US012624349B2

(12) United States Patent
Meyerson et al.

(10) Patent No.: US 12,624,349 B2
(45) Date of Patent: May 12, 2026

(54) METHODS OF HIGH-THROUGHPUT IDENTIFICATION OF T CELL EPITOPES BY CAPTURING CYTOKINES ON THE SURFACE OF ANTIGEN-PRESENTING CELLS

(71) Applicant: DANA-FARBER CANCER INSTITUTE, INC., Boston, MA (US)

(72) Inventors: Matthew Meyerson, Concord, MA (US); Mark N. Lee, Arlington, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1059 days.

(21) Appl. No.: 17/760,532

(22) PCT Filed: Sep. 23, 2020

(86) PCT No.: PCT/US2020/052164
§ 371 (c)(1),
(2) Date: Mar. 15, 2022

(87) PCT Pub. No.: WO2021/061736
PCT Pub. Date: Apr. 1, 2021

(65) Prior Publication Data
US 2022/0364079 A1     Nov. 17, 2022

Related U.S. Application Data

(60) Provisional application No. 62/904,473, filed on Sep. 23, 2019.

(51) Int. Cl.
| | |
|---|---|
| *C12N 15/10* | (2006.01) |
| *C07K 14/74* | (2006.01) |
| *C07K 16/24* | (2006.01) |

(52) U.S. Cl.
CPC .... *C12N 15/1034* (2013.01); *C07K 14/70539* (2013.01); *C07K 16/246* (2013.01); *C07K 16/249* (2013.01); *C12N 15/1037* (2013.01)

(58) Field of Classification Search
CPC ............ C07K 14/70539; C07K 16/246; C07K 16/249; C12N 15/1034; C12N 15/1037; C12N 15/1138; C12N 15/907; C12N 2310/20; C12N 2740/16043; G01N 33/505; G01N 33/6863
See application file for complete search history.

(56) References Cited

U.S. PATENT DOCUMENTS

| | | |
|---|---|---|
| 9,115,380 B2 | 8/2015 | Jendrisak et al. |
| 2018/0320230 A1 | 11/2018 | LaBaer |

FOREIGN PATENT DOCUMENTS

| | | |
|---|---|---|
| WO | 2017176806 A1 | 10/2017 |
| WO | 2019031938 A2 | 2/2019 |

OTHER PUBLICATIONS

Ku et al. (J. Allergy Clin. Immunol., 2016, 137(3):945-948) (Year: 2016).*
Trotta et al. (Nat. Med., 2018, 24(7):1005-1014, doi:10.1038/s41591-018-0070-2) (Year: 2018).*

* cited by examiner

*Primary Examiner* — Jeremy C Flinders
(74) *Attorney, Agent, or Firm* — ArentFox Schiff LLP; Daniel W. Clarke

(57) ABSTRACT

The present disclosure relates to methods that combine identification of T cell-secreted cytokines by modified antigen-presenting cells (APCs), cell sorting, and next-generation sequencing to identify class I- and class II-restricted epitopes starting from massively-complex peptide-encoding oligonucleotide pools. APCs are modified to express anti-cytokine antibodies, a library of DNA-encoded peptides, and multiple HLA class I or II molecules. Upon co-culture with T cells, these modified APCs form HLA/epitope/TCR complexes, enabling the production of T cell activation-dependent cytokines with the DNA that encodes the presented peptide. After co-culture, the APCs are sorted, and the peptide-encoding DNA is sequenced to determine the identity of the immunogenic peptides. Thus, the disclosure allows pooled screening of thousands of encoded peptides to enable epitope discovery for orphan T cell receptors.

26 Claims, 78 Drawing Sheets

Specification includes a Sequence Listing.

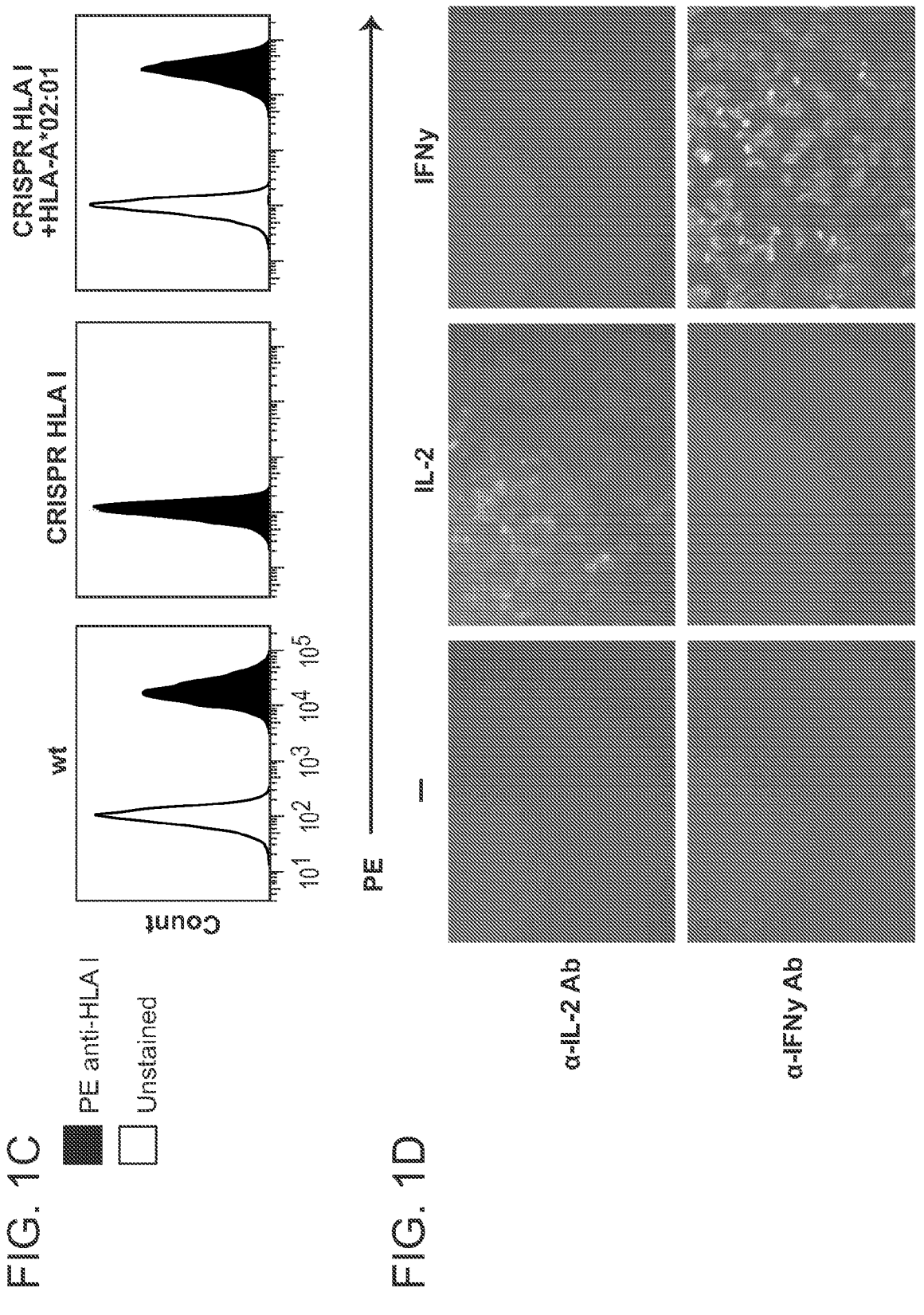

Figure 5A:
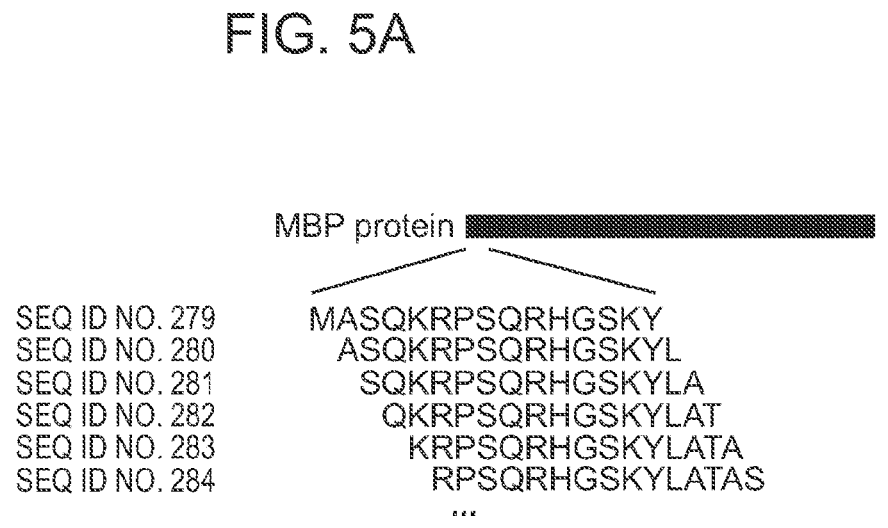

MBP protein ▓▓▓▓▓▓▓▓▓▓▓▓▓▓▓▓▓▓▓▓

SEQ ID NO. 279          MASQKRPSQRHGSKY
SEQ ID NO. 280           ASQKRPSQRHGSKYL
SEQ ID NO. 281            SQKRPSQRHGSKYLA
SEQ ID NO. 282             QKRPSQRHGSKYLAT
SEQ ID NO. 283              KRPSQRHGSKYLATA
SEQ ID NO. 284               RPSQRHGSKYLATAS
                              ...

FIG. 5B

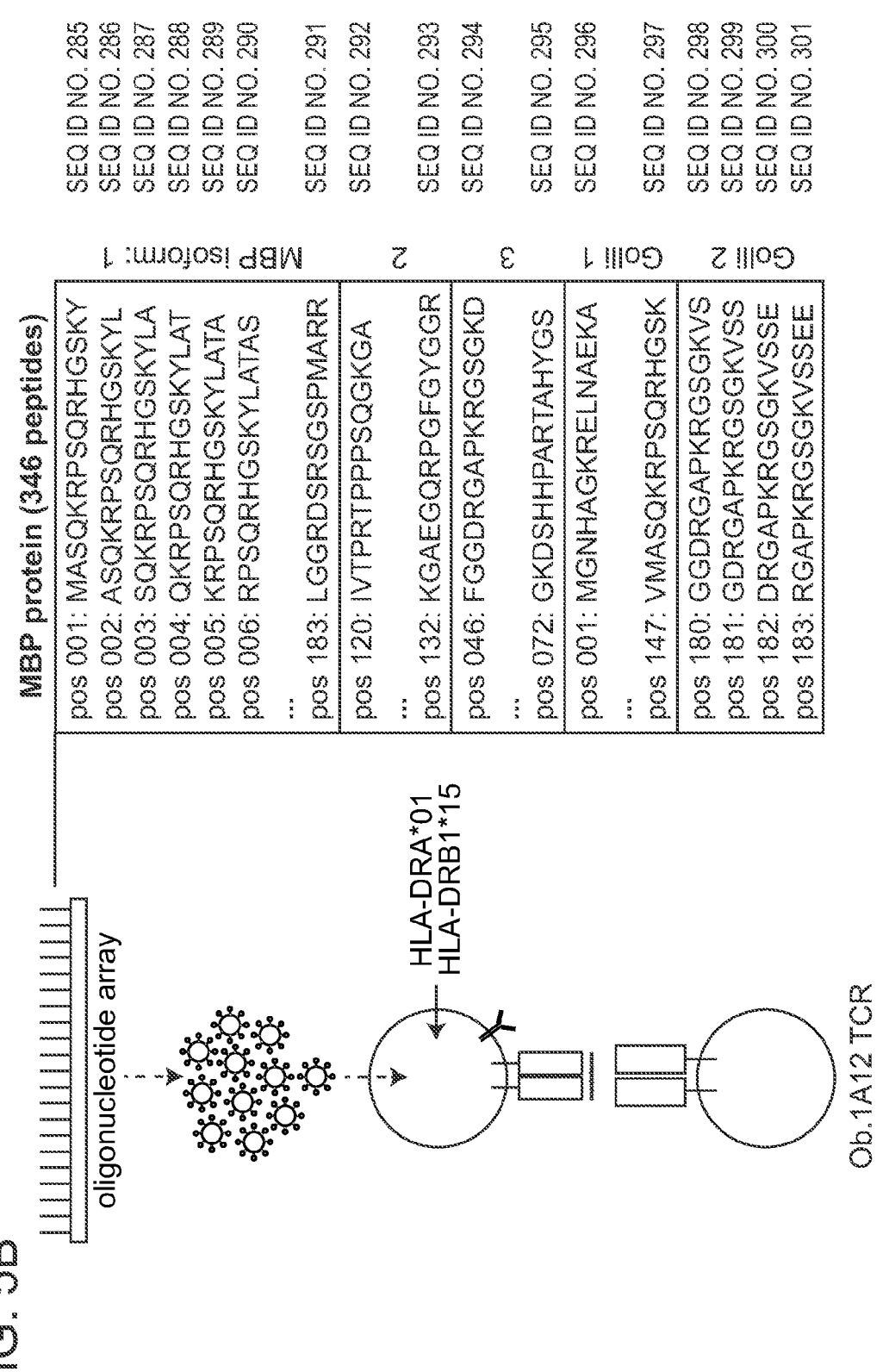

MBP protein (346 peptides)

| MBP isoform: 1 | | |
|---|---|---|
| pos 001: MASQKRPSQRHGSKY | SEQ ID NO. 285 |
| pos 002: ASQKRPSQRHGSKYL | SEQ ID NO. 286 |
| pos 003: SQKRPSQRHGSKYLA | SEQ ID NO. 287 |
| pos 004: QKRPSQRHGSKYLAT | SEQ ID NO. 288 |
| pos 005: KRPSQRHGSKYLATA | SEQ ID NO. 289 |
| pos 006: RPSQRHGSKYLATAS | SEQ ID NO. 290 |
| ...: | |
| pos 183: LGGRDSRSGSPMARR | SEQ ID NO. 291 |

| 2 | |
|---|---|
| pos 120: IVTPRTPPPSQGKGA | SEQ ID NO. 292 |
| ...: | |
| pos 132: KGAEGQRPGFGYGGR | SEQ ID NO. 293 |

| 3 | |
|---|---|
| pos 046: FGGDRGAPKRGSGKD | SEQ ID NO. 294 |
| ...: | |
| pos 072: GKDSHHPARTAHYGS | SEQ ID NO. 295 |

| GolII 1 | |
|---|---|
| pos 001: MGNHAGKRELNAEKA | SEQ ID NO. 296 |
| ...: | |
| pos 147: VMASQKRPSQRHGSK | SEQ ID NO. 297 |

| GolII 2 | |
|---|---|
| pos 180: GGDRGAPKRGSGKVS | SEQ ID NO. 298 |
| pos 181: GDRGAPKRGSGKVSS | SEQ ID NO. 299 |
| pos 182: DRGAPKRGSGKVSSE | SEQ ID NO. 300 |
| pos 183: RGAPKRGSGKVSSEE | SEQ ID NO. 301 | oligonucleotide array

HLA-DRA*01
HLA-DRB1*15

Ob.1A12 TCR

HGRTQDENPVVHFFK = -0.09%    SEQ ID NO. 302
GRTQDENPVVHFFKN = 0.04%    SEQ ID NO. 303
RTQDENPVVHFFKNI = -0.15%    SEQ ID NO. 304
TQDENPVVHFFKNIV = -0.09%    SEQ ID NO. 305
QDENPVVHFFKNIVT = 0.49%    SEQ ID NO. 306
DENPVVHFFKNIVTP = 2.05%    SEQ ID NO. 307
ENPVVHFFKNIVTPR = 1.59%    SEQ ID NO. 308
NPVVHFFKNIVTPRT = 1.82%    SEQ ID NO. 309
PVVHFFKNIVTPRTP = 1.78%    SEQ ID NO. 310
VVHFFKNIVTPRTPP = -0.27%    SEQ ID NO. 311

HLA-ORA*01
HLA-ORBQ*15      SEQ. ID NO: 317

5.1%

+TQDENPVVHFFKNN      SEQ. ID NO: 318

0.45%

+QDENPVVHFFKNVI      SEQ. ID NO: 319

4.2%

+DENPVVHFFKNIVTP      SEQ. ID NO: 320

32.35%

+ENPVVHFFKNIVTPR      SEQ. ID NO: 321

55.45%

+NPVVHFFKNIVTPRT      SEQ. ID NO: 322

43.75%

+PVVHFFKNIVTPRTP      SEQ. ID NO: 763

52.25%

+VVHFFKNIVTPRTPP      SEQ. ID NO: 323

0.45%

Count $10^1\ 10^2\ 10^3\ 10^4\ 10^5$
PC anti-IL2

FIG. 6A

Public TCRβ (infection, associated)

TCRα (single-cell sequencing)

Epitope (library)
HLAI (typing)

FIG. 6B

| | | TCRβ | | CMV+/- [12] |
|---|---|---|---|---|
| SEQ ID NO. 325 | TRC #1 | TRBV11-2 CASSSGQETQYF TRBJ2-5 | | 2.8% / 0.3% |
| SEQ ID NO. 326 | TRC #5 | TRBV9 CASSVTGGTDTQYF TRBJ2-3 | | 11.5% / 6.4% |
| SEQ ID NO. 327 | TRC #6 | TRBV9 CASSAGQGVTYEQYF TRBJ2-7 | | 3.7% / 0% |

| | TCRα | Candidate HLAI | Epitope | |
|---|---|---|---|---|
| | TRAV8-3 CAVASYGNKLVF TRAJ47 | B*51 | u/k | SEQ ID NO. 328 |
| | TRAV19 CALSEGFQTGANNLFF TRAJ36 | A*01, B*08 | u/k | SEQ ID NO. 329 |
| | TRAV21 CAVRSGGYQKVTF TRAJ13 | A*01, B*08 | u/k | SEQ ID NO. 330 |

TCR #1 HLA-A*24:02 + HLA-B*07:02 + HLA*51:01 + Filtered library

LPLKMLNI

TCR #5 HLA-A*01:01 + HLA-B*08:01 + Tiled library

QQIFLEVQAIRETVELRQYDPVAALFFFDIDLLLQRGPQYSEHPTFTSQY

SEQ ID NO. 333

TCR #6 HLA-A*01:01 + HLA-B*08:01 + Tiled library

TLLNCAVTKLPCTLRIVTEHDTLLYVASRNGLFAVENFLTEEPFGRGDPF

SEQ ID NO. 334

Peptide-encoding oligo

FIG. 7C

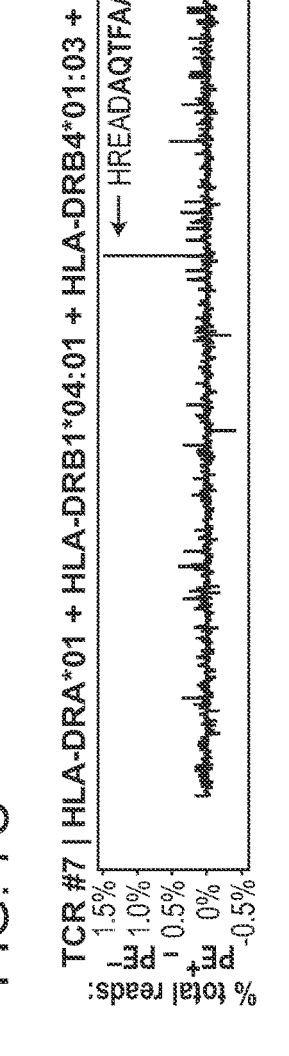

TCR #7 | HLA-DRA*01 + HLA-DRB1*04:01 + HLA-DRB4*01:03 + HLA-DRB5*01:01 + Tiled library

← HREADAQTFAATHNPWASQAGCLSDVLYNTRHRERLGYNSKFYSPCAQYF
SEQ ID NO. 363

% total reads: PE⁻/PE⁺
1.5%
1.0%
0.5%
0%
-0.5%

FIG. 7D

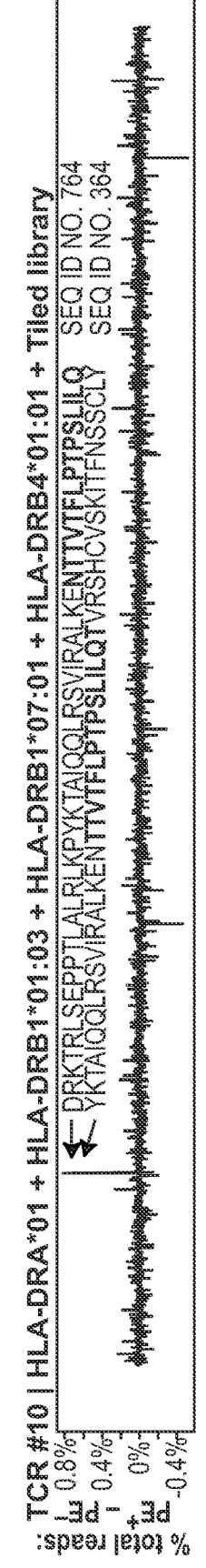

TCR #10 | HLA-DRA*01 + HLA-DRB1*01:03 + HLA-DRB1*07:01 + HLA-DRB4*01:01 + Tiled library ← DRKTRLSEPPTLALRLKPYKTAIQQLRSVIRALKENTTVTFLPTPSLILQ  SEQ ID NO. 764
← YKTAIQQLRSVIRALKENTTVTFLPTPSLILQTVRSHCVSKITFNSSCLY  SEQ ID NO. 364

% total reads: PE⁻/PE⁺
0.8%
0.4%
0%
-0.4%

Peptide-encoding oligo

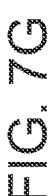

FIG. 7G

HRE 50-mer:HREADAQTFAATHNPWASQAGCLSDVLYNTRHRERLGYNSKFYSPCAQYF   SEQ ID NO. 365

AQTFAATHNPWASQA   SEQ ID NO. 366

Legend:
- ● HLA-DRB1*04:01
- ◑ HLA-DRB4*01:03
- ○ HLA-DRB5*01:01

Peptide (15 aa)

-log(Rank)
NetMHCIIpan 4.0

DRK 50-mer:DRKTRLSEPPTLALRLKPYKTAIQQLRSVIRALKENTTVTFLPTPSLILQ   SEQ ID NO. 367

YKT 50-mer YKTAIQQLRSVIRALKENTTVTFLPTPSLILQTVRSHCVSKITFNSSCLY   SEQ ID NO. 368

SEQ ID NO. 706   TTVTFLPTPSLILQT→
SEQ ID NO. 707   NTTVTFLPTPSLILQ→

Legend:
- ● HLA-DRB1*01:03
- ◑ HLA-DRB1*07:01
- ○ HLA-DRB4*01:01

Peptide (15 aa)

-log(Rank)
NetMHCIIpan 4.0

Figure 8A:
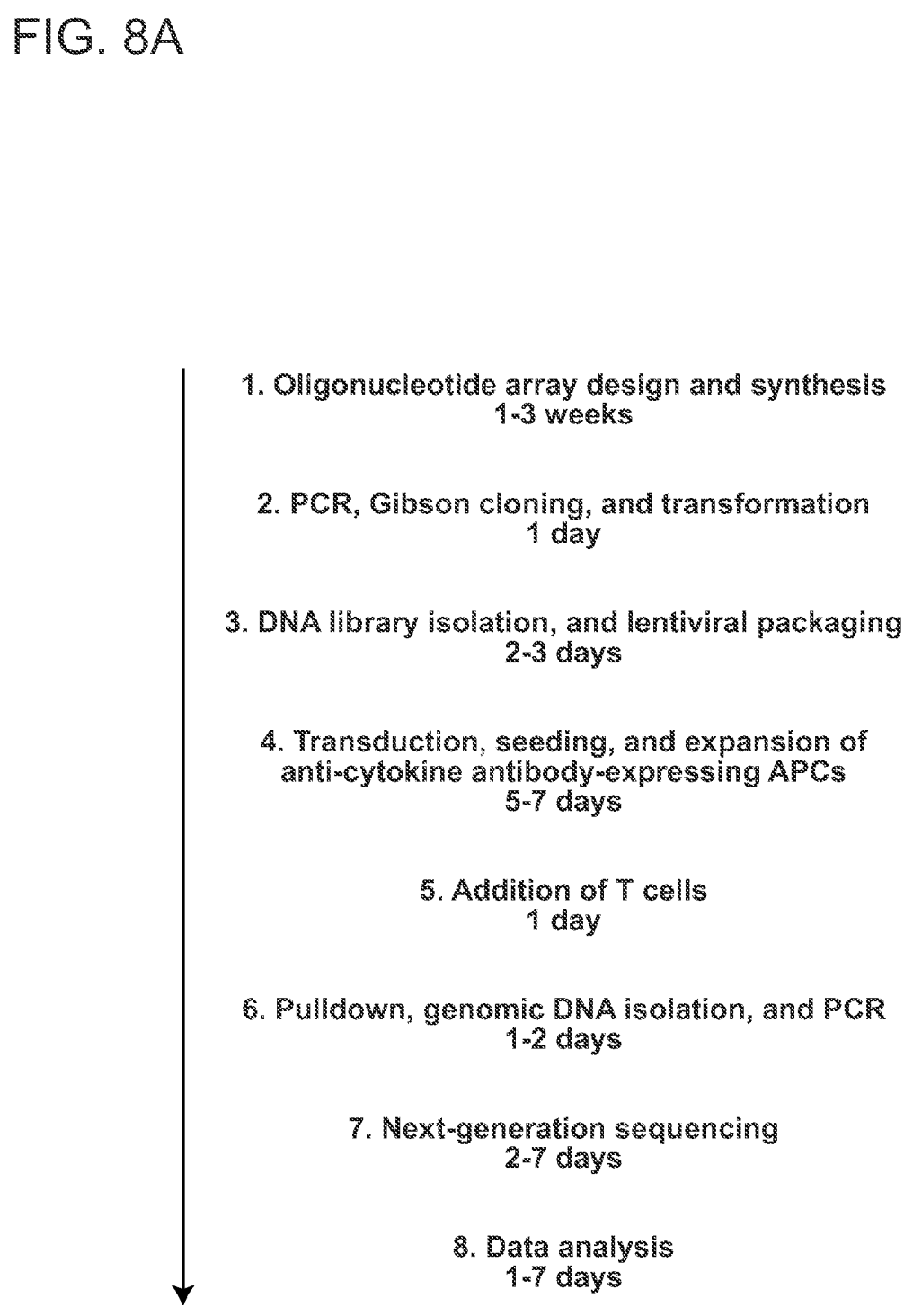

1. Oligonucleotide array design and synthesis
1-3 weeks

2. PCR, Gibson cloning, and transformation
1 day

3. DNA library isolation, and lentiviral packaging
2-3 days

4. Transduction, seeding, and expansion of
anti-cytokine antibody-expressing APCs
5-7 days 5. Addition of T cells
1 day 6. Pulldown, genomic DNA isolation, and PCR
1-2 days 7. Next-generation sequencing
2-7 days 8. Data analysis
1-7 days wild-type,
isotype ctrl wild-type,
FITC anti-HLA I CRISPR HLA,
FITC anti-HLA I wt

CRISPR TCR

CRISPR TCR,
KRAS TCR

☐ –
■ Influenza JM22 TCR
▧ NY-ESO-1 1G4 TCR

FIG. 10G

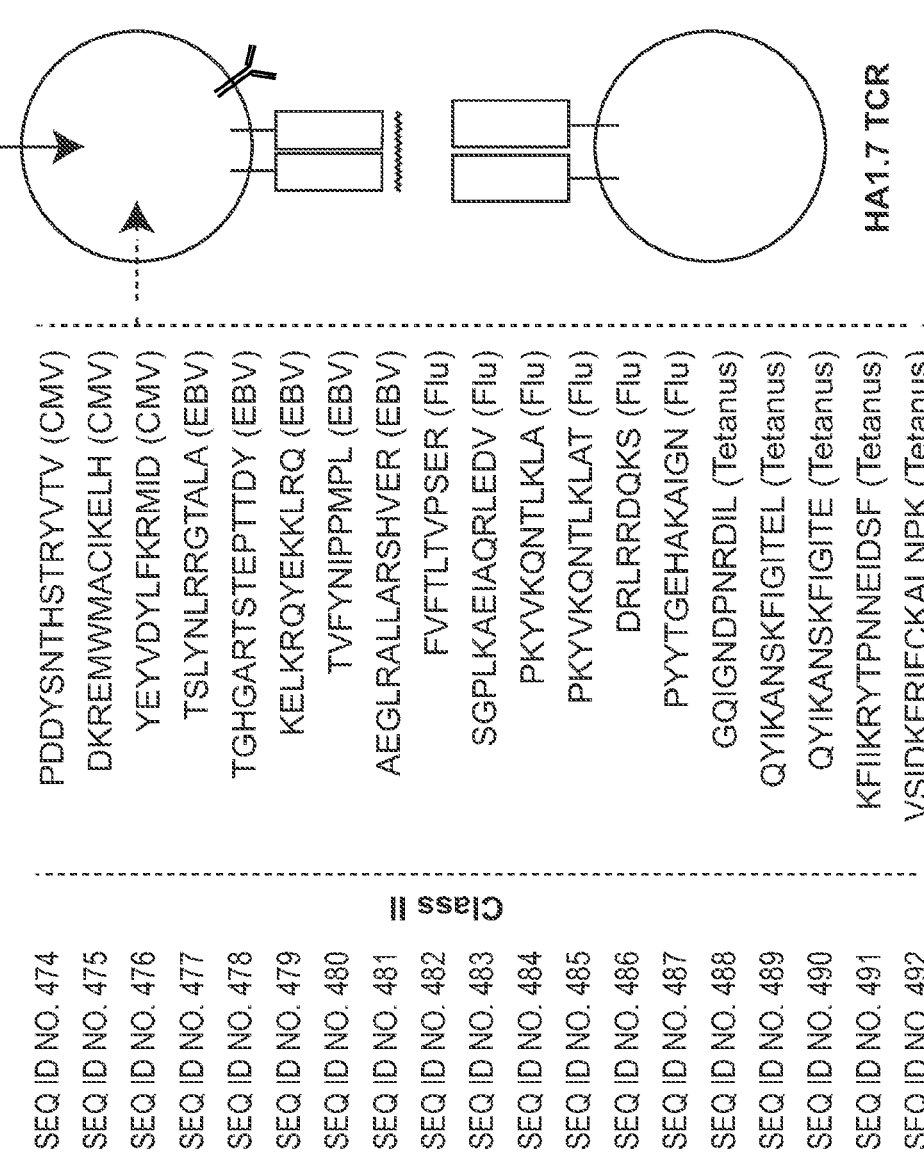

HLA-DRA*01
HLA-DRB1*01

HA1.7 TCR

Class II

| | |
|---|---|
| SEQ ID NO. 474 | PDDYSNTHSTRYVTV (CMV) |
| SEQ ID NO. 475 | DKREMWMACIKELH (CMV) |
| SEQ ID NO. 476 | YEYVDYLFKRMID (CMV) |
| SEQ ID NO. 477 | TSLYNLRRGTALA (EBV) |
| SEQ ID NO. 478 | TGHGARTSTEPTTDY (EBV) |
| SEQ ID NO. 479 | KELKRQYEKKLRQ (EBV) |
| SEQ ID NO. 480 | TVFYNIPPMPL (EBV) |
| SEQ ID NO. 481 | AEGLRALLARSHVER (EBV) |
| SEQ ID NO. 482 | FVFTLTVPSER (Flu) |
| SEQ ID NO. 483 | SGPLKAEIAQRLEDV (Flu) |
| SEQ ID NO. 484 | PKYVKQNTLKLA (Flu) |
| SEQ ID NO. 485 | PKYVKQNTLKLAT (Flu) |
| SEQ ID NO. 486 | DRLRRDQKS (Flu) |
| SEQ ID NO. 487 | PYYTGEHAKAIGN (Flu) |
| SEQ ID NO. 488 | GQIGNDPNRDIL (Tetanus) |
| SEQ ID NO. 489 | QYIKANSKFIGITEL (Tetanus) |
| SEQ ID NO. 490 | QYIKANSKFIGITE (Tetanus) |
| SEQ ID NO. 491 | KFIIKRYTPNNEIDSF (Tetanus) |
| SEQ ID NO. 492 | VSIDKFRIFCKALNPK (Tetanus) |

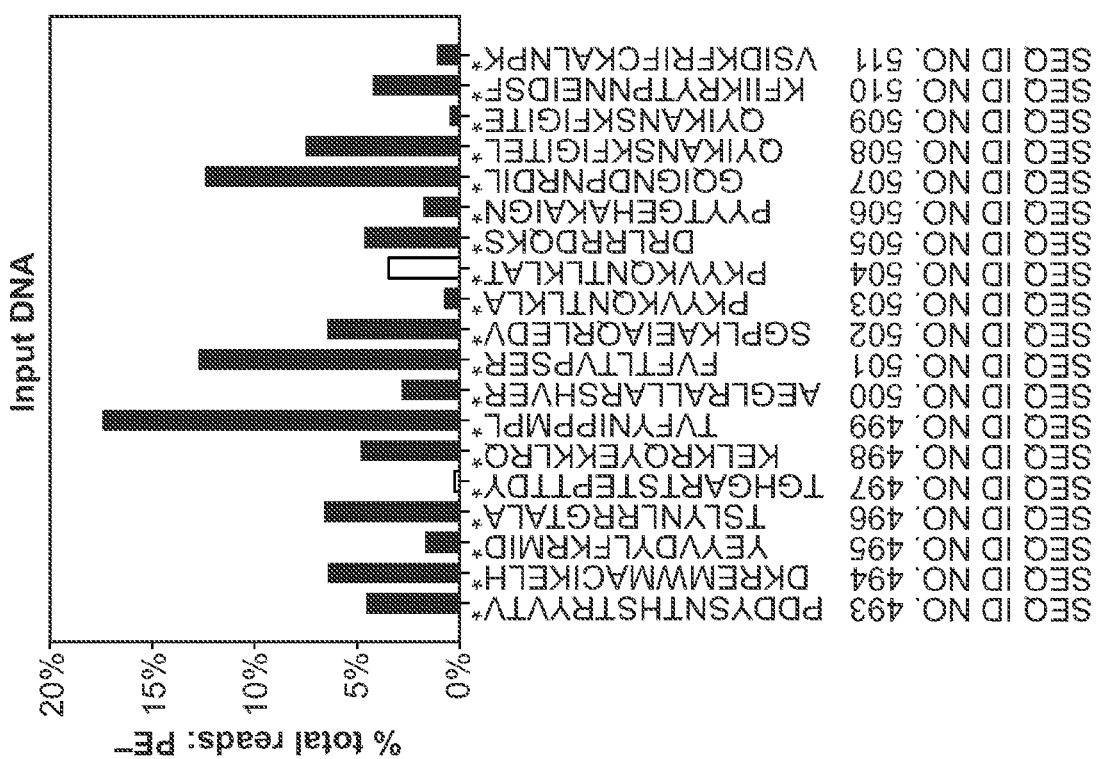
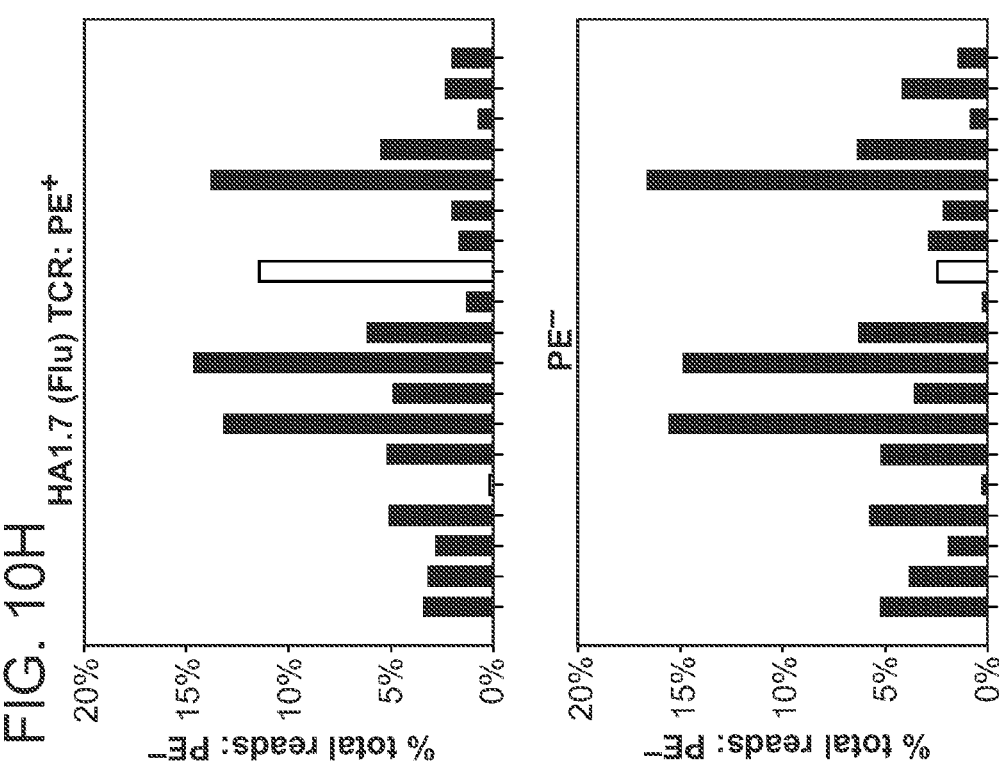

Run #1

GADGVGKSAL SEQ ID NO. 535

Run #2

GADGVGKSAL SEQ ID NO. 536

Encoded peptides

```
MBP.1        ------------------------------------------------------------
MBP.2        ------------------------------------------------------------
MBP.3        ------------------------------------------------------------
MBP.4        ------------------------------------------------------------
Golli.1      MGNHAGKRELNAEKASTNSETNRGESEKKRNLGELSRTTSEDNEVFGEADANQNNGTSSQ    SEQ ID NO. 537
Golli.2      MGNHAGKRELNAEKASTNSETNRGESEKKRNLGELSRTTSEDNEVFGEADANQNNGTSSQ    SEQ ID NO. 538
```

-73 to -14

```
MBP.1        ------------------------------------------------------------
MBP.2        ------------------------------------------------------------
MBP.3        ------------------------------------------------------------
MBP.4        ------------------------------------------------------------
Golli.1      DTAVTDSKRTADPKNAWQDAHPADPGSRPHLIRLFSRDAPGREDNTFKDRPSESDELQTI    SEQ ID NO. 539
Golli.2      DTAVTDSKRTADPKNAWQDAHPADPGSRPHLIRLFSRDAPGREDNTFKDRPSESDELQTI    SEQ ID NO. 540
```

-13 to 47

```
MBP.1        ------------MASQKRPSQRHGSKYLATASTMDHARHGFLPRHRDTGILDSIGRFFG    SEQ ID NO. 541
MBP.2        ------------MASQKRPSQRHGSKYLATASTMDHARHGFLPRHRDTGILDSIGRFFG    SEQ ID NO. 542
MBP.3        ------------MASQKRPSQRHGSKYLATASTMDHARHGFLPRHRDTGILDSIGRFFG    SEQ ID NO. 543
MBP.4        ------------MASQKRPSQRHGSKYLATASTMDHARHGFLPRHRDTGILDSIGRFFG    SEQ ID NO. 544
Golli-MBP.1  QEDSAATSESLDVMASQKRPSQRHGSKYLATASTMDHARHGFLPRHRDTGILDSIGRFFG    SEQ ID NO. 545
Golli-MBP.2  QEDSAATSESLDVMASQKRPSQRHGSKYLATASTMDHARHGFLPRHRDTGILDSIGRFFG    SEQ ID NO. 546
```

| | | |
|---|---|---|
| MBP.1 | GDRGAPKRGSGKVPWLKPGRSPLPSHARSQPGLCNMYKDSHHPARTAHYGSLPQKSHGRT | SEQ ID NO. 547 |
| MBP.2 | GDRGAPKRGSGKVPWLKPGRSPLPSHARSQPGLCNMYKDSHHPARTAHYGSLPQKSHGRT | SEQ ID NO. 548 |
| MBP.3 | GDRGAPKRGSGKD-------------------------SHHPARTAHYGSLPQKSHGRT | SEQ ID NO. 549 |
| MBP.4 | GDRGAPKRGSGKD-----------------------------SHHPARTAHYGSLPQKSHGRT | SEQ ID NO. 550 |
| Golli-MBP.1 | GDRGAPKRGSGKD-------------------------SHHPARTAHYGSLPQKSHGRT | SEQ ID NO. 551 |
| Golli-MBP.2 | GDRGAPKRGSGKV----------------------------SSEE-------------- | SEQ ID NO. 552 |

108 to 167

| | | |
|---|---|---|
| MBP.1 | QDENPVVHFFKNIVTPRTPPPSQGKGRGLSLSRFSWGAEGQRPGFGYGGRASDYKSAHKG | SEQ ID NO. 553 |
| MBP.2 | QDENPVVHFFKNIVTPRTPPPSQGKGRGLSLSRFSWGAEGQRPGFGYGGRASDYKSAHKG | SEQ ID NO. 554 |
| MBP.3 | QDENPVVHFFKNIVTPRTPPPSQGKG-------AEGQRPGFGYGGRASDYKSAHKG | SEQ ID NO. 555 |
| MBP.4 | QDENPVVHFFKNIVTPRTPPPSQGKG-------AEGQRPGFGYGGRASDYKSAHKG | SEQ ID NO. 556 |
| Golli-MBP.1 | QDENPVVHFFKNIVTPRTPPPSQGKGRGLSLSRFSWGAEGQRPGFGYGGRASDYKSAHKG | SEQ ID NO. 557 |
| Golli-MBP.2 | -------------------------------------------------------------- | |

168 to 197

| | | |
|---|---|---|
| MBP.1 | FKGVDAQGTLSKIFKLGGRDSRSGSPMARR | SEQ ID NO. 558 |
| MBP.2 | FKGVDAQGTLSKIFKLGGRDSRSGSPMARR | 171 | SEQ ID NO. 559 |
| MBP.3 | FKGVDAQGTLSKIFKLGGRDSRSGSPMARR | 160 | SEQ ID NO. 560 |
| MBP.4 | FKGVDAQGTLSKIFKLGGRDSRSGSPMARR | 304 | SEQ ID NO. 561 |
| Golli-MBP.1 | FKGVDAQGTLSKIFKLGGRDSRSGSPMARR | 197 | SEQ ID NO. 562 |
| Golli-MBP.2 | ------------------------------ | |

Encoded peptides (15 aa)

TCR #2 | HLA-A*24:02 + HLA-B*07:02 + HLA-B*51:01 + Filtered library

VYAIFIFQL SEQ ID NO. 765

Peptide-encoding oligo

% total reads:
PE+ − PE−

TCR #2

SEQ ID NO. 645     VYAIFIFQL z-score

Frequency

TCR #2:

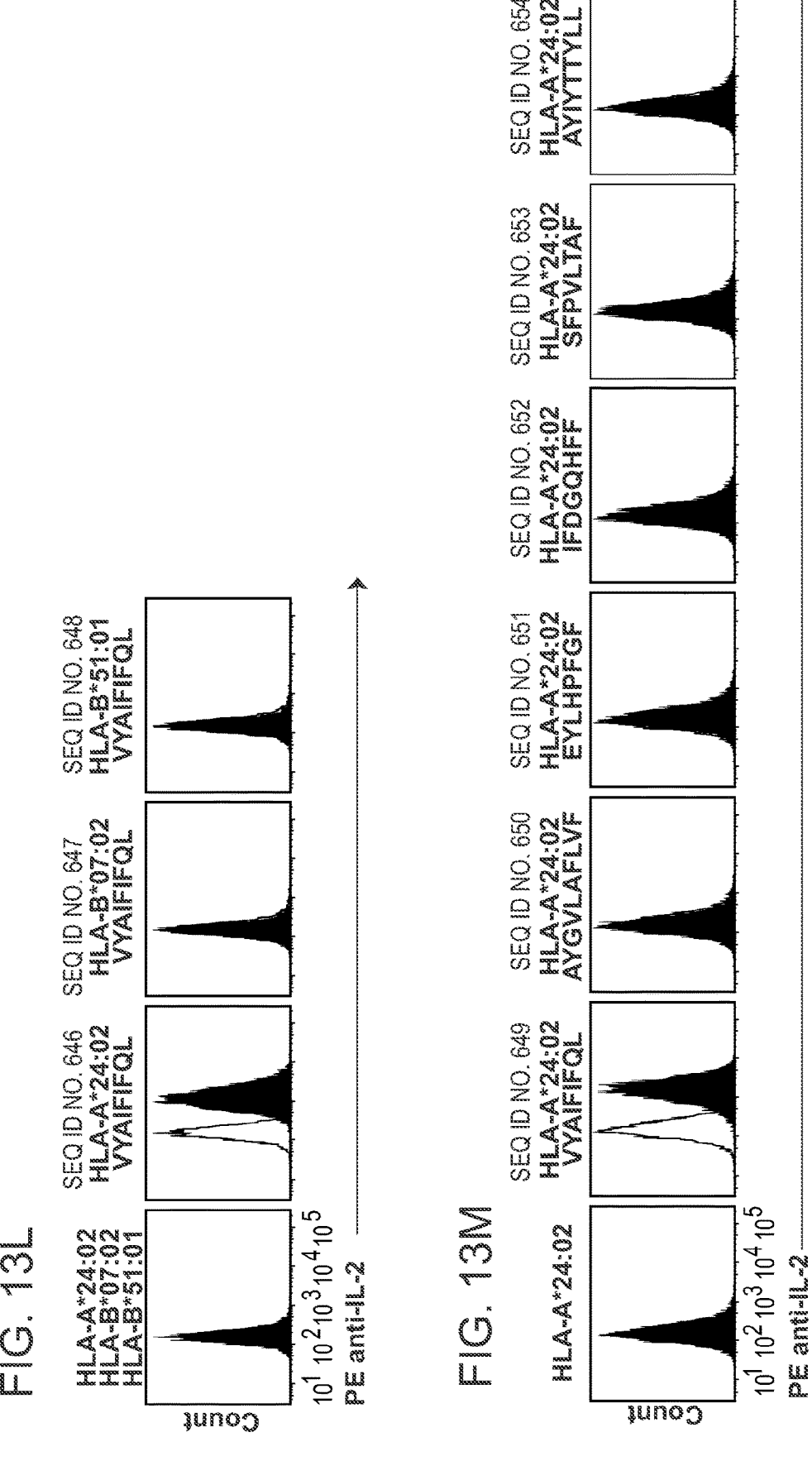

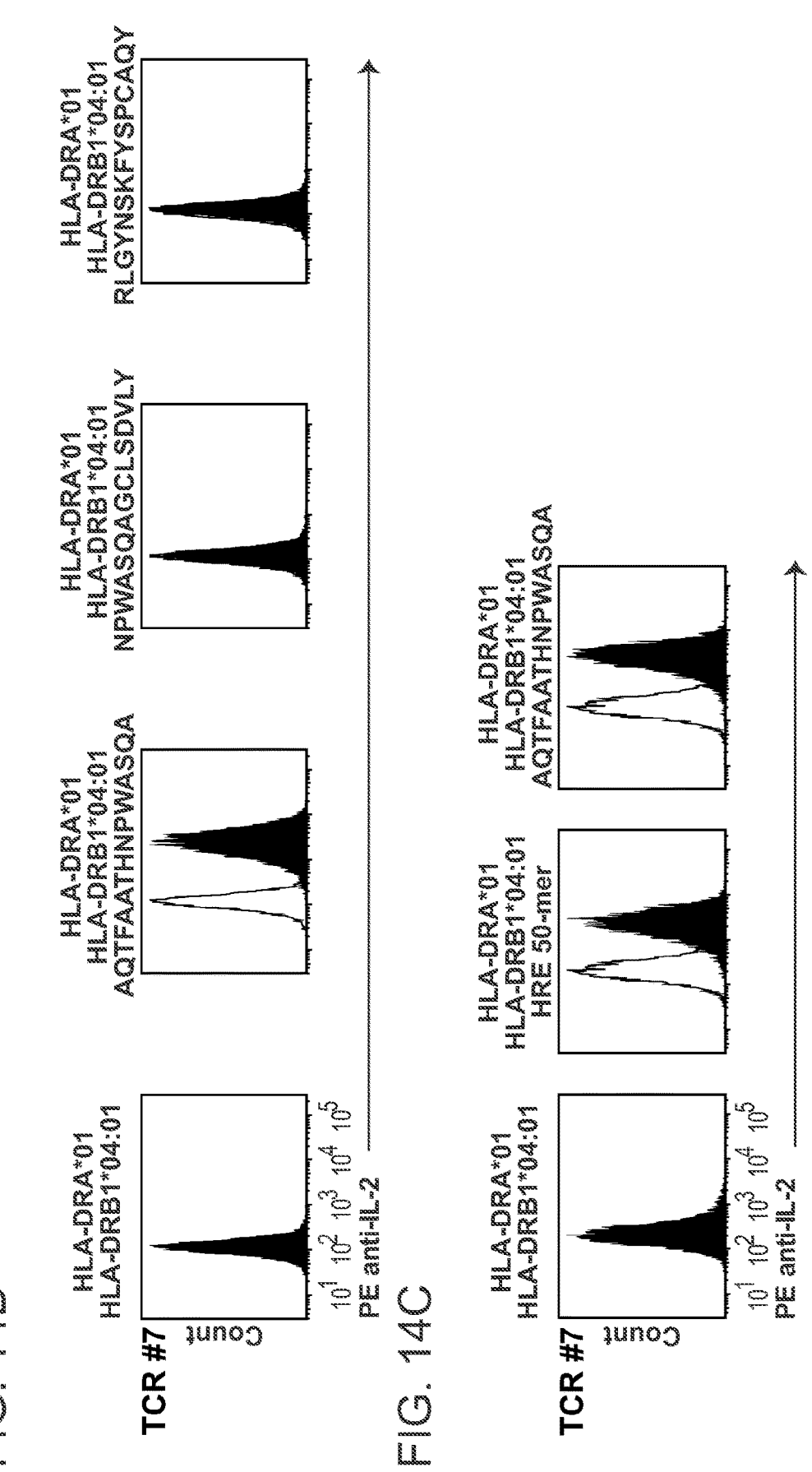

METHODS OF HIGH-THROUGHPUT IDENTIFICATION OF T CELL EPITOPES BY CAPTURING CYTOKINES ON THE SURFACE OF ANTIGEN-PRESENTING CELLS

RELATED APPLICATIONS

This application is a National Stage application, filed under 35 U.S.C. § 371, of International Application No. PCT/US2020/052164, filed Sep. 23, 2020, which claims the benefit of priority under 35 U.S.C. § 119(e) to U.S. Provisional Application No. 62/904,473, filed on Sep. 23, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 2, 2020, is named 52095-639001WO_SL.txt and is 239.79 kilobytes in size.

GOVERNMENT LICENSE RIGHTS

This invention was made with government support under grant number R35 CA197568 awarded by the National Institutes of Health. The government has certain rights in the invention.

BACKGROUND OF THE INVENTION

T cell activation cascade is critical for the initiation of the immune response and within the human system revolves around three stages. The first stage involves binding between a T cell receptor (TCR) with programmed specificity to a particular foreign molecule (antigen), specifically an epitope of the antigen presented on an antigen presenting cell (APC). The second stage involves binding of a T cell to the APC to initiate T cell proliferation. The third stage involves secretion of cytokines from activated T cells that send signals to different types of immune responder cells. Activation of T cells enables cytotoxic CD8 T cells to develop cell-mediated immune system mechanisms. It also promotes the engagement of accessory immune cells such as macrophages. Further, the activation cascade increases antibody responses through the T-helper cells (CD4) and the enhancement of antibody production by B cells. (T-Cell Activation, Susan Pross, *xPharm: The Comprehensive Pharmacology Reference,* 2007). Improper or defective T cell activation cause a variety of autoimmune diseases (e.g., type 1 diabetes mellitus in infancy, hypothyroidism, and Addison's disease) which attack a subject's own immune cells, as well as uncontrolled cell proliferation associated with cellular checkpoint blockades in cancer immunotherapies. T cell receptors (TCRs) on the surface of T cells are used by the immune system to identify foreign molecules in order to trigger an immune response. TCRs recognize small peptides, called epitopes that are bound to human leukocyte (HLA) antigen proteins. The number of possible candidate epitopes is large.

Variation in human leukocyte antigen (HLA) and T cell receptor (TCR) genes is associated with risk of infection and autoimmunity (International HIV Controllers Study et al., 2010 Science, 330:1551-7; Gutierrez-Arcelus et al., 2016 Nat. Rev. Genet., 17:160-174; Miyadera et al., 2015 J. Hum.

Genet., 60:697-702), and can influence patient survival to checkpoint blockade immunotherapy (Zaretsky et al., 2016 N. Engl. J. Med., 375:819-829; Chowell et al., 2018 Science, 359:582-587). Identification of the specific complexes between HLA molecules epitopes, and TCRs—resulting in T cell stimulation—provides fundamental information about disease pathogenesis (Miyadera et al., 2015 J. Hum. Genet., 60:697-702; Latorre et al., 2018 Nature, 562:63-68; Tran et al., 2016 N. Engl. J. Med., 375:2255-2262; Zacharakis et al., 2018 Nat. Med., 24:724-730).

Productive interactions between a T cell (e.g., cytotoxic T cell) and an antigen, such as an antigen presented by an APC, are rare. They may often occur among fewer than one out of one million target cells. An antigen recognized by a given T cell is typically present at exceedingly low frequencies, e.g., 1 in 100,000 antigens or less. Further, not every target cell displaying a given antigen will encounter its cognate T cell, especially given the specificities of mixed T cell populations.

Other factors of a technological nature present barriers to identifying which HLA, epitopes, and TCRs that productively lead to T cell activation. These barriers, in part, emerge from the significant inter- and intra-individual variation in HLA (Dendrou et al., 2018 Nat. Rev. Immunol., 18:325-339 (2018)) and TCR genes (Robins et al., 2009 Blood., 114:4099-107; Robins et al., 2010 Sci. Transl. Med., 2, 47ra64; Emerson et al., 2017 Nat. Genet., 49:659-665), as well as the vast potential space of candidate peptide epitopes (Lundegaard et al., 2010 Immunome Res., 6:S3623-629).

Accordingly, efforts to identify T cell receptor interactions with epitopes thereof have focused on individual or small numbers of pairs of interactions based on direct measurement of T cell responses. Functional assays, notably enzyme-linked immunospot (ELISpot) assays (Czerkinsky et al., 1988 J. Immunol. Methods., 110:29-36) and HLA multimer assays (Altman et al., 1996 Science., 274:94-6; Newell et al., 2013 Nat. Biotechnol., 31:623-629; Bentzen et al., 2016 Nat. Biotechnol., 34:1037-1045), have been in widespread use to detect HLA-epitope-TCR complexes (Sharma et al., 2014 Hum. Immunol., 75:514-519). The ELISpot assay is a highly sensitive immunoassay that measures the frequency of cytokine-secreting cells at the single-cell level. In this assay, cells are cultured on a surface coated with a specific capture antibody in the presence or absence of stimuli. Proteins, such as cytokines, that are secreted by the cells are captured by the specific antibodies on the surface. After an appropriate incubation time, cells are removed and the secreted molecule is detected using a detection antibody. The detection antibody is either biotinylated and followed by a streptavidin-enzyme conjugate or the antibody is directly conjugated to an enzyme. By using a substrate with a precipitating rather than a soluble product, the end result is visible spots on the surface. Each spot corresponds to an individual cytokine-secreting cell.

Traditional candidate epitope identification technologies, including functional assays such as ELISPOT (enzyme-linked immunospot) and ICS (intracellular cytokine staining), are in widespread use to detect HLA-epitope-TCR complexes. ELISPOT and ICS rely on capture of T cell activation-dependent cytokines—endogenous signals with high signal: noise. These methods have had broad and important applications, e.g. to identify epitopes targeted by both CD8+ and CD4+ T cells in disease contexts such as cancer and natural/vaccine-elicited immunity against pathogens. However, these types of assays are particularly limited in candidate epitope dimensionality due to the high costs of peptide synthesis (Hondowicz et al., 2012 PLoS One, 7:

doi:10.1371/journal.pone.0029949; Siewert et al., 2012 Nat. Med., 18:824-828). A means to address this limitation is to use massively-complex oligonucleotide pools (Tian et al., 2004 Nature, 432:1050-4; Kosuri et al., 2014 Nat. Methods., 11:499-507) to encode peptides (Hondowicz et al., 2012 PLoS One, 7: doi:10.1371/journal.pone.0029949). However, use of these pools in turn creates a technical challenge of selecting target oligonucleotides from the mixture.

Alternative methods utilize oligonucleotide pools (Birnbaum et al., 2014 Cell., 157:1073-87; Li et al., 2019 Nat. Methods, 16:183-190; Joglekar et al., 2019 Nat. Methods., 16: 191-198; Kula et al., 2019 Cell., 178:1016-1028.e13). However, their specificity, robustness, and adoptability are imperfect or unclear. For example, a method to screen yeast-displayed peptide-MHC libraries using TCR multimers is scalable to millions of candidate epitopes (Birnbaum et al., 2014 Cell., 157:1073-87). However, this method relies on the technically complex synthesis of each TCR multimer, the extensive optimization of each MHC allele, and attempts to infer target epitope sequences from surrogate hits (Birnbaum et al., 2014 Cell., 157:1073-87; Gee et al., 2018 Cell, 172:549-563.e16; Saligrama et al., 2019 Nature, 572:481-487). Moreover, the ability to screen both HLA class I and class II-presented candidate epitopes remains unclear with many of these alternative methods and/or their ability to concurrently test multiple HLA alleles is limited, secondary to the need for extensive optimization of each recombinant HLA or to fusion of peptide libraries to an HLA molecule (Li et al., 2019 Nat. Methods, 16:183-190; Joglekar et al., 2019 Nat. Methods., 16: 191-198; Kula et al., 2019 Cell., 178: 1016-1028.e13).

A need remains for a high-throughput epitope identification method that takes into account both HLA and peptide diversity.

SUMMARY OF THE INVENTION

Described herein is a high-throughput assay for identifying epitopes that activate T cells by capturing cytokine(s) on the surface of antigen-presenting cells (APCs).

Accordingly, an aspect of the disclosed invention pertains to methods for identifying complexes of HLA/epitope/TCR indicative of T cell activation. Even when the number of possible candidate epitopes is large, the invention described herein allows for vastly greater efficiency, both in time and cost, relative to traditional methods. The input of the assay is a mixture of a plurality, e.g., thousands, of different candidate epitopes. The core part of the assay entails mixing (also referred to as "co-culturing") 1) antigen presenting cells (APCs) engineered so as to express a) a nucleic acid encoding an epitope complex comprising a candidate epitope and an HLA molecule, and b) a nucleic acid encoding an anti-cytokine antibody with 2) T cells that display TCRs on their surface. Alternatively, the APCs are genetically engineered to express a) a nucleic acid encoding a candidate epitope or a nucleic acid encoding a peptide, e.g., a long peptide, e.g., >24 amino acids in length, that may be processed into a candidate epitope, b) a nucleic acid encoding an HLA molecule, and c) a nucleic acid encoding an anti-cytokine antibody. The mixing or contacting is conducted under conditions suitable for contacting as between the modified APCs and the T cells that allows for epitope recognition by the TCRs. If a TCR recognizes the HLA/epitope complex, an HLA/epitope/TCR complex is formed, the T cell becomes activated and secretes a cytokine. The cytokine binds the anti-cytokine antibody present on the APC. The cytokine is then labeled. The APCs coated with captured cytokine are identified and separated by sorting. The identified and integrated candidate epitope nucleic acid (also referred to as gene and oligonucleotide) is sequenced, e.g., using next generation sequencing (NGS). The output of the assay may include a list of epitopes that caused T cell activation.

In some embodiments, the APCs are professional APC cells. Examples of professional APCs include dendritic cells, macrophages, monocytes and B cells.

In some embodiments, the APCs are non-professional cells such as a human immortalized cell line.

In some embodiments, the APCs are human cells.

In some embodiments, the epitope is an infectious disease-associated epitope, an autoimmune disease-associated epitope, or a tumor-associated epitope.

In some embodiments, an HLA molecule is an HLA class I (i.e., MHC class I) or HLA class II (i.e., MHC class II) molecule. For example, the HLA molecule is an HLA-A, HLA-B, HLA-C, HLA-DP, HLA-DQ, or HLA-DR molecule.

Examples of cytokines secreted by activated T cells include interferon gamma (IFN-γ) and interleukin-2 (IL-2). Accordingly, in some embodiments, the anti-cytokine antibody on the surface of the APCs is an anti-IFN-γ antibody or an anti-IL-2 antibody.

In some embodiments, the activated T cells are CD8$^+$ and CD4$^+$ cells.

The APCs that bear a T cell-activating HLA/epitope complex (or T cell-activating epitope) may be identified and sorted (separated) by contacting them with a detectable label that binds the cytokine. In some cases, the detectable label is a fluorescently-labeled secondary, anti-cytokine antibody. In some embodiments, labeled APCs are separated from non-labeled APCs that do not bear a T cell-activating HLA/epitope complex by magnetic or flow cytometry.

Yet another aspect of the present invention is directed to a library of APCs wherein the respective APCs contain different nucleic acids that encode a different candidate epitope that is expressed on the respective APC surface.

A related aspect of the present invention is directed to a modified antigen presenting cell (APC) that expresses a) a nucleic acid encoding an epitope complex comprising a candidate epitope and an HLA molecule, and b) a nucleic acid encoding an anti-cytokine antibody.

Also provided is a modified APC, wherein the modified APC expresses a) a nucleic acid encoding a candidate epitope or a nucleic acid encoding a peptide, e.g., a long peptide, that may be processed into a candidate epitope, b) a nucleic acid encoding an HLA molecule, and c) a nucleic acid encoding an anti-cytokine antibody.

Identifying functional T-cell epitopes in accordance with the present invention offers several possible commercial applications, including, for example: (i) TCR based therapeutics (e.g., in cellular therapies) in which identifying TCRs that recognize HLA/epitope complexes on cancer cells are used in new cellular therapies; (ii) vaccine components in which identifying TCRs that recognize cancer cells are used to develop cancer vaccines or to prevent or treat infectious diseases; and (iii) infectious disease diagnostic testing in which knowledge of functional HLA/epitope/TCR complexes are used to inform new diagnostic tests.

BRIEF DESCRIPTION OF THE DRAWINGS

FIG. 2A-2G is a series of schematics showing engineered APCs capture cytokines in an HLA class I or II epitope-specific manner.

FIG. 5A-5E is a series of schematics showing identification of a minimal epitope sequence using tiled encoded peptides.

FIG. 7A-7J is a series of schematics and charts showing identification of previously unknown epitopes targeted by orphan, class II-restricted T cell receptors.

FIG. 8A-8H is a series of schematics, bar graphs, and scatterplots establishing a system for epitope identification using APC-bound anti-cytokine antibodies.

FIG. 10A-10K is a series of schematics, bar graphs, photomicrographs, and scatterplots showing identification of target epitopes from pooled oligonucleotide libraries.

FIG. 12A-12H is an alignment of sequences, a series of histograms, and a series of scatter plots showing identification of a minimal epitope sequence using tiled encoded peptides.

FIG. 13A-13M is a series of schematics and charts showing identification of previously unknown epitopes targeted by orphan T cell receptors.

FIG. 14A-14L is a series of schematics and charts showing identification of previously unknown epitopes targeted by orphan, class II-restricted T cell receptors.

DETAILED DESCRIPTION OF THE INVENTION

Definitions

Figure 1A:
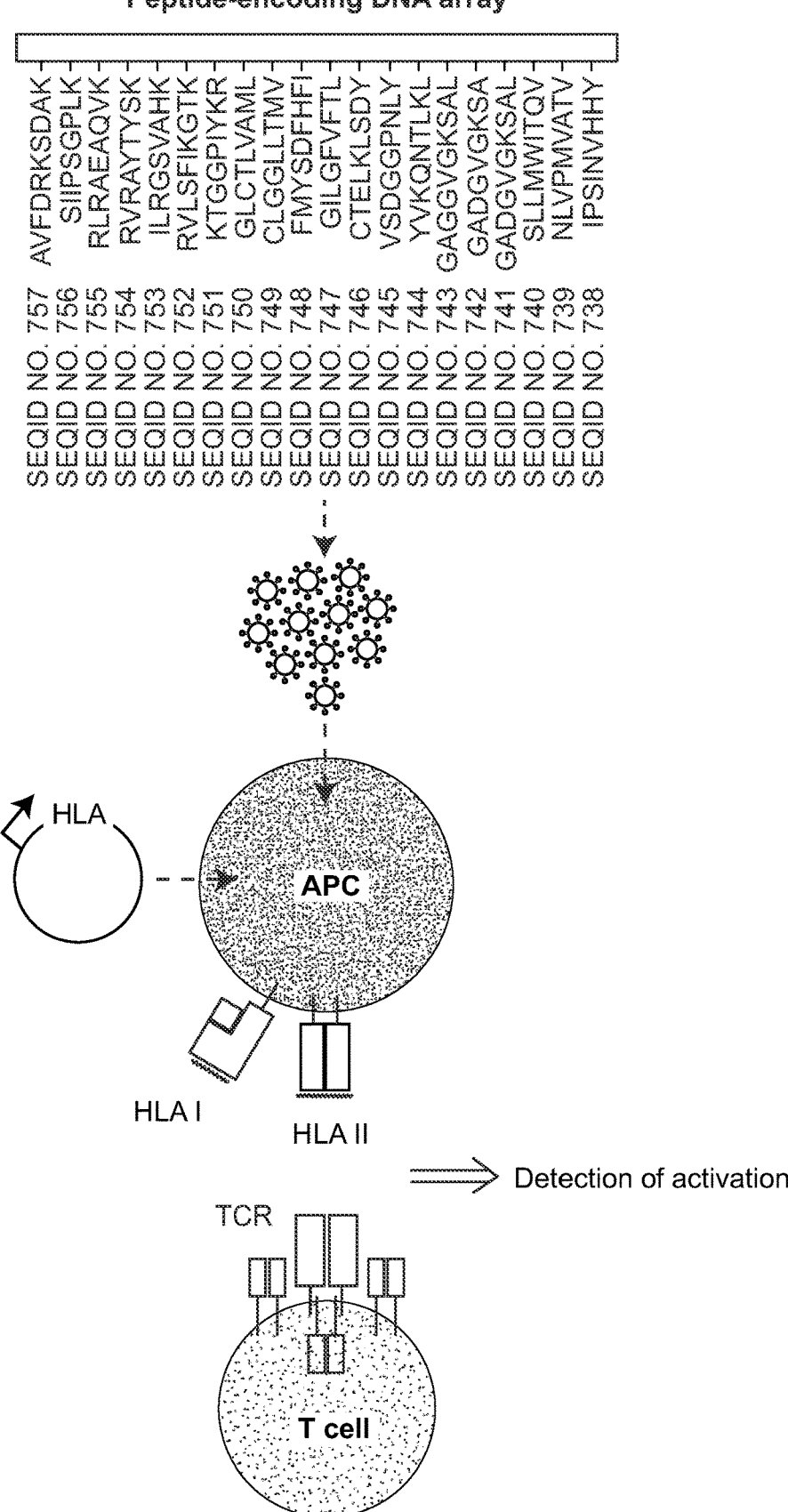
FIG. 1A-IE is a series of schematics and photomicrographs establishing a system for epitope identification by APC cytokine capture.

An antigen refers to a molecule capable of inducing an immune response in the host organism that is specifically recognized by T cells.

An antibody (Ab), commonly known as an immunoglobulin, is a class of protein produced by the immune system to neutralize pathogens such as pathogenic bacteria and viruses by recognizing and specifically binding antigens. The basic structure of an antibody is a Y-shaped unit composed of four polypeptide chains, two heavy chains, and two light chains. Antibodies are further divided into 5 classes based on the types of Y units and heavy chains: IgG, IgM, IgA, IgD, and IgE.

An epitope refers to the portion of antigen that is recognized by B cells or T Cells, and the portion of the antigen to which an antibody binds. An epitope refers more specifically to the portion of antigen that is recognized by B cells or T Cells, and the portion of the antigen to which an antibody binds. An epitope is typically a small peptide of 2 or more amino acids (e.g., 2, 3, 4, 5, 6, 7, 8, 9, 10, 11, 12, 13, 14, 15, 16, 17, 18, 19, 20, 21, 22, 23, or 24 amino acids). Class I epitopes are typically about 8-15 amino acids in length, and more typically about 8-12 amino acids in length. Class II epitopes are typically about 8-24 amino acids in length, and more typically about 15 amino acids in length.

A cytokine is a low-molecular-weight glycoprotein such as an interleukin or an interferon that is secreted by different cells in the body, mainly cells of the immune system including T cells. Cytokines act as messengers to influence cellular interactions. These interactions provoke inflammatory responses, which can be both anti-inflammatory and pro-inflammatory. While cytokines are produced by a variety of cell populations, they are most heavily produced by the helper T cells and macrophages.

An antigen presenting cell (APC) refers to any nucleated cell that is able to process antigens and present them on its surface to other cells of the immune system such as a T cell in order to activate the immune system and trigger an immune response to the antigen. APCs useful in the practice of the present invention include professional and non-professional APCs. APCs that have naturally endogenous mechanisms for processing antigens are characterized as professional APCs. They possess both HLA class I and class II molecules. Non-professional APCs possess HLA class I.

The term library refers to a collection of genetic material (nucleic acids) encoding candidate epitopes or encoding long peptides, e.g., >24 amino acids in length, e.g., about 50 amino acids in length, that may be processed into candidate epitopes, e.g., about 8-24 amino acids in length. The term library can also refer to a collection of APC cells that display the library of candidate epitopes or long peptides.

The human leukocyte antigen (HLA) system or complex is a group of related proteins encoded by the human major histocompatibility complex (MHC) gene complex. These cell-surface proteins are responsible for the regulation of the immune system. Exemplary HLA proteins (also referred to herein as "molecules") include MHC Class 1 and MHC Class 2.

A vector refers to a vehicle by which a polynucleotide sequence (e.g., a foreign or exogenous gene) can be introduced into a host cell, so as to transform the host and promote expression (e.g., transcription and translation) of the introduced sequence. Vectors capable of directing the expression of genes to which they are operatively linked are referred to herein as "expression vectors."

"Binding to" a molecule refers to having a physicochemical affinity for that molecule.

"Detecting" refers to identifying the presence, absence, or amount of the agent (e.g., a nucleic acid molecule, for example deoxyribonucleic acid (DNA) or ribonucleic acid (RNA)) to be detected.

"Contacting" refers to bringing into the state or condition of immediate proximity or direct contact.

Unless specifically stated or obvious from context, as used herein, the term "or" is understood to be inclusive. Unless specifically stated or obvious from context, as used herein, the terms "a", "an", and "the" are understood to be singular or plural.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Overview of Assay Methods

The inventive assay methods are highly scalable. They allow epitope pools of enormous complexity to be screened for productive HLA-epitope-TCR interactions. This feature enables selection of only those epitopes that bind a TCR and cause activation of the T cells.

Figure 1B:
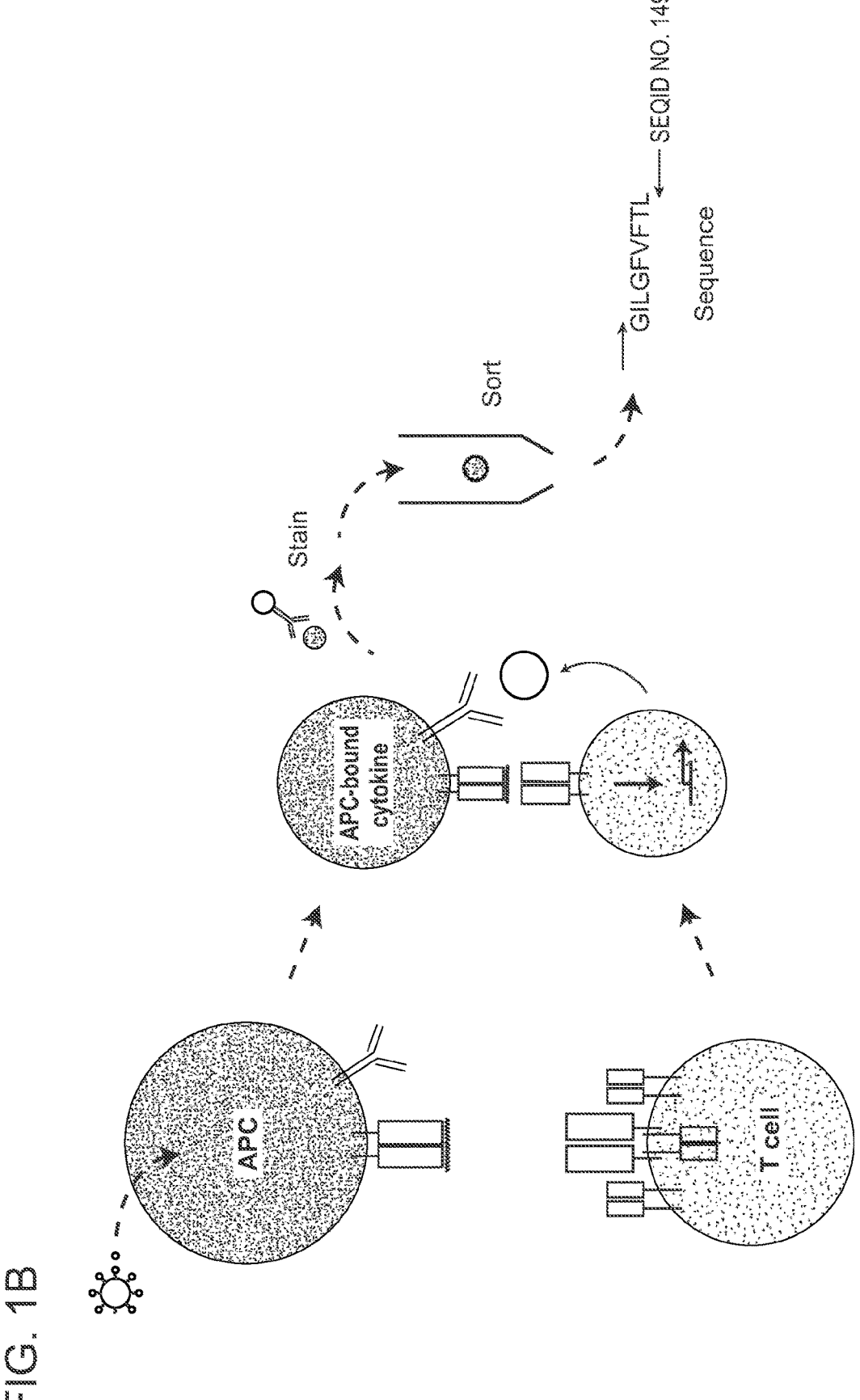
Figure 1E:
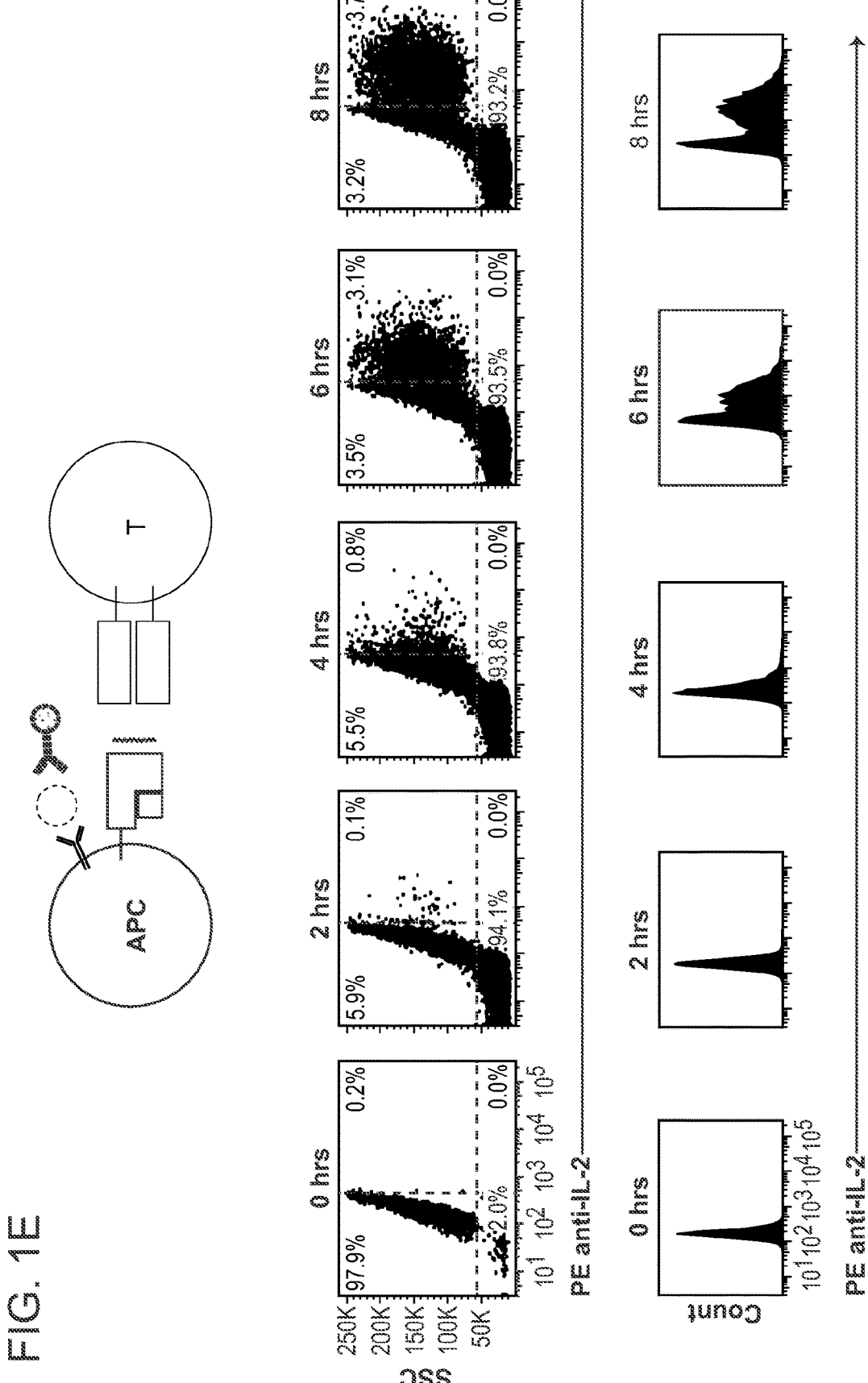
Figure 3A:
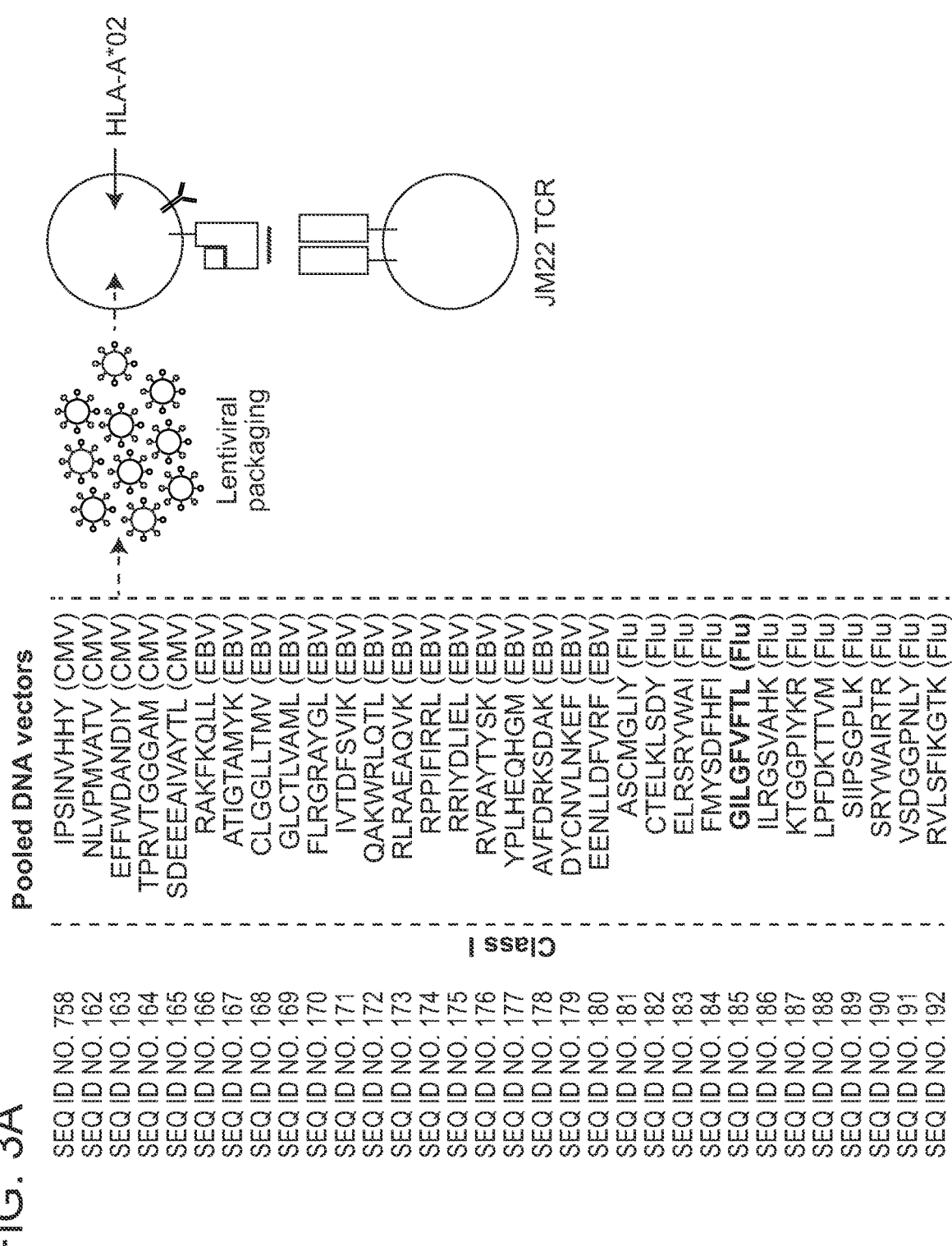
FIG. 3A-3E is a series of schematics, photomicrographs, and bar graphs showing identification of a target epitope from a pooled oligonucleotide library.
Figure 3B:
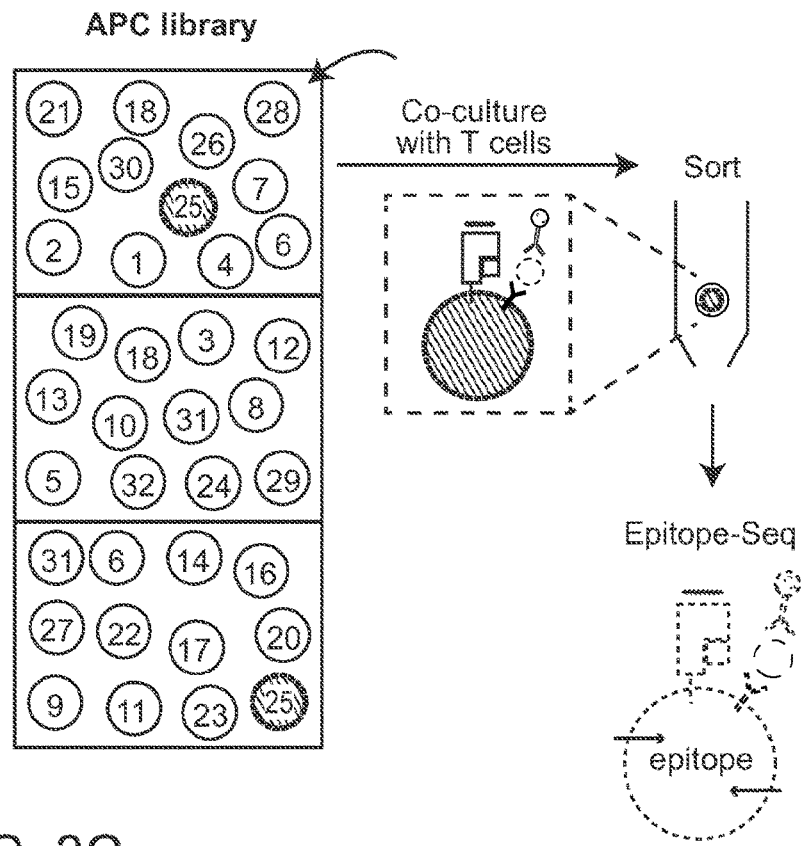

The specificity of the inventive assay methods is aided by the use of untethered HLA-epitope complexes, a functional readout of T cell activation, and a signal of T cell activation, namely cytokine secretion that is widely used as a readout for productive HLA-epitope-TCR interactions (Sharma et al., 2014 Hum. Immunol., 75:514-519). Moreover, and as described in detail below, the strength of the signal builds as activated T cells progressively secrete cytokine (FIG. 1E). Background signal is present due to cytokine capture by APCs in physical proximity. However, the number of transduced APCs is large relative to library diversity and productive epitopes are comparatively few. Therefore, the background is distributed across APCs expressing different epitopes while signal accrues (FIG. 3B). Signal leakage is further limited by physically partitioning cells into wells. As shown in the working examples, cells may be seeded at numbers less than or comparable to library diversity (FIG. 3B). In some embodiments, APCs that are coated with cytokine are sorted by flow cytometry. In other embodiments, given localization of the signal at the cell surface, APCs that are coated with cytokine can be sorted within minutes using magnetic beads. This feature facilitates scalability of the assay.

Individually and collectively, these features enable single-round selection to result in wide separation of the target epitope from non-targeted epitopes. The present assay methods offer many potential advantages over existing systems, particularly those in which signal is generated solely through binding interactions (Birnbaum et al., 2014 Cell., 157:1073-871; Li et al., 2019 Nat. Methods, 16:183-190), systems that require tethered peptide-MHC complexes that may alter peptide binding affinities (Birnbaum et al., 2014 Cell., 157:1073-87; Li et al., 2019 Nat. Methods, 16:183-190; Joglekar et al., 2019 Nat. Methods., 16: 191-198; Kisielow et al., 2019 Nat. Immunol., 20:652-662) and those wherein signal and background distributions greatly overlap (Li et al., 2019 Nat. Methods, 16:183-190; Kula et al., 2019 Cell., 178:1016-1028.e13) thus necessitating computational methods to infer true targets using surrogate hits (Birnbaum et al., 2014 Cell., 157:1073-87; Li et al., 2019 Nat. Methods, 16:183-190; Kisielow et al., 2019 Nat. Immunol., 20:652-662) and iterative rounds of selection (Gee et al., 2018 Cell, 172:549-563.e16; Saligrama et al., 2019 Nature, 572:481-487).

Because many of the components are genetically encoded, they are switchable. That is, the methods described herein can be tailored as necessary. For example, while current assays have been shown to work only with either HLA class I or class II. The results presented herein demonstrate screening of both HLA class I and class II epitopes simply by "knocking out" endogenous HLA mechanisms through processes known in the art (e.g., CRISPR) following the introduction of different HLA-encoding, peptide-encoding, and/or antibody encoding constructs into the HLA-negative APCs (i.e., a non-professional APC) through transduction.

In addition, the readout, cytokine secretion, is common to both HLA class I- and class II-restricted T cells. As described in detail below, the encoded anti-cytokine antibody on the APC can also be switched (FIG. 1D), allowing selection of T cell subsets through their differential cytokine secretion (Haining, 2012 Proc. Natl. Acad. Sci. U.S.A, 109:1359-60). Accordingly, this method helps solve bottlenecks in identifying HLA class II epitopes involved in autoimmune disease pathophysiology (Rosenblum, et al., 2012 Sci. Transl. Med., 4:1-10). The methods described herein have yet other potential advantages over systems in which extensive optimization is needed to screen different MHC molecules (Birnbaum et al., 2014 Cell., 157:1073-87) the design of which may be intractable for certain MHC (Saligrama et al., 2019 Nature, 572:481-487) or in which readouts may be restricted to screening HLA class I alone (Kula et al., 2019 Cell., 178:1016-1028.e13).

In order to more fully realize the versatility of the system, several adaptations of the methods described herein could be readily envisioned. Co-culture of the screening APCs with primary T cells allows for the identification of epitopes using endogenous TCRs. Alternatively, screening many cloned TCRs in parallel—e.g. those derived from single-cell TCR sequencing of tissue—is conceivable given the assay's efficiency. Finally, enormous increases of epitope library diversity are achievable.

In conjunction with strategies to identify paired T cell receptor genes (Howie et al., 2015 Sci. Transl. Med., 7:301ra131), the methods may allow discovery of novel immunogenic tumor antigens. They may also offer a way to tile whole genomes of infectious organisms, and suggests a path towards identification of elusive T cell targets, such as autoimmune epitopes. As recent advances have been made using knowledge of HLA-epitope-TCR complexes to develop diagnostics (Emerson et al., 2017 Nat. Genet., 49:659-665) and therapeutics (Tran et al., 2016 N. Engl. J. Med., 375:2255-2262; Zacharakis et al., 2018 Nat. Med., 24:724-730; Trotta et al., 2018 Nat. Med. 24:1005-1014), need for such enhancements in HLA-epitope-TCR complex identification will likely continue to grow.

The invention described herein allows an orders-of-magnitude increase in the number of candidate epitopes (possibly greater than 2-4 logs) with costs that do not correspond to scale. Accordingly, the invention allows increased efficiencies of cost and time, and potentially allows identification of HLA/epitope/TCR complexes and the epitopes themselves that previously could not be solved.

Antigen Presenting Cells (APCs)

In some embodiments, the APCs are professional APC cells. Examples of professional APCs include dendritic cells, macrophages, monocytes and B cells. Practice of the present invention does not require use of professional APCs. More broadly, the type of APC for use in the present invention and its origin (human or non-human) is not particularly limited provided that it is amenable to introduction of exogenous nucleic acid encoding a candidate epitope and an anti-cytokine antibody, and can endogenously process and present on its surface, the candidate epitope on an HLA molecule (e.g. HLA-A, HLA-B, HLA-C, HLA-DP, HLA-DQ, or HLA-DR that may be endogenous or exogenous), and the anti-cytokine antibody (or at least a cytokine-binding portion thereof). This is believed to be the case for almost all human cells and other mammalian cells which contain a nucleus, which are known in the art as non-professional APC cells. Therefore, the present assay methods can also be used with single-chain HLA-epitope fusions that bypass the need for endogenous antigen processing. Representative examples of APCs that may be suitable for use in the present invention include all human cells containing a nucleus (e.g. human immortalized cell lines such as HeLa, HEK293T, A549, and THP-1) and primary human cells. Additional examples of APCs that may be useful in the practice of the present invention include vascular endothelial cells, microglia of the brain, and various epithelial and mesenchymal cell types. APCs can be engineered to express particular HLA by knocking out endogenous HLA (e.g., by CRISPR) and stably expressing (e.g., by transduction) defined HLA constructs.

Professional APCs that endogenously express HLA-Class I and HLA-Class II include dendritic cells, macrophages, monocytes and B-cells. Primary dendritic cells and primary B cells can be used for autologous screening. If APCs are autologous, there is no need to transduce professional APCs with HLA. By contrast, if APCs are allogeneic, i.e., not from the same person, professional APCs must be HLA-matched allogeneic APCs or transduced with HLA.

APCs for use in the present invention can be genetically modified to express nucleic acids encoding candidate epitopes, HLA-Class I/II molecules (e.g, HLA-A, HLA-B, HLA-C, HLA-DP, HLA-DQ, or HLA-DR), and antibodies recognizing cytokines (e.g., IL-2, IFN-γ).

Epitopes and Epitope Libraries

The terms "epitope" and "candidate epitope" are used interchangeably and refer to a peptide encoded by an exogenous nucleic acid introduced into the APC target intended for use in the screening methods described herein. Epitopes useful for practicing the inventive method may belong to a variety of causative pathologies. For example, epitopes may be a part of the causative agents in any number of infectious diseases. The term "infectious disease" as used herein, refers to any disease that is caused by an infectious organism or pathogen. Infectious organisms and pathogens may comprise viruses, (e.g., single stranded RNA viruses, single stranded DNA viruses, HIV, hepatitis A, B, and C virus, HSV, CMV EBV, HPV), parasites (e.g., protozoan and metazoan pathogens such as Plasmodia species, *Leishmania* species, *Schistosoma* species, *Trypanosoma* species), bacteria (e.g., Mycobacteria, in particular, *M. tuberculosis, Salmonella*, Streptococci, *E. coli*, Staphylococci), fungi (e.g., *Candida* species, *Aspergillus* species), *Pneumocystis carinii*, and prions (known prions infect animals to cause scrapie, a transmissible, degenerative disease of the nervous system of sheep and goats, as well as bovine spongiform encephalopathy (BSE) and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI)). As used herein "prion" includes all forms of prions causing all or any of these diseases or others in any animals used—and in particular in humans and domesticated farm animals. The pathogen can be virtually any pathogen for which genetic information (e.g., gene sequences) is available.

In other embodiments, the epitopes may be implicated as the causative agent in an autoimmune disorder or cancer. In some embodiments, an epitope is derived from a tumor-associated antigen. In some embodiments, an epitope is derived from a pathogen-associated target antigen. Examples of such antigens include viruses, bacteria, fungi, yeast, protozoa and parasites. Representative examples of viruses include cytomegalovirus (CMV), adenovirus, Epstein Barr virus (EBV), respiratory syncytial virus (RSV), herpes simplex virus 6 (HSV6), parainfluenza 3, influenza B, BK virus, and JC virus.

Libraries, as described herein, comprise APC cells that include the introduced candidate epitope(s) or long peptides. In some embodiments, a library of APCs comprises a plurality of peptides derived from any of, for example, pathogens, pathogen infected cells, cancer cells, cells involved in (e.g., targeted in) autoimmune disease, and/or cells from healthy subjects, wherein an epitope is displayed on the surface of the target cell such that they are presented with MHC class I and/or MHC class II molecules General methods for the construction of large, genome-scale libraries of sequences for the expression of encoded peptides, such as in the generation of the candidate epitope libraries to be introduced into the modified APCs, are known in the art. See, e.g., Xu et al., Science. 2015; 348(6239); Larman et al., Biotechnol. 2011; 29(6):535-41; and Zhu et al., Nat Biotechnol. 2013 April; 31(4):331-4.

In some embodiments, the candidate epitopes are encoded by genomic DNA. The genomic DNA may be isolated from a subject (e.g., human) or from infectious organisms or combinations thereof. In some embodiments, the subject is healthy. In some embodiments, the subject has a disease. In some embodiments, the infectious organisms are pathogens, including but not limited to bacteria, viruses, bacteria, fungi, protozoa, and multicellular parasitic organisms. In some embodiments, the plurality of candidate epitopes from which the library is generated represents a substantially complete set of epitopes from the genome of a healthy subject or a subject with a disease (for example, diseases including but not limited to cancer, autoimmune disease, cardiovascular disease, infectious disease etc.). In some embodiments, the plurality of candidate epitopes represents a substantially complete set of peptides from a pathogen or group of pathogens, viruses, bacteria, or fungi (e.g., all pathogenic viruses, bacteria or fungi).

In some embodiments, long peptides, e.g., >24 amino acids in length, e.g., about 50 amino acids in length, are encoded by genomic DNA. These long peptides may be processed, i.e., cut, within the cell to produce candidate epitopes, e.g., about 8-24 amino acids in length, by the cell's antigen processing machinery.

In some embodiments, each APC contains and expresses a single nucleic acid, perhaps in multiple copies, to thereby present a single candidate epitope with an HLA molecule (i.e., an MHC Class I and/or MHC Class II molecule). The epitope will most often be encoded at single copy at the DNA level and will be produced, processed, and presented on MHC, typically at tens to thousands of molecules per cell. Even single epitopes on the surface of the modified APC can be recognized by T cells such as cytotoxic lymphocytes. Therefore, the present assay methods may be functional even at very low copies of surface expressed epitope.

In other embodiments, each modified APC contains and expresses a handful of different nucleic acids expressing different candidate epitopes, thereby presenting several candidate epitopes (e.g., 2, 3, 4, 5, 6, 7, 8, 9, 10 or more) with an HLA molecule (i.e., an HLA-Class I and/or HLA-Class II molecule).

In some embodiments, the libraries contain about $10^2$ to about $10^{14}$ modified APC cells. In some embodiments, each candidate epitope is presented on between about 10 and 10,000 modified APCs.

Modifying the APCs

Any appropriate method of expressing candidate antigens can be used to modify APCs. Delivery of nucleotides sequences and/or expression constructs to target cells can be achieved in a variety of ways including transfection, transduction, electroporation, viral infection, encapsulation of the polynucleotide(s) in liposomes, direct microinjection of the DNA into nuclei, genetic modification and cloning. Transfection refers to transient or stable introduction of exogenous nucleic acids into cultured cells by various methods comprising chemical, biological or physical methods. Transduction refers to transient or stable introduction of exogenous nucleic acid into eukaryotic cells using biological particles, such as viruses, as a carrier, optionally with a transfection agent or delivery vehicle that enhances the entry of nucleic acid into cells. Nucleotide sequences can be readily electroporated into primary cells without inducing significant cell death.

An exemplary type of genetic modification includes Clustered Regularly Interspaced Short Palindromic Repeats/Cas9 (CRISPR/CAS9). This is a powerful system used for genetic editing that increases efficiency and precision by allowing for site specific genomic targeting. The system utilizes ribonucleic acid (RNA) to allow insertion or deletion of genetic material. The disruptions are created by using single guide RNA (sgRNA) that is specific to a deoxyribonucleic acid (DNA) target to direct CAS9 nuclease to the specific genomic location, where it facilitates double stranded breaks in the DNA. The breaks are repaired via non-homologous end joining (NHEJ) DNA pathway, allowing error prone insertions to disrupt gene function.

Cloning entails use of vectors to introduce nucleic acid into a cell. Exemplary vectors may be episomal, e.g., plasmids, virus derived vectors such cytomegalovirus, adenovirus, etc., or may be integrated into the target cell genome, through homologous recombination or random integration, e.g., retrovirus derived vectors such MMLV, HIV-1, ALV, etc. Lentiviral vectors such as those based on HIV or FIV gag sequences can be used to transfect non-dividing cells. In some embodiments, combinations of retroviruses and an appropriate packaging cell line may also find use, where the capsid proteins will be functional for infecting the target cells according to methods known in the art.

Many viral vectors or virus-associated vectors are known in the art. Such vectors can be used as carriers of a nucleic acid construct into the cell. Constructs may be integrated and packaged into non-replicating, defective viral genomes like adenovirus, adeno-associated virus (AAV), or herpes simplex virus (HSV) or others, including retroviral and lentiviral vectors, for infection or transduction into cells. Other vectors that may be used in connection with alternate embodiments will be apparent to those of skill in the art.

The constructs may include viral sequences for transfection, if desired. Alternatively, the construct may be incorporated into vectors capable of episomal replication, e.g., EPV and EBV vectors. The inserted material of the vectors may be operatively linked to an expression control sequence that controls and regulates the transcription and translation of that polynucleotide sequence.

Representative examples of nucleic acids that may be useful for modifying the APCs may encode HLA-A, HLA-B, HLA-C, HLA-DP, HLA-DQ, or HLA-DR.

An exemplary nucleic acid sequence of the HLA-A Class I molecule is provided at NCBI Accession No. NM_001242758, version NM_001242758.1, incorporated herein by reference, and reproduced below (SEQ ID NO: 1):

```
   1 gagaagccaa tcagtgtcgt cgcggtcgct gttctaaagt
     ccgcacgcac ccaccgggac 61 tcagattctc cccagacgcc gaggatggcc gtcatggcgc
     cccgaaccct cctcctgcta 121 ctctcggggg ccctggccct gacccagacc tgggcgggct
     cccactccat gaggtatttc 181 ttcacatccg tgtcccggcc cggccgcggg gagccccgct
     tcatcgccgt gggctacgtg 241 gacgacacgc agttcgtgcg gttcgacagc gacgccgcga
     gccagaagat ggagccgcgg 301 gcgccgtgga tagagcagga ggggccggag tattgggacc
     aggagacacg gaatatgaag 361 gcccactcac agactgaccg agcgaacctg gggaccctgc
     gcggctacta caaccagagc 421 gaggacggtt ctcacaccat ccagataatg tatggctgcg
     acgtggggcc ggacgggcgc 481 ttcctccgcg ggtaccggca ggacgcctac gacggcaagg
     attacatcgc cctgaacgag 541 gacctgcgct cttggaccgc ggcggacatg gcagctcaga
     tcaccaagcg caagtgggag 601 gcggtccatg cggcggagca gcggagagtc tacctggagg
     gccggtgcgt ggacgggctc 661 cgcagatacc tggagaacgg gaaggagacg ctgcagcgca
     cggaccccc caagacacat 721 atgacccacc accccatctc tgaccatgag gccaccctga
     ggtgctgggc cctgggcttc 781 taccctgcgg agatcacact gacctggcag cgggatgggg
     aggaccagac ccaggacacg 841 gagctcgtgg agaccaggcc tgcaggggat ggaaccttcc
     agaagtgggc ggctgtggtg 901 gtgccttctg gagaggagca gagatacacc tgccatgtgc
     agcatgaggg tctgcccaag 961 cccctcaccc tgagatggga gctgtcttcc cagcccacca
     tccccatcgt gggcatcatt 1021 gctggcctgg ttctccttgg agctgtgatc actggagctg
     tggtcgctgc cgtgatgtgg
```

-continued

```
1081  aggaggaaga  gctcagatag  aaaaggaggg  agttacactc aggctgcaag  cagtgacagt 1141  gcccagggct  ctgatgtgtc  tctcacagct  tgtaaagtgt gagacagctg  ccttgtgtgg 1201  gactgagagg  caagagttgt  tcctgccctt  ccctttgtga cttgaagaac  cctgactttg 1261  tttctgcaaa  ggcacctgca  tgtgtctgtg  ttcgtgtagg cataatgtga  ggaggtgggg 1321  agagcacccc  accccatgt   ccaccatgac  cctcttccca cgctgacctg  tgctccctct 1381  ccaatcatct  ttcctgttcc  agagaggtgg  ggctgaggtg tctccatctc  tgtctcaact 1441  tcatggtgca  ctgagctgta  acttcttcct  tccctattaa aattagaacc  tgagtataaa 1501  tttactttct  caaattcttg  ccatgagagg  ttgatgagtt aattaaagga  gaagattcct 1561  aaaatttgag  agacaaaatt  aatggaacgc  atgagaacct tccagagtcc  a
```

An exemplary amino acid sequence of the HLA-A Class I molecule is provided at NCBI Accession No. NP_001229687, version NP_001229687.1, incorporated herein by reference, and reproduced below (SEQ ID NO: 2):

```
1    mavmaprtll  lllsgalalt  qtwagshsmr  yfftsvsrpg rgeprfiavg  yvddtqfvrf 61   dsdaasqkme  prapwieqeg  peywdqetrn  mkahsqtdra nlgtlrgyyn  qsedgshtiq 121  imygcdvgpd  grflrgyrqd  aydgkdyial  nedlrswtaa dmaaqitkrk  weavhaaeqr 181  rvylegrcvd  glrrylengk  etlqrtdppk  thmthhpisd heatlrcwal  gfypaeitlt 241  wqrdgedqtq  dtelvetrpa  gdgtfqkwaa  vvvpsgeeqr ytchvqhegl  pkpltlrwel 301  ssqptipivg  iiaglvllga  vitgavvaav  mwrrkssdrk ggsytqaass  dsaqgsdvsl 361  tackv
```

An exemplary nucleic acid sequence of the HLA-B Class I molecule is provided at NCBI Accession No. NM_005514, version NM_005514.8., incorporated herein by reference, and reproduced below (SEQ ID NO: 3):

```
1    agagtctcct  cagacgccga  gatgctggtc  atggcgcccc gaaccgtcct  cctgctgctc
```

-continued

```
61   tcggcggccc  tggccctgac  cgagacctgg  gccggctccc actccatgag  gtatttctac 121  acctccgtgt  cccggcccgg  ccgcggggag  ccccgcttca tctcagtggg  ctacgtggac 181  gacacccagt  tcgtgaggtt  cgacagcgac  gccgcgagtc cgagagagga  gccgcgggcg 241  ccgtggatag  agcaggaggg  gccggagtat  tgggaccgga acacacagat  ctacaaggcc 301  caggcacaga  ctgaccgaga  gagcctgcgg  aacctgcgcg gctactacaa  ccagagcgag 361  gccgggtctc  acaccctcca  gagcatgtac  ggctgcgacg tggggccgga  cgggcgcctc 421  ctccgcgggc  atgaccagta  cgcctacgac  ggcaaggatt acatcgccct  gaacgaggac 481  ctgcgctcct  ggaccgccgc  ggacacggcg  gctcagatca cccagcgcaa  gtgggaggcg 541  gcccgtgagg  cggagcagcg  gagagcctac  ctggagggcg agtgcgtgga  gtggctccgc 601  agatacctgg  agaacgggaa  ggacaagctg  gagcgcgctg accccccaaa  gacacacgtg 661  acccaccacc  ccatctctga  ccatgaggcc  accctgaggt gctgggccct  gggtttctac 721  cctgcgcgaga  tcacactgac  ctggcagcgg  gatggcgagg accaaactca  ggacactgag 781  cttgtggaga  ccagaccagc  aggagataga  accttccaga agtgggcagc  tgtggtggtg 841  ccttctggag  aagagcagag  atacacatgc  catgtacagc atgaggggct  gccgaagccc 901  ctcaccctga  gatgggagcc  gtcttcccag  tccaccgtcc ccatcgtggg  cattgttgct 961  ggcctggctg  tcctagcagt  tgtggtcatc  ggagctgtgg tcgctgctgt  gatgtgtagg 1021 aggaagagtt  caggtggaaa  aggagggagc  tactctcagg ctgcgtgcag  cgacagtgcc 1081 cagggctctg  atgtgtctct  cacagcttga  aaagcctgag acagctgtct  tgtgagggac 1141 tgagatgcag  gatttcttca  cgcctcccct  ttgtgacttc aagagcctct  ggcatctctt 1201 tctgcaaagg  cacctgaatg  tgtctgcgtc  cctgttagca taatgtgagg  aggtggagag
```

15

```
1261  acagcccacc cttgtgtcca ctgtgacccc tgttcccatg ctgacctgtg tttcctcccc 1321  agtcatcttt cttgttccag agaggtgggg ctggatgtct ccatctctgt ctcaacttta 1381  cgtgcactga gctgcaactt cttacttccc tactgaaaat aagaatctga atataaattt 1441  gttttctcaa atatttgcta tgagaggttg atggattaat taaataagtc aattcctgga 1501  atttgagaga gcaaataaag acctgagaac cttcca
```

An exemplary amino acid sequence of the HLA-B Class I molecule is provided at NCBI Accession No. NP_005505, version NP_005505.2, incorporated herein by reference, and reproduced below (SEQ ID NO: 4):

```
1    mlvmaprtvl lllsaalalt etwagshsmr yfytsvsrpg rgeprfisvg yvddtqfvrf 61   dsdaaspree prapwieqeg peywdrntqi ykaqaqtdre slrnlrgyyn qseagshtlq 121  smygcdvgpd grllrghdqy aydgkdyial nedlrswtaa dtaaqitqrk weaareaeqr 181  raylegecve wlrrylengk dkleradppk thvthhpisd heatlrcwal gfypaeitlt 241  wqrdgedqtq dtelvetrpa gdrtfqkwaa vvvpsgeeqr ytchvqhegl pkpltlrwep 301  ssqstvpivg ivaglavlav vvigavvaav mcrrkssggk ggsysqaacs dsaqgsdvsl 361  ta
```

An exemplary nucleic acid sequence of the HLA-C Class I molecule is provided at NCBI Accession No. NM_001243042, version NM_001243042.1, incorporated herein by reference, and reproduced below (SEQ ID NO: 5):

```
1    tccgcagtcc cggttctaaa gtccccagtc acccacccgg actcacattc tccccagagg 61   ccgagatgcg ggtcatggcg ccccgagccc tcctcctgct gctctcggga ggcctggccc 121  tgaccgagac ctgggcctgc tcccactcca tgaggtattt cgacaccgcc gtgtcccggc 181  ccggccgcgg agagccccgc ttcatctcag tgggctacgt ggacgacacg cagttcgtgc 241  ggttcgacag cgacgccgcg agtccgagag gggagccgcg ggcgccgtgg gtggagcagg 301  aggggccgga gtattgggac cgggagacac agaactacaa gcgccaggca caggctgacc
```

16

```
361  gagtgagcct gcggaacctg cgcggctact acaaccagag cgaggacggg tctcacaccc 421  tccagaggat gtatggctgc gacctggggc ccgacgggcg cctcctccgc gggtatgacc 481  agtccgccta cgacggcaag gattacatcg ccctgaacga ggacctgcgc tcctggaccg 541  ccgcggacac cgcggctcag atcacccagc gcaagttgga ggcggcccgt gcggcggagc 601  agctgagagc ctacctggag ggcacgtgcg tggagtggct ccgcagatac ctggagaacg 661  ggaaggagac gctgcagcgc gcagaacccc caaagacaca cgtgacccac cacccctct 721  ctgaccatga ggccaccctg aggtgctggg ccctgggctt ctaccctgcg gagatcacac 781  tgacctggca gcgggatggg gaggaccaga cccaggacac cgagcttgtg gagaccaggc 841  cagcaggaga tggaaccttc cagaagtggg cagctgtggt ggtgccttct ggacaagagc 901  agagatacac gtgccatatg cagcacgagg ggctgcaaga gcccctcacc ctgagctggg 961  agccatcttc ccagcccacc atccccatca tgggcatcgt tgctggcctg gctgtcctgg 1021 ttgtcctagc tgtccttgga gctgtggtca ccgctatgat gtgtaggagg aagagctcag 1081 gtggaaaagg agggagctgc tctcaggctg cgtgcagcaa cagtgcccag ggctctgatg 1141 agtctctcat cacttgtaaa gcctgagaca gctgcctgtg tgggactgag atgcaggatt 1201 tcttcacacc tctcctttgt gacttcaaga gcctctggca tctctttctg caaaggcgtc 1261 tgaatgtgtc tgcgttcctg ttagcataat gtgaggaggt gggagagacag cccacccccg 1321 tgtccaccgt gacccctgtc cccacactga cctgtgttcc ctccccgatc atctttcctg 1381 ttccagagag gtggggctgg atgtctccat ctctgtctca aattcatggt gcactgagct 1441 gcaacttctt acttccctaa tgaagttaag aacctgaata taaatttgtg ttctcaaata
```

-continued
```
1501 tttgctatga agcgttgatg gattaattaa ataagtcaat tcctagaagt tgagagagca 1561 aataaagacc tgagaacctt ccagaa
```

An exemplary amino acid sequence of the HLA-C Class I molecule is provided at NCBI Accession No. NP_001229971, version NP_001229971.1, incorporated herein by reference, and reproduced below SEQ ID NO: 6):

```
  1 mrvmaprall lllsgglalt etwacshsmr yfdtavsrpg rgeprfisvg yvddtqfvrf 61 dsdaasprge prapwveqeg peywdretqn ykrqaqadrv slrnlrgyyn qsedgshtlq 121 rmygcdlgpd grllrgydqs aydgkdyial nedlrswtaa dtaaqitqrk leaaraaeql 181 raylegtcve wlrrylengk etlqraeppk thvthhplsd heatlrcwal gfypaeitlt 241 wqrdgedqtq dtelvetrpa gdgtfqkwaa vvvpsgqeqr ytchmqhegl qepltlswep 301 ssqptipimg ivaglavlvv lavlgavvta mmcrrkssgg kggscsqaac snsaqgsdes 361 litcka
```

An exemplary nucleic acid sequence of the HLA-DRA Class II molecule is provided at NCBI Accession No. NM_019111, version NM_019111.5, incorporated herein by reference, and reproduced below (SEQ ID NO: 615):

```
  1 attcttgtct gttctgcctc actcccgagc tctactgact cccaacagag cgcccaagaa 61 gaaaatggcc ataagtggag tccctgtgct aggatttttc atcatagctg tgctgatgag 121 cgctcaggaa tcatgggcta tcaaagaaga acatgtgatc atccaggccg agttctatct 181 gaatcctgac caatcaggcg agtttatgtt tgactttgat ggtgatgaga ttttccatgt 241 ggatatggca aagaaggaga cggtctggcg gcttgaagaa tttggacgat ttgccagctt 301 tgaggctcaa ggtgcattgg ccaacatagc tgtggacaaa gccaacctgg aaatcatgac 361 aaagcgctcc aactatactc cgatcaccaa tgtacctcca gaggtaactg tgctcacaaa 421 cagccctgtg gaactgagag agcccaacgt cctcatctgt ttcatagaca agttcacccc 481 accagtggtc aatgtcacgt ggcttcgaaa tggaaaacct gtcaccacag gagtgtcaga
```

-continued
```
541 gacagtcttc ctgcccaggg aagaccacct tttccgcaag ttccactatc tccccttcct 601 gccctcaact gaggacgttt acgactgcag ggtggagcac tggggcttgg atgagcctct 661 tctcaagcac tgggagtttg atgctccaag ccctctccca gagactacag agaacgtggt 721 gtgtgccctg ggcctgactg tgggtctggt gggcatcatt attgggacca tcttcatcat 781 caagggattg cgcaaaagca atgcagcaga acgcaggggg cctctgtaag gcacatggag 841 gtgatggtgt ttcttagaga gaagatcact gaagaaactt ctgctttaat ggctttacaa 901 agctggcaat attacaatcc ttgacctcag tgaaagcagt catcttcagc attttccagc 961 cctatagcca ccccaagtgt ggatatgcct cttcgattgc tccgtactct aacatctagc 1021 tggcttccct gtctattgcc ttttcctgta tctattttcc tctatttcct atcattttat 1081 tatcaccatg caatgcctct ggaataaaac atacaggagt ctgtctctgc tatggaatgc 1141 cccatggggc atctcttgtg tacttattgt ttaaggtttc ctcaaactgt gatttttctg 1201 aacacaataa actattttga tgatcttggg tggaa
```

An exemplary amino acid sequence of the HLA-DRA Class II molecule is provided at NCBI Accession No. NP_061984, version NP_NP_061984.2, incorporated herein by reference, and reproduced below (SEQ ID NO: 616):

```
  1 maisgvpvlg ffiiavlmsa qeswaikeeh viiqaefyln pdqsgefmfd fdgdeifhvd 61 makketvwrl eefgrfasfe aqgalaniav dkanleimtk rsnytpitnv ppevtvltns 121 pvelrepnvl icfidkftpp vvnvtwlrng kpvttgvset vflpredhlf rkfhylpflp 181 stedvydcrv ehwgldepll khwefdapsp lpettenvvc algltvglvg iiigtifiik 241 glrksnaaer rgpl
```

An exemplary nucleic acid sequence of the HLA-DRB1 Class II molecule is provided at NCBI Accession No. NM_002124, version NM_002124.4, incorporated herein by reference, and reproduced below (SEQ ID NO: 617):

```
   1 agtaacttcc tccctataac ttggaatgtg ggtggagggg ttcatagttc tccctgagtg 61 agacttgcct gcttctctgg cccctggtcc tgtcctgttc tccagcatgg tgtgtctgaa 121 gctccctgga ggctcctgca tgacagcgct gacagtgaca ctgatggtgc tgagctcccc 181 actggctttg tctgggggaca cccgaccacg tttcctgtgg cagcctaaga gggagtgtca 241 tttcttcaat gggacggagc gggtgcggtt cctggacaga tacttctata accaggagga 301 gtccgtgcgc ttcgacagcg acgtggggga gttccgggcg gtgacggagc tggggcggcc 361 tgacgctgag tactggaaca gccagaagga catcctggag caggcgcggg ccgcggtgga 421 cacctactgc agacacaact acggggttgt ggagagcttc acagtgcagc ggcgagtcca 481 acctaaggtg actgtatatc cttcaaagac ccagcccctg cagcaccaca acctcctggt 541 ctgctctgtg agtggtttct atccaggcag cattgaagtc aggtggttcc tgaacggcca 601 ggaagagaag gctgggatgg tgtccacagg cctgatccag aatggagact ggaccttcca 661 gaccctggtg atgctgaaa cagttcctcg aagtggagag gtttacacct gccaagtgga 721 gcacccaagc gtgacaagcc ctctcacagt ggaatggaga gcacggtctg aatctgcaca 781 gagcaagatg ctgagtggag tcggggggctt tgtgctgggc ctgctcttcc ttggggccgg 841 gctgttcatc tacttcagga atcagaaagg acactctgga cttcagccaa caggattcct 901 gagctgaaat gcagatgacc acattcaagg aagaactttc tgccccggct ttgcaggatg 961 aaaagctttc ctgcttggca gttattcttc cacaagagag ggctttctca ggacctggtt 1021 gctactggtt cggcaactgc agaaaatgtc ctcccttgtg gcttcctcag ctcctgcct 1081 tggcctgaag tcccagcatt gatggcagcg cctcatcttc aacttttgtg ctcccctttg 1141 cctaaaccgt atggcctccc gtgcatctgt attcaccctg tatgacaaac acattacatt 1201 attaaatgtt tctcaaagat gga
```

An exemplary amino acid sequence of the HLA-DRB1 Class II molecule is provided at NCBI Accession No. NP_061984, version NP_NP_061984.2, incorporated herein by reference, and reproduced below (SEQ ID NO: 618):

```
   1 mvclklpggs cmtaltvtlm vlssplalsg dtrprflwqp krechffngt ervrfldryf 61 ynqeesvrfd sdvgefravt elgrpdaeyw nsqkdileqa raavdtycrh nygvvesftv 121 qrrvqpkvtv ypsktqplqh hnllvcsvsg fypgsievrw flngqeekag mvstgliqng 181 dwtfqtlvml etvprsgevy tcqvehpsvt spltvewrar sesaqskmls gvggfvlgll 241 flgaglfiyf rnqkghsglq ptgfls
```

T cells that are activated in the course of the practice of the present assay methods may produce one or more of IFNg, GM-CSF, IFNa, IL-2, IL-4, IL-5, IL-10, IL-12, IL-13, and IL-17. Antibodies that bind these cytokines ("anti-cytokine antibodies") and nucleic acids encoding them useful for practicing the inventive assay methods are available from commercial sources, such as those identified in the examples and in Table 2. Typically, a nucleic acid encoding the light chain and a nucleic acid encoding the heavy chain of the anti-cytokine antibody are introduced into the APC.

Representative examples of nucleic acid molecules encoding anti-cytokine antibodies (and their respective light and heavy chains) that may be useful for modifying the APCs are listed in Table 2.

T Cells

The T cells used in the inventive assay methods are T lymphocytes that express TCRs, either endogenously or via transformation of nucleic acid encoding a TCR. As is known in the art, a TCR is a grouping of proteins on the surface of T cells that bind to antigens on foreign or abnormal cells (cancer cells, cells from other organisms, and cells infected with virus or bacteria). The grouping of proteins is composed of six different chains that when fused together form an a/P heterodimer. Engagement of the TCR results in the activation of both positive and negative cellular signaling cascades responsible for cellular proliferation, differentiation, cytokine production, and/or activation-induced cell death. The T cells also secrete at least one cytokine upon activation.

T cells that may be suitable for use in the present invention include experimentally produced T cells and T cells obtained from individuals having an infectious disease, from individuals having a known autoimmune disorder, from individuals having an identified cancer, or from healthy individuals. T cells suitable for use in the present assay methods include CD8+ T cells and CD4+ T cells. Cytotoxic CD8+ T cells express their endogenous TCRs. Alternatively, a non-cytotoxic CD4+ T cell may be modified to express an exogenous TCR. The specificity of a T cell is contained in the sequence of its T cell receptor. Introducing a TCR from one T cell into another can retain the effector functions of the recipient cell while transferring the specificity of the new TCR. Moreover, a TCR from a CD8+ T cell can drive the effector functions of CD4+ T cells when introduced into donor CD4+ cells. In some embodiments, the exogenous T cell receptor is from a T helper (Th1 or Th2) or a regulatory T cell. Other types of cytotoxic cells can be used in the assays, such as natural killer cells, that have been engineered to express a TCR.

The T cells and cytotoxic lymphocytes or NK cells can be obtained from a variety of sources. Typically the cytotoxic lymphocytes are obtained from a biological sample.

General Assay Conditions

The assay methods may be advantageously practiced with multi-well (e.g., 96-well or 384-well) plates or larger plates (e.g., 10-cm or 15-cm plates) or flasks (e.g. T75 or T175). T cells and APCs may be mixed in ratios ranging generally from 1:1 to about 25:1 and in some embodiments at a ratio between about 2:1 and 16:1. The conditions suitable for epitope recognition by TCRs typically includes an incubation at about 37° C. for a time period that typically ranges from about 0-28 hours. T cells and APCs may be dissociated with reagents known in the art (e.g., 0.25% trypsin-EDTA and enzyme-free cell dissociation buffer). The cells may be pooled. Labelling of the anti-cytokine antibody may be conducted prior to or after dissociation. At least one wash step may be conducted e.g., to remove excess label.

Labels

Representative labels that may be suitable for use in the present invention and be attached to the anti-cytokine antibody include radioactive isotopes, fluorescers, chemiluminescers, chromophores, enzymes, enzyme substrates, enzyme cofactors, enzyme inhibitors, dyes, metal ions and metal sols.

In some embodiments, the label is fluorescent. Representative examples of non-proteinaceous fluorescent labels include allophycocyanins (tradename XL665); luminescent organic molecules, such as rhodamines, cyanines (e.g., Cy5), squaraines, coumarins, proflavins, acridines, fluoresceins, boron-dipyrromethene derivatives (commercially available under the tradename "BODIPY"), fluorophores known under the name "Atto", fluorophores known under the name "DY", compounds known under the name "Alexa", and nitrobenzoxadiazole. The "Alexa" compounds are commercially available, e.g., from Invitrogen; the "Atto" compounds are commercially available from Atto-tec; the "DY" compounds are commercially available from Dyomics; and the "Cy" compounds are commercially available from Amersham Biosciences. Fluorescently labeled anti-cytokine antibodies are commercially available.

Proteinaceous fluorescent labels may also be useful. Representative examples of fluorescent polypeptides include yellow fluorescent protein (YFP), cyan fluorescent protein (CFP), GFP, mRFP, RFP (tdimer2), and HCRED.

Biotin-based labels may also be useful. Biotinylation of target molecules, including antibodies, is well known in the art. Biotinylated anti-cytokine antibodies may be detected by binding of a detectably labeled biotin binding partner, such as avidin or streptavidin.

Isolating APCs Bearing HLA/Epitope/TCR Complexes

Isolating and/or sorting of APCs bearing HLA/epitope/TCR complexes, indicative of T cell activation, may be conducted using a variety of methods and/or devices known in the art. The methods and/or devices may depend on the type of nature of the label. Representative examples include flow cytometry (e.g., fluorescence activated cell sorting (FACS) or Ramen flow cytometry), fluorescence microscopy, optical tweezers, micro-pipettes, affinity purification, and microfluidic magnetic separation devices and methods.

Sequencing of Genes of Epitopes that Cause T Cell Activation

APCs identified as having a candidate epitope that caused activation of a T cell antigen can be further processed to isolate the encoding gene. In some embodiments, the candidate epitope gene may be isolated by PCR amplification using primer sequences complementary to the candidate epitope gene. In other embodiments, RT-PCR can be used to amplify the transcribed form of the epitope cassette. If the candidate epitope is expressed episomally such as by part of a viral genome or plasmid, the episomal nucleic acid can be isolated.

Determination of the sequence of the candidate epitope can be accomplished by use of high-throughput systems such as DNA sequencing. Numerous DNA sequencing techniques are known in the art. Examples include fluorescence-based sequencing methods, automated sequencing techniques, methods that provide parallel sequencing of partitioned amplicons, parallel oligonucleotide extension, the Church polony technology, the 454 picotiter pyrosequencing technology, the Solexa single base addition technology, the Lynx massively parallel signature sequencing technology, and the Adessi PCR colony technology.

In some embodiments, the sequence of the candidate epitope is determined by next-generation sequencing (NGS). These methods share the common feature of massively parallel, high-throughput strategies at relatively low lower costs compared to older sequencing methods. As known in the art, NGS methods can be broadly divided into those that typically use template amplification and those that do not. Amplification-requiring methods include pyrosequencing (commercially available from Roche as the 454 technology platforms (e.g., GS 20 and GS FLX)), the Solexa platform (commercially available from ILLUMINA™), and the Supported Oligonucleotide Ligation and Detection™ (SOLiD) platform (commercially available from APPLIED BIOSYSTEMS™. Non-amplification approaches, also known as single-molecule sequencing, may also be used. Examples include the HELISCOPE™ platform (commercially available from HELICOS BIOSYSTEMS™, and newer, real-time platforms (e.g., commercially available from VISIGEN™, OXFORD NANOPORE TECHNOLOGIES LTD., and PACIFIC BIOSCIENCES™).

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Materials and Methods

Cells, Viruses, and Reagents.

Jurkat cells were obtained from ATCC, and maintained in RPMI (Thermo Fisher Scientific) supplemented with 10% FBS (Gemini Bio-Products). HeLa and 293T cells were maintained in DMEM (Thermo Fisher Scientific) supplemented with 10% FBS. Self-inactivating minimal HIV-1 virus was produced in 293T cells using the vectors pLX301 (Broad Institute, Addgene plasmid #25895) or pLX303 (Broad Institute, Addgene plasmid #25897), the packaging construct psPAX2, and the envelope plasmid pCMV-VSVG. Recombinant IL-2 and IFN-γ were obtained from Peprotech. Antibodies were obtained from the following sources: PE-conjugated anti-IL-2 (N7.48 A; Miltenyi), Vio515-conjugated anti-IL-2 (N7.48 A; Miltenyi), PE-conjugated anti-IFN-γ (IFN-γ Detection; IFN-γ Secretion Assay; Miltenyi), APC-conjugated anti-CD45 (HI30; BioLegend), FITC-conjugated anti-HLA-A/B/C (W6/32, BioLegend), FITC-conjugated anti-HLA-DR (T036, BioLegend), FITC-conjugated anti-HLA-DP/DQ/DR (T039, BioLegend), PE-conjugated anti-HLA-DM (MaP.DM1, BioLegend), and PE-conjugated anti-TCR α/β (IP26, BioLegend).

Antigen-Presenting Cell Preparation.

HLA class I knockout (HLA class I KO) APCs were prepared as follows. Genomic DNA from HeLa and HEK293T cells was extracted (DNeasy Blood & Tissue Kit; Qiagen), and HLA typed by next-generation sequencing (CD Genomics). HeLa cells were typed as HLA-A*68:02 (homozygous), HLAB*15:03 (homozygous), HLA-C*12:03 (heterozygous c.391G>A (p.G131R)), DPA1*02:01:08 (homozygous), DPB1*01:01:01 (homozygous), DQA1*01:01:01 (homozygous), DQB1*05:01:01 (heterozygous c.186C>T (p.H62Q)), DRB1*01:02:01 (homozygous), DRB345 not present. 293T cells were typed as HLA-A*02:01 (homozygous), HLAB*07:02 (homozygous), HLHLC*07:02 (homozygous), DPA*01:03:01 (homozygous), DPB1*04:02:01 (homozygous), DQA1*01:02:01 (homozygous), DQB1*06:02:01 (homozygous), DRB1*15:01:01 (homozygous), DRB5*01:01:01 (homozygous). Two CRISPR/Cas9 cassettes directed to cleave relatively conserved sequences in all of the above HLA-A, HLA-B, and HLA-C genes were cloned into the lentiviral, Cas9-containing vector pXPR_001 (Broad Institute, Addgene plasmid #49535); sequences are listed in Table 1.

TABLE 1

| PCR Primers | sequence [Nucleic Acid] | SEQ ID NO |
|---|---|---|
| CRISPR HLA class I forward #1 | caccgAGGTCAGTGTGATCTCCGCA | 11 |
| CRISPR HLA class I reverse #1 | AAACTGCGGAGATCACACTGACCTC | 12 |
| CRISPR HLA class I forward #2 | caccgCGGCTACTACAACCAGAGCG | 13 |
| CRISPR HLA class I reverse #2 | AAACCGCTCTGGTTGTAGTAGCCGC | 14 |
| CRISPR TCRa forward | CACCGGCTGGTACACGGCAGGGTCA | 15 |
| CRISPR TCRa reverse | AAACTGACCCTGCCGTGTACCAGCC | 16 |
| CRISPR TCRb forward | CACCGCGTAGAACTGGACTTGACAG | 17 |
| CRISPR TCRb reverse | AAACCTGTCAAGTCCAGTTCTACGC | 18 |
| Mutate CRISPR site in TCRa, reverse primer | CAGGCTACTGCTGAATTAGATTTAAA ATCCATAGACCTCATGTCTAGCACAG T | 19 |
| Mutate CRISPR site in TCRa, forward primer | GGATTTTAAATCTAATTCAGCAGTAG CCTGGAGCAACAAATCTGACTTTGCA | 20 |
| Mutate CRISPR site in TCRb, reverse primer | ACCATAAAATTGTACCTGGCATCGAA AGTGGTTGCGGGGGTTC | 21 |
| Mutate CRISPR site in TCRb, forward primer | TCGATGCCAGGTACAATTTTATGGTCT CTCGGAGAATGACGAGTGGA | 22 |
| barcoded HLA I Epitope-Seq forward primer #1 | CGATGTGCAACTCCTGTCTTGCATTG | 23 |
| barcoded HLA I Epitope-Seq forward primer #2 | ACATGTGCAACTCCTGTCTTGCATTG | 24 |
| barcoded HLA I Epitope-Seq forward primer #3 | GCCAATGCAACTCCTGTCTTGCATTG | 25 |
| barcoded HLA I Epitope-Seq forward primer #4 | TAGCTTGCAACTCCTGTCTTGCATTG | 26 |

TABLE 1-continued

| PCR Primers | sequence [Nucleic Acid] | SEQ ID NO |
|---|---|---|
| barcoded HLA I Epitope-Seq forward primer #5 | GGCTAGGCAACTCCTGTCTTGCATTG | 27 |
| barcoded HLA I Epitope-Seq reverse primer #1 | CGATGTCCACATAGCGTAAAAGGAGCA | 28 |
| barcoded HLA I Epitope-Seq reverse primer #2 | ACATGTCCACATAGCGTAAAAGGAGCA | 29 |
| barcoded HLA I Epitope-Seq reverse primer #3 | GCCAATCCACATAGCGTAAAAGGAGCA | 30 |
| barcoded HLA I Epitope-Seq reverse primer #4 | GATCAGCCACATAGCGTAAAAGGAGCA | 31 |
| barcoded HLA I Epitope-Seq reverse primer #5 | GGCTAGCCACATAGCGTAAAAGGAGCA | 32 |
| barcoded HLA II Epitope-Seq forward primer #1 | TAGCTTACCGCCTACTTCCTGTACCA | 33 |
| barcoded HLA II Epitope-Seq forward primer #2 | GGCTAGACCGCCTACTTCCTGTACCA | 34 |
| barcoded HLA II Epitope-Seq reverse primer #1 | CGATGTCGTATTTTGTGGCATTCTGC | 35 |
| barcoded HLA II Epitope-Seq reverse primer #2 | GCCAATCGTATTTTGTGGCATTCTGC | 36 |
| CRISPR HLA-DPA forward | CACCGCGTCACATGGCTGTGCAATG | 37 |
| CRISPR HLA-DPA reverse | AAACCATTGCACAGCCATGTGACGC | 38 |
| CRISPR HLA-DPB forward | CACCGCGAAGCGCGCGTACTCCTCC | 39 |
| CRISPR HLA-DPB reverse | AAACGGAGGAGTACGCGCGCTTCGC | 40 |
| CRISPR HLA-DQA forward | CACCGAATGGGCAGTCAGTCACAGA | 41 |
| CRISPR HLA-DQA reverse | AAACTCTGTGACTGACTGCCCATTC | 42 |
| CRISPR HLA-DQB forward | CACCGAACTACGAGGTGGCGTACCG | 43 |
| CRISPR HLA-DQB reverse | AAACCGGTACGCCACCTCGTAGTTC | 44 |
| CRISPR HLA-DRB forward | CACCGAAGATGCATCTATAACCAAG | 45 |
| CRISPR HLA-DRB reverse | AAACCTTGGTTATAGATGCATCTTC | 46 |
| barcoded HLA I and HLA II (3' fusion) Epitope-Seq reverse primer #1 | CGATGTCCACATAGCGTAAAAGGAGCA | 47 |
| barcoded HLA I and HLA II (3' fusion) Epitope-Seq reverse primer #2 | ACATGTCCACATAGCGTAAAAGGAGCA | 48 |
| barcoded HLA I and HLA II (3' fusion) Epitope-Seq reverse primer #3 | GCCAATCCACATAGCGTAAAAGGAGCA | 49 |
| barcoded HLA I and HLA II (3' fusion) Epitope-Seq forward primer #4 | CAGATCCCACATAGCGTAAAAGGAGCA | 50 |
| barcoded HLA I and HLA II (3' fusion) Epitope-Seq reverse primer #5 | GATCAGCCACATAGCGTAAAAGGAGCA | 51 |
| barcoded HLA I and HLA II (3' fusion) Epitope-Seq reverse primer #6 | GGCTAGCCACATAGCGTAAAAGGAGCA | 52 |

TABLE 1-continued

| PCR Primers | sequence [Nucleic Acid] | SEQ ID NO |
|---|---|---|
| HLA II (3' fusion) Epitope-Seq forward primer #1 | GGTGTGACCAAGCAGGATCT | 53 |
| HLA II (3' fusion) Epitope-Seq forward primer #2 | GTGACCAAGCAGGATCTGG | 54 |
| barcoded HLA II (CLIP replacement) Epitope-Seq forward primer #1 | CGATGTACCGCCTACTTCCTGTACCA | 55 |
| barcoded HLA II (CLIP replacement) Epitope-Seq forward primer #2 | ACATGTACCGCCTACTTCCTGTACCA | 56 |
| barcoded HLA II (CLIP replacement) Epitope-Seq forward primer #3 | TAGCTTACCGCCTACTTCCTGTACCA | 57 |
| barcoded HLA II (CLIP replacement) Epitope-Seq forward primer #4 | GGCTAGACCGCCTACTTCCTGTACCA | 58 |
| barcoded HLA II (CLIP replacement) Epitope-Seq reverse primer #1 | CGATGTCGTATTTTGTGGCATTCTGC | 59 |
| barcoded HLA II (CLIP replacement) Epitope-Seq reverse primer #2 | GCCAATCGTATTTTGTGGCATTCTGC | 60 |
| barcoded HLA II (CLIP replacement) Epitope-Seq reverse primer #3 | TAGCTTCGTATTTTGTGGCATTCTGC | 61 |
| barcoded HLA II (CLIP replacement) Epitope-Seq reverse primer #4 | GCCAATCGTATTTTGTGGCATTCTGC | 62 |

35

The targeting vectors were transiently transfected into HeLa or HEK293T cells using TransIT-LT1 (Mirus). Single-cell clones were established and tested for knockout of HLA class I cell surface expression by flow cytometry. To create HLA-matched APCs, an HLA class I KO APC clone was transduced with selected HLA class I or II cDNAs.

TABLE 2

| Name | Sequence [Amino Acid] | SEQ. ID No. | Sequence [Nucleic Acid] | SEQ ID No. |
|---|---|---|---|---|
| anti-IL2 antibody, heavy chain | MYRMQLLSCIALSLALV TNSQVQLVQSGGGWQP GRSLRLSCAASGFTFSN YAMNWVRQAPGKGLE WVTLISYDGSQKYYADS VKGRFTTSRDNSKNTLY LQMNSLRAEDTAVYYC ARDSTTLGAFDVWGQG TMVTVSSASTKGPSVFP LAPSSKSTSGGTAALGC LVKDYFPEPVTVSWNSG ALTSGVHTFPAVLQSSG LYSLSSVVTVPSSSLGTQ TYICNVNHKPSNTKVDK KVEPKSCDKTHTCPPCP APELLGGPSVFLFPPKPK DTLMISRTPEVTCVVVD VSHEDPEVKFNWYVDG VEVHNAKTKPREEQYNS TYRVVSVLTVLHQDWL NGKEYKCKVSNKALPA PIEKTISKAKGQPREPQV YTLPPSREEMTKNQVSL TCLVKGFYPSDIAVEWE SNGQPENNYKTTPPVLD SDGSFFLYSKLTVDKSR WQQGNVFSCSVMHEAL | 63 | ATGTACAGGATGCAACTCCTGTCTTGCATTGCACTAAGTCTTGCACT TGTCACGAATTCACAGGTACAGCTTGTCCAATCTGGGGGTGGCTGG CAACCAGGGCGCAGCCTGAGACTTTCCTGTGCGGCCTCAGGGTTTA CTTTTAGTAATTACGCAATGAATTGGGTCAGGCAAGCTCCGGGTAA AGGTCTTGAGTGGGTCACTCTCATCTCATACGATGGTAGCCAGAAA TATTACGCTGACAGTGTTAAGGGTAGGTTCACCACATCTCGAGATA ATAGTAAGAACACCCTGTACCTTCAGATGAACAGTCTGCGAGCCGA AGACACCGCTGTTTACTACTGTGCGCGAGATAGTACCACACTCGGA GCGTTCGACGTTTGGGGACAGGGCACGATGGTGACCGTCTCAAGTG CTAGCACCAAGGGCCCATCGGTCTTCCCCCTGGCACCCTCCTCCAAG AGCACCTCTGGGGGCACAGCGGCCCTGGGCTGCCTGGTCAAGGACT ACTTCCCCGAACCGGTGACGGTGTCGTGGAACTCAGGCGCCCTGAC CAGCGGCGTGCACACCTTCCCGGCTGTCCTACAGTCCTCAGGACTCT ACTCCCTCAGCAGCGTGGTGACCGTGCCCTCCAGCAGCTTGGGCAC CCAGACCTACATCTGCAACGTGAATCACAAGCCCAGCAACACCAAG GTGGACAAGAAAGTTGAGCCCAAATCTTGTGACAAAACTCACACAT GCCCACCGTGCCCAGCACCTGAACTCCTGGGGGGACCGTCAGTCTT CCTCTTCCCCCCAAAACCCAAGGACACCCTCATGATCTCCCGGACCC CTGAGGTCACATGCGTGGTGGTGGACGTGAGCCACGAAGACCCTGA GGTCAAGTTCAACTGGTACGTGGACGGCGTGGAGGTGCATAATGCC AAGACAAAGCCGCGGGAGGAGCAGTACAACAGCACGTACCGTGTG GTCAGCGTCCTCACCGTCCTGCACCAGGACTGGCTGAATGGCAAGG AGTACAAGTGCAAGGTCTCCAACAAAGCCCTCCCAGCCCCCATCGA GAAAACCATCTCCAAAGCCAAAGGGCAGCCCCGAGAACCACAGGT GTACACCCTGCCCCCATCCCGGGAGGAGATGACCAAGAACCAGGTC AGCCTGACCTGCCTGGTCAAAGGCTTCTATCCCAGCGACATCGCCGT GGAGTGGGAGAGCAATGGGCAGCCGGAGAACAACTACAAGACCAC | 71 |

TABLE 2-continued

| Name | Sequence [Amino Acid] | SEQ. ID No. | Sequence [Nucleic Acid] | SEQ ID No. |
|---|---|---|---|---|
| | HNHYTQKSLSLSPGK* | | GCCTCCCGTGCTGGACTCCGACGGCTCCTTCTTCCTCTACAGCAAGC TCACCGTGGACAAGAGCAGGTGGCAGCAGGGGAACGTCTTCTCATG CTCCGTGATGCATGAGGCTCTGCACAACCACTACACGCAGAAGAGC CTCTCCCTGTCTCCGGGTAAATGA | |
| anti-IL2 antibody, light chain | MYRMQLLSCIALSLALV TNSSYELTQPPSVSVSPG QTARITCSGDALPRKFA YWYQQKSGQAPVMVIY EDSKRPPGIPERFSGSSS GTMATLTITGAQVEDEA DYYCYSTDSGGDVSVFG GGTKLTVLGQPKAAPSV TLFPPSSEELQANKATLV CLISDFYPGAVTVAWKA DSSPVKAGVETTTPSKQ SNNKYAASSYLSLTPEQ WKSHRSYSCQVTHEGST VEKTVAPTECS* | 64 | ATGTACAGGATGCAACTCCTGTCTTGCATTGCACTAAGTCTTGCACT TGTCACGAATTCATCATACGAACTGACTCAGCCTCCGTCAGTCTCAG TTAGCCCCGGTCAAACCGCACGGATCACGTGCTCCGGGGATGCTTT GCCCCGGAAGTTTGCTTATTGGTATCAGCAGAAGTCCGGGCAAGCA CCAGTCATGGTTATCTACGAGGATAGCAAGCGACCCCCTGGAATCC CTGAGAGATTCAGCGGGTCCAGTAGCGGGACTATGGCAACACTGAC AATAACCGGCGCACAAGTCGAGGACGAGGCGGATTACTACTGTTAT AGCACTGATAGTGGTGGCGACGTTAGCGTCTTTGGTGGCGGAACCA AGCTGACGGTTCTTGGACAGCCCAAGGCTGCCCCCTCGGTCACTCTG TTCCCGCCCTCCTCTGAGGAGCTTCAAGCCAACAAGGCCACACTGG TGTGTCTCATAAGTGACTTCTACCCGGGAGCCGTGACAGTGGCCTG GAAGGCAGATAGCCAGCCCCGTCAAGGCGGGAGTGGAGACCACCAC ACCCTCCAAACAAAGCAACAACAAGTACGCGGCCAGCAGCTATCTG AGCCTGACGCCTGAGCAGTGGAAGTCCCACAGAAGCTACAGCTGCC AGGTCACGCATGAAGGGAGCACCGTGGAGAAGACAGTGGCCCCTA CAGAATGTTCATAG | 72 |
| anti-IFNγ antibody, heavy chain | MYRMQLLSCIALSLALV TNSEVQLLESGGGLVQP GGSLRLSCAASGFTFSSY AMSWVRQAPGKGLEW VSAISGSGGSTYYADSV KGRFTISRDNSKNTLYL QMNSLRAEDTAVYYCA KDGSSGWYVPHWFDPW GQGTLVTVSSASTKGPS VFPLAPSSKSTSGGTAAL GCLVKDYFPEPVTVSWN SGALTSGVHTFPAVLQS SGLYSLSSVVTVPSSSLG TQTYICNVNHKPSNTKV DKKVEPKSCDKTHTCPP CPAPELLGGPSVFLFPPK PKDTLMISRTPEVTCVV VDVSHEDPEVKFNWYV DGVEVHNAKTKPREEQ YNSTYRVVSVLTVLHQD WLNGKEYKCKVSNKAL PAPIEKTISKAKGQPREP QVYTLPPSREEMTKNQV SLTCLVKGFYPSDIAVE WESNGQPENNYKTTPPV LDSDGSFFLYSKLTVDK SRWQQGNVFSCSVMHE ALHNHYTQKSLSLSPGK * | 65 | ATGTACAGGATGCAACTCCTGTCTTGCATTGCACTAAGTCTTGCACT TGTCACGAATTCAGAGGTGCAGCTGTTGGAGTCTGGGGGAGGCTTG GTACAGCCTGGGGGGTCCCTGAGACTCTCCTGTGCAGCCTCTGGATT CACCTTTAGCAGCTATGCCATGAGCTGGGTCCGCCAGGCTCCAGGG AAGGGGCTGGAGTGGGTCTCAGCTATTAGTGGTAGTGGTGGTAGCA CATACTACGCAGACTCCGTGAAGGGCCGGTTCACCATCTCCAGAGA CAATTCCAAGAACACGCTGTATCTGCAAATGAACAGCCTGAGAGCC GAGGACACGGCCGTATATTACTGTGCGAAAGATGGTAGCAGTGGCT GGTACGTACCACACTGGTTCGACCCCTGGGGCCAGGGCACCCTGGT CACCGTCTCCTCAGCTAGCACCAAGGGCCCATCGGTCTTCCCCCTGG CACCCTCCTCCAAGAGCACCTCTGGGGGCACAGCGGCCCTGGGCTG CCTGGTCAAGGACTACTTCCCCGAACCGGTGACGGTGTCGTGGAAC TCAGGCGCCCTGACCAGCGGCGTGCACACCTTCCCGGCTGTCCTAC AGTCCTCAGGACTCTACTCCCTCAGCAGCGTGGTGACCGTGCCCTCC AGCAGCTTGGGCACCCAGACCTACATCTGCAACGTGAATCACAAGC CCAGCAACACCAAGGTGGACAAGAAAGTTGAGCCCAAATCTTGTGA CAAAACTCACACATGCCCACCGTGCCCAGCACCTGAACTCCTGGGG GGACCGTCAGTCTTCCTCTTCCCCCCAAAACCCAAGGACACCCTCAT GATCTCCCGGACCCCTGAGGTCACATGCGTGGTGGTGGACGTGAGC CACGAAGACCCTGAGGTCAAGTTCAACTGGTACGTGGACGGCGTGG AGGTGCATAATGCCAAGACAAAGCCGCGGGAGGAGCAGTACAACA GCACGTACCGTGTGGTCAGCGTCCTCACCGTCCTGCACCAGGACTG GCTGAATGGCAAGGAGTACAAGTGCAAGGTCTCCAACAAAGCCCTC CCAGCCCCCATCGAGAAAACCATCTCCAAAGCCAAAGGGCAGCCCC GAGAACCACAGGTGTACACCCTGCCCCCATCCCGGGAGGAGATGAC CAAGAACCAGGTCAGCCTGACCTGCCTGGTCAAAGGCTTCTATCCC AGCGACATCGCCGTGGAGTGGGAGAGCAATGGGCAGCCGGAGAAC AACTACAAGACCACGCCTCCCGTGCTGGACTCCGACGGCTCCTTCTT CCTCTACAGCAAGCTCACCGTGGACAAGAGCAGGTGGCAGCAGG GGAACGTCTTCTCATGCTCCGTGATGCATGAGGCTCTGCACAACCACT ACACGCAGAAGAGCCTCTCCCTGTCTCCGGGTAAATGA | 73 |
| anti-IFNγ antibody, light chain | MYRMQLLSCIALSLALV TNSNFMLTQPHSVSESP GKTVTISCTRSSGSIASN YVQWYQQRGSSPTTVIY EDNQRPSGVPDRFSGSID SSSNSASLTISGMFGGGT KLTVLGQPKAAPSVTLF PPSSEELQANKATLVCLI SDFYPGAVTVAWKADS SPVKAGVETTTPSKQSN NKYAASSYLSLTPEQWK SHRSYSCQVTHEGSTVE KTVAPTECS* | 66 | ATGTACAGGATGCAACTCCTGTCTTGCATTGCACTAAGTCTTGCACT TGTCACGAATTCAAATTTTATGCTGACTCAGCCCCACTCTGTGTCGG AGTCTCCGGGGAAGACGGTAACCATCTCCTGCACCCGCAGCAGTGG CAGCATTGCCAGCAACTATGTGCAGTGGTACCAGCAGCGCCCGGGC AGTTCCCCCACCACTGTCATCTATGAGGATAACCAAAGACCTTCTG GGGTCCCTGACCGGTTCTCTGGCTCCATCGACAGCTCCTCCAATTCT GCCTCCCTCACCATCTCTGGGATGTTCGGCGGAGGGACCAAGCTGA CCGTCCTAGGTCAGCCCAAGGCTGCCCCCTCGGTCACTCTGTTCCCG CCCTCCTCTGAGGAGCTTCAAGCCAACAAGGCCACACTGGTGTGTC TCATAAGTGACTTCTACCCGGGAGCCGTGACAGTGGCCTGGAAGGC AGATAGCAGCCCCGTCAAGGCGGGAGTGGAGACCACCACACCCTCC AAACAAAGCAACAACAAGTACGCGGCCAGCAGCTATCTGAGCCTG ACGCCTGAGCAGTGGAAGTCCCACAGAAGCTACAGCTGCCAGGTCA CGCATGAAGGGAGCACCGTGGAGAAGACAGTGGCCCCTACAGAAT GTTCATAG | 74 |
| IL2 signal sequence | MYRMQLLSCIALSLALV TNS | 67 | ATGTACAGGATGCAACTCCTGTCTTGCATTGCACTAAGTCTTGCACT TGTCACGAATTCA | 75 |
| CD74 | MHRRRSRSCREDQKPV MDDQRDLISNNEQLPML GRRPGAPESKCSRGALY | 68 | ATGCACAGGAGGAGAAGCAGGAGCTGTCGGGAAGATCAGAAGCCA GTCATGGATGACCAGCGCGACCTTATCTCCAACAATGAGCAACTGC CCATGCTGGGACGGCGCCCTGGTGCACCAGAATCAAAATGTTCAAG | 76 |

TABLE 2-continued

| Name | Sequence [Amino Acid] | SEQ. ID No. | Sequence [Nucleic Acid] | SEQ ID No. |
|------|----------------------|-------------|-------------------------|------------|
| | TGFSILVTLLLAGQATTA<br>YFLYQQQGRLDKLTVTS<br>QNLQLENLRMKLPKPPK<br>PVSKMRMATPLLMQAL<br>PMGALPQGPMQNATKY<br>GNMTEDHVMHLLQNAD<br>PLKVYPPLKGSFPENLR<br>HLKNTMETIDWKVFES<br>WMHHWLLFEMSRHSLE<br>QKPTDAPPKESLELEDPS<br>SGLGVTKQDLGPVPM* | | AGGAGCCCTATACACAGGCTTTTCCATCCTGGTGACTCTGCTCCTCG<br>CTGGCCAGGCCACCACCGCCTACTTCCTGTACCAGCAGCAGGGCCG<br>GCTGGACAAACTGACAGTCACCTCCCAGAACCTGCAGCTGGAGAAC<br>CTGCGCATGAAGCTTCCCAAGCCTCCCAAGCCTGTGAGCAAGATGC<br>GCATGGCCACCCCGCTGCTGATGCAGGCGCTGCCCATGGGAGCCCT<br>GCCCCAGGGGCCCATGCAGAATGCCACAAAATACGGTAATATGACT<br>GAAGACCATGTGATGCACCTGCTCCAGAATGCTGACCCCCTGAAGG<br>TGTACCCGCCACTGAAGGGGAGCTTCCCGGAGAACCTCAGGCATTT<br>GAAAAATACGATGGAGACCATAGACTGGAAGGTCTTTGAGAGCTGG<br>ATGCACCATTGGCTCCTGTTTGAAATGAGCAGGCACTCCTTGGAGC<br>AAAAGCCCACTGACGCTCCACCGAAAGAGTCACTGGAACTGGAGG<br>ACCCGTCTTCTGGGCTGGGTGTGACCAAGCAGGATCTGGGCCCAGT<br>CCCCATGTGA | |
| cathepsin S cleavage site | GRWHTVGL | 69 | GGAAGATGGCACACCGTGGGACTG | 77 |
| CLIP | MRMATPLLM | 70 | | |

To create HLA class I and II knockout cells, HLA class I KO HeLa cells were first transduced with CIITA cDNA. Single-cell clones were established and tested for presence of endogenous HLA class II cell surface expression by flow cytometry. Messenger RNA was isolated (RNeasy Mini kit; Qiagen) from a positive clone, and cDNA was prepared (iScript cDNA Synthesis Kit; Bio-Rad) and used to type HLA class II genes using degenerate primers (Table 1). HeLa-CIITA cells were typed as DPA1*02:01:08, DPB1*01:01:01, DQA1*01:01:01, DQB1*05:01:01, and DRB1*01:02:01. CRISPR/Cas9 cassettes directed to each of these genes were cloned into pXPR_001; sequences are listed in Table 1. The targeting vectors were transiently transfected into the CIITA-expressing HLA class I KO HeLa clone. The cells were then tested for knockout of HLA class II cell surface expression by flow cytometry.

To express surface-bound antibodies, anti-cytokine antibody heavy and light chain cDNAs were cloned separately into pLX303 vectors. Anti-IL-2 antibody and anti-IFN-γ antibody sequences (Table 2) were previously described). Lentivirus containing heavy and light chain genes were co-transduced into the HLA class I KO APCs. Cells were used directly, or single-cell cloned and selected for anti-cytokine antibody expression.

Encoded Peptide Library Construction.

For HLA class I-presented peptides, the human IL-2 signal sequence was cloned into the lentiviral vector pLX301. Peptide-encoding oligonucleotides were then cloned in-frame 3' of the signal sequence, using Gibson Assembly Master Mix (New England Biolabs). Individual oligonucleotides encoding peptides were synthesized by Integrated DNA Technologies (IDT). Oligonucleotide library pools were synthesized by CustomArray/Genscript or Twist Bioscience. Long (i.e., 50 amino acid) peptides for HLA class I processing and presentation were cloned 3' of a methionine; the spacer sequence encoding HTVGLYM was added between the methionine and the peptide to facilitate cloning. For HLA class II-presented peptides, the CD74 gene was fused to a cathepsin S cleavage site (amino acid sequence: GRWHTVGL (SEQ ID. NO 78) followed by a peptide-encoding sequence (Table 2). For long peptides for HLA class II processing and presentation, an additional YM spacer sequence was added between the cathepsin S cleavage site and the peptide to facilitate cloning. Alternatively, the CLIP-encoding sequence (amino acid sequence: MRMATPLLM (SEQ ID NO. 79) in CD74 was replaced with a peptide-encoding sequence. Peptide-encoding oligonucleotide sequences are listed in Table 3.

To construct the CMV libraries, sequence data was downloaded for all 169 ORFs (open reading frames) that were annotated in the complete genome sequence of CMV strain Merlin in NCBI (accession AY446894). The sequence data for all 168 ORFs that were annotated in the reference proteome of CMV strain Merlin in UniProt (proteome ID UP000000938) was added, as well as all 190 ORF sequences that were annotated in the reference proteome of CMV strain AD169 (UniProt proteome ID UP000008991). Finally, sequence data for 57 CMV ORFs from mass spectrometry data of CMV (strain Merlin)-infected cells was added. To construct the tiled genomic library, for all CMV ORFs, 50 amino acid peptides were tiled, each with 32 amino acid overlaps. For ORFs with lengths <50 amino acids, full-length ORFs were constructed. In total, this resulted in 4,867 unique peptides. To construct the NetMHC-filtered library, all ORF sequences were run through the NetMHCpan 4.0 server (Jurtz et al. 2017 J. Immunol., 199:3360-3368), specifying peptide lengths of 8-10 amino acids, and alleles HLA-A*24:02, HLA-B*07:02, and HLA-B51:01. One thousand four hundred and seven peptides (1,407) were obtained for HLA-A*24:02 (% Rank </=0.5), 947 peptides for HLA-B*07:02 (% Rank </=0.2), and 631 peptides for HLA-B*51:01 (% Rank </=0.2); for a total of 2,852 unique peptides. Peptide-encoding oligonucleotide sequences are listed in Table 3.

TABLE 3

| Epitope name | Amino Acid Sequence | SEQ ID NO. | Nucleic Acid sequence | HLA | SEQ ID NO. |
|--------------|--------------------|------------|-----------------------|-----|------------|
| CMV pp65 (495-503) | NLVPMV ATV* | 80 | AACCTCGTTCCT ATGGTCGCCAC CGTCTAG | HLA-A*02: 01 | 92. |
| Influenza MP (58-66) | GILGFVF TL* | 81 | GGCATTCTGGG GTTCGTTTTCAC CCTGTAA | HLA-A*02: 01 | 93. |

33

TABLE 3-continued

| Epitope name | Amino Acid Sequence | SEQ ID NO. | Nucleic Acid sequence | HLA | SEQ ID NO. |
|---|---|---|---|---|---|
| NY-ESO-1 (157-165) (C165V) | SLLMWIT QV* | 82 | AGCCTCTTGATG TGGATCACGCA GGTTTAG | HLA-A*02: 01 | 94. |
| KRAS G12 (wt) | GAGGVG KSAL* | 83 | GGAGCAggaGGC GTGGGTAAGTC AGCTCTGTGA | | 95. |
| KRAS G12D | GADGVG KSAL* | 84 | GGAGCAgacGGC GTGGGTAAGTC AGCTCTGTGA | HLA-C*08: 02 | 96. |
| KRAS G12C | GACGVG KSAL* | 85 | GGAGCAtgcGGC GTGGGTAAGTC AGCTCTGTGA | | 97. |
| KRAS G12V | GAVGVG KSAL* | 86 | GGAGCAgtgGGC GTGGGTAAGTC AGCTCTGTGA | | 98. |
| KRAS G12R | GARGVG KSAL* | 87 | GGAGCAagaGGC GTGGGTAAGTC AGCTCTGTGA | | 99. |
| MBP (85-99) epitope | ENPVVHF FKNIVTP R* | 88 | GAAAACCCAGT GGTGCACTTTTT TAAGAATATAG TCACTCCCCGGT GA | HLA-DRA*01: 01 + HLA-DRB1*15: 01 | 100. |
| MBP (89-101) | VHFFKNI VTPRTP* | 89 | | HLA-DRA*01: 01 + HLA-DRB1*15: 01 | |
| influenza HA | PKYVKQ NTLKLAT | 90 | CCGAAGTATGT GAAGCAAAATA | HLA-DRA*01: | 101. |

34

TABLE 3-continued

| Epitope name | Amino Acid Sequence | SEQ ID NO. | Nucleic Acid sequence | HLA | SEQ ID NO. |
|---|---|---|---|---|---|
| (307-319) | * | | CATTGAAACTC GCTACGTGA | 01 + HLA-DRB1*01: 01 | |
| influenza HA (309-317) | YVKQNT LKL* | 91 | | HLA-DRA*01: 01 + HLA-DRB1*01: 01 | |

T Cell Receptor Expression.

TCR knockout (KO) T cells were first prepared using CRISPR/Cas9. Briefly, CRISPR/Cas9 cassettes directed to cleave the constant regions of the T cell receptor alpha and T cell receptor beta loci were cloned into pXPR_001. Sequences are listed in Table 1. Jurkat cells were transduced with lentivirus containing the CRISPR/Cas9 cassettes. Single-cell clones were established and tested for knockout of TCR cell surface expression by flow cytometry.

TCR cDNAs Preparation

TCR cDNAs were prepared as follows. The TCR constant regions (TRAC and TRBC1) were modified in two ways. Silent mutations were introduced into the T cell receptor alpha and beta constant regions to avoid CRISPR/Cas9 targeting. Cysteine mutations (TRAC T48C and TRBC S57C) were also introduced to stabilize TCR heterodimerization and increase TCR cell surface expression (J. M. Boulter et al., 2003 Protein Eng. Des. Sel., 16:707-711; Kuball et al., 2007 Blood, 109:2331-8). Specific TCR alpha and TCR beta variable regions were fused in-frame to the respective modified TCR constant region, and the TCR alpha and TCR beta genes were cloned into pLX301 vectors separately. Lentivirus containing TCR alpha and TCR beta genes were co-transduced into the TCR KO Jurkat cells. TCR-encoding sequences are listed in Table 4.

TABLE 4

| TCR name | Target epitope [aa] | SEQ ID No. | HLA restriction | TRBV | CDR3 beta | SEQ ID No. |
|---|---|---|---|---|---|---|
| C25 TCR | NLVPMVATV (CMV) | 102 | HLA-A*02:01 | TRBV7-6 | CASSLAPGTTNEKLFF | 112 |
| JM22 TCR | GILGFVFTL (Flu) | 103 | HLA-A*02:01 | TRBV19 | CASSSRSSYEQYF | 113 |
| 1G4 TCR | SLLMWITQV (NY-ESO-1 C165V) | 104 | HLA-A*02:01 | TRBV6-5 | CASSYVGNTGELFF | 114 |
| 1A TCR | TPRVTGGGAM (CMV) | 105 | HLA-B*07:02 | TRBV7-9 | CASSDHSVTGISSPLHF | 115 |
| IPS TCR | IPSINVHHY (CMV) | 106 | HLA-B*35:01 | TRBV11-2 | CASSADSNGELFF | 116 |
| 3B TCR | TAFTIPSI (HIV) | 107 | HLA-B*51:01 | TRBV7-3 | CASSLTGGGELFF | 117 |
| KRAS p.G12 D TCR | GADGVGKSAL (KRAS p.G12D) | 108 | HLA-C*08:02 | TRBV10-2 | CASSDPGTEAFF | 118 |
| HA1.7 TCR | PKYVKQNTLKLAT (Flu) | 109 | HLA-DRB1*01:01 | TRBV28 | CASSSTGLPYGYTF | 119 |
| Ob.1A 12 TCR | ENPVVHFFKNIVTPR (MBP) | 110 | HLA-DRB1*15:01 | TRBV20 | CSARDLTSGANNEQFF | 120 |
| Ob.2F 3 TCR | ENPVVHFFKNIVTPR (MBP) | 111 | HLA-DRB1*15:01 | TRBV20 | CSARDLTSGSLNEQFF | 121 |
| TCR #1 | na | | na | TRBV11-2 | CASSSGQVQETQYF | 619 |
| TCR #2 | na | | na | TRBV7-9 | CASSFPTSGQETQYF | 620 |
| TCR #3 | na | | na | TRBV7-9 | CASSHRDRNYEQYF | 621 |

TABLE 4-continued

| | | | | CDR3 | SEQ ID No. | |
|---|---|---|---|---|---|---|
| TCR #4 | na | | na | TRBV15 | CATSRVAGETQYF | 622 |
| TCR #5 | na | | na | TRBV9 | CASSVTGGTDTQYF | 623 |
| TCR #5b | na | | na | TRBV9 | CASSVTGGTDTQYF | 624 |
| TCR #6 | na | | na | TRBV9-1 | CASSAGQGVTYEQYF | 625 |
| TCR #7 | na | | na | TRBV12-3 | CASSLGGPGDTQYF | 626 |
| TCR #7-4 | na | | na | TRBV12-4 | CASSLGGPGDTQYF | 627 |
| TCR #8 | na | | na | TRBV12-3 | CASSLGGAGDTQYF | 628 |
| TCR #8-4 | na | | na | TRBV12-4 | CASSLGGAGDTQYF | 629 |
| TCR #9 | na | | na | TRBV20-1 | CSASDHEQYF | 630 |
| TCR #10 | na | | na | TRBV14 | CASSLNRGQETQYF | 631 |

| TRBJ | TRAV | CDR3 alpha | SEQ ID No. | TRAJ | Note |
|---|---|---|---|---|---|
| TRBJ1-4 | TRAV26-2 | CILDNNNDMRF | 122 | TRAJ43 | |
| TRBJ2-7 | TRAV27 | CAGAGSQGNLIF | 123 | TRAJ42 | |
| TRBJ2-2 | TRAV21 | CAVRPTSGGSYIPTF | 124 | TRAJ6 | |
| TRBJ1-6 | TRAV38-2 | CAYRSARDSSYKLIF | 125 | TRAJ12 | |
| TRBJ2-2 | TRAV5 | CAERGWDNDMRF | 126 | TRAJ43 | |
| TRBJ2-2 | TRAV17 | CATDDDSARQLTF | 127 | TRAJ22 | |
| TRBJ1-1 | TRAV12-2 | CAAAMDSSYKLIF | 128 | TRAJ12 | |
| TRBJ1-2 | TRAV8-4 | CAVSESPFGNEKLTF | 129 | TRAJ48 | |
| TRBJ2.1 | TRAV17 | CATDTTSGTYKYIF | 130 | TRAJ40 | |
| TRBJ2.1 | TRAV17 | CATDATSGTYKYIF | 131 | TRAJ40 | |
| TRBJ2-5 | TRAV8-3 | CAVASYGNKLVF | 632 | TRAJ47 | |
| TRBJ2-5 | TRAV9-2 | CALSDNYGQNFVF | 633 | TRAJ26 | |
| TRBJ2-7 | TRAV12-2 | CAVNVDTDKLIF | 634 | TRAJ34 | |
| TRBJ2-5 | TRAV17 | CATEGNFGNEKLTF | 635 | TRAJ48 | |
| TRBJ2-3 | TRAV19 | CALSEGFQTGANNLFF | 636 | TRAJ36 | The TCRβ was found in 2 different individuals, paired with |
| TRBJ2-3 | TRAV29 | CAAPGGSTLGRLYF | 637 | TRAJ 18 | different TCRα |
| TRBJ2-7 | TRAV21 | CAVRSGGYQKVTF | 638 | TRAJ 13 | |
| TRBJ2-3 | TRAV3 | CAVSQPSGGSYIPTF | 639 | TRAJ6 | TRBV12-3 & TRBV12-4 could not be distinguished |
| TRBJ2-3 | TRAV3 | CAVSQPSGGSYIPTF | 640 | TRAJ6 | in TCR-seq data |
| TRBJ2-3 | TRAV3 | CAVTDASGGSYIPTF | 641 | TRAJ6 | TRBV12-3 & TRBV12-4 could not be distinguished |
| TRBJ2-3 | TRAV3 | CAVTDASGGSYIPTF | 642 | TRAJ6 | in TCR-seq data |
| TRBJ2-7 | TRAV34 | CGADSRGSTLGRLYF | 643 | TRAJ18 | |
| TRBJ2-5 | TRAV21 | CAVRRGTDKLIF | 644 | TRAJ34 | |

Enzyme-Linked Immunosorbent Assay (ELISA).

HLA class I KO APCs expressing desired HLA and peptide-encoding genes were seeded in a 96-well plate. T cells were added to the APCs at a ratio of about 10:1. Eighty (80) ng/mL phorbol 12-myristate 13-acetate (PMA; Sigma-Aldrich) was added to help Jurkat cells stimulate antigen-dependent IL-2 production. After 24 hours of incubation at 37° C., supernatants were collected. IL-2 secretion was quantitated by IL-2 ELISA (Human IL-2 ELISA MAX Deluxe; Biolegend).

APC Cytokine Labeling Assay.

HLA class I KO APCs expressing desired HLA, encoded peptides, and surface-bound anti-cytokine antibodies were seeded in 96-well or 384-well plates. T cells were added to the APCs at a ratio between 2:1 and 16:1. 80 ng/mL PMA was added to help Jurkat cells stimulate antigen-dependent IL-2 production. After incubation at 37° C. for 0-28 hours, cells were washed with phosphate buffered saline (PBS; Thermo Fisher Scientific) or DMEM supplemented with 10% FBS. Cells were dissociated with 0.25% trypsin-EDTA (Thermo Fisher Scientific) or enzyme-free cell dissociation buffer (Thermo Fisher Scientific), pooled, and stained with fluorescently-labeled anti-IL-2 or anti-IFN-γ antibody. Alternatively, cells were stained in-well prior to dissociation. Stained cells were then washed with DMEM supplemented with 10% FBS to remove excess antibody. A subset of the cells was imaged (Zeiss Axiovert 40 CFL, Olympus CK40, or Olympus IX73) to assess fluorescence staining, or analyzed by flow cytometry (BD LSRFortessa; Dana-Farber Cancer Institute Flow Cytometry Core). For pulldowns, PE+ cells were magnetically labeled using Anti-PE MicroBeads (Miltenyi) or PE Positive Selection Kit (StemCell Technologies), and separated from unlabeled cells using a MACS Separator (Miltenyi) or EasySep Magnet (StemCell Technologies).

Amplification of Encoded Peptides and Sequencing

Genomic DNA was extracted (DNeasy Blood & Tissue Kit; Qiagen) from PE-labeled cells (pulldown) and from unlabeled cells (flow-through). The integrated epitope sequences were amplified by PCR (Kapa HotStart Ready-Mix; Kapa Biosystems) using barcoded primers complementary to sequences flanking the peptide-encoding sequences. Primer sequences are listed in Table 1. NGS libraries were prepared from the PCR products and sequenced by the Massachusetts General Hospital (MGH) Center for Computational & Integrative Biology (CCIB) DNA Core (Boston, MA).

Data Analysis

For each NGS read, the 5' and 3' barcodes were identified to demultiplex the reads into associated samples, e.g. PE+

(pulldown) cells, PE⁻ (flow-through) cells, and input DNA. For long encoded peptides, paired end reads were joined using fastq-join. For each read, common sequences flanking the peptide-encoding sequence were identified, and the intervening peptide-encoding sequences were enumerated for each sample. For each sample, the fractional abundance of each encoded peptide in the pulldown was calculated and graphed. The difference in fractional abundance of each encoded peptide between pulldown and flow-through samples (annotated as % enrichment) was calculated and graphed. Peptide-HLA binding predictions were performed using NetMHCpan 4.0 (Jurtz et al., 2017 J. Immunol., 199:3360-3368) and NetMHC 4.0 servers (Nielsen et al., 2003 Protein Sci., 12:1007-17; Andreatta et al., 2016 Bioinformatics, 32:511-517).

Peptide-HLA binding predictions were performed using NetMHCpan 4.097, NetMHCpan 4.166, and NetMHCIIpan 4.059 servers using default parameters, including rank thresholds for strong binding (SB) peptides (0.5% for NetMHCpan, 2% for NetMHCIIpan) and weak binding (WB) peptides (2% for NetMHCpan, 10% for NetMHCIIpan).

Statistical Analysis

Data are reported as mean±s.d. P values were calculated using an unpaired Student's t-test. *P<0.05, P<0.005, *P<0.0005.

Figure 8B:
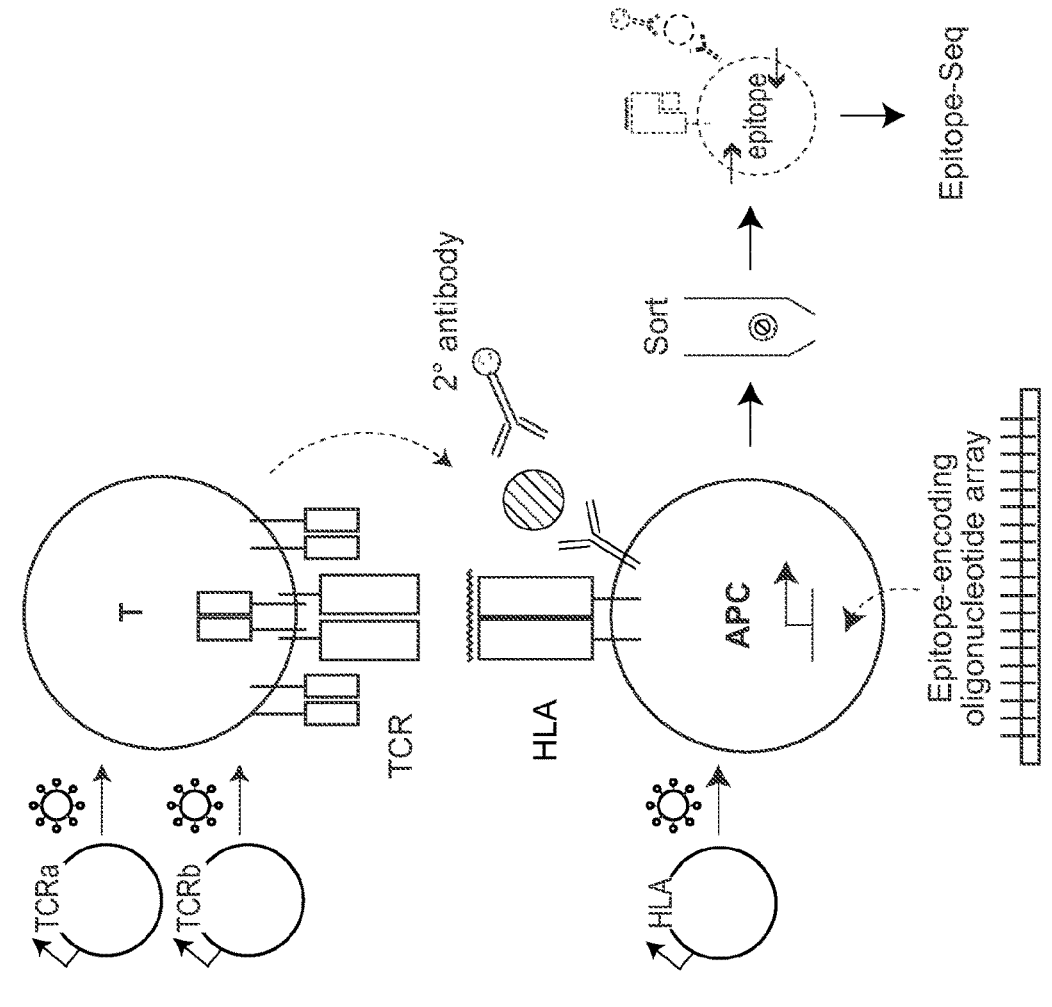
Figure 8B:
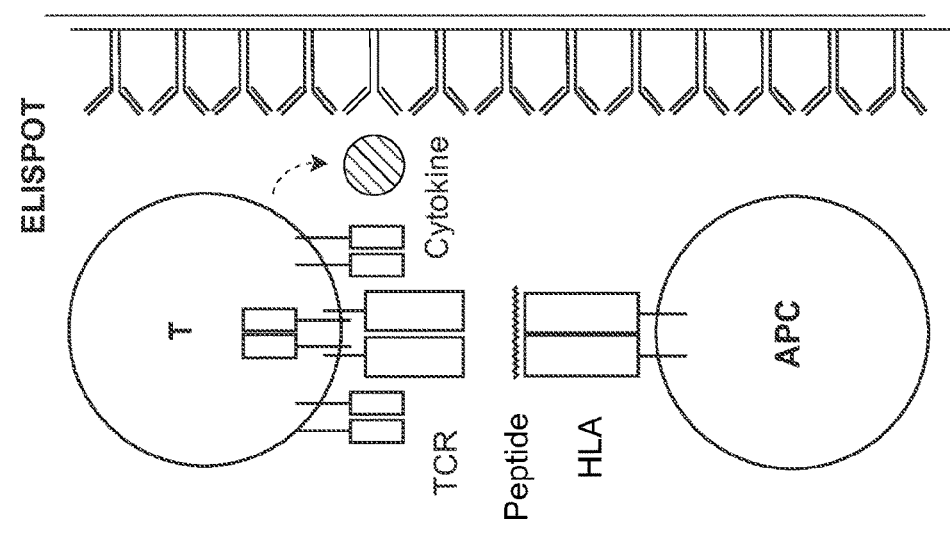

Example 2: Establishing a System for Epitope Identification Using Antigen-Presenting Cell-Bound Anti-Cytokine Antibodies The present assay methods (schematically shown in FIG. 8A) accept highly complex epitope-encoding oligonucleotide pools as an input (FIG. 1A), and use a cytokine readout to pinpoint TCR-targeted epitopes (FIG. 1B). In cytokine detection assays such as the ELISPOT, antibodies linked to solid phase capture cytokines secreted by activated T cells (FIG. 8B). In contrast, the present assay methods which, inter alia, feature (i) stably encoding the peptide library within antigen-presenting cells (APCs) and (ii) expressing an anti-cytokine antibody on the APC surface instead of on solid phase (FIG. 1B and FIG. 8B) give them the ability to sort epitopes using activation-dependent cytokines.

Figure 8C:
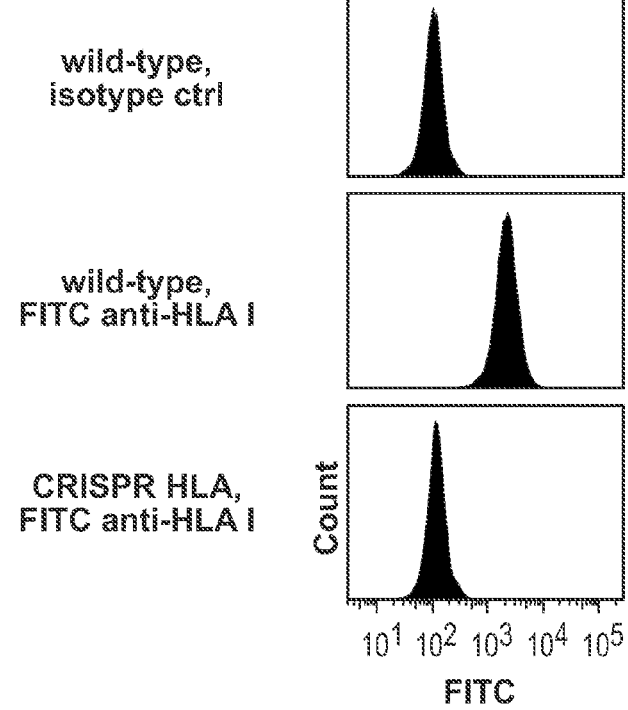
Figure 8E:
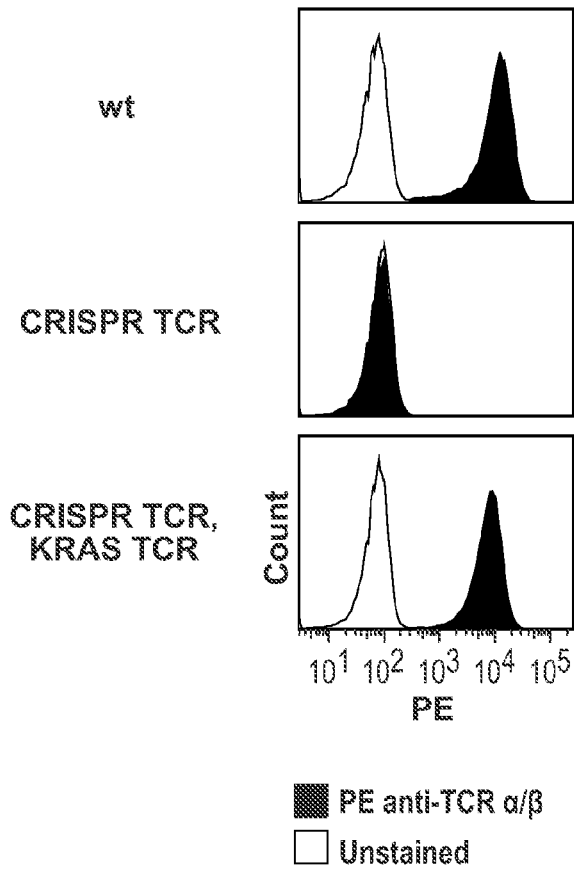
Figure 8D:
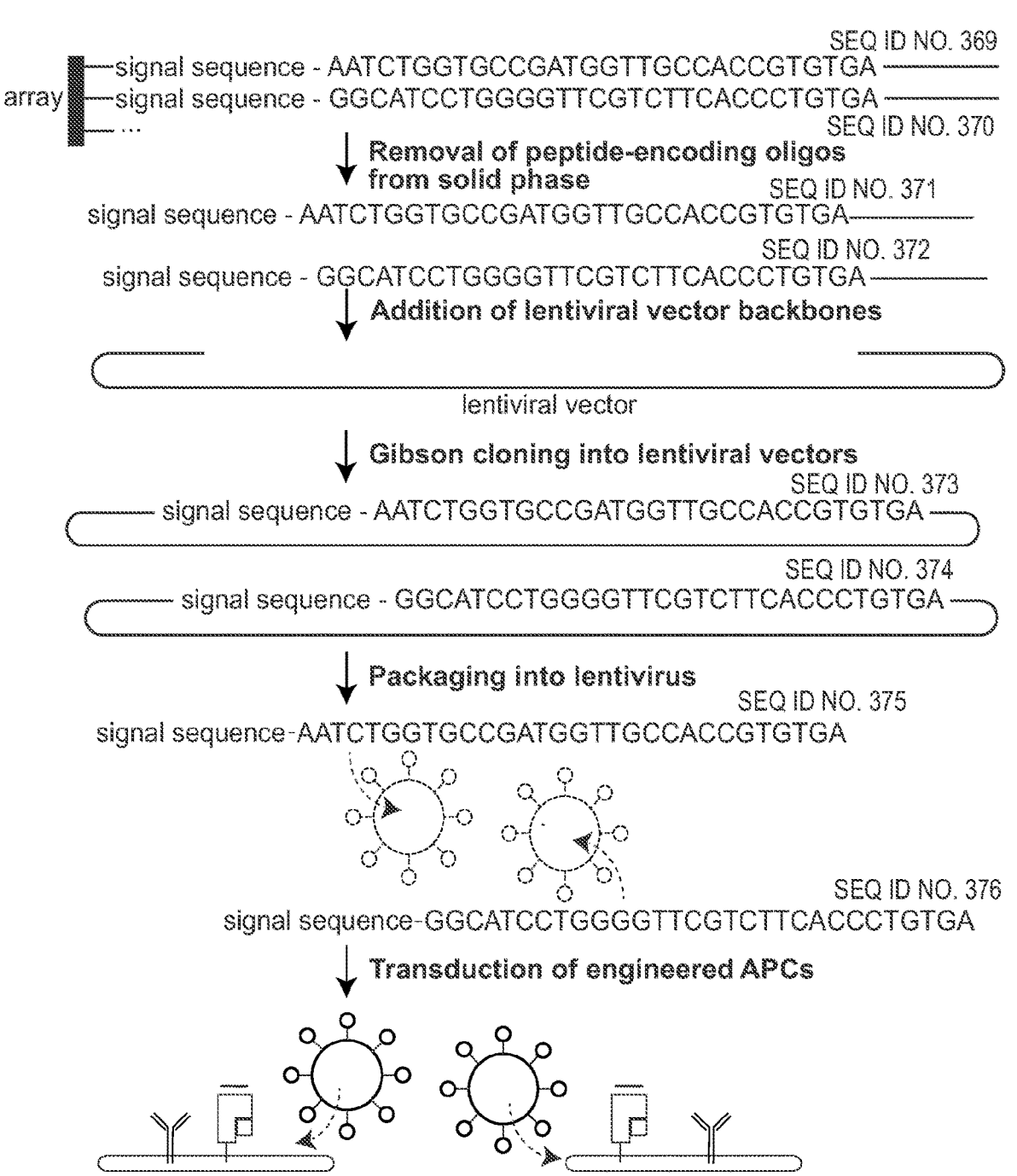
Figures 8F, 8G, 8H:
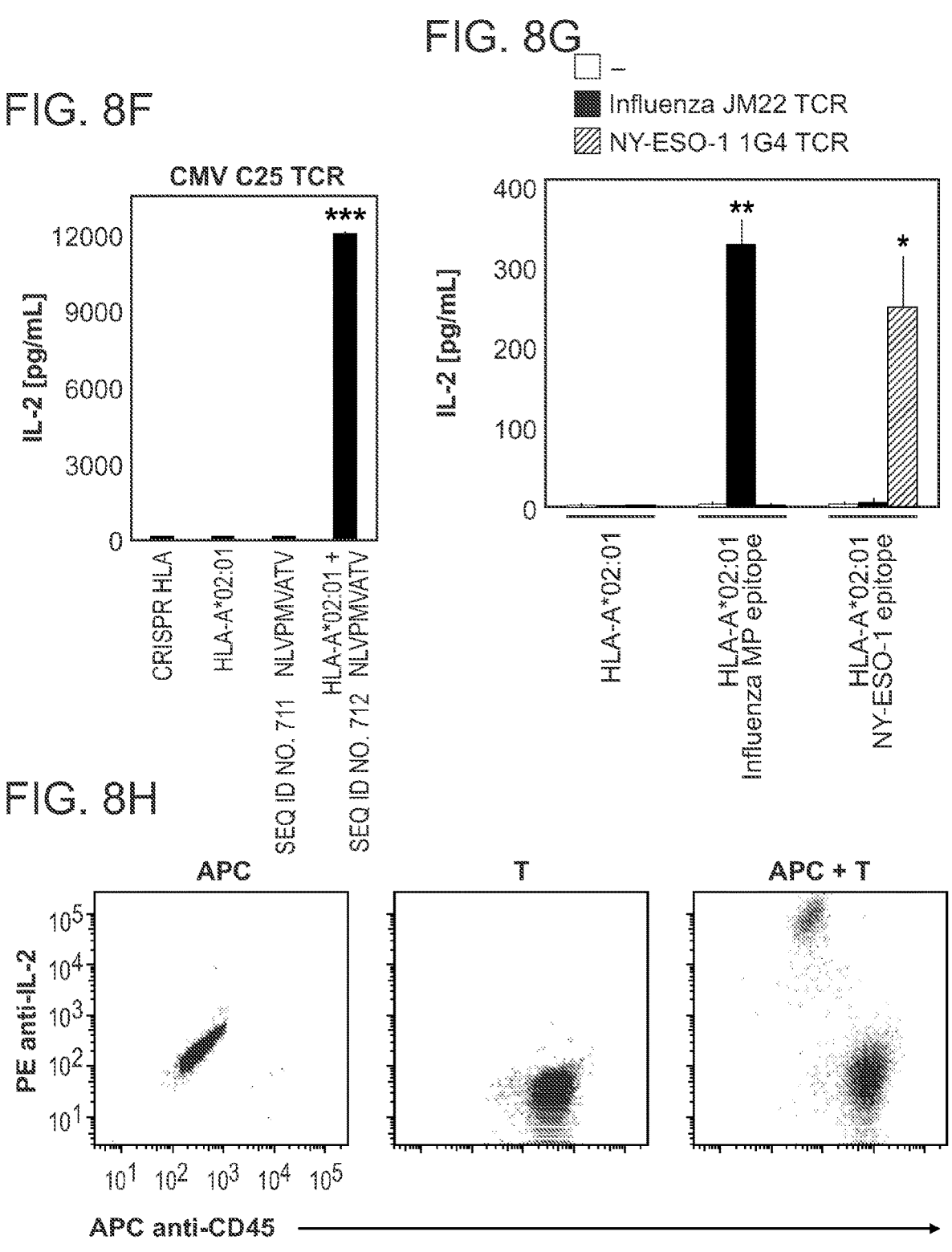

To make human APCs express defined HLA genes as well as defined peptides, HLA class I knockout (HLA class I KO) APC lines were generated through transient expression of CRISPR/Cas9 cassettes targeting HLA class I loci (Table 1). Following CRISPR/Cas9 transfection, HLA class I cell surface expression was eliminated from APC lines, including HeLa and HEK293T cells, which were used as model APCs (FIG. 1C and FIG. 8C). After several passages to dilute the expression of the CRISPR constructs, stable expression of exogenous HLA genes in the HLA class I KO APCs was achieved (FIG. 1C). For presentation on HLA class I, peptide-encoding minigenes 3' of a signal sequence were then cloned into a lentiviral vector backbone in order to stably express defined peptide-encoding sequences (FIG. 8D). Peptide-encoding genes were synthesized individually, or thousands were synthesized in parallel on an oligonucleotide array and pooled. To confirm the stimulatory capacity and specificity of these HLA- and peptide-expressing APCs, the APCs were co-cultured with exogenous TCR-expressing Jurkat cells (Table 4) in which the endogenous Jurkat TCR was knocked out using CRISPR/Cas9 (TCR KO T cells) (FIG. 8E and Table 1). IL-2 was secreted only after co-culture of the T cells with APCs expressing the corresponding HLA and epitope combinations (FIG. 8F and FIG. 8G).

In order to capture these cytokines on the surface of APCs, an antibody-encoding gene was expressed—in this case expressing antibodies to IL-2 or IFN-γ—that can affix cytokine to the APC surface (FIG. 1B and Table 2). These modified APCs were tested by adding recombinant IL-2 or IFN-γ to the cells. Addition of cytokine to cells expressing surface-bound antibody affixed cytokine to the APC surface in a cytokine-specific manner (FIG. 1D).

An assay for capture of cytokine was performed during the co-culture of the APCs with T cells. A previously-described TCR, C25 (Yang et al., 2015 J. Biol. Chem., 290:29106-29119), that recognizes the human cytomegalovirus (CMV) pp65 epitope sequence, NLVPMVATV, (SEQ ID NO. 655) when presented on HLA-A*02:01 was used. For various time intervals, APCs expressing HLA-A*02:01, a NLVPMVATV-encoding gene, and a surface-bound anti-IL-2 antibody-encoding gene were co-cultured with TCR KO T cells expressing C25 TCRα- and TCRβ-expressing genes. The surface of the APCs was stained with a fluorescently-labeled secondary anti-IL-2 antibody, and quantitated staining by flow cytometry. Negligible surface IL-2 staining was seen with APCs alone, while cytokine staining on the APCs increased during co-culture (FIG. 1E and FIG. 8H).

Taken together, these results establish development of an engineered APC that can present integrated epitopes on defined HLA molecules (e.g. HLA-A, HLA-B, HLA-C, HLA-DP, HLA-DQ, or HLA-DR), and can capture cytokine signal from activated T cells.

Example 3: Engineered APCs Capture Cytokine Only in the Context of Functional HLA-Epitope-TCR Complexes To encode peptides for class I presentation, defined peptide-encoding genes 3' of a signal sequence (FIG. 2A and FIG. 8D) were cloned, so that the peptide was predicted to cleave off from the signal sequence without an N-terminal methionine (Martoglio et al., 1998 Trends Cell Biol., 8:410-415) and could potentially be presented by HLA proteins. Alternatively, longer peptide-encoding genes could be synthesized that undergo further processing in the APC prior to presentation; in this latter case, the specific sequence context could alter processing efficiency, which may be cell type- and cell state-dependent (Blum et al., 2013 Annu. Rev. Immunol., 31:443-73).

Figure 2A:
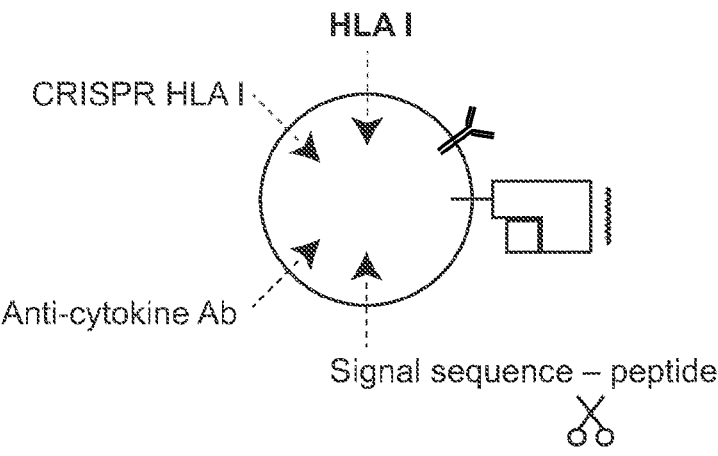
Figure 2B:
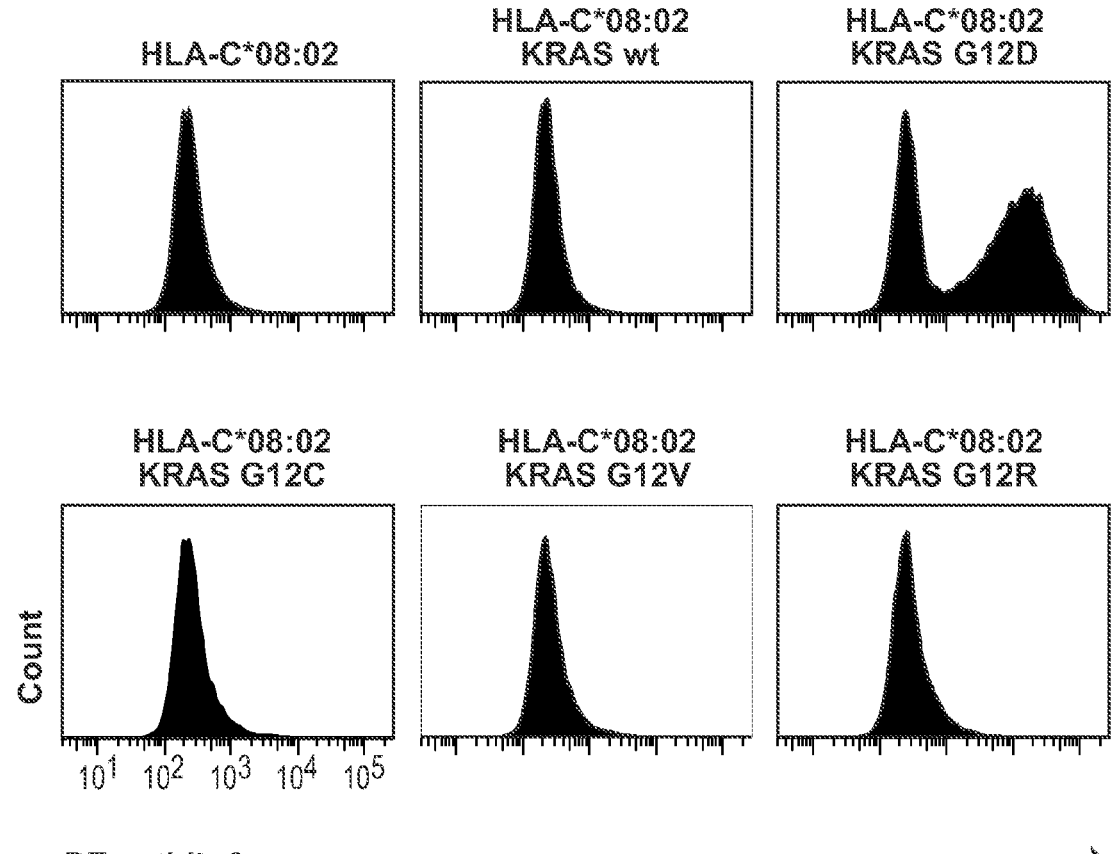
Figure 9A:
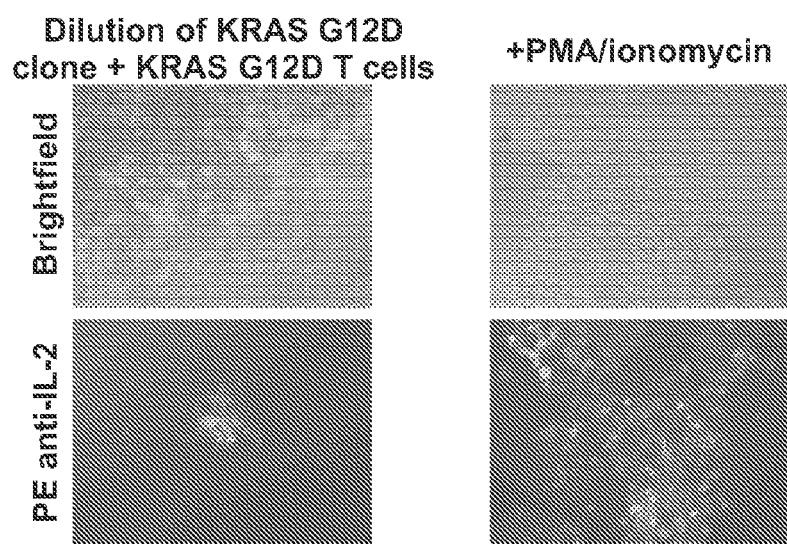
FIG. 9A-9M is a series of schematics and photomicrographs showing engineered APCs capture cytokines in an HLA class I or II epitope-specific manner.

In order to test the specificity of the assay, the target specificity of a KRAS p.G12D mutant-reactive TCR that was identified among the tumor-infiltrating lymphocytes (TILs) of a patient with colorectal adenocarcinoma was assessed (Tran et al., 2016 N. Engi. J. Med., 375:2255-2262). An anti-IL-2 antibody-expressing APCs were transduced with HLA-C*08:02 alone, or in combination with wild-type or mutant KRAS peptide-encoding genes cloned 3' of a signal sequence (FIG. 2A and FIG. 2B). The KRAS mutant-reactive ICR was specific for the p.GT2D mutant, and did not recognize the respective wild-type peptide, as expected (Tran et al., 2016 N. Engl. J. Med., 375:2255-2262), nor peptides containing the common (Cox et al., 2014 Nat. Rev. Drug Discov., 13:828-851) KRAS p.GT2C, p.G12V, or p.G12R mutants (FIG. 2B and FIG. 9A), consistent with in silico predictions that these variants do not bind strongly to HLA-C*08:02 (Table 5).

TABLE 5

| Peptide [aa] | HLA | Affinity [nM], NetMHC 4.0 | % Rank, NetMHC 4.0 | % Rank, NetMHCpan 4.0 | SEQ. ID. No. | Note |
|---|---|---|---|---|---|---|
| | | HLA Binding Affinity Predictions | | | | |
| GACGVGKSAL | HLA-C*08:02 | 42331.36 | 60.00 | 14.1194 | ~~122~~ 728 | |
| GADGVGKSAL | HLA-A*02:01 | 23041.70 | 32.00 | 14.3478 | ~~123~~ 729 | |
| GADGVGKSAL | HLA-B*07:02 | 6646.79 | 5.50 | 2.2886 | ~~124~~ 730 | |
| GADGVGKSAL | HLA-C*08:02 | 24523.65 | 9.00 | 0.3508 (SB) | ~~125~~ 731 | Known HLA Specificity |
| GAGGVGKSAL | HLA-C*08:02 | 42640.73 | 60.00 | 8.0828 | ~~126~~ 732 | |
| GARGVGKSAL | HLA-C*08:02 | 43315.93 | 65.00 | 7.1688 | ~~127~~ 733 | |
| GAVGVGKSAL | HLA-C*08:02 | 43325.76 | 65.00 | 5.8520 | ~~128~~ 734 | |
| GILGFVFTL | HLA-A*02:01 | 15.71 | 0.20 (SB) | 0.0833 (SB) | ~~129~~ 735 | Known HLA Specificity |
| GILGFVFTL | HLA-B*07:02 | 16630.17 | 12.00 | 7.6525 | ~~130~~ 736 | |
| GILGFVFTL | HLA-C*08:02 | 35493.90 | 26.00 | 2.2706 | ~~131~~ 737 | |
| IPSINVHHY | HLA-B*35:01 | 33.76 | 0.20 (SB) | 0.0171 (SB) | 132 | Known HLA Specificity |
| IPSINVHHY | HLA-B*51:01 | 10281.49 | 2.50 | 1.2283 (WB) | 133 | |
| NLVPMVATV | HLA-A*02:01 | 25.85 | 0.40 (SB) | 0.0839 (SB) | 134 | Known HLA Specificity |
| ALVPMVATV | HLA-A*02:01 | 12.03 | 0.15 (SB) | 0.0389 (SB) | 135 | |
| NAVPMVATV | HLA-A*02:01 | 2141.23 | 6.00 | 2.8557 | 136 | |
| NLAPMVATV | HLA-A*02:01 | 12.32 | 0.15 (SB) | 0.0359 (SB) | 137 | |
| NLVAMVATV | HLA-A*02:01 | 31.27 | 0.40 (SB) | 0.2511 (SB) | 138 | |
| NLVPAVATV | HLA-A*02:01 | 37.04 | 0.50 (SB) | 0.0618 (SB) | 139 | |
| NLVPMAATV | HLA-A*02:01 | 65.46 | 0.80 (WB) | 0.2476 (SB) | 140 | |
| NLVPMVAAV | HLA-A*02:01 | 23.24 | 0.40 (SB) | 0.1146 (SB) | 141 | |
| NLVPMVATA | HLA-A*02:01 | 188.84 | 1.60 (WB) | 0.3889 (SB) | 142 | |
| TAFTIPSI | HLA-B*51:01 | 3194.50 | 0.70 (WB) | 0.0145 (SB) | 143 | Known HLA Specificity |
| TAFTIPSI | HLA-C*08:02 | 37721.18 | 33.00 | 5.8485 | 144 | |
| TPRVTGGGAM | HLA-A*02:01 | 38342.11 | 75.00 | 41.1667 | 145 | |
| TPRVTGGGAM | HLA-B*07:02 | 3.86 | 0.01 (SB) | 0.0372 (SB) | 146 | Known HLA Specificity |
| TPRVTGGGAM | HLA-B*35:01 | 257.49 | 0.80 (WB) | 0.6671 (WB) | 147 | |
| TPRVTGGGAM | HLA-C*08:02 | 44796.35 | 75.00 | 10.0892 | 148 | |

-Rank threshold for Strong Binding (SB) Peptides: 0.500%
-Rank for Weak Binding (WB) Peptides: 2.000%

Figure 9D:
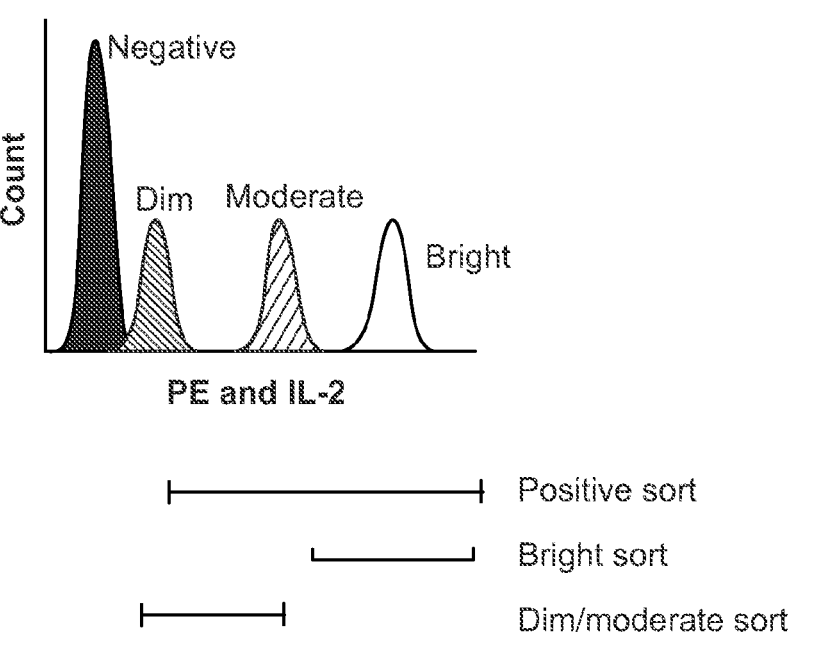
Figures 9B, 9C:
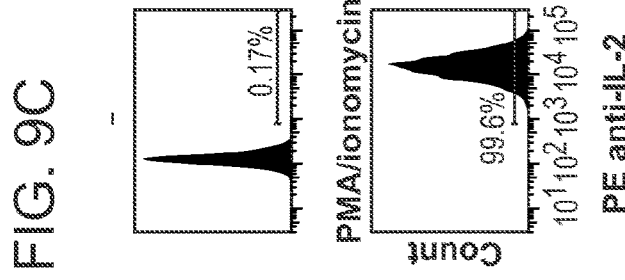

In addition, the anti-IL-2 antibody-expressing APCs were transduced with HLA-A*02:01 alone, or in combination with influenza A MP (58-66), CMV pp65 (495-503), or NY-ESO-1 (157-165) (C165V) epitope-encoding genes (FIG. 9B). These APCs were co-cultured with T cells expressing JM22 TCR (influenza MP (58-66)-reactive) (Stewart-Jones et al., 2003 Nat. Immunol., 4:657-663), C25 TCR (CMV pp65 (495-503)-reactive) (Yang et al., 2015 J. Biol. Chem., 290:29106-29119), or 1G4 TCR (NY-ESO-1 (157-165) (C165V)-reactive) (Chen et al., 2005 J. Exp. Med., 201:1243-1255), respectively. Surface-bound IL-2 was detectable only when the APCs expressed HLA and epitope pairs corresponding to the expected TCR specificities (FIG. 9B).

Figure 2C:
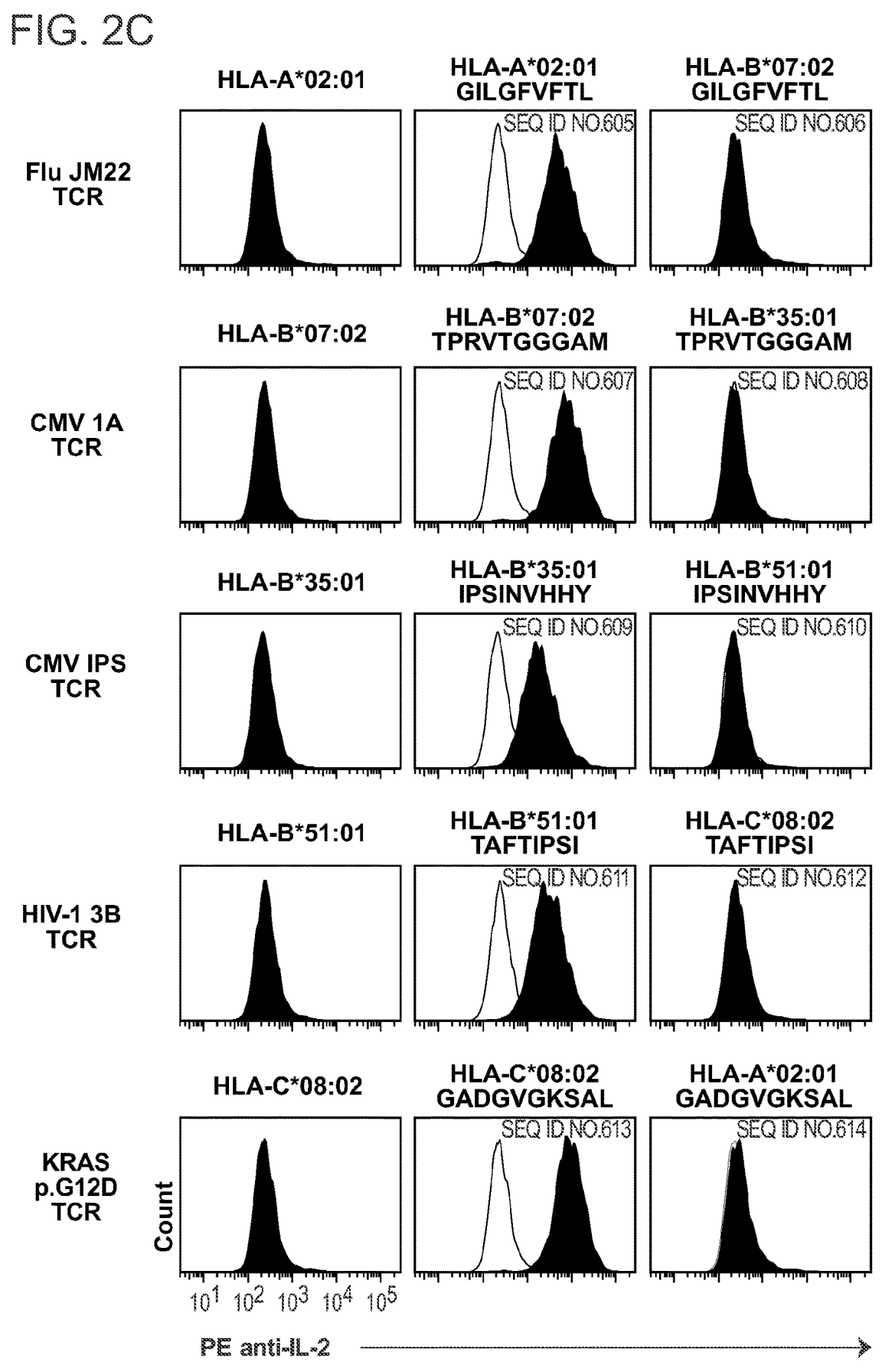

Next, recognition of epitopes presented by different HLA-A, —B, or -C proteins (FIG. 2C) was tested. Anti-IL-2 antibody-expressing APCs were transduced with: HLA-A*02:01 and a GILGFVFTL (influenza MP (58-66))-encoding gene and co-cultured these APCs with T cells expressing JM22 TCR; HLA-B*07:02 and a TPRVTGGGAM (SEQ ID NO. 656) (CMV pp65 (417-426))-encoding gene and co-cultured these APCs with T cells expressing 1A TCR (Dossinger et al., 2013 PLoS One, 8:doi:10.1371/journal.pone.0061384); HLA-B*35:01 and a IPSINVHHY (SEQ ID NO. 657) (CMV pp65 (123-131))-encoding gene and co-cultured these APCs with T cells expressing IPS TCR (Schub et al., 2009 J. Immunol., 183:6819-6830); HLA-B*51:01 and a TAFTIPSI (SEQ ID NO. 658) (HIV-1 RT (128-135))-encoding gene and co-cultured these APCs with T cells expressing 3B TCR (Motozono et al., 2014 J. Immunol., 192:3428-3434); or HLA-C*08:02 and a GAD-GVGKSAL (SEQ ID NO. 659) (KRAS p.G12D)-encoding gene and co-cultured these APCs with T cells expressing KRAS p.G12D TCR. Surface-bound IL-2 was detected after co-culture with each known HLA-epitope-TCR complex (FIG. 2C). The HLA genes were permuted, such that the HLA are not predicted to bind to the epitopes (Table 5) or the TCRs are not expected to detect the HLA-epitope complex (Table 4). Co-culture in the context of these alternative HLA did not result in substantial surface-bound IL-2 relative to the cognate HLA alone (FIG. 2C). These results show that signal can be generated (and detected) by the engineered APCs in the context of various HLA-A, HLA-B, or HLA-C proteins.

Figure 2D:
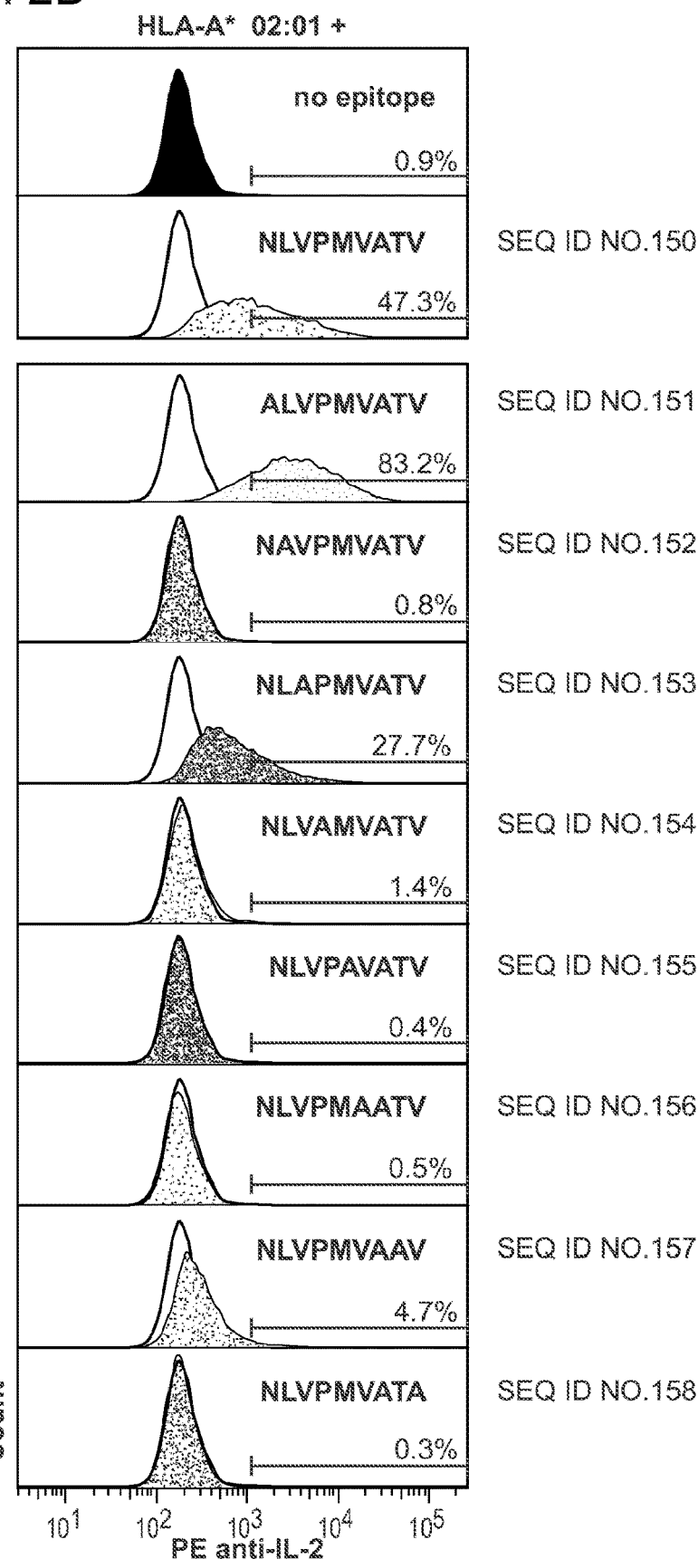

Given the ability to generate near-complete separation between unstimulated and stimulated cells when optimized (FIG. 9C), bright PE anti-IL-2 staining APCs could potentially be separated by flow cytometry from intermediate staining or dim staining APCs (FIG. 9D). This could potentially be used to separate epitopes that elicit different signal strengths. To demonstrate the quantitative nature of the signal, an alanine scan library of the NLVPMVATV (SEQ ID NO. 655) epitope (Table 3) was created, individually transduced each of these peptide-encoding constructs into anti-IL-2 antibody-expressing APCs with the HLA-A*02:01 gene, and co-cultured these APCs with C25 TCR-expressing T cells (FIG. 2D). Expression of the p.N495A (ALVPM-VATV (SEQ ID NO. 660)) mutant consistently resulted in brighter signal (83.2% of cells gated in a representative experiment) than expression of the wild-type epitope (47.3% of cells gated); expression of the p.V497A (NLAPMVATV (SEQ ID NO. 655)) mutant resulted in intermediate signal (27.7% of cells gated); and expression of the p.T502A (NLVPMVAAV SEQ ID NO. 661) mutant resulted in dim signal (4.7% of cells gated) (FIG. 2D). Expression of the other mutants (p.L496A, p.P498A, p.M499A, p.V500A, and p.V503A) did not elicit substantial signal (0.8%, 1.4%, 0.4%, and 0.3% of cells gated, respectively) relative to expression of HLA-A*02:01 alone (0.9% of cells gated) (FIG. 2D). These results are consistent with a crystal structure of this HLA-epitope-TCR complex (Yang et al., 2015 J. Biol. Chem., 290:29106-29119) that had shown that the C25 TCR makes extensive interactions with the methionine at position 499, and also interacts with positions 498 and 500. Position 496 is predicted to bind poorly to HLA-A*02:01 (Table 5), as this position is a known anchor residue for HLA-A*02:01 (Falk et al., 1991 Nature, 351:290-296).

Figures 2E, 2F:
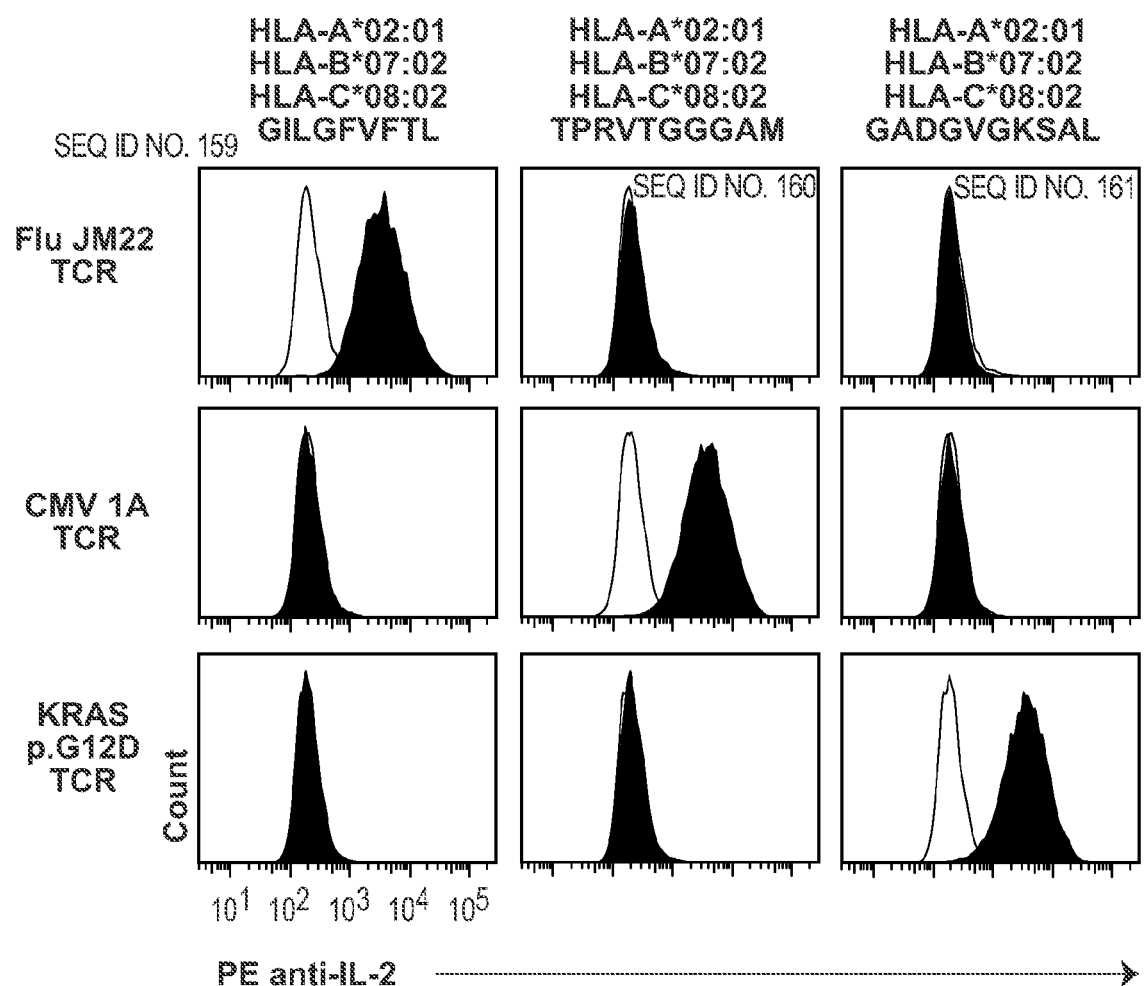

Finally, it was reasoned that increase the number of HLA genes that could be tested could be increased by concurrently co-transducing the APCs with multiple HLA constructs. To demonstrate this, the anti-IL-2 antibody-expressing APCs was transduced with HLA-A*02:01, HLA-B*07:02, and HLA-C*08:02 together (FIG. 2E). These APCs were transduced with GILGFVFTL (SEQ ID NO. 662), TPRVTGGGAM (SEQ ID NO. 663), or GADGVGKSAL (SEQ ID NO. 664) peptide-encoding genes. These APCs were then co-cultured with T cells expressing JM22 TCR, 1A TCR, or KRAS mutant-reactive TCR. Surface-bound IL-2 was detectable when the APCs expressed epitopes corresponding to the expected TCR specificities (FIG. 2E).

Taken together, these results suggest that the engineered APCs could express epitopes presented by HLA-A, HLA-B, or HLA-C; could be co-transduced with multiple HLA; could be labeled in a T cell activation-dependent manner; and could quantitatively distinguish epitopes eliciting high signal strength from those eliciting low signal strength.

Example 4: Adapting the System to Identify HLA Class II Epitopes

Figure 9E:
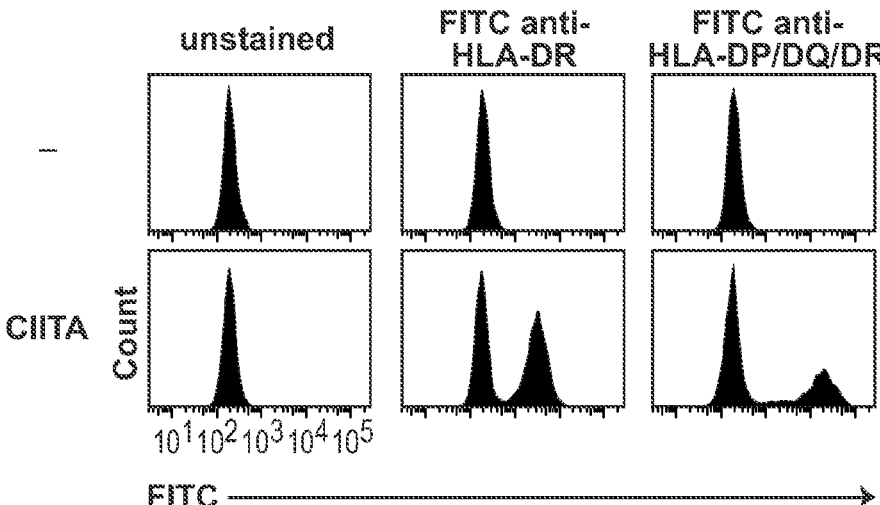
Figure 9F:
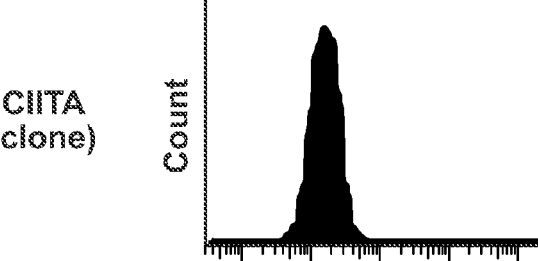
Figure 9F:
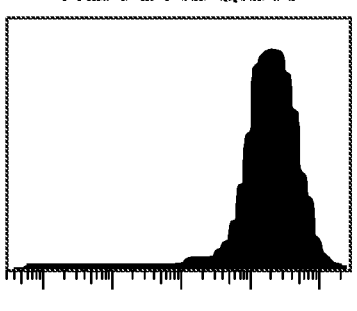
Figure 9G:
Figure 9G:
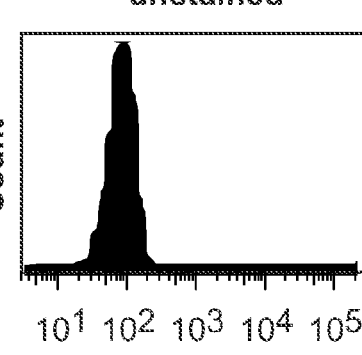
Figure 9G:
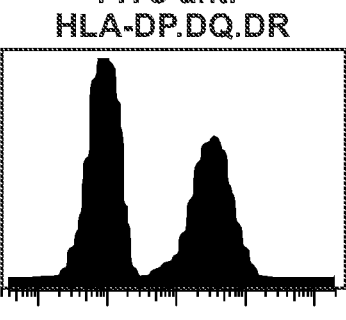
Figure 9I:
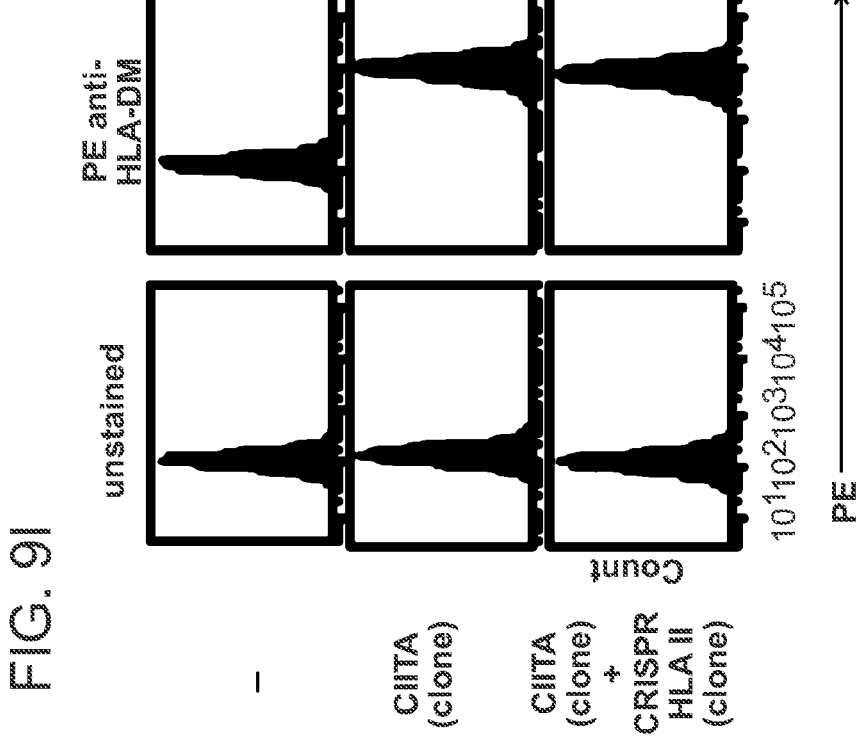
Figure 9H:
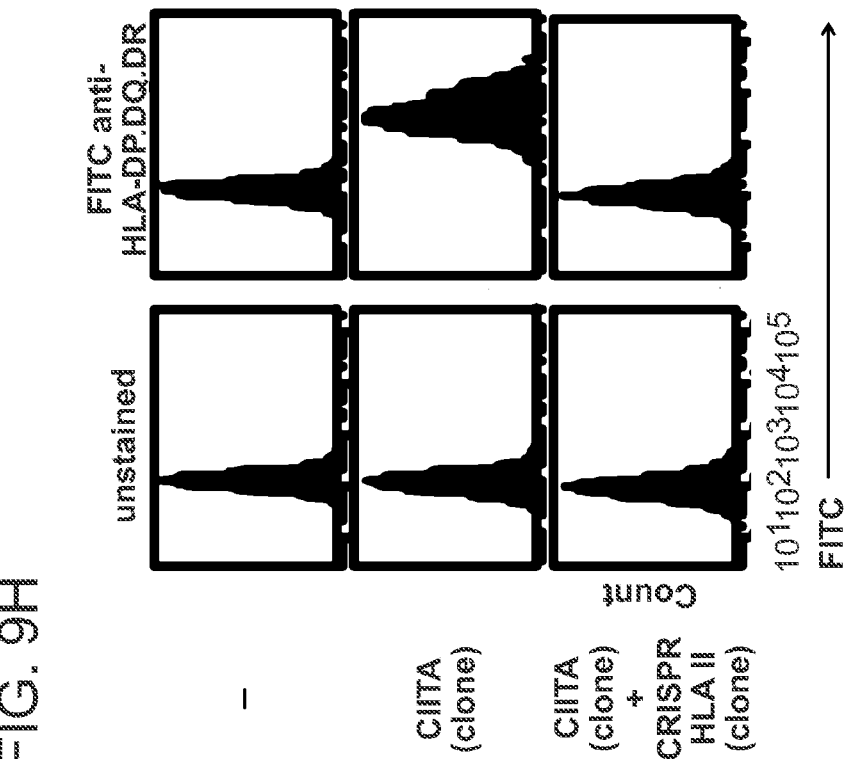
Figure 9J:
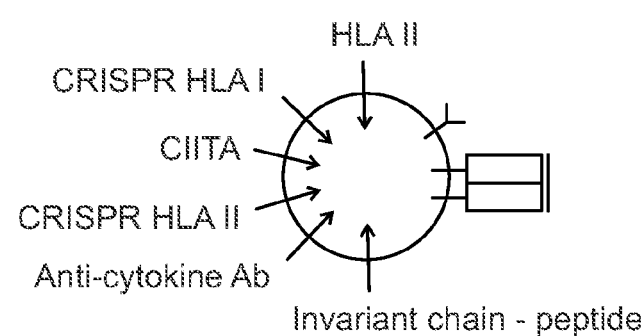
Figure 9K:
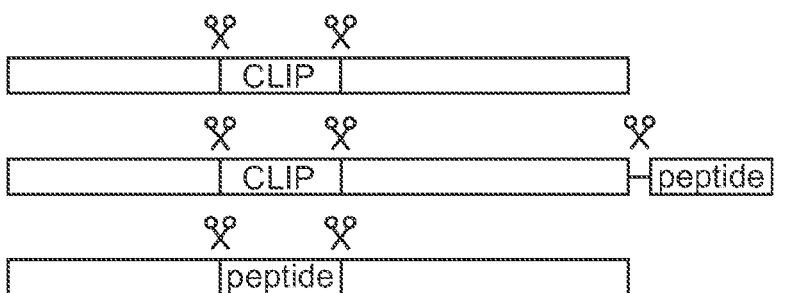

By modifying the HLA constructs and the peptide-encoding strategy, an analogous system to label HLA class II epitope-expressing APCs was designed (FIG. 2F). While the HLA class I KO APCs do not express HLA class II on their surface at baseline (FIG. 9E), non-professional APCs can support HLA class II expression, either after transduction with the HLA class II master transcriptional activator, CIITA (Chang et al., 1994 J. Exp. Med., 180:1367-74; Steimle et al., 1994 Science, 265:106-9) or after expression of HLA class II and the invariant chain (Ii) gene, CD74 (Bergen et al., 1997 Proc. Natl. Acad. Sci. U.S.A, 94:7499-502). As transduction of CIITA induces endogenous HLA class II expression (FIG. 9E and FIG. 9F), transient expression of CRISPR/Cas9 cassettes targeting endogenous HLA class II loci (Table 1) are needed to knockout endogenous HLA class II genes (FIG. 9G, FIG. 9H, and FIG. 9I) so that only specified HLA class II genes could be expressed (FIG. 9J). In order to direct encoded peptides into endosomal compartments for HLA class II presentation, epitope-encoding minigenes can be fused to CD74 (Chang et al., 1994 J. Exp. Med., 180:1367-74; Steimle et al., 1994 Science, 265:106-9). Here, two different fusion constructs were tested. In one version, the peptide-encoding minigene was fused to the 3' end of CD74 with an intervening cathepsin S cleavage sequence (Nakano et al., 1997 Science., 275:678-83) (FIG. 2F and FIG. 9K). In the second version, the peptide sequence was encoded in place of the CLIP-encoding (Class II-associated invariant chain peptide) region in CD74 (Bergen et al., 1997 Proc. Natl. Acad. Sci. U.S.A, 94:7499-502; Malcherek et al., 1998 Eur. J. Immunol., 28:1524-1533). (FIG. 2F and FIG. 9K).

Figure 2G:
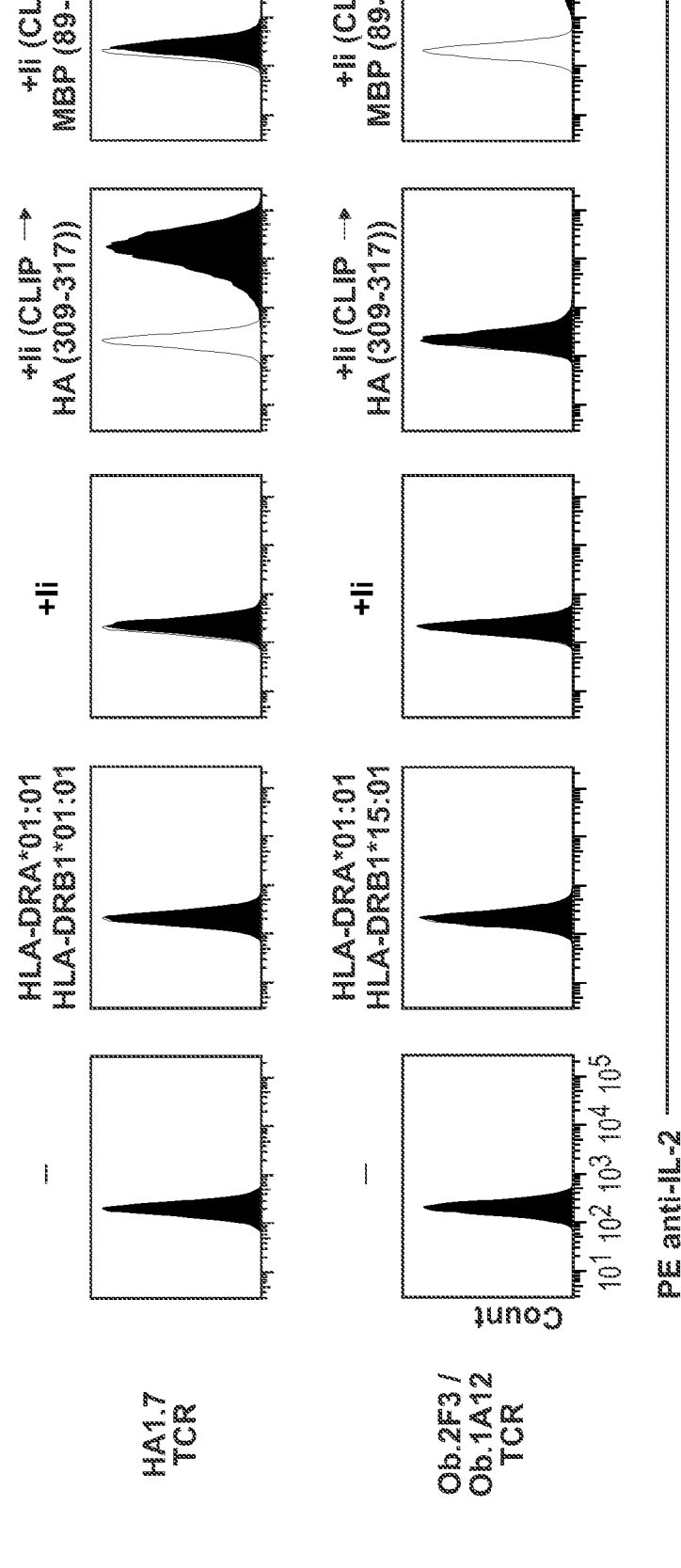
Figure 9L:
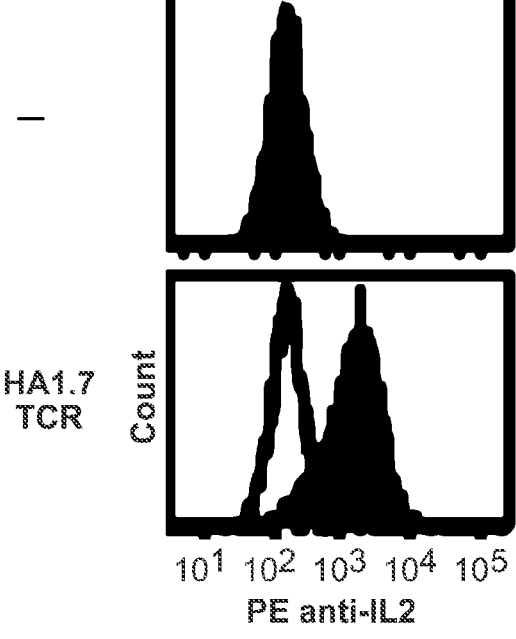
Figure 9M:
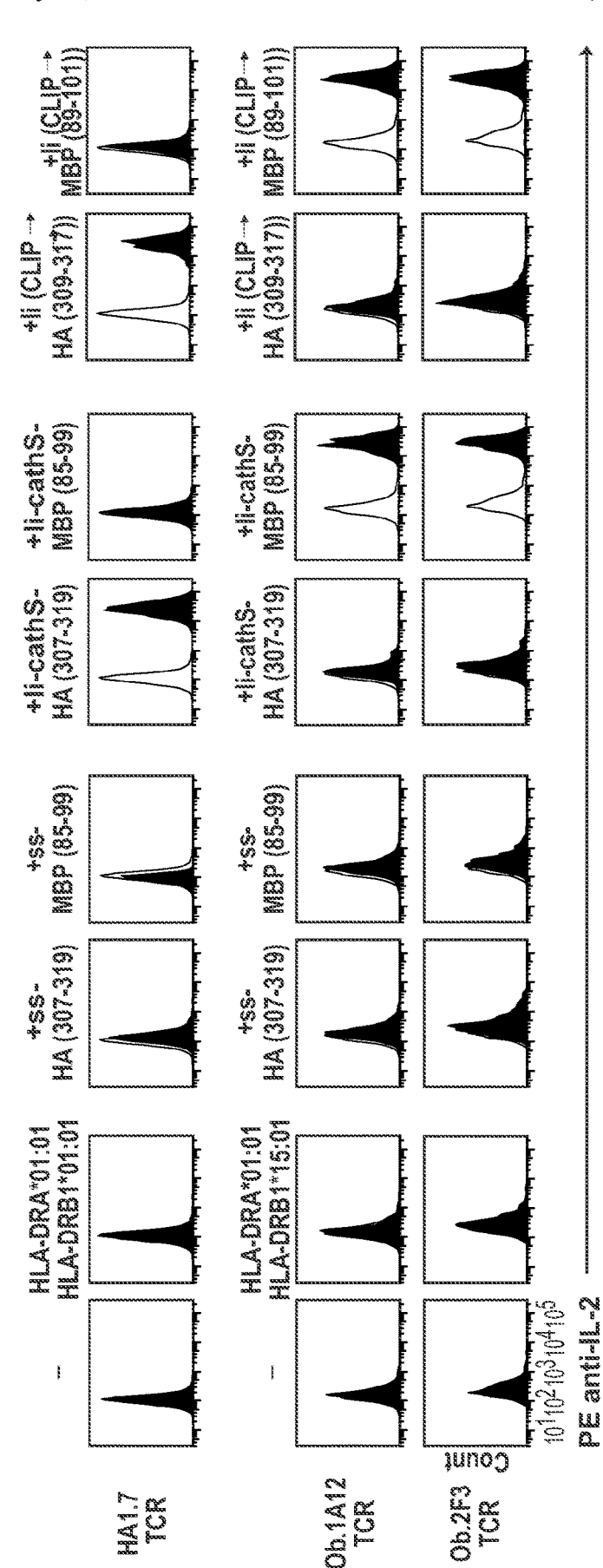

It was tested if the engineered APCs can stimulate class II-restricted TCRs in an epitope-specific manner. First, HLA I/II KO APCs was co-transduced with HLA-DRA*01:01, HLA-DRB1*01:01, and a viral class II epitope-encoding gene from influenza A hemagglutinin (HA) fused to the 3' end of CD74. In parallel, TCR KO T cells were transduced with an influenza A HA-reactive TCR, HA1.7. Co-culture of these APCs and T cells led to robust levels of surface-bound IL-2 on the APCs (FIG. 9L). Second, these cells were transduced with a viral class II epitope-encoding gene from influenza A hemagglutinin (HA) (Hennecke et al., 2000 EMBO J., 19:5611-24) or with an autoimmune class II epitope-encoding gene from myelin basic protein (MBP) (Table 3) (Hausmann et al., 1999 J. Immunol. 162, 338-44). In parallel, TCR KO T cells were transduced with an influenza A HA-reactive TCR, HA1.7 (Hennecke et al., 2000 EMBO J., 19:5611-24), or with the MBP-reactive TCRs, Ob.1A12 or Ob.2F3 (Hausmann et al., 1999 J. Immunol. 162, 338-44). After co-culture of the APCs and T cells, expression of the epitope-encoding sequences either fused to the invariant chain or replacing CLIP led to robust levels of surface-bound IL-2 on the APCs (FIG. 2G and FIG. 9M). Surface-bound IL-2 was detectable only when the APCs expressed HLA and epitope pairs corresponding to the expected TCR specificities (FIG. 2G and FIG. 9M). In contrast, expression of the epitope-encoding sequences fused to a signal sequence—the design that was used for class I epitopes (FIG. 2A)—did not result in efficient stimulation of the T cells (FIG. 9M).

Taken together, these results demonstrated that the engineered APCs can capture cytokine in the context of both HLA class I and II epitopes, and their respective TCRs.

Figure 10A:
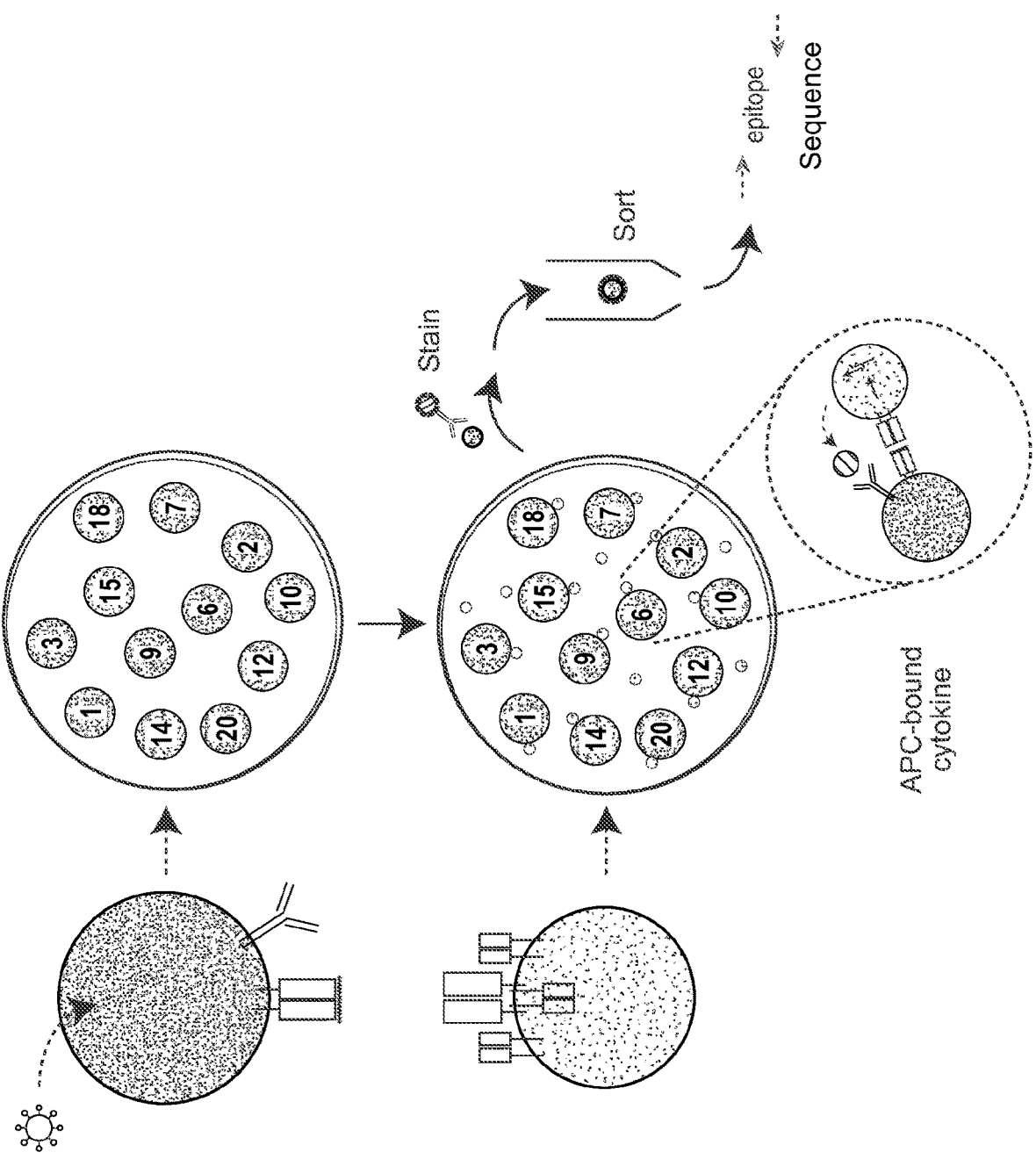
Figure 10B:
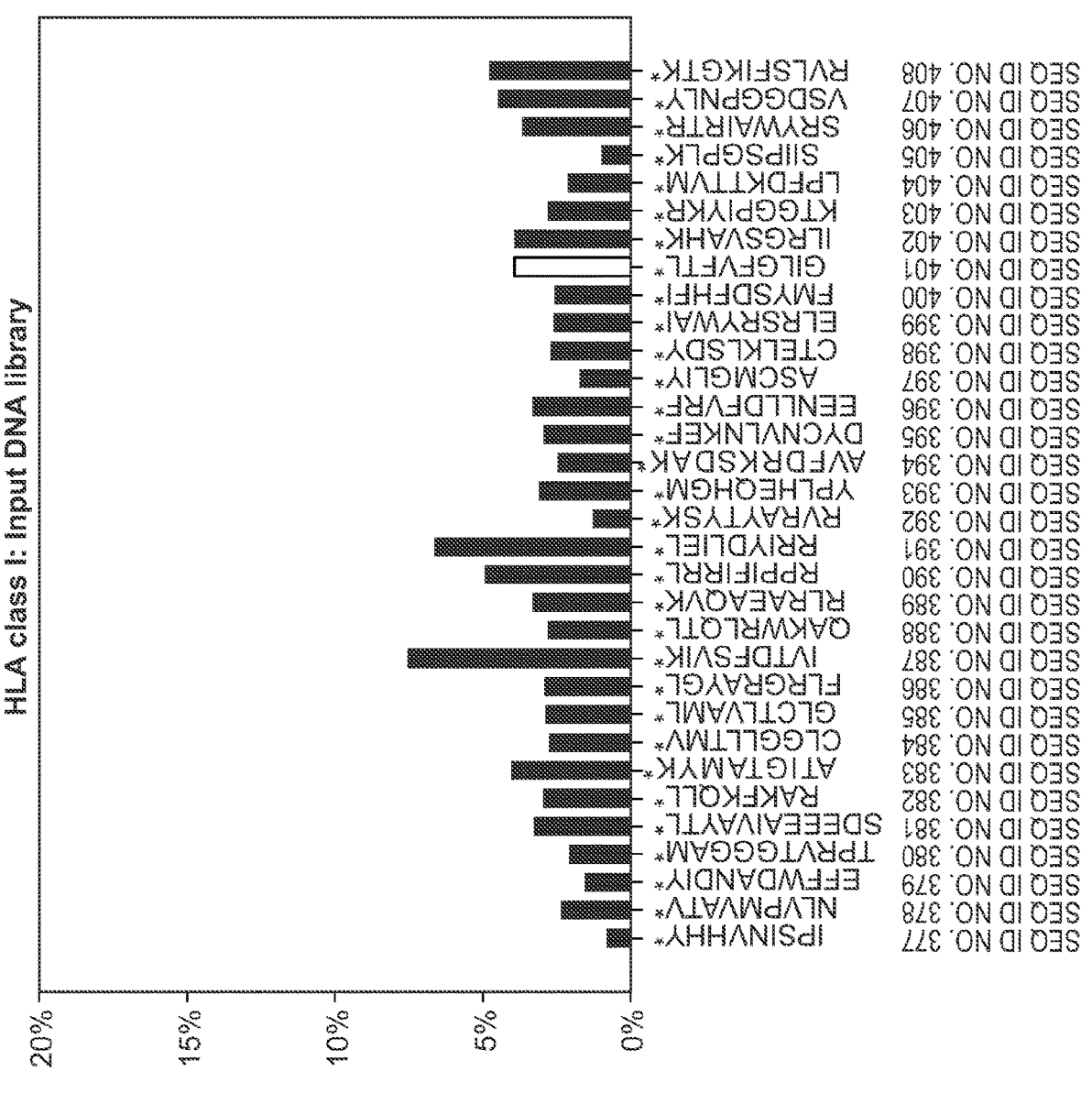

Example 5: Identification of a T Cell Epitope from a Pooled Oligonucleotide Library Using these APCs, a method to locate a specific epitope amongst a pool of peptide-encoding oligonucleotides was developed (FIG. 10A). First, a pooled DNA library consisting of 32 common CMV, Epstein-Barr virus (EBV), or influenza (Flu) epitope-encoding genes (FIG. 3A and Table 3) was created, selected from an expanded CEF (CMV, EBV, Flu) epitope set (Currier et al., 2002 J. Immunol. Meth., 260:157-72). Sequencing of the DNA pool showed representation of each epitope in the library (FIG. 10B). The CEF library was transduced into HLA-A*02:01-expressing APCs at a multiplicity of infection (m.o.i.)<1 to create a library of epitope-expressing APCs (FIG. 3B and FIG. 10A).

Figure 3C:
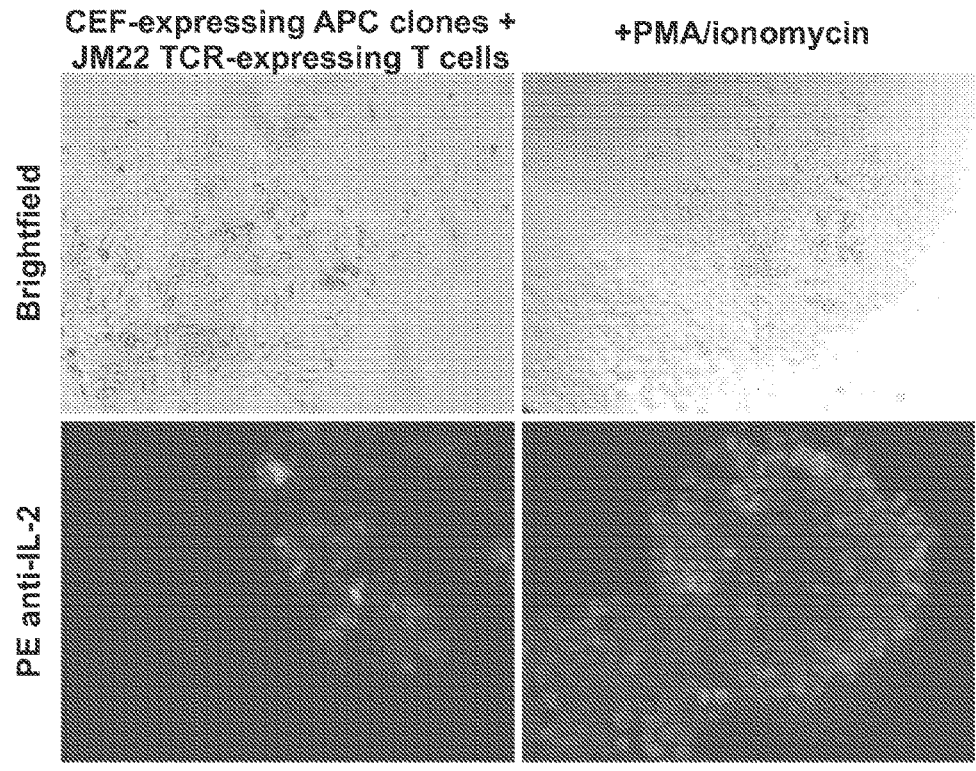
Figure 10C:
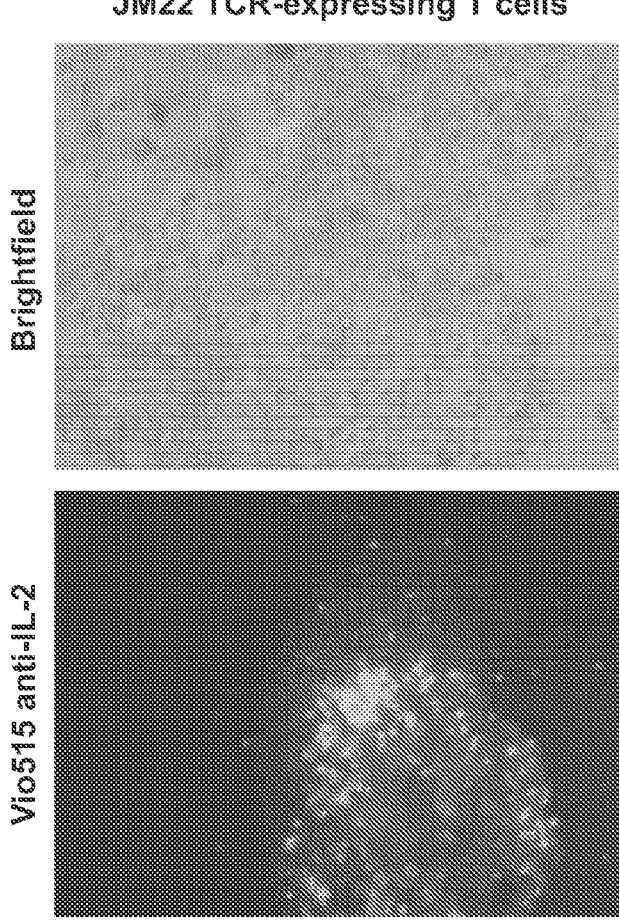

The APC library was seeded at low density relative to library diversity (i.e 3.5-10 APCs/well relative to 32 possible epitope-expressing APCs), aiming for <1 positive clone per well to limit the possibility of signal leakage (FIG. 3B and FIG. 10A). In total, >1000 cells were seeded (i.e., 1000-8000) so that each epitope in the library was represented multiple times (FIG. 3B). The cells were allowed to clonally expand into clusters (FIG. 3C and FIG. 10C). To each well, T cells expressing the influenza MP (58-66)-reactive TCR, JM22 (Stewart-Jones et al., 2003 Nat. Immunol., 4:657-663), which recognizes the peptide, GILGFVFTL, when presented on HLA-A*02:01 were added. After co-culture, supernatant was removed, the APCs were stained with phycoerythrin (PE)-conjugated anti-IL-2 antibody (FIG. 3C), the PE-labeled and unlabeled APCs were separated by magnetic separation, the epitope-encoding genes from the PE⁺ and PE⁻ cell populations were amplified using primers flanking the epitope sequences, and the PCR products were sequenced by NGS.

Figure 3D:
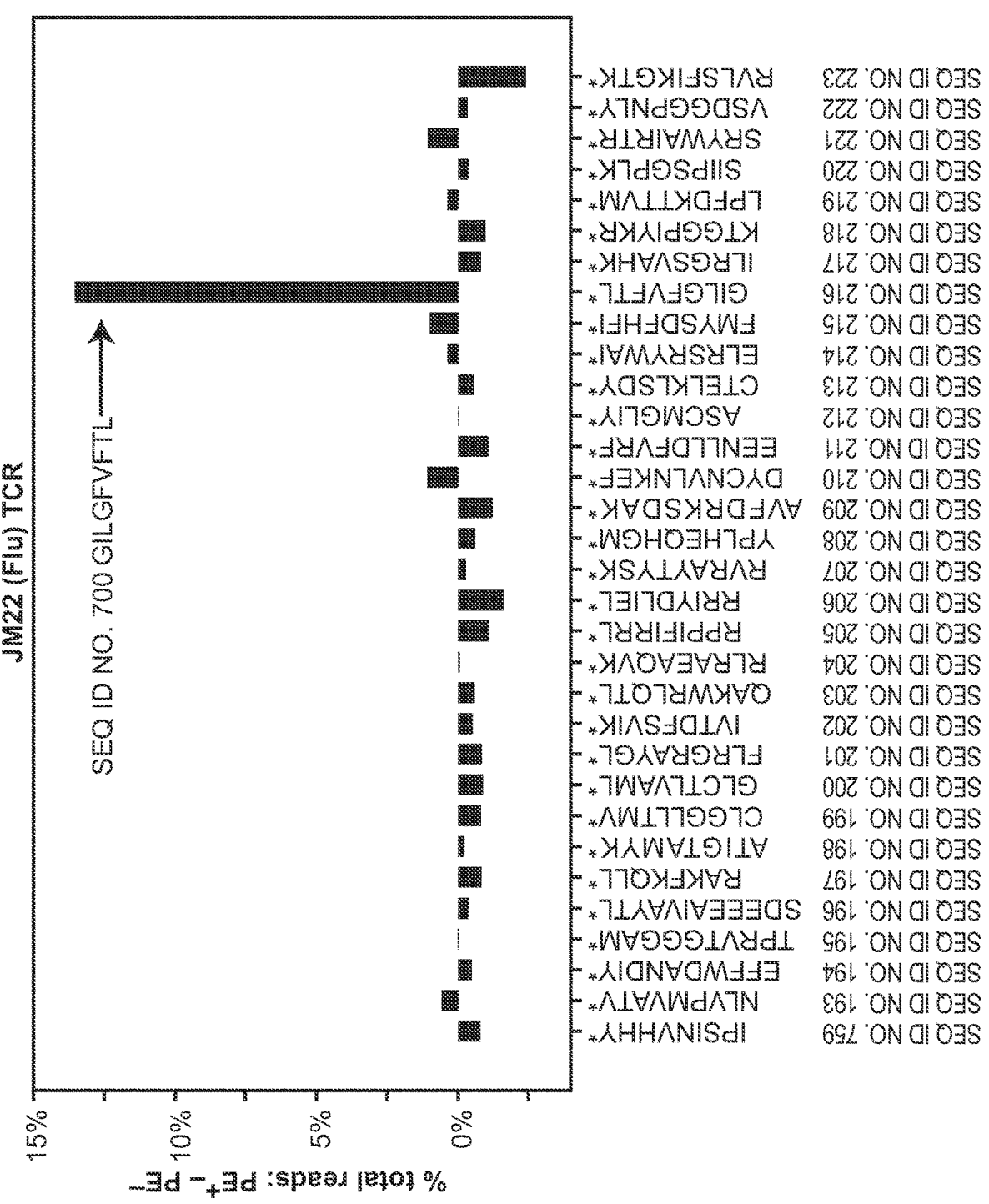
Figure 3E:
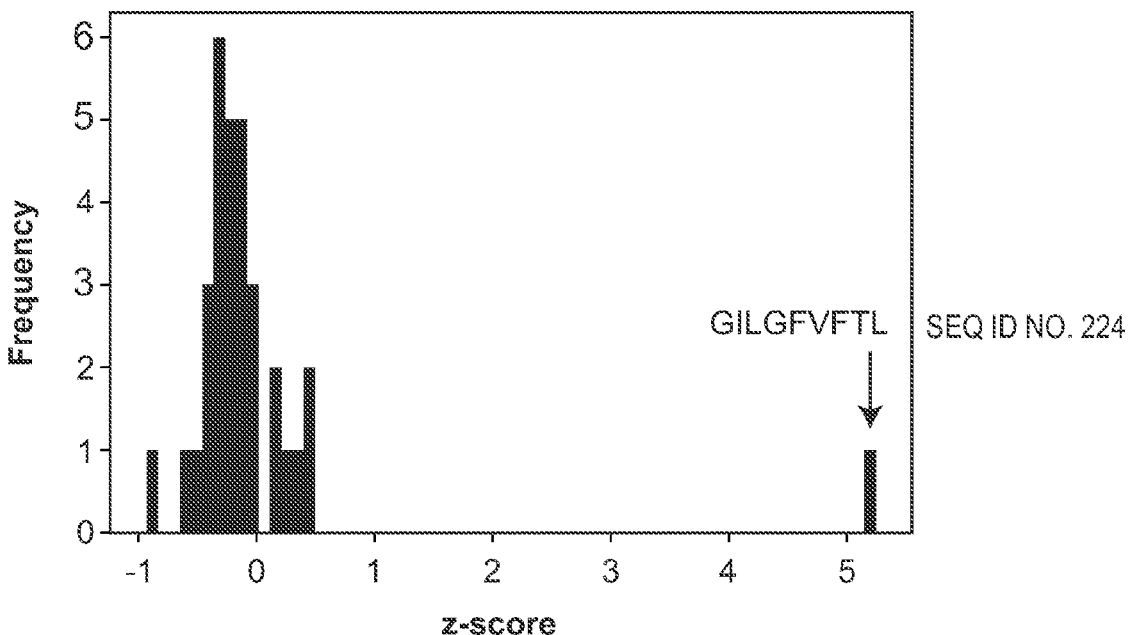
Figure 10D:
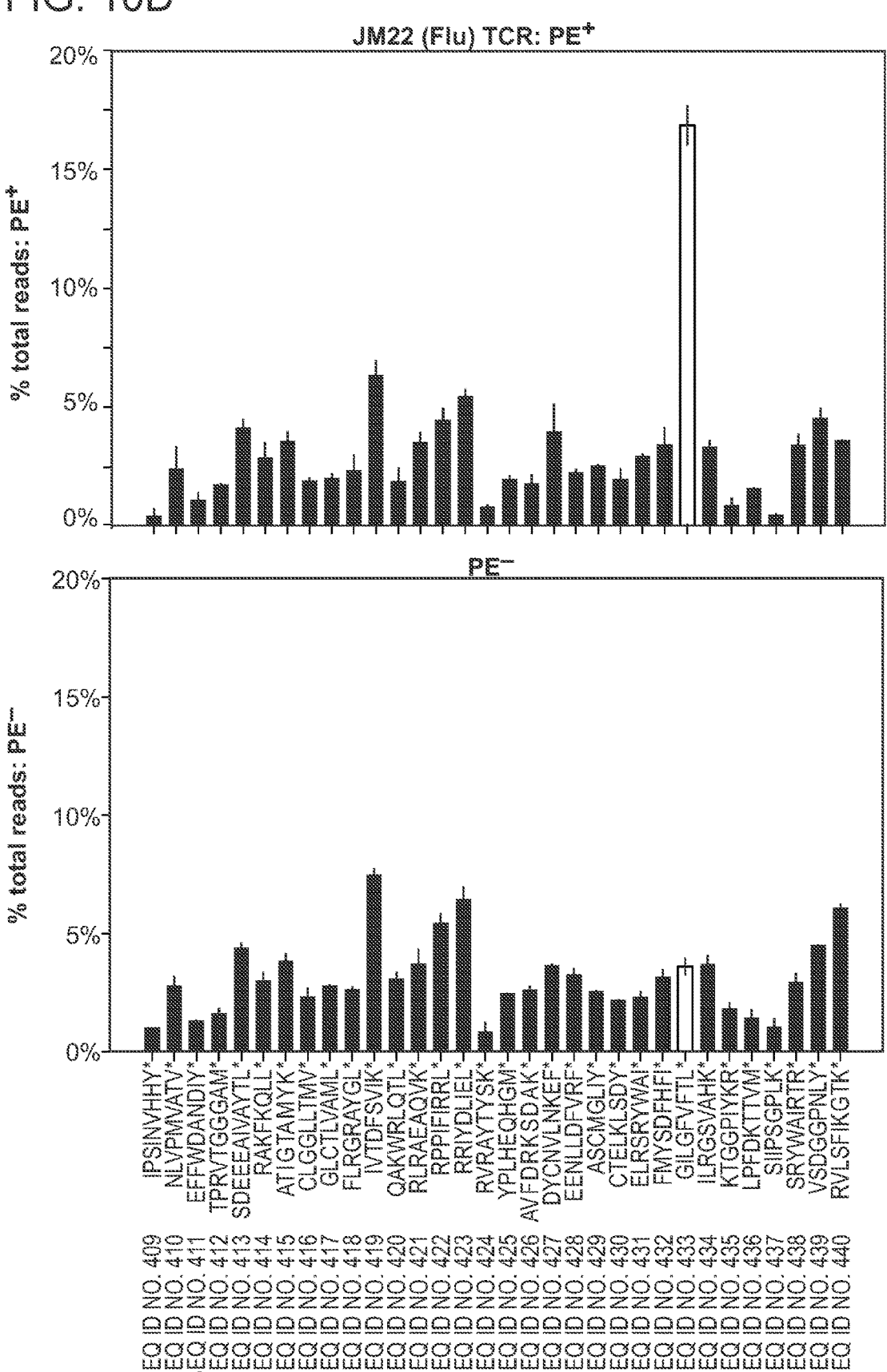
Figure 10E:
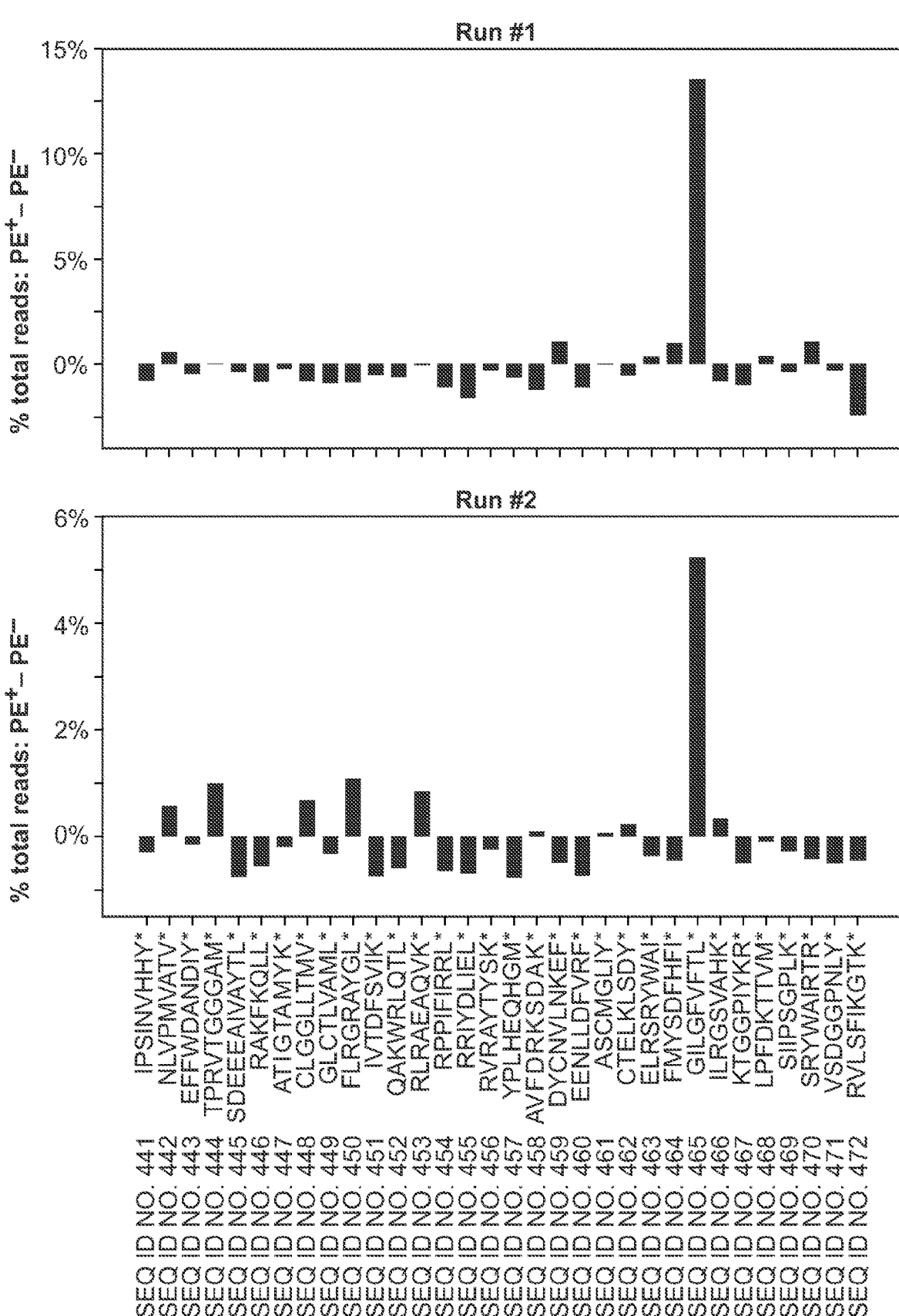
Figure 10F:
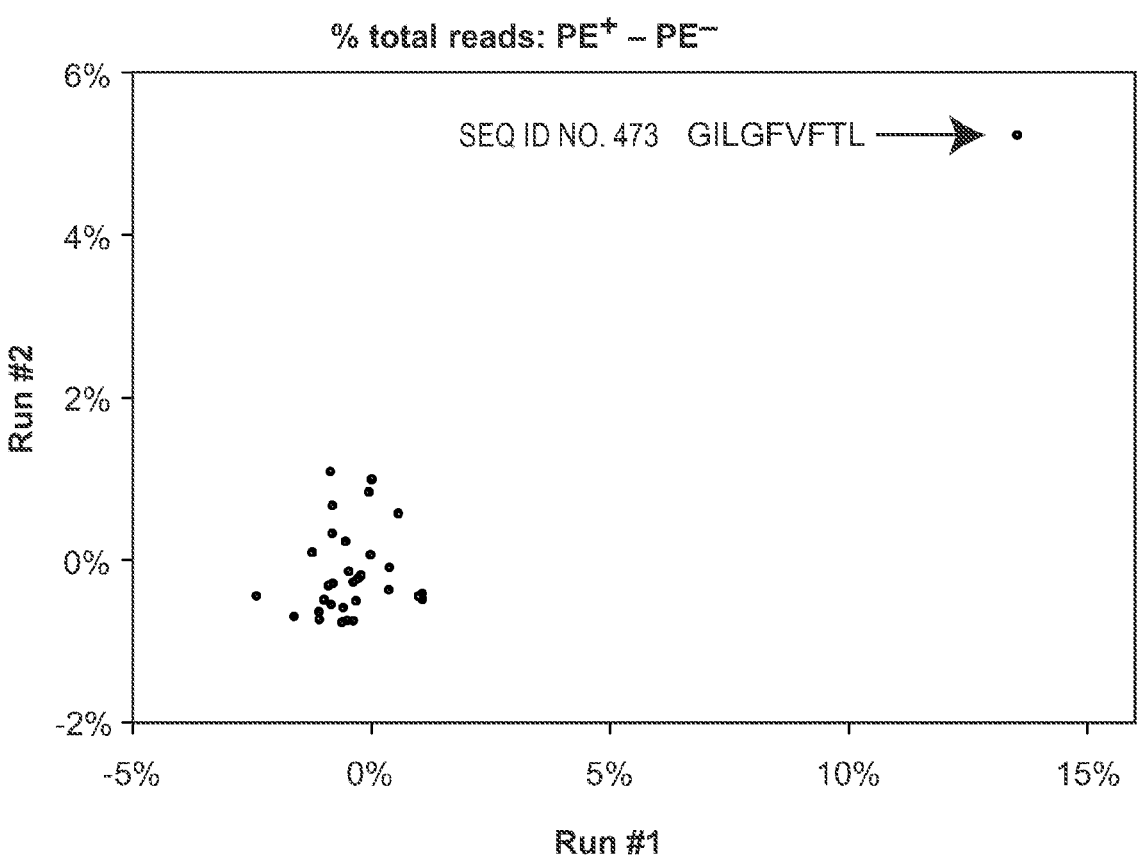

In a representative experiment, in the pulldown of PE-labeled cells, 17.4% of the total epitope-encoding reads encoded the JM22 target, GILGFVFTL (SEQ ID NO. 665) (FIG. 10D). In comparison, GILGFVFTL (SEQ ID NO. 665) was represented by 3.9% of epitope-encoding reads in the unlabeled population (FIG. 10D). This difference of 13.5% (FIG. 3D) was the most significant outlier among the 32 class I epitopes, with a z-score of 5.2 (FIG. 3E). All 31 of the other epitopes had a z-score <1 (FIG. 3E). Replication of this workflow showed similar results (FIG. 10E and FIG. 10F). These results demonstrated that the assay can identify a targeted epitope starting from a mixed pool of peptide-encoding oligonucleotides.

Example 6: Identification of an HLA Class II Epitope from a Pooled Oligonucleotide Library An analogous screen was performed with HLA class II epitopes, testing the ability of the assay to locate a specific epitope among a pooled DNA library consisting of 19 CMV, EBV, influenza (flu), or *Clostridium tetani* (tetanus) (CEFT) class II epitope-encoding genes (FIG. 10G and Table 3) (Vita et al., 2009 Nucleic Acids Res., 38:doi:10.1093/nar/gkp1004; Planas et al., 2018 Sci. Transl. Med., 10:1-16). The HLA class II epitope library was transduced into HLA-DRA*01:01 and HLA-DRB*01:01 co-expressing APCs at a m.o.i. <1. APCs were seeded (i.e., 5000-20000) at low density. After clonal expansion, the APCs were co-cultured with T cells expressing the HA1.7 TCR. The PE anti-IL-2 antibody-labeled APCs were separated from unlabeled cells.

Figure 10I:
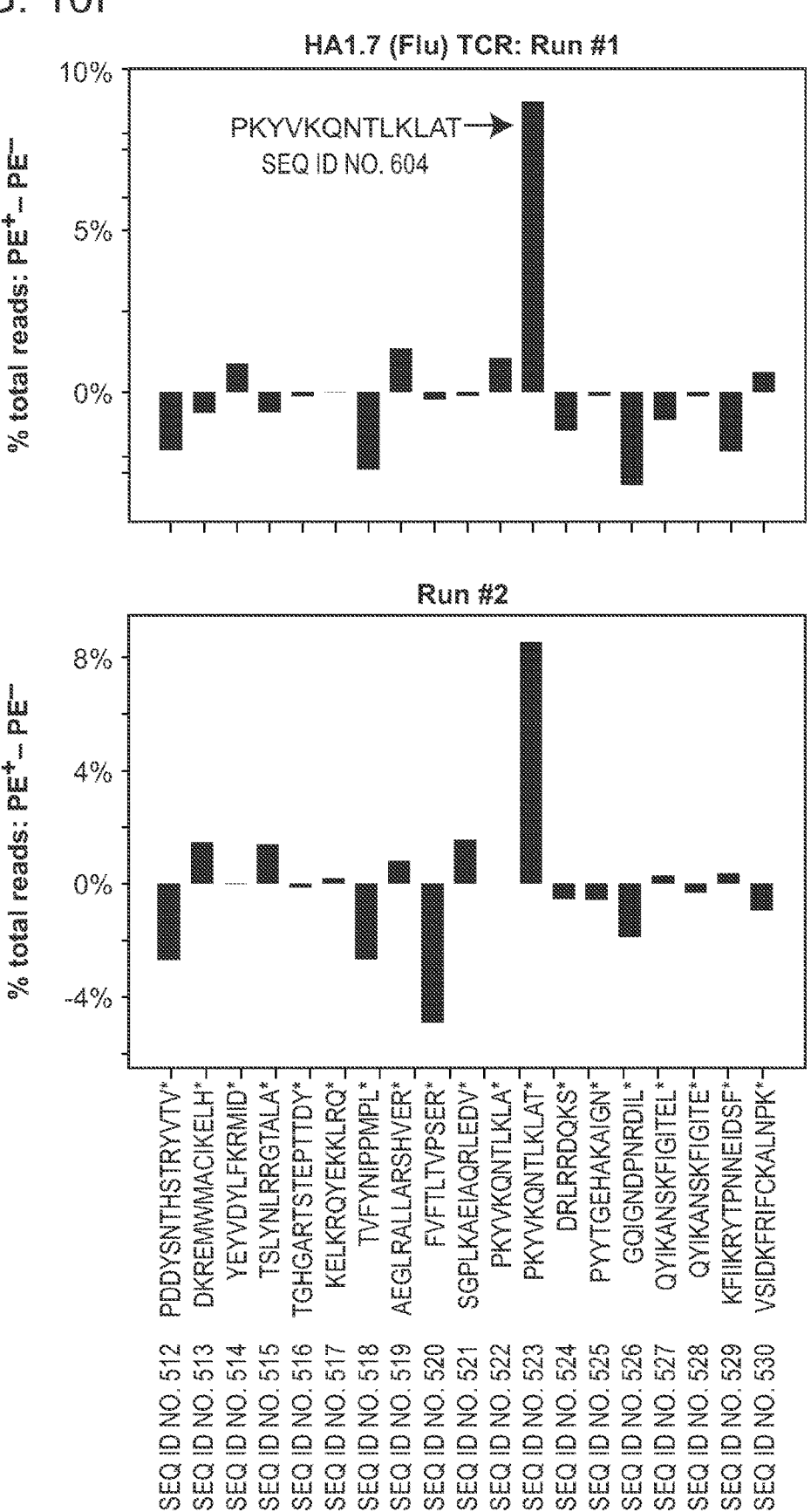
Figure 10J:
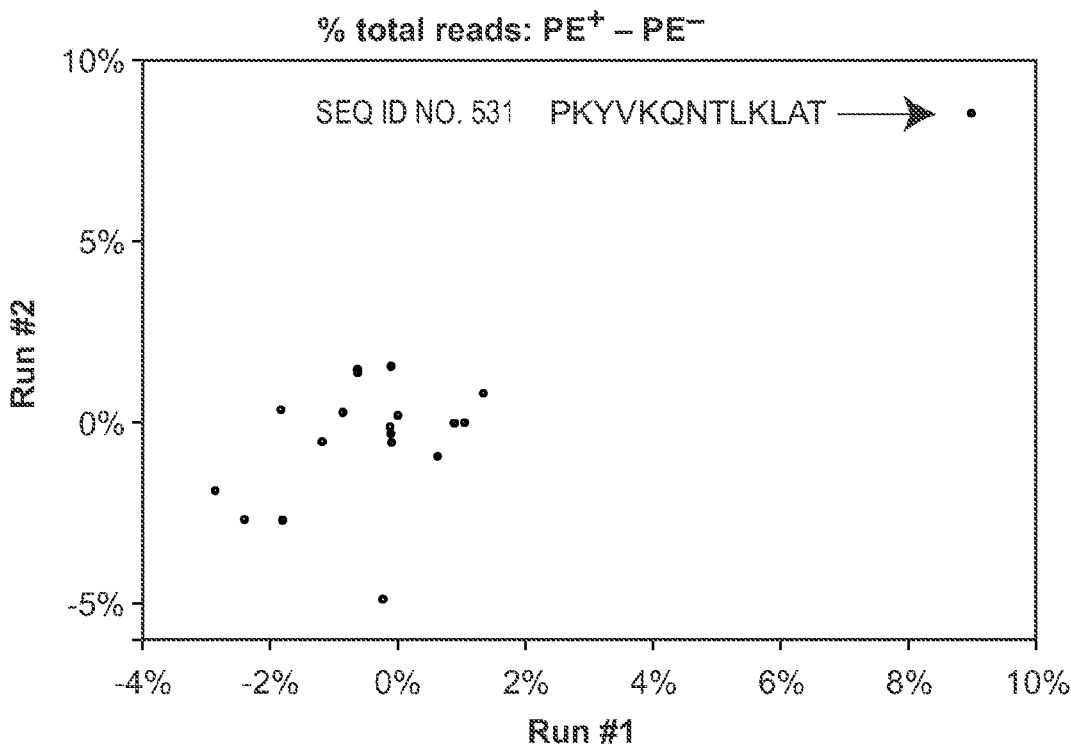
Figure 10K:
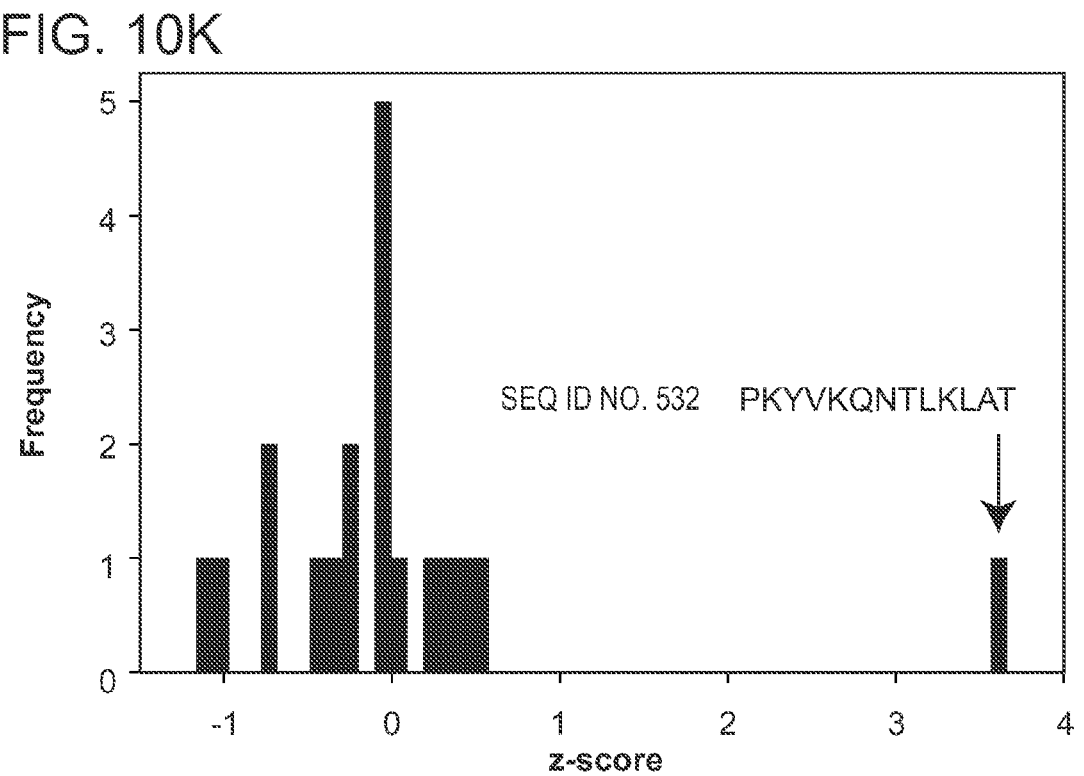

In a representative experiment in the pulldown of PE-labeled cells, 11.4% of the total epitope-encoding reads encoded the influenza HA (307-319) epitope, PKYVKQNTLKLAT (SEQ ID NO. 666) (FIG. 10H). In comparison, PKYVKQNTLKLAT (SEQ ID NO. 666) was represented by 2.4% of epitope-encoding reads in the unlabeled population (FIG. 10H). This difference of 9.0% (FIG. 10I and FIG. 10J) was the most significant outlier among the 19 HLA class II epitopes, with a z-score of 3.7 (FIG. 10K). Replication of this workflow showed similar results (FIG. 10I and FIG. 10J). Taken together, these results demonstrated that the assay can be used to identify HLA class II epitopes starting from mixed pools of peptide-encoding oligonucliotide.

Figure 4A:
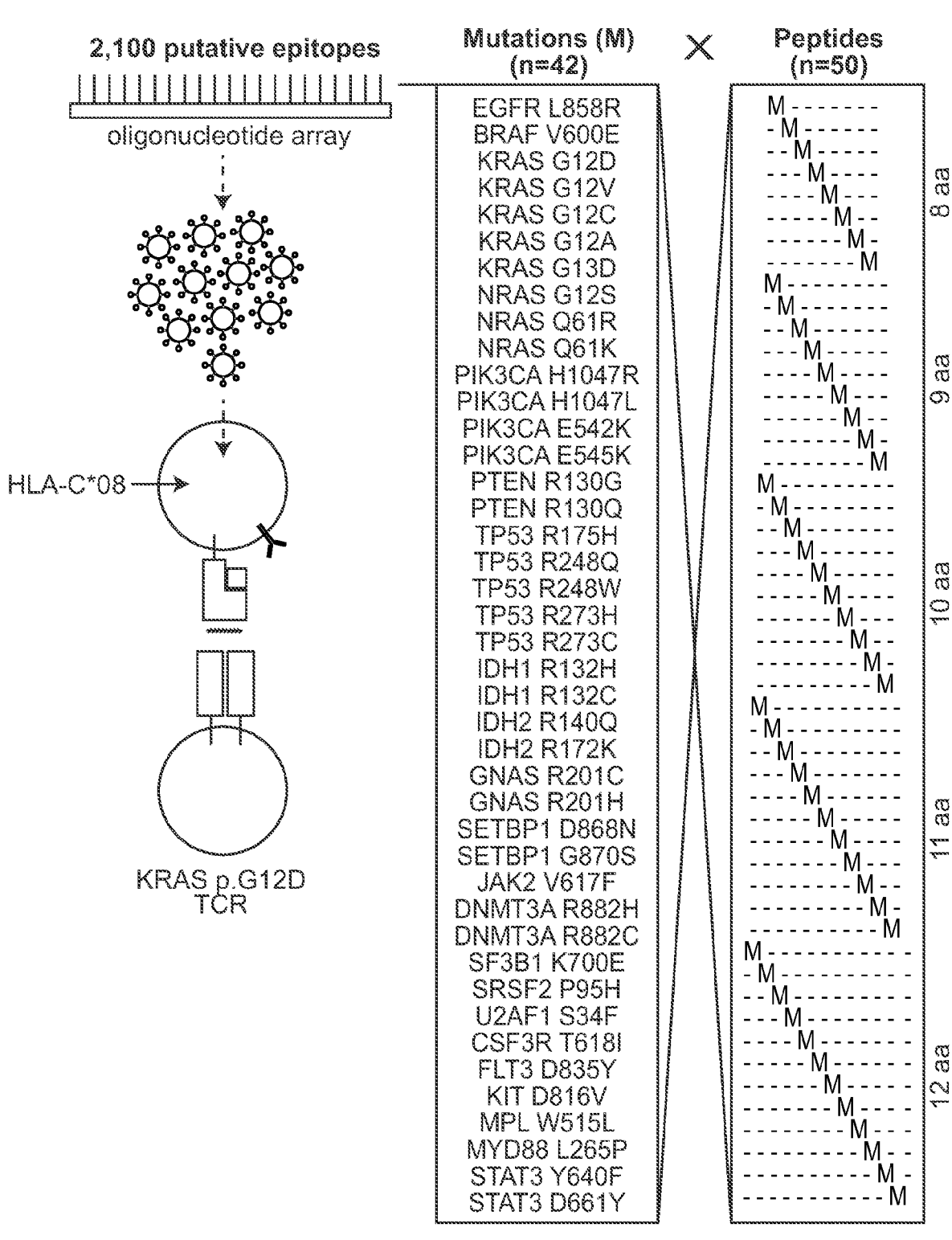
FIG. 4A-4F is a series of schematics showing scale-up to identify a targeted neoepitope from an oligonucleotide array.
Figure 4B:
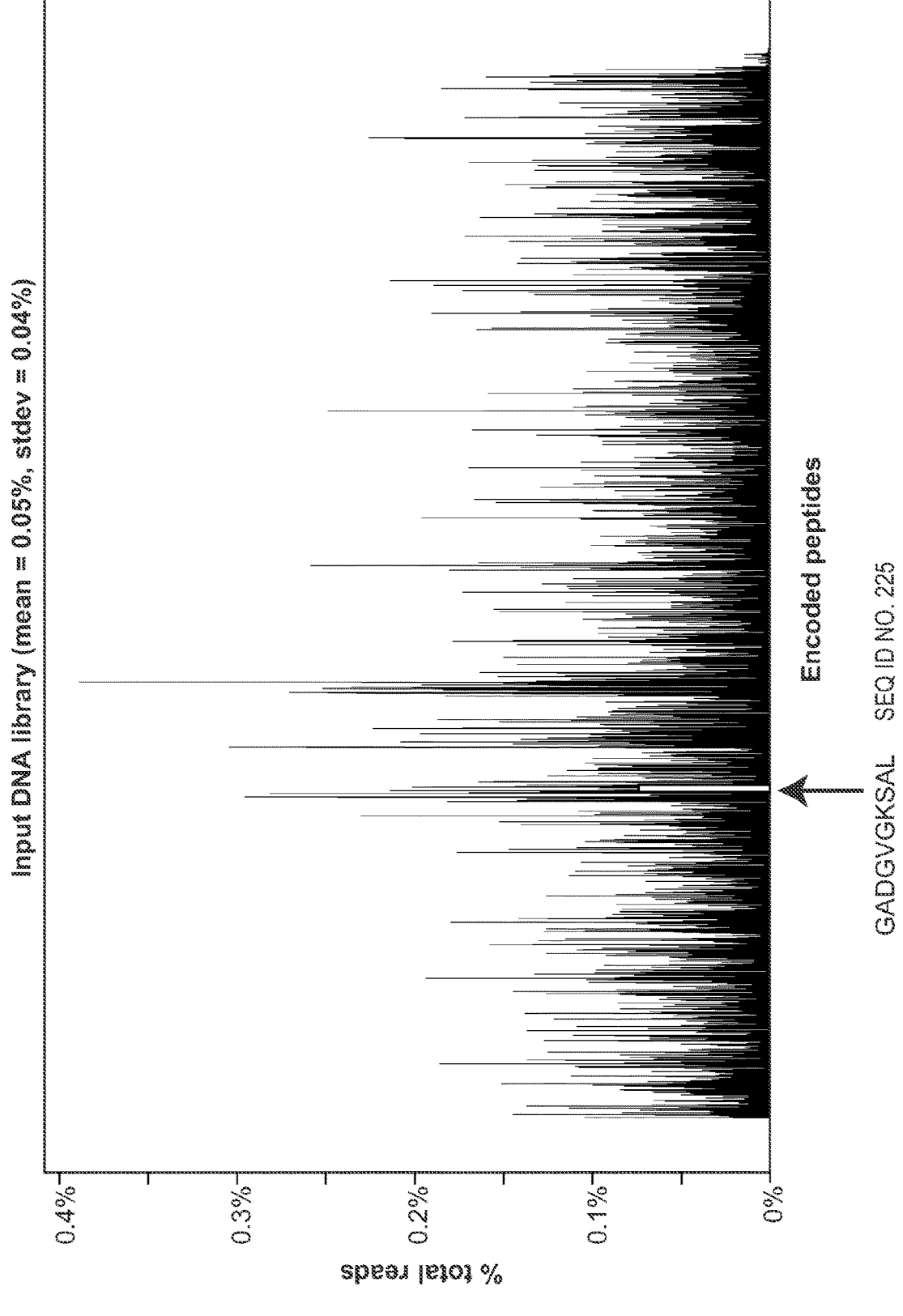
Figure 11A:
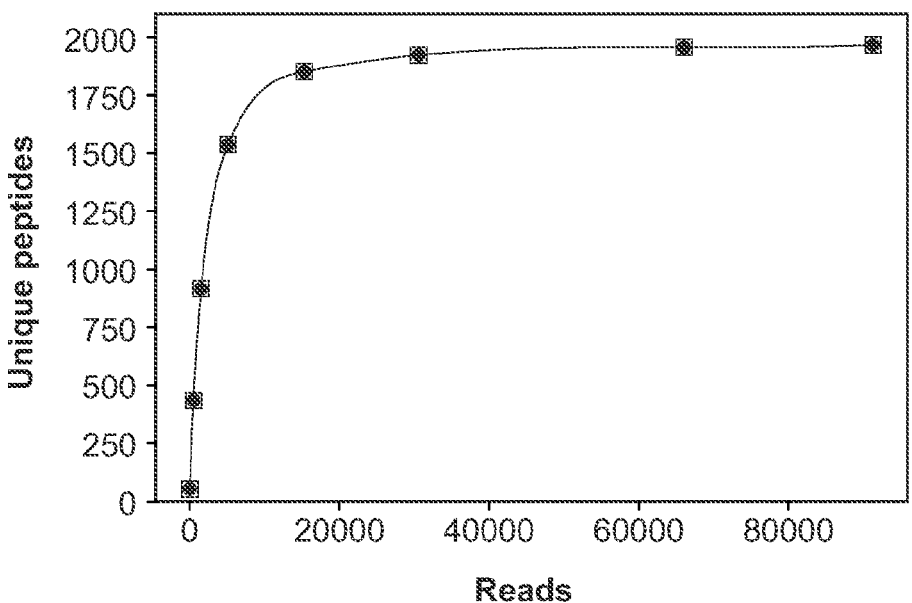
FIG. 11A-11C is a line graph and a series of histograms showing the scale-up to identify a targeted neoepitope from an oligonucleotide array.

Example 7: Scale-Up of the Assay to Identify a Targeted Neoepitope from an Oligonucleotide Array It was then determined whether the neoepitope target of a tumor-infiltrating T cell could be identified amongst a pool of thousands of putative epitopes. As a proof-of-principle, the previously-described KRAS p.G12D mutant-reactive TCR was used (Zacharakis et al., 2018 Nat. Med., 24:724-730). A pooled library of 2,100 oligonucleotides encoding all 8, 9, 10, 11, and 12 amino acid peptides that contain one of 42 common driver mutations (FIG. 4A and Table 3) was created. One thousand nine hundred sixty seven of the peptide-encoding sequences (ninety three percent of expected library diversity) were identified in the input DNA library (FIG. 4B) at the depth sequenced (FIG. 11A). The library was transduced into HLA-C*08:02-expressing APCs at a m.o.i. <1. The APCs were seeded at a density of 100-1000 cells/well using a total of 50,000-200,000 cells. After clonal expansion, the APCs were co-cultured with T cells expressing the KRAS p.G12D-reactive TCR, and separated PE anti-IL-2 antibody-labeled APCs from unlabeled cells.

Figure 4C:
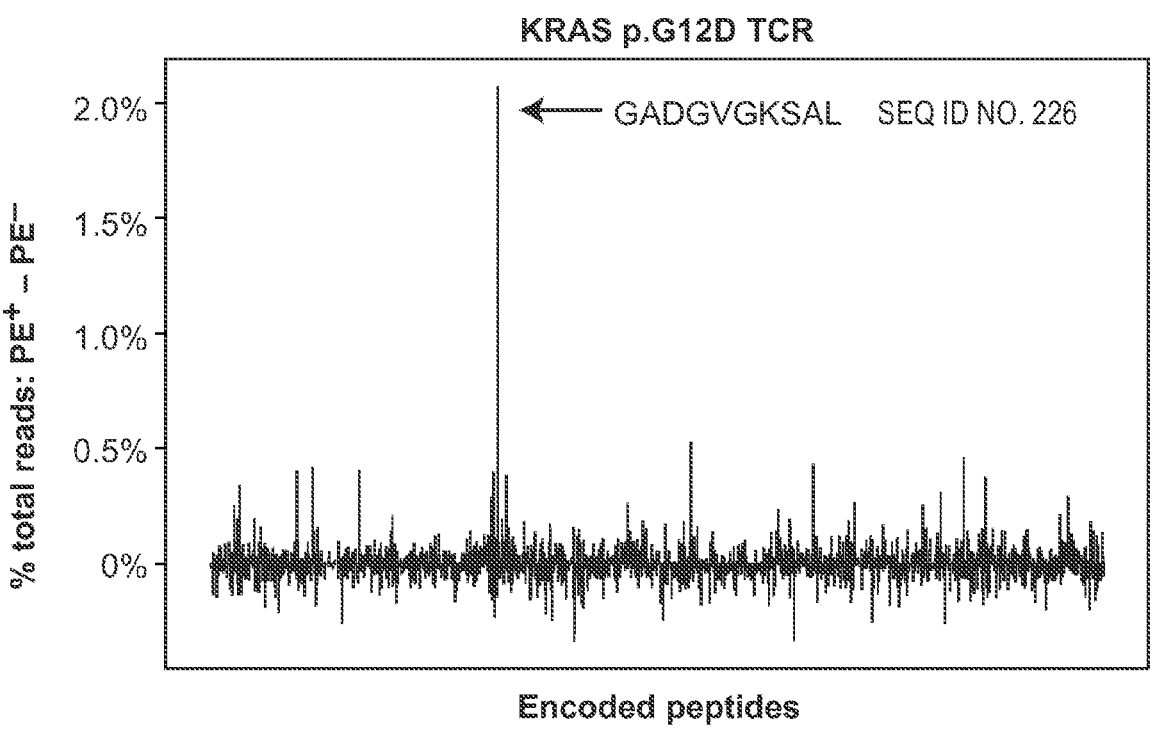
Figure 4D:
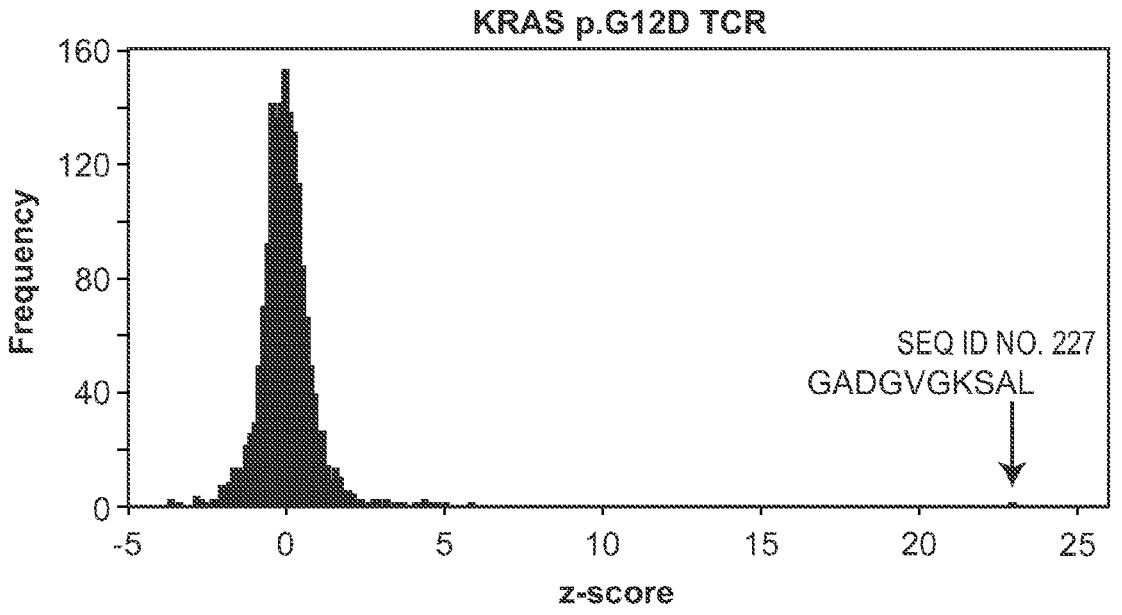
Figure 4E:
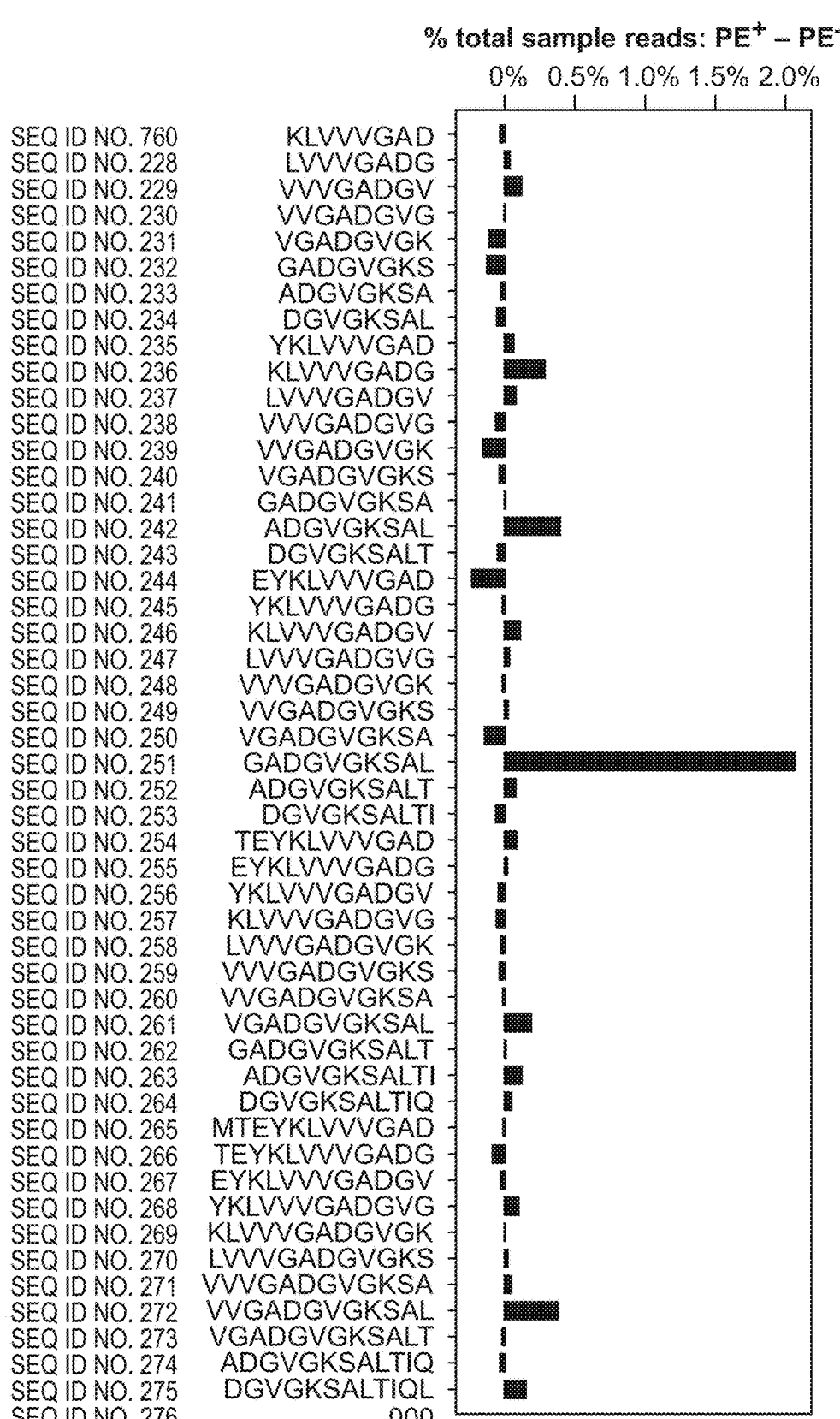
Figure 4F:
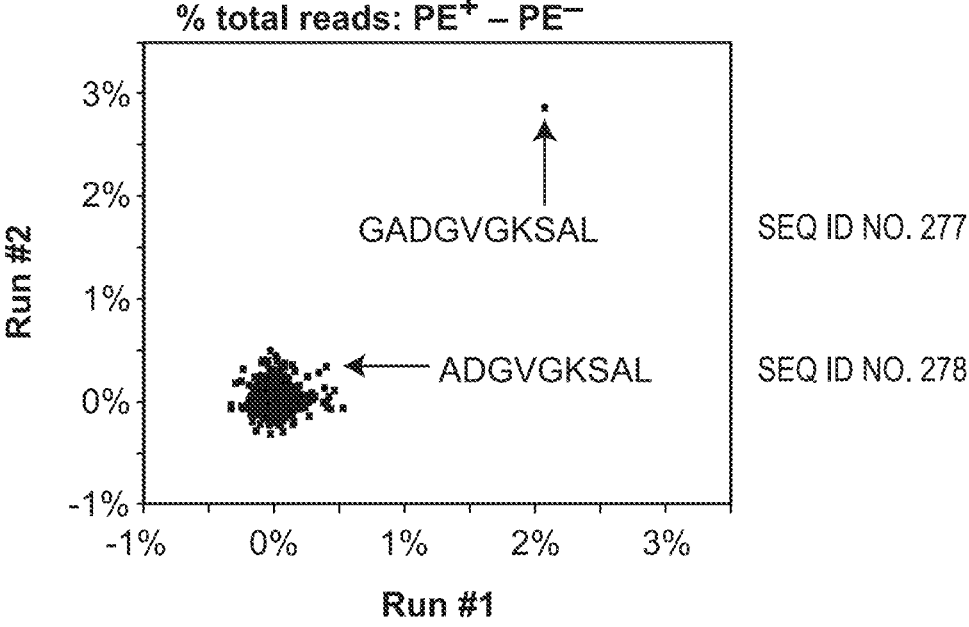
Figure 11B:
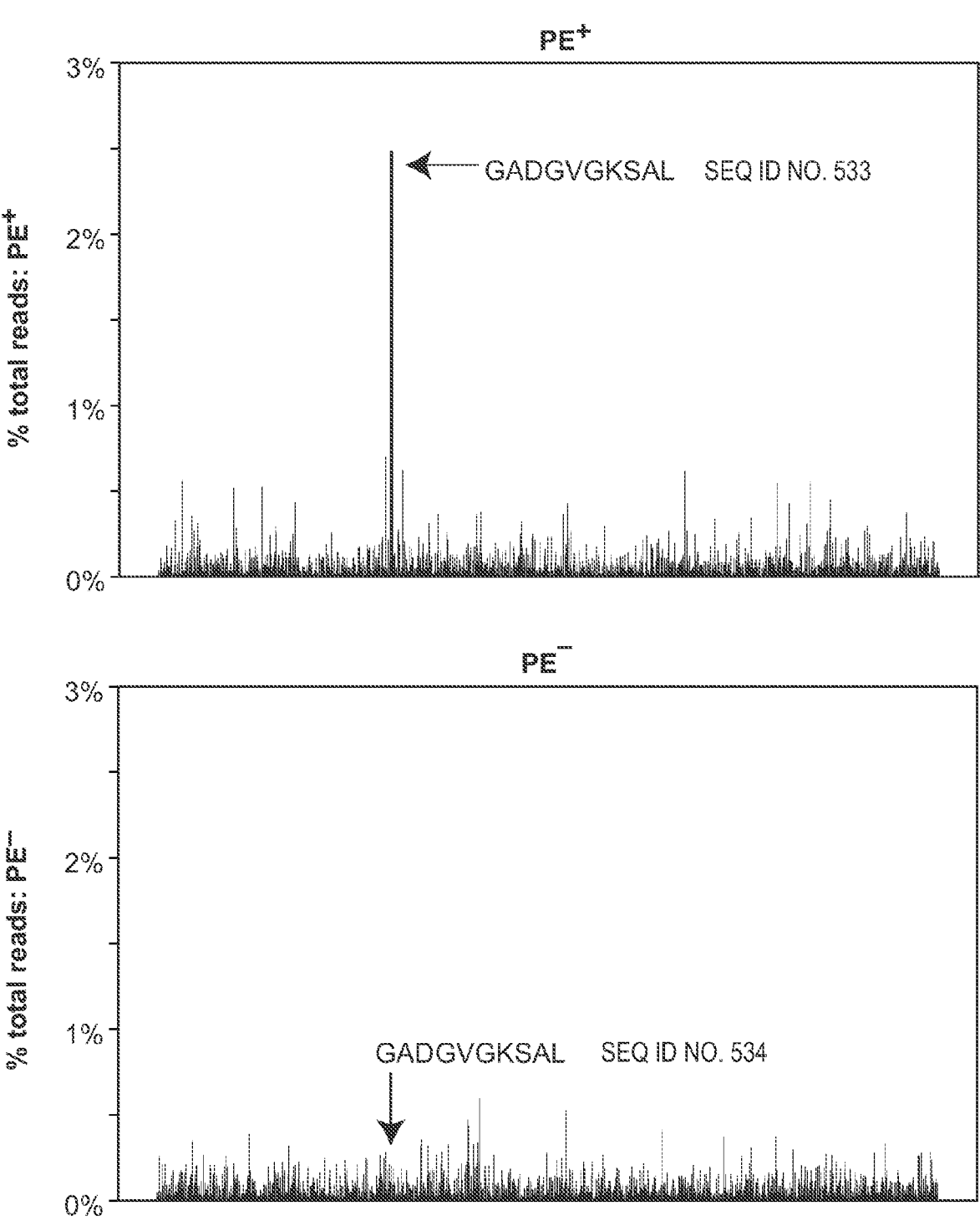
Figure 11C:
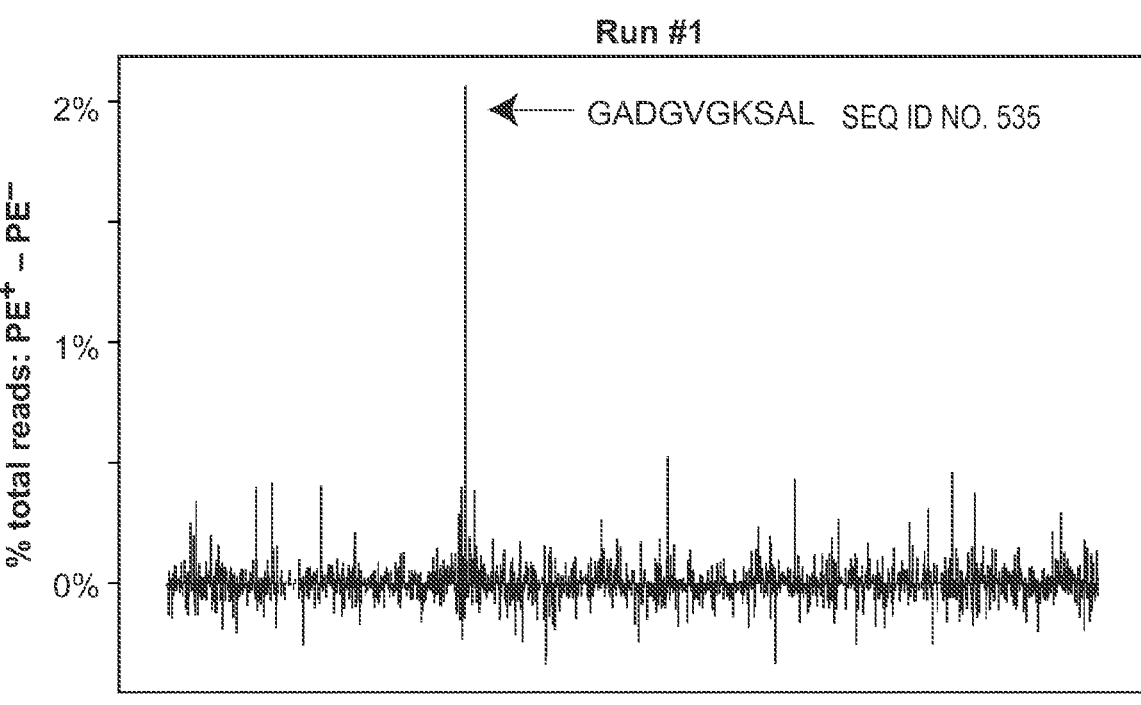
Figure 11C:
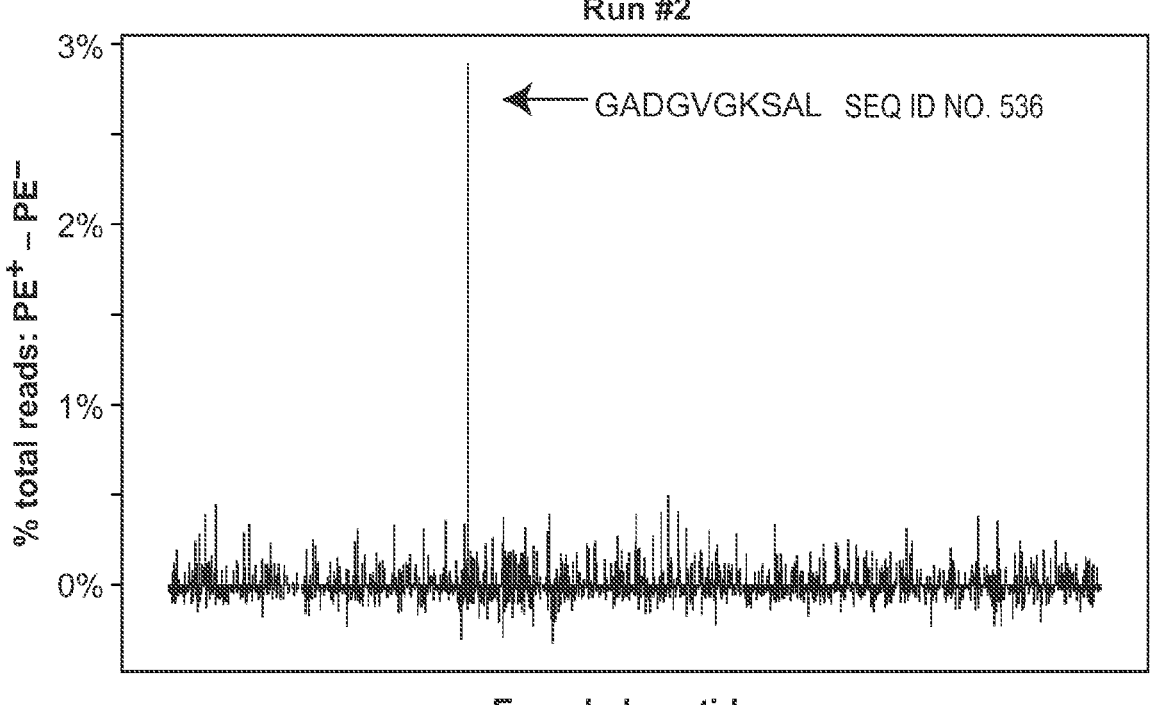

In a representative experiment in the pulldown of PE-labeled cells, 2.2% of the total peptide-encoding reads encoded the KRAS p.G12D TCR target, GADGVGKSAL (SEQ ID NO. 667) (FIG. 11B). In comparison, GAD-GVGKSAL (SEQ ID NO. 667) was represented by 0.09% of peptide-encoding reads in the unlabeled population (FIG. 11B). This difference of 2.1% (FIG. 4C) was the most significant outlier among the encoded peptide library, with a z-score of 23.0 (FIG. 4D). Other sequences that encompass the p.G12D mutation but at a shifted starting position (e.g. ADGVGKSALT (SEQ ID NO. 668)) and/or different length (e.g. GADGVGKSA(SEQ ID NO. 669) or VGAD-GVGKSAL (SEQ ID NO. 670)) were not significantly enriched (FIG. 4E). Replication of this workflow showed similar results (FIG. 4F and FIG. 11C).

Taken together, these results demonstrated that the assay can identify a TCR-targeted epitope—in this case a tumor neoepitope—amongst a library of thousands of peptide-encoding oligonucleotides.

Example 8: Fine Mapping Epitope Sequences Using Tiled Encoded Peptides

It was reasoned that the method can be used to identify the minimal epitope targeted by a reactive T cell, e.g. the minimal epitope targeted within a pathogen genome (Addo et al., 2003 J. Virol., 77:2081-2092; Pereyra et al., 2014 J. Virol., 88:12937-12948) or within an autoimmune disease-targeted gene or genome (Latorre et al., 2018 Nature, 562:63-68; Ota et al., 1990 Nature., 346:183-187) To demonstrate this, the Ob.1A12 TCR was used, which a class 11-restricted myelin basic protein (MBP)-reactive TCR identified in a patient with multiple sclerosis (Wucherpfennig et al., 1994 J. Immunol., 152:5581-92).

Figure 12B:
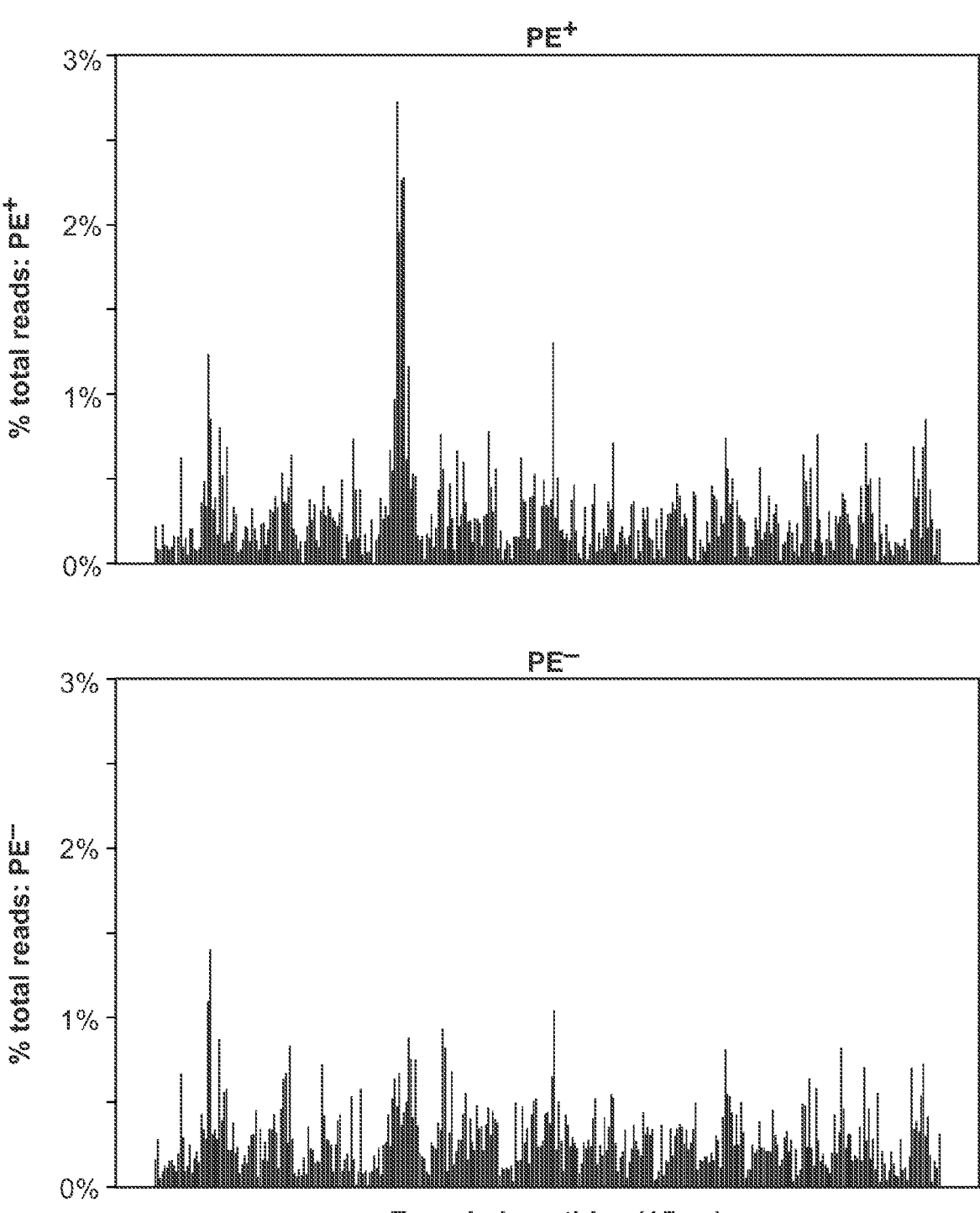
Figure 12C:
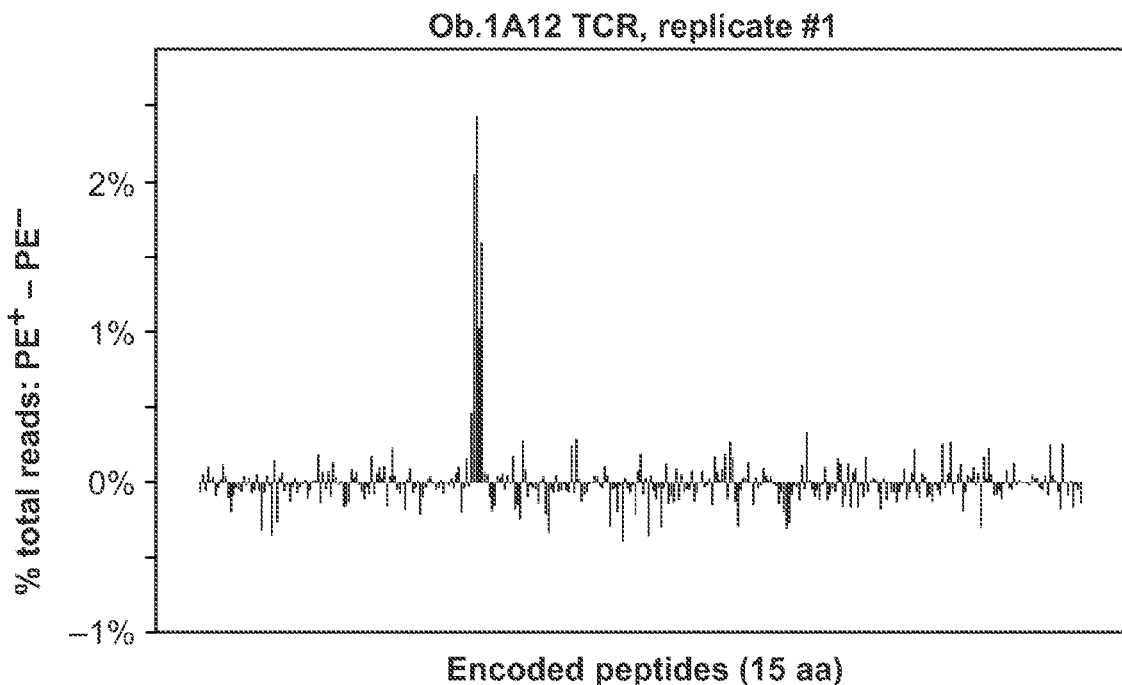
Figure 12D:
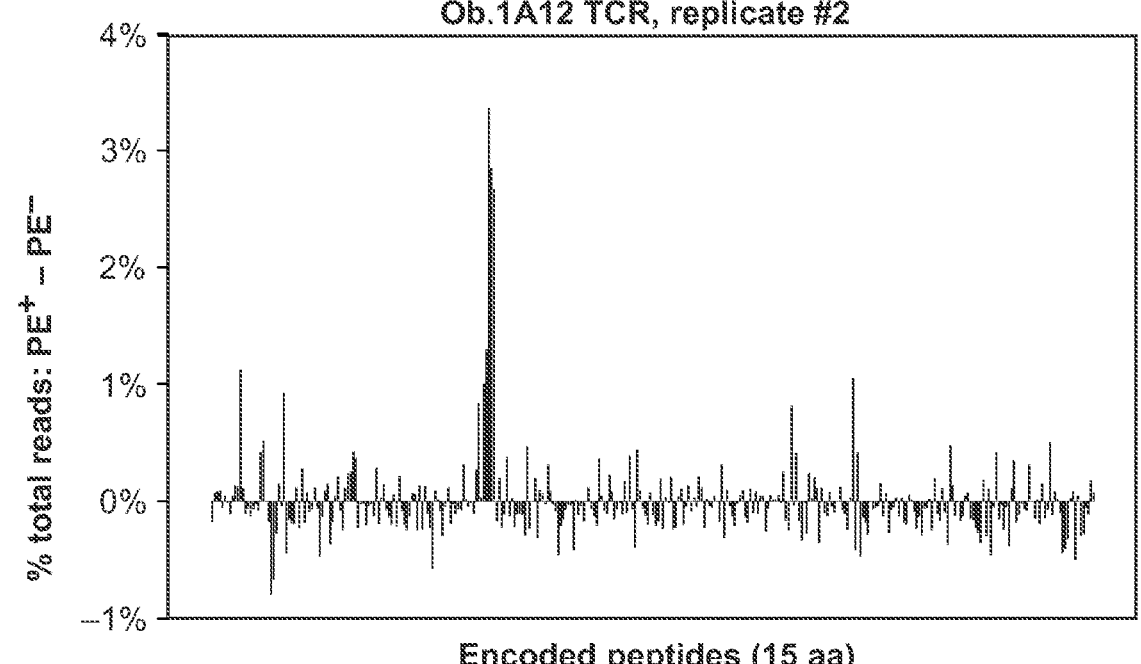
Figures 12E, 12F:
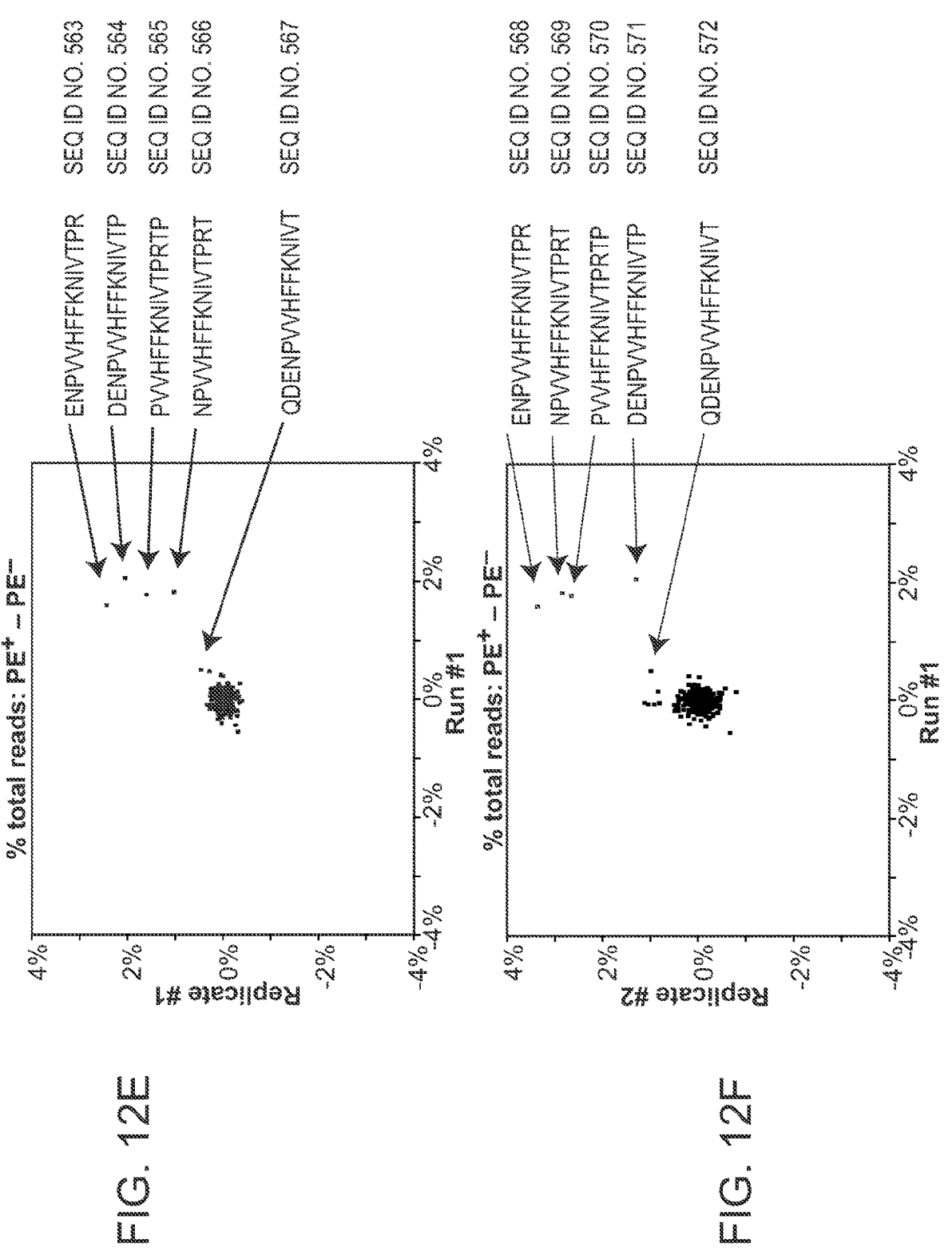

A pooled DNA library that encodes all 15 amino acid peptides (i.e., with 14 amino acid overlaps) in the myelin basic protein (MBP) was created—covering MBP isoform 1, isoform 2, isoform 3, isoform 4, Golli isoform 1, and Golli isoform 2 (FIG. 5A, FIG. 5B, FIG. 12A, and Table 3) (Pribyl et al., 1996 J. Comp. Neurol., 374, 342-53)- and created fusions with the invariant chain gene (FIG. 9K, middle panel). This library was transduced into HLA-DRA*01:01 and HLA-DRB*15:01 co-expressing APCs at a m.o.i. <1. About 300 APCs were seeded in each well of a single 96-well plate. After clonal expansion, the APCs were co-cultured with T cells expressing the Ob.1A12 TCR. The PE anti-IL-2 antibody-labeled APCs were separated from unlabeled cells.

Figure 5C:
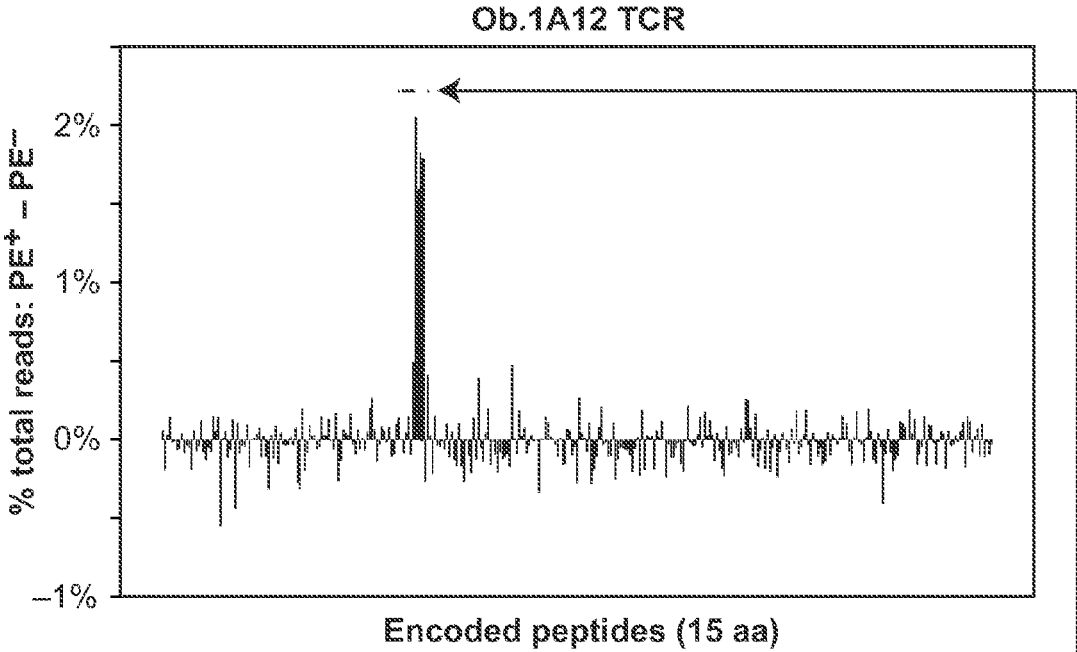
Figure 5D:
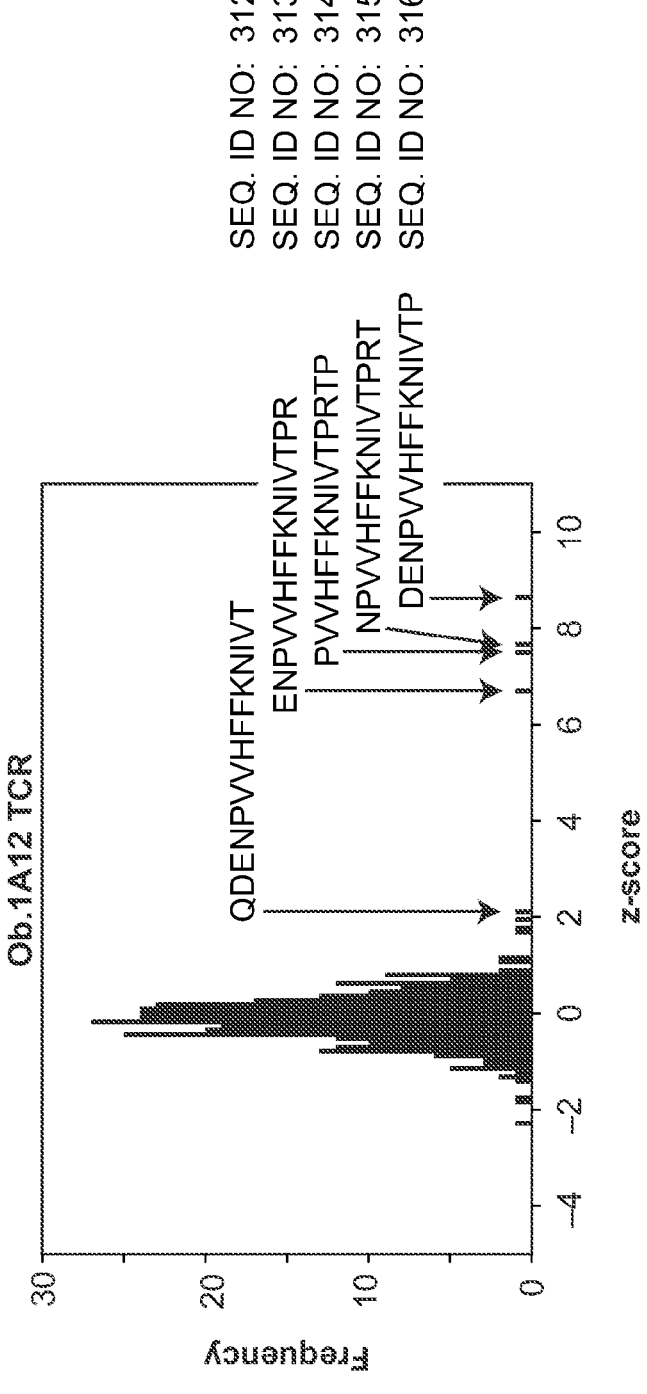

In a representative experiment in the pulldown of PE-labeled cells, several overlapping peptides—QDEN-PVVHFFKNIVT (SEQ ID NO. 671), DEN-PVVHFFKNIVTP (SEQ ID NO. 672), ENPVVHFFKNIVTPR (SEQ ID NO. 673), NPVVHFFKNIVTPRT (SEQ ID NO. 674), and PVVHFFKNIVTPRTP (SEQ ID NO. 675)—were outliers (FIG. 5C and FIG. 12B) with a z-score >2 (FIG. 5D). ENPVVHFFKNIVTPR (SEQ ID NO. 673) was previously identified as an optimal 15 amino acid epitope within MBP (Ota et al., 1990 Nature., 346:183-187; Wucherpfennig et al., 1994 J. Exp. Med., 179:279-90), but the other epitopes identified here were not tested (Wucherpfennig et al., 1994 J. Exp. Med., 179:279-90). Consistent with the peptides identified, a crystal structure had shown VVHFFK (SEQ ID NO. 674) as the critical region of HLA binding and TCR recognition (Hahn et al., 2005 Nat. Immunol., 6:490-496). This experiment was performed in triplicate, with similar results (FIG. 12C-FIG. 12F). Consistent with these results, a crystal structure had shown VVHFFK (SEQ ID NO. 674) as the critical region of HLA binding and TCR recognition (Hahn et al., 2005. Nat. Immunol. 6:490-496).

Figure 5E:
Figure 5E:
Figure 12G:
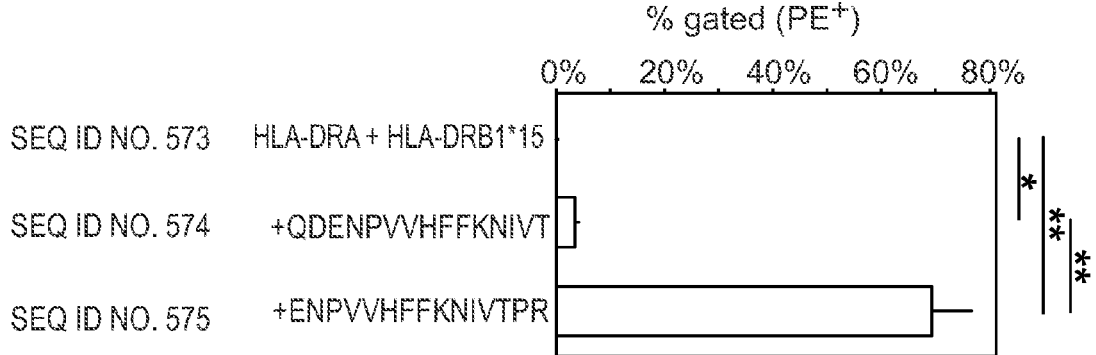

The screening results were confirmed using single peptide-encoding oligonucleotides, which showed that each of the five epitopes above elicited T cell activation, while the flanking peptides, VVHFFKNIVTPRTPP (SEQ ID NO. 675) and TQDENPVVHFFKNIV (SEQ ID NO. 676), did not elicit substantial signal relative to expression of HLA alone (FIG. 5E). Expression of QDENPVVHFFKNIVT (SEQ ID NO. 677) consistently resulted in dimmer signal (4.0% of cells gated in a representative experiment) relative to expression of the other four epitopes (37.3%, 61.4%, 49.7%, and 83.7% of cells gated) (FIG. 5E and FIG. 12G), consistent with its weaker enrichment in the screen (FIG. 5C).

Figure 12H:
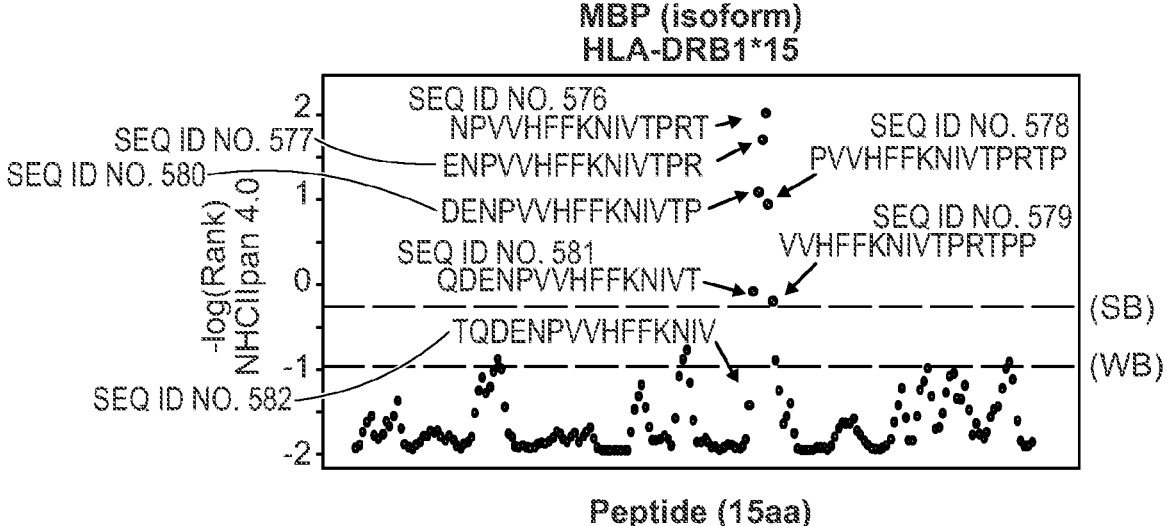

Using NetMHCIIpan 4.059, predicted HLA II binding affinities were compared with the results. Consistent with the functional screen, the four strongest T cell-activating peptides (FIG. 5E) were the top four predicted binders to HLA-DRB1*15:01 (FIG. 12H). The flanking peptides QDENPVVHFFKNIVT (SEQ ID NO. 677) and VVHFFKNIVTPRTPP (SEQ ID NO. 675), described above, were also predicted to be strong binders, though with lower % Rank scores. These results show that multiple stimulatory epitopes could be simultaneously identified in a single pulldown. The enrichment scores can be semi-quantitative (FIG. 9D). This information taken together can be used to fine map epitopes.

Example 9: Identification of Epitopes Targeted by Orphan T Cell Receptors

Having established the ability to identify known class I and II epitopes from pooled libraries, the methods was used for the discovery of epitopes targeted by T cell receptor sequences that are common in the population, so called "public" T cell receptor sequences, but whose targets remain unknown, i.e., "orphan" TCRs. A published database of 89,840,865 TCRβ sequences identified in the peripheral blood of 666 healthy donors (Emerson, et al., 2017 Nat. Genet. 49: 659-665) was used. Analysis of this dataset had shown that 164 TCRβ sequences were shared by at least 12 individuals and were statistically associated with CMV seropositive status (Emerson, et al., 2017 Nat. Genet. 49: 659-665) While prior data suggested that five of the TCRβ sequences recognize known CMV epitopes—i.e., the class I epitopes NLVPMVATV (SEQ ID NO. 655), TPRVTGG-GAM (SEQ ID NO. 678), MLNIPSINV (SEQ ID NO. 679), or RPHERNGFTVL (SEQ ID NO. 680)—155 of 164 of the target epitopes remain unknown (Emerson, et al., 2017 Nat. Genet. 49: 659-665).

To identify targets of the orphan TCRs, the following populations needed to be defined (i) the TCRα genes whose protein products form heterodimers with the selected TCRβ proteins, (ii) the HLA presenting the epitope to the TCRs, and (iii) a putative epitope set (FIG. 6A).

Figure 13A:
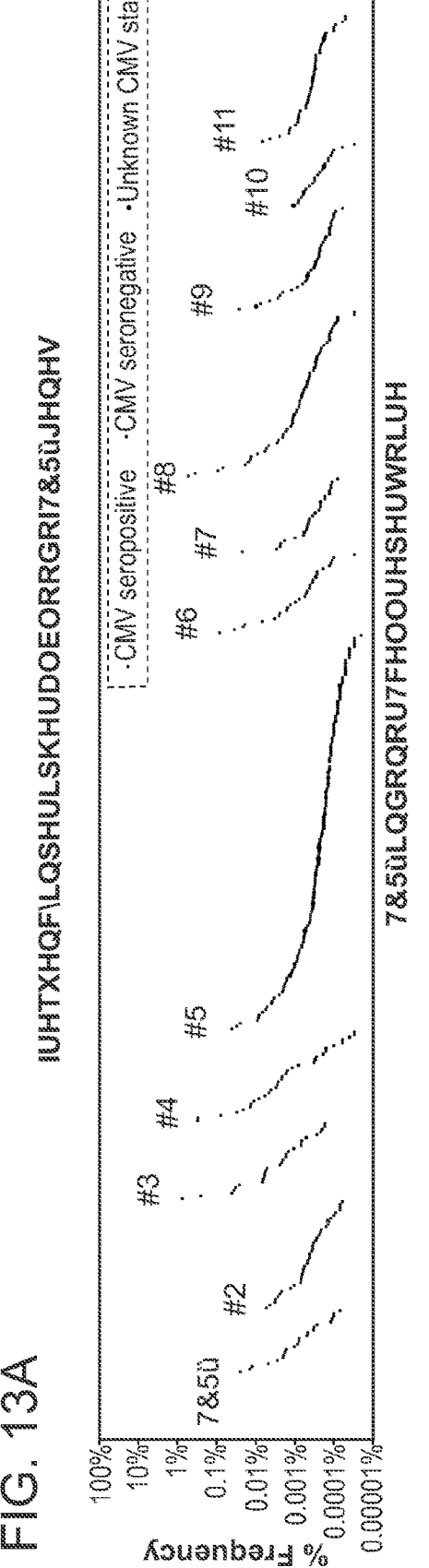

Because these are public TCRβ, the databases were searched to find single-cell TCR sequences (Tanno et al., 2020 Proc. Natl. Acad. Sci. U.S.A, 117:532-540; Guo et al., 2018 Nat. Med., 24:978-985; Zheng et al., 2017 Cell, 169:1342-1356.e16; Sade-Feldman et al., 2018 Cell, 175: 998-1013.e20) for the exact TCRβ, leading to identification of 11 of the 155 TCRβ sequences with paired TCRα sequences. The TCR KO T cells were transduced with each TCRβ-TCRα pair (13 in total, given TCR gene segment ambiguities and promiscuous TCRβ-TCRα pairing). Of note, from the single-cell datasets, some TCR sequences were identified in total T cells from peripheral blood (TCRs #7-9) (Tanno et al., 2020 Proc. Natl. Acad. Sci. U.S.A., 117:532-540) some in sorted memory T cells from blood (TCR #10) (Tanno et al., 2020 Proc. Natl. Acad. Sci. U.S.A, 117:532-540) some in T cells from tumor tissue (TCRs #5 and #11) (Guo et al., 2018 Nat. Med., 24:978-985; Sade-Feldman et al., 2018 Cell, 175:998-1013.e20) potentially as bystander T cells (Simoni et al., 2018 Nature, 557:575-579), some in T cells from normal tissue (TCR #4) (Zheng et al, 2017 Cell, 169:1342-1356.e16), and some in T cells from both peripheral blood and tissue samples from the same patient (TCRs #1-3 and #6) (Guo et al., 2018 Nat. Med., 24:978-985). The frequencies (of the TCRβ in some donors suggested that they were found in expanded T cell clones (FIG. 13A).

To identify candidate HLAs, all available HLA typing data was gathered for each individual in whom the TCRβ was found, as well as any available CD8 or CD4 expression data to narrow candidates to HLA class I or class II. Candidate HLA class I or II were identified for 10 of 11 TCRs, although full HLA typing data was not available which represented a potential source of negative screening results. For four TCRs (TCRs #1-4), candidate HLA were narrowed to a single HLA class I type (HLA-A*24:02, HLA-B*07:02, or HLA-B*51:01) based on statistical association with the TCRβ (Emerson, et al., 2017 Nat. Genet. 49: 659-665). Similarly, for two TCRs (TCRs #5-6), candidate HLAs were narrowed to two HLA class I types (HLA-A*01: 01 and HLA-B*08:01).

Figure 6C:
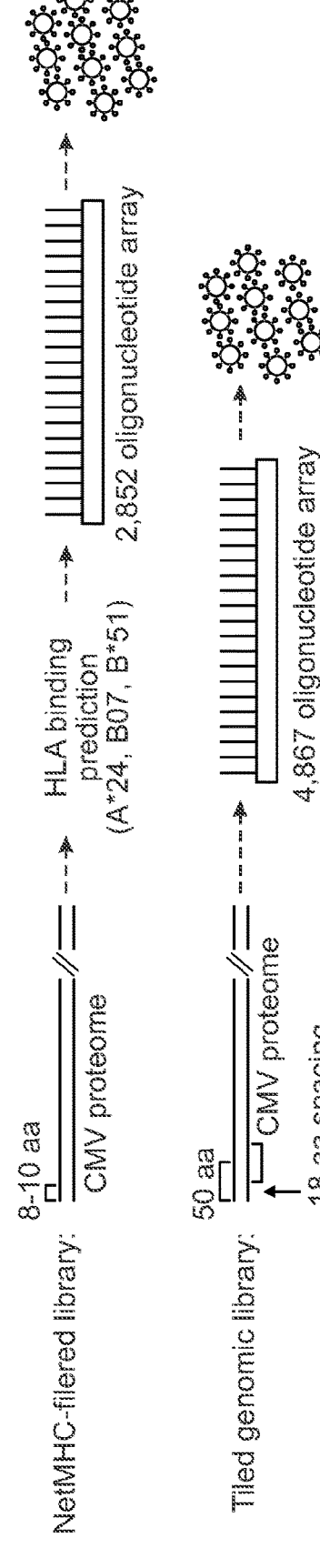
FIG. 6A-6N is a series of schematics and charts showing identification of previously unknown epitopes targeted by orphan T cell receptors.
Figure 13B:
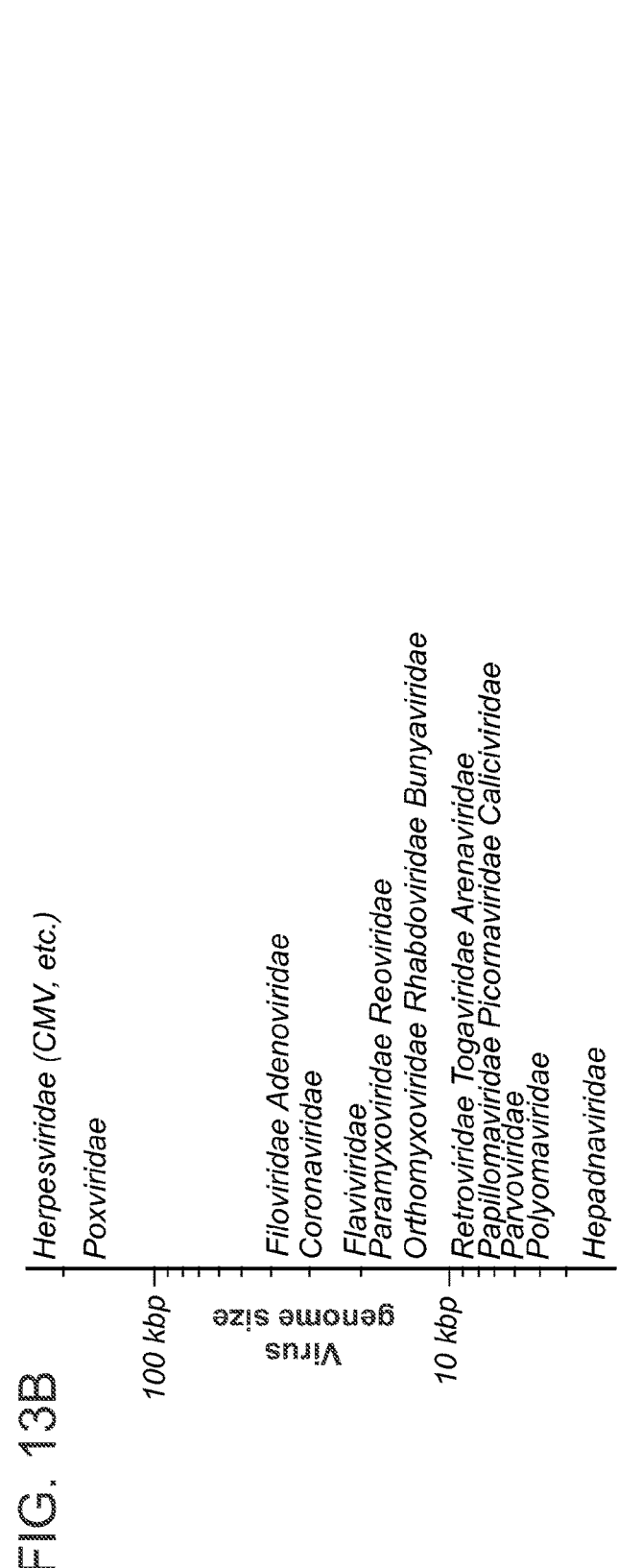

As a source for the candidate epitopes, the top 236 kbp CMV genomes—the largest among viruses that cause disease in humans (Sijmons et al., 2015 J. Virol. 89:7673-7695) (FIG. 13B)—were used as the most likely antigen source given the TCRs' association with CMV seropositive status (FIG. 6B and FIG. 13A). Two peptide-encoding libraries were synthesized (FIG. 6C): (i) a library of 2,852 oligo-nucleotides, each encoding 8-10 amino acid peptides from CMV that were predicted to bind to HLA-A*24:02, HLA-B*07:02, or HLA-B*51:01 (our "NetMHC-filtered" set);

and (ii) a library of 4,867 oligonucleotides, each encoding 50 amino acid peptides (with 32 amino acid overlaps) tiling the entire CMV genome. The NetMHC-filtered library was transduced into HLA-A*24:02, HLA-B*07:02, and HLA-B*51:01 co-expressing APCs (to screen TCRs #1-4). The tiled genomic library was transduced into APCs co-expressing HLA-A*01:01 and HLA-B*08:01 (to screen TCR #5-6); APCs co-expressing HLA-DRA*01:01, HLA-DRB1*04:01, HLA-DRB4*01:03, and HLA-DRB5*01:01 (to screen TCRs #7-9); or APCs co-expressing HLA-DRA*01:01, HLA-DRB1*01:03, HLA-DRB1*07:01, and HLA-DRB4*01:01 (to screen TCR #10). For class II presentation, oligonucleotides encoding peptides were fused to CD74.

Figure 13C:
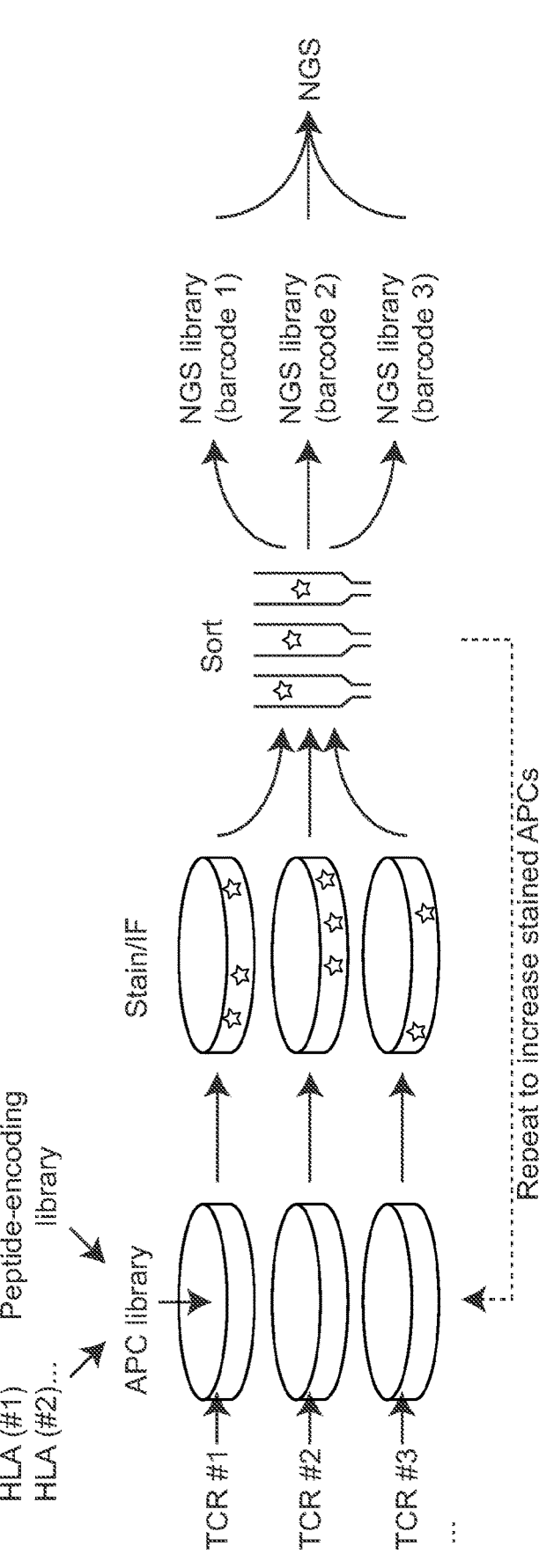

In order to screen all TCRs concurrently, the technical aspect of the workflow was s streamlined to facilitate multiplexing. First, the oligonucleotide library was transduced at m.o.i. >1 (approximately 4-10) to increase the rate of positive clones, and second, was plated at a density of approximately 300,000 APCs in a single 10-cm plate for each TCR tested (rather than partitioning the library among wells as we had done in the earlier screens). (FIG. 13C). Then added TCR-expressing TCR KO T cells were added to each 10-cm plate, the APCs were stained with PE anti-IL2 antibody after 20.75 hours of co-culture, the number of PE⁺ cells were estimated under a fluorescent microscope, and the cells were sorted using anti-PE beads and magnetic columns (FIG. 13C). To increase the number of PE+ cells, the first round of sorted APCs were cultured and re-incubated with T cells before a second sort was perfumed. Barcoded libraries were generated from the pulldown and flow-through cells and sequenced the libraries by NGS (FIG. 13C).

Out of the ten TCRs with unique TCRβ genes, the immunofluorescence (data not shown) and NGS results suggested that an identification of seven hits. For the screens in which PE⁺ signal was not apparent and few cells were in the pulldown (i.e., for TCRs #3, 4, and 8), NGS libraries were not prepared. Four of the potential hits were found in the class I libraries (FIG. 6D-FIG. 6N and FIG. 13D-FIG. 13K).

Figures 6D, 6E, 6F:
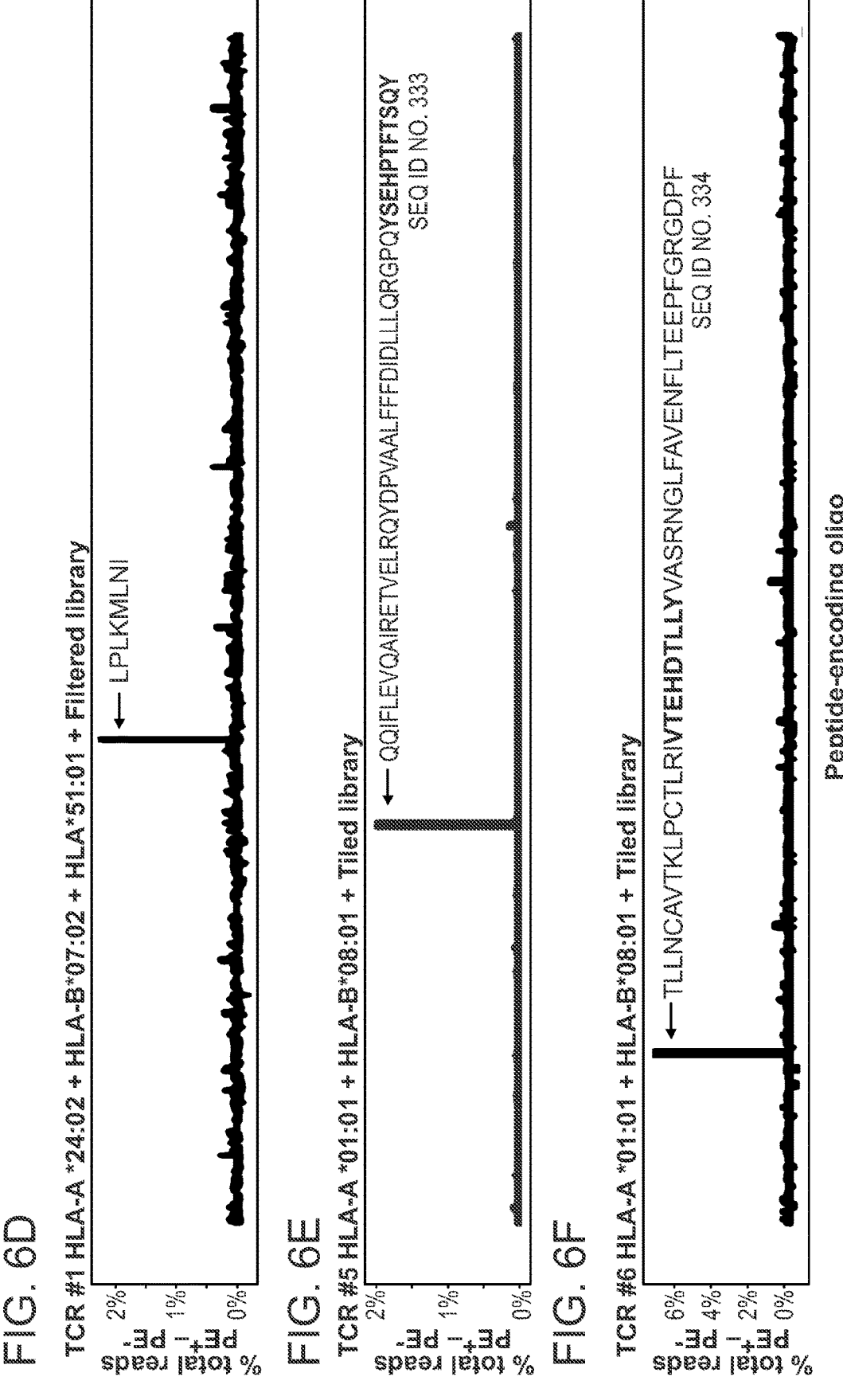
Figure 13D:
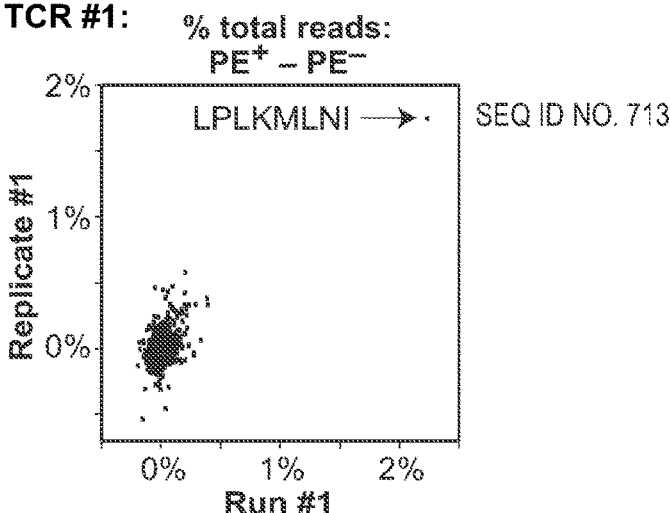

For TCR #1, using the NetMHC-filtered library, the 8 amino acid peptide, LPLKMLNI (SEQ ID NO. 681), was identified from the CMV UL83 protein as the top hit (FIG. 6D), with a z-score of 34.1 (FIG. 6E). Replication of the second round of screening showed similar results (FIG. 13D). It was confirmed that LPLKMLNI (SEQ ID NO. 681) stimulates TCR #4-expressing T cells, and that recognition is restricted by HLA-B*51:01 (FIG. 6I).

Figures 6G, 6H, 6I:
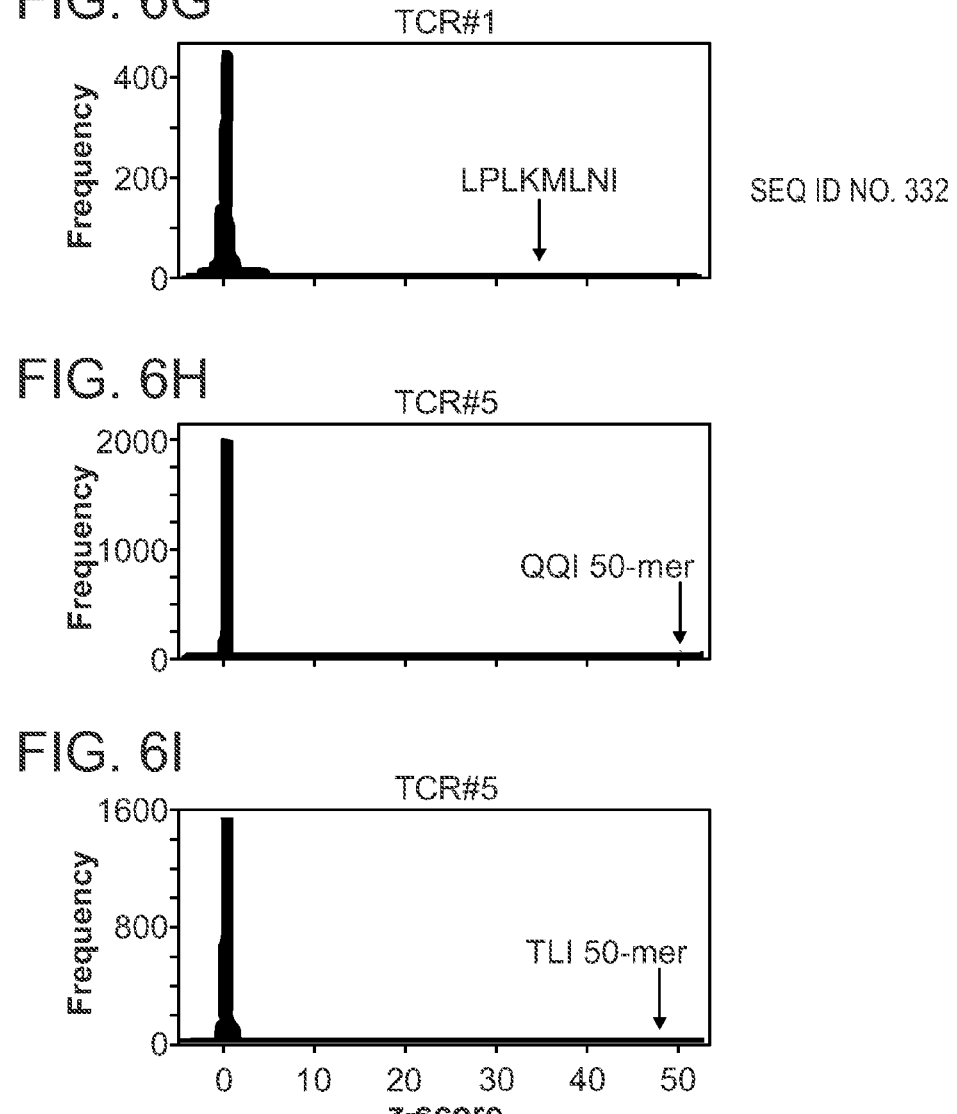
Figures 6J, 6K:
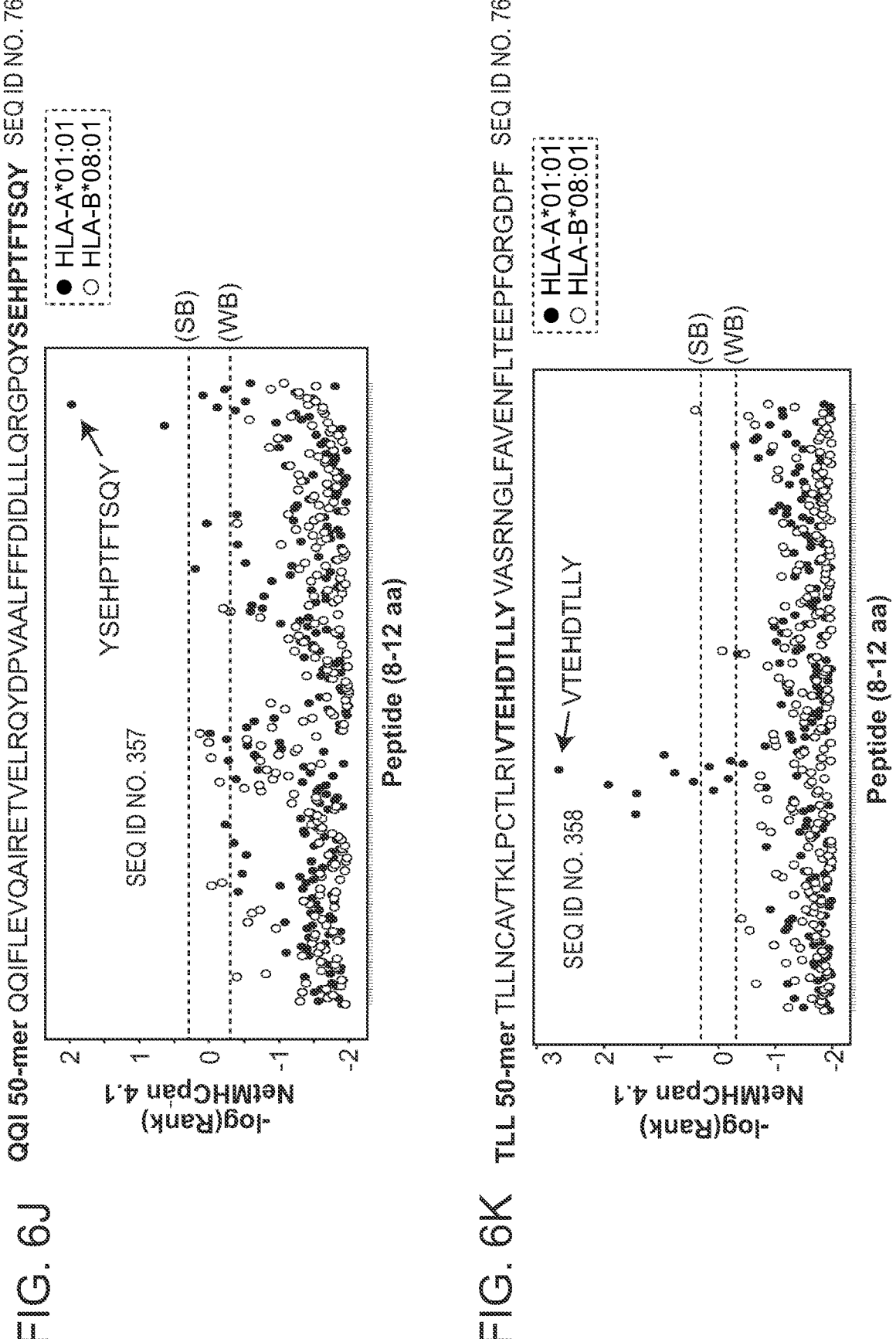
Figure 6L:
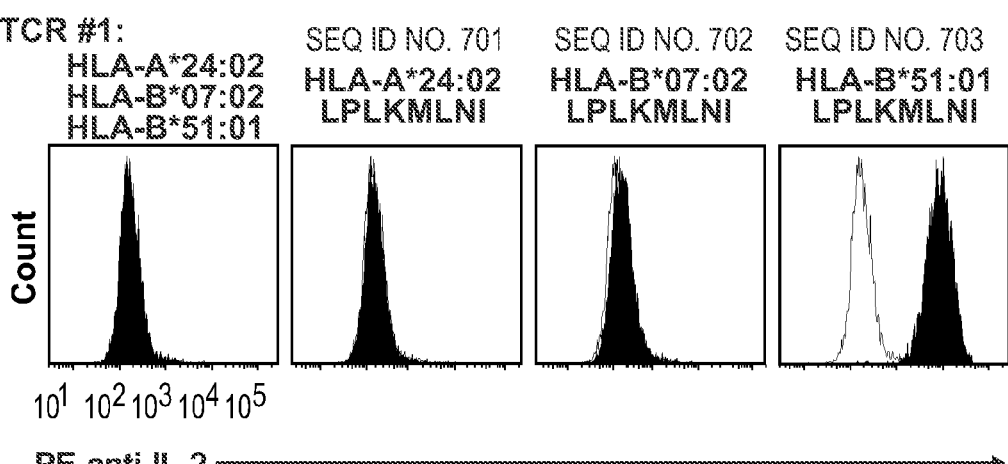
Figure 6M:
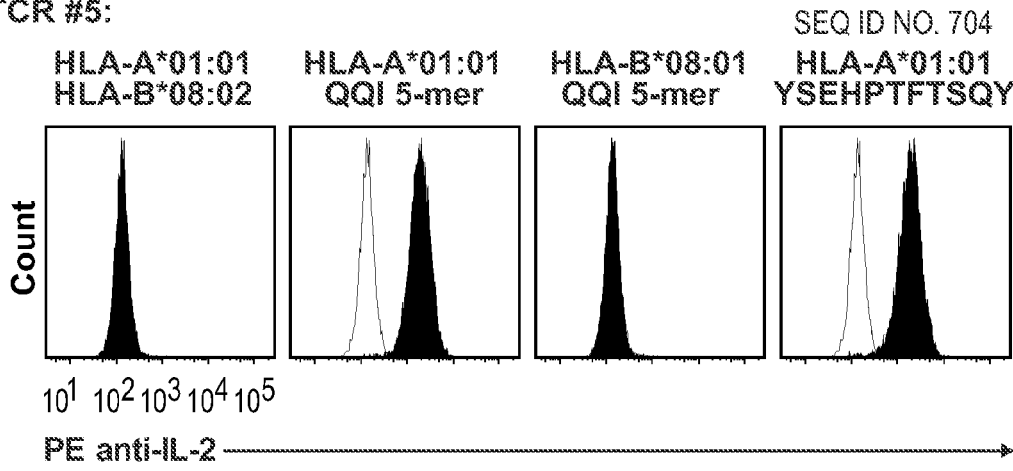
Figure 13E:
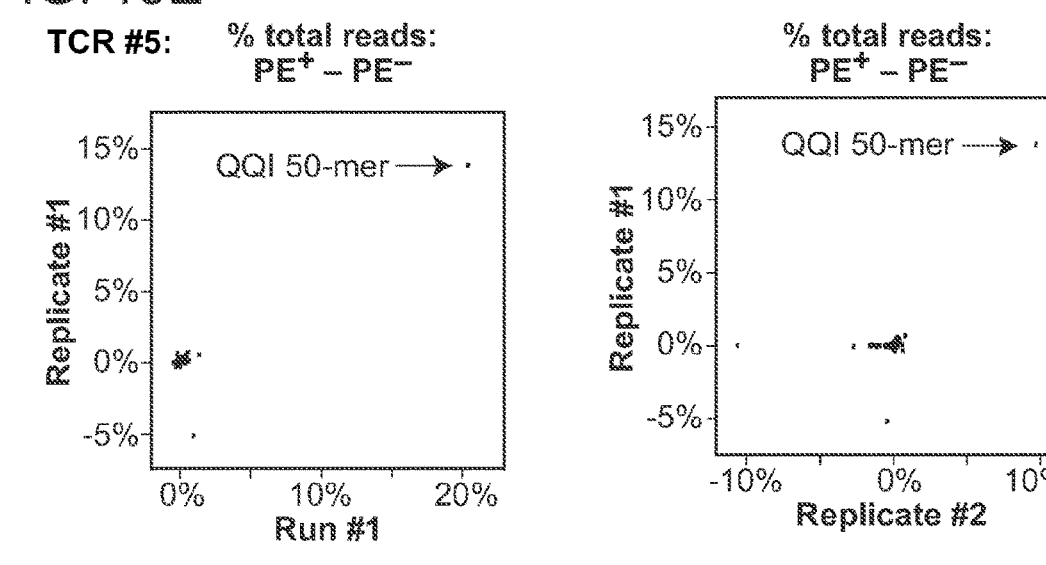
Figure 13F:
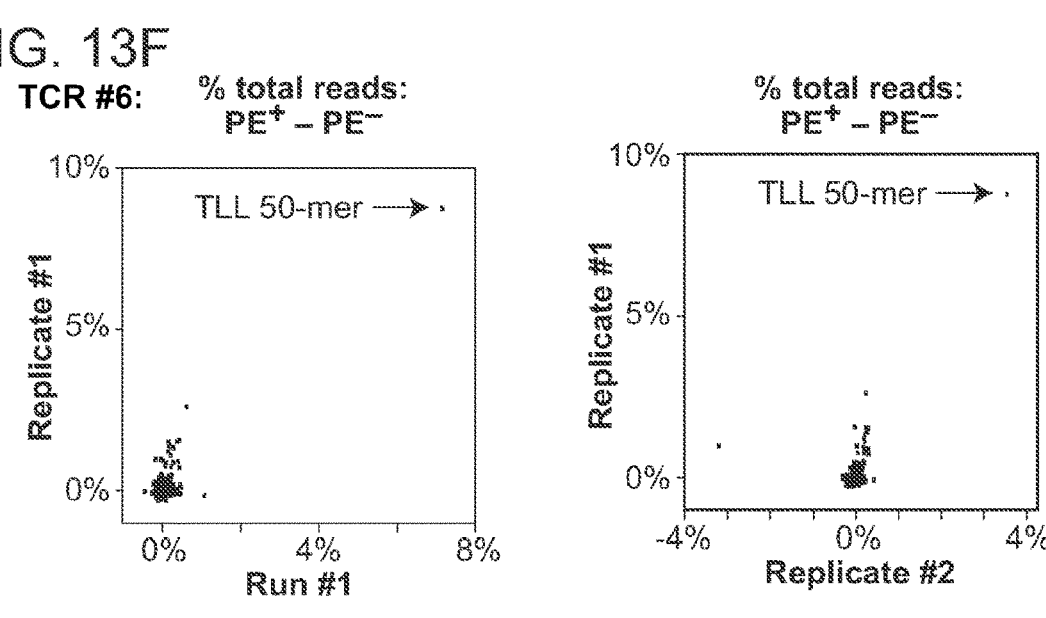
Figures 13G, 13H:
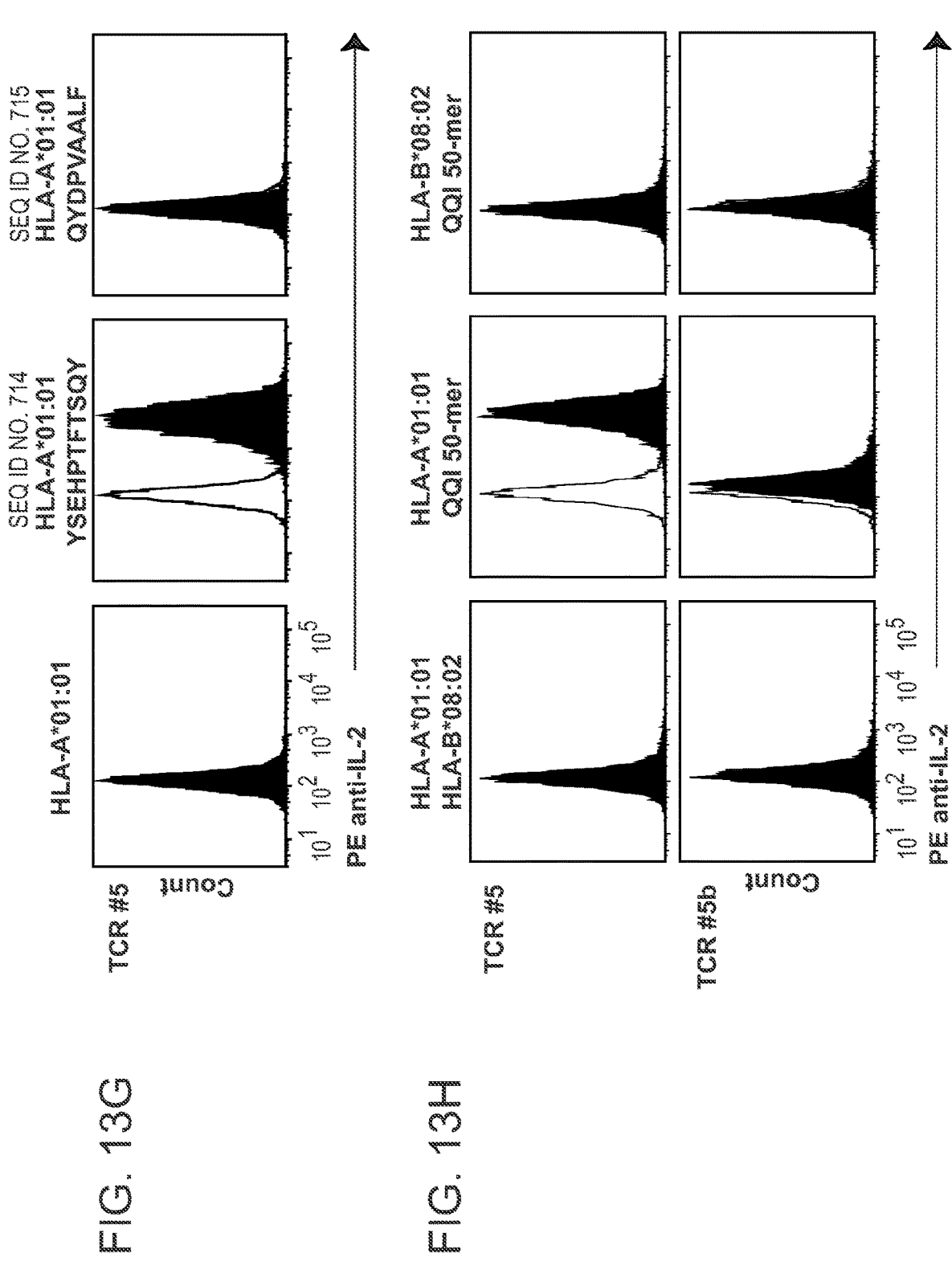

For TCR #5, QQI-FLEVQAIRETVELRQYDPVAALFFFDIDLLLQRGPQY-SEHPTFTSQY (SEQ ID NO. 682) was identified from the CMV UL83 protein as the top hit using the tiled genomic library (FIG. 6F), with a z-score of 50.3 (FIG. 6G). Replication of the second round of screening showed similar results (FIG. 13E). This 50 amino acid peptide (QQI 50-mer) was confirmed to stimulate TCR #5-expressing T cells, and it was found that its recognition is restricted by HLA-A*01:01 (FIG. 6M). Within the QQI 50-mer, the 11 amino acid peptide YSEHPTFTSQY (SEQ ID NO. 683) was the top ranked peptide predicted (by NetMHCpan 4.1 (Reynisson et al., 2020 Nucleic Acids Res. 48:W449-W454)) to bind to HLA-A*01:01 (FIG. 6J). It was confirmed that this 10 amino acid peptide stimulates TCR #29-expressing T cells (FIG. 6M and FIG. 13G). In addition to TCR #5, there was another T cell (TCR #5b) in the single-cell data which expressed the same TCRβ but with an alternative TCRα. TCR #5b did not show substantial activation by the QQI 50-mer (FIG. 13H). The promiscuous pairing of this TCRβ is consistent with its expression in a higher percentage of CMV seronegative donors than the other TCRβs (Emerson et al., 2017 Nat. Genet., 49:659-665) (FIG. 13A), suggesting that some of these TCRβ-TCRα pairs target a non-CMV antigen.

Figure 6N:
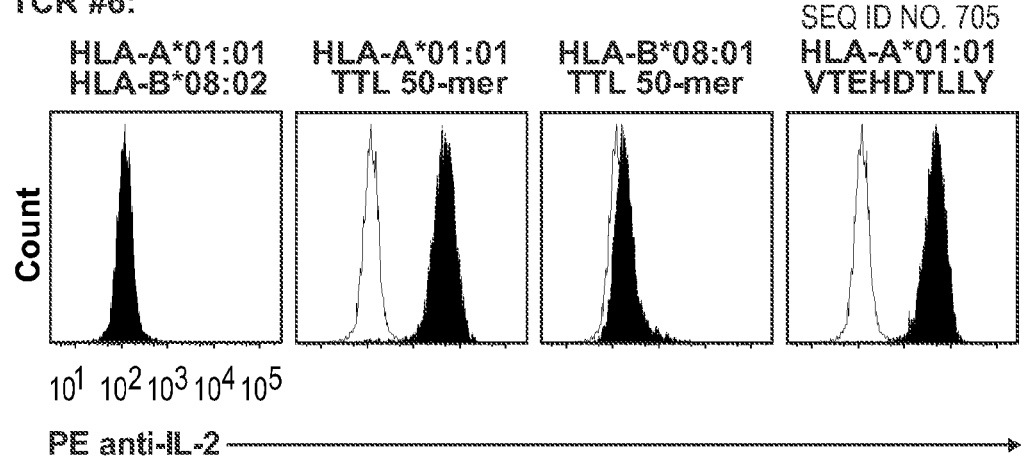

For TCR #6, TLLNCAVTKLPCTLRIVTEHDTLLY-VASRNGLFAVENFLTEEPFQRGDPF (SEQ ID NO. 684) was identified from the CMV UL44 protein as the top hit using the tiled genomic library (FIG. 6H), with a z-score of 48.2 (FIG. 6I). Replication of the second round of screening showed similar results (FIG. 13F). It was confirmed that the TLL 50-mer stimulated TCR #6-expressing T cells, and found that recognition is restricted by HLA-A*01:01 (FIG. 6N). Within the TLL 50-mer, the 9 amino acid peptide VTEHDTLLY (SEQ ID NO. 685) was the top ranked peptide predicted (by NetMHCpan 4.1 (Reynisson et al., 2020 Nucleic Acids Res. 48:W449-W454)) to bind to HLA-A*01:01 (FIG. 6K). It was confirmed that this 9 amino acid peptide stimulates TCR #1-expressing T cells when presented on HLA-A*01:01 (FIG. 6N).

Figure 13I:
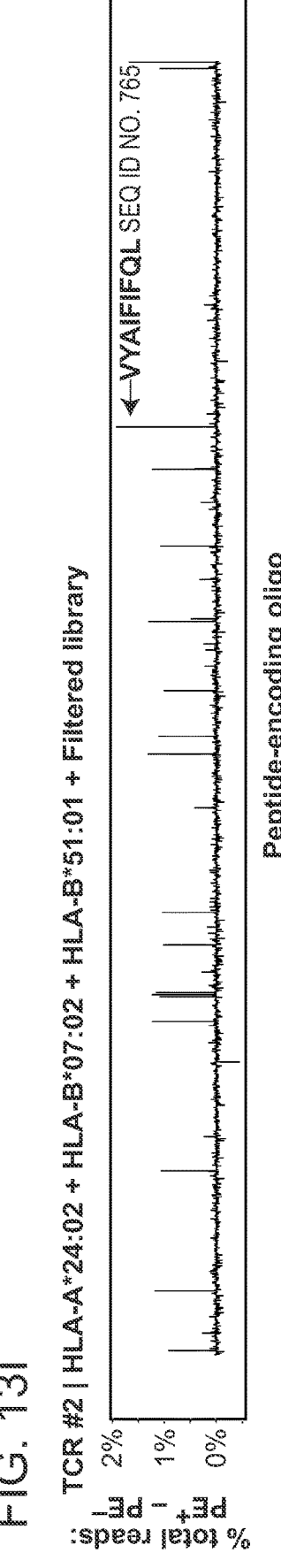
Figure 13J:
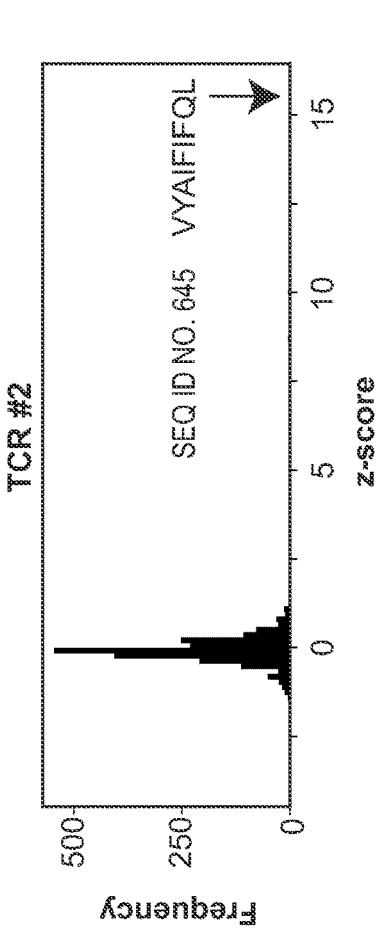
Figure 13K:
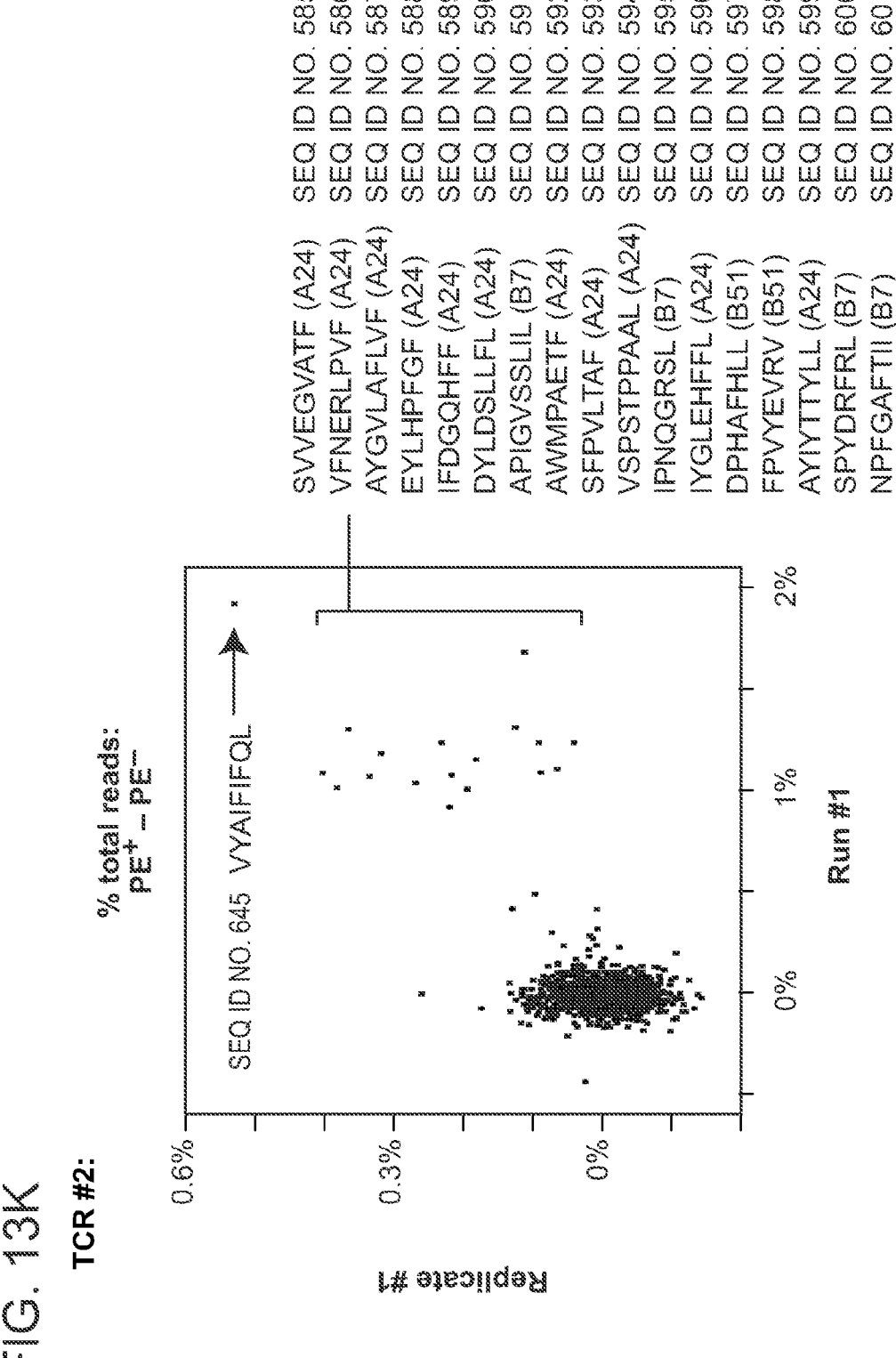

For TCR #2, using the NetMHC-filtered library, 18 hits that appeared to be outliers relative to background were identified. These hits were reproducible after replication of the second round of screening (FIG. 13I-FIG. 13K). VYAI-FIFQL (SEQ ID NO. 686) from the CMV US20 protein was consistently the top hit (FIG. 13K). It was confirmed that VYAIFIFQL (SEQ ID NO. 686) stimulates TCR #2-expressing T cells, and that recognition is restricted by HLA-A*24:02 (FIG. 13L). The other hits in the TCR #2 screen did not appear to have sequence similarity to VYAIFIFQL (SEQ ID NO. 686). Thus, it was hypothesized that the other hits were false positives caused by (i) transduction of the oligonucleotide library at m.o.i. >1 (approximately 4-10) combined with (ii) selection of a small number of clones in the first round of the screen. This "bottleneck" effect would cause APCs expressing VYAIFIFQL (SEQ ID NO. 686) to be selected (and VYAIFIFQL (SEQ ID NO. 686) to be slightly enriched), but "passenger" peptides within VYAIFIFQL (SEQ ID NO. 686)-expressing APCs to also be selected. With higher m.o.i., the screening workflow depended upon many different clones to be selected, so that the passenger peptides are distributed towards background while the target epitope is enriched (FIG. 3B), which did not appear to occur in the TCR #2 screen. Testing of several of the putative passenger peptides confirmed that they did not stimulate TCR #2 (FIG. 13M) in contrast to VYAIFIFQL (SEQ ID NO. 686).

Altogether, epitopes were identified for four of six TCRs with unique TCRβ genes that were screened on class I libraries. For each epitope, the HLA restriction and fine map 50-mers to 8-12 amino acid peptides were determined using HLA binding prediction. Three of four of these epitopes have been described (Vita et al., 2019 Nucleic Acids Res., 47:D339-D343). YSEHPTFTSQY (SEQ ID NO. 687) and VTEHDTLLY (SEQ ID NO. 688) have previously been shown to stimulate T cells from multiple individuals (Vita et al., 2019 Nucleic Acids Res., 47:D339-D343), consistent with the associated TCRβ genes being public. LPLKMLNI (SEQ ID NO. 689) has previously been shown to stimulate T cells from at least one individual (Nastke et al., 2005 Cell. Mol. Life Sci., 62: 77-86). Notably, the VYAIFIFQL (SEQ ID NO. 686) epitope has not been previously described (Vita et al., 2019 Nucleic Acids Res., 47:D339-D343).

Figures 7A, 7B:
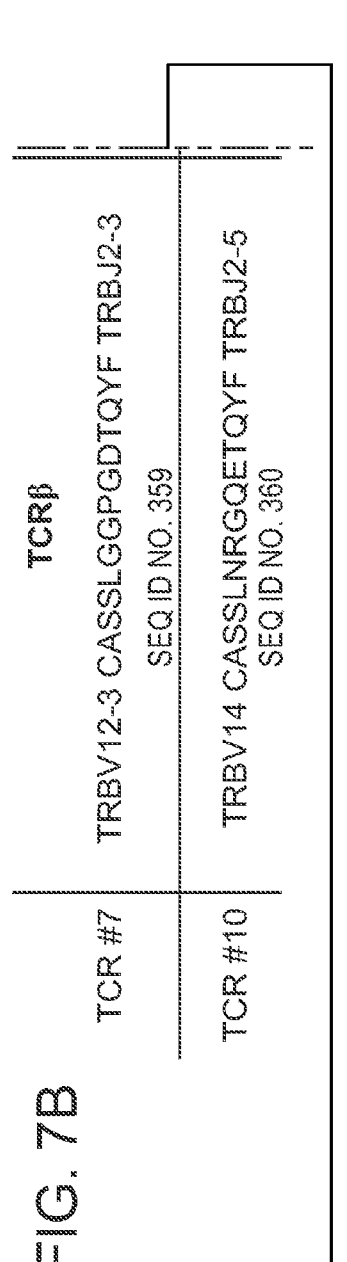

Example 10: Identification of Epitopes Targeted by Orphan, Class II-Restricted T Cell Receptors Out of the four TCRs screened on class II libraries (FIG. 7A) with unique TCRβ genes, the immunofluorescence (data not shown) and NGS results suggested three hits (FIG. 7C-FIG. 7J) and FIG. 14A-FIG. 14e). It was sought to (i) confirm the hits using single encoded peptides, and if confirmed, (ii) identify their HLA class II restrictions, and (iii) further fine map long peptides to 15 amino acid sequences.

Figure 7E:
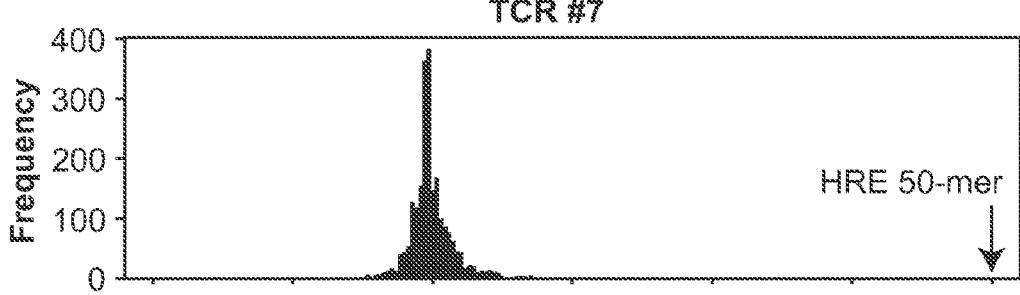
Figure 14A:
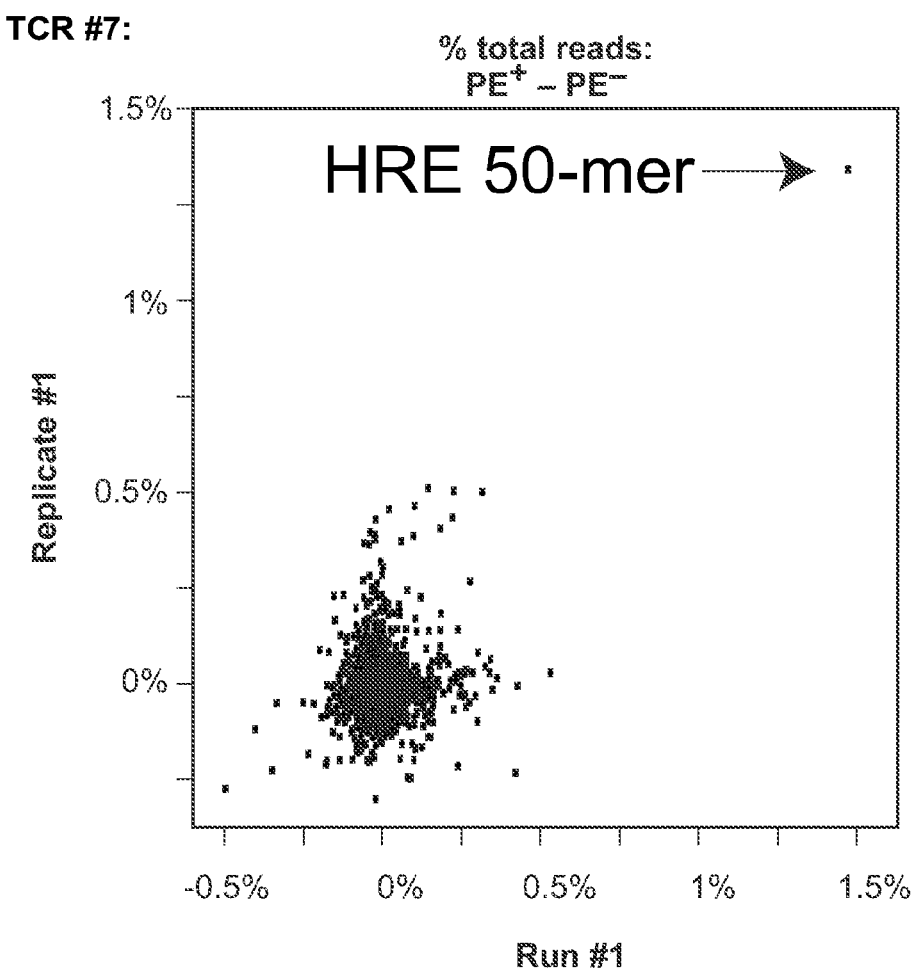

For TCR #7, HREADAQTFAATHNP-WASQAGCLSDVLYNTRHRERLGYNSKFYSPCAQYF (SEQ ID NO. 690) was identified from the CMV UL86 protein as the top hit using the tiled genomic library (FIG. 7C), with a z-score of 19.7 (FIG. 7D). Replication of the second round of screening showed similar results (FIG. 14A). It was confirmed that the HRE 50-mer stimulated TCR #7-expressing T cells, and found that recognition was restricted by HLA-DRB1*04:01 (FIG. 7I). Within the HRE 50-mer, the 15 amino acid peptide AQTFAATHNPWASQA (SEQ ID NO. 691) was the top ranked peptide predicted (by NetMHCIIpan 4.0 (Reynisson et al., 2020 J. Proteome Res., 19:2304-2315)) to bind to HLA-DRB1*04:01 (FIG. 7G), with the HLA binding core (Reynisson et al., 2020 J. Proteome Res., 19:2304-2315) predicted to be FAATH-NPWA. It was confirmed that AQTFAATHNPWASQA (SEQ ID NO. 691) stimulated TCR #7-expressing T cells when presented on HLA-DRB1*04:01 (FIG. 7I and FIG. 14B-FIG. 14C).

Figures 14D, 14E, 14F:
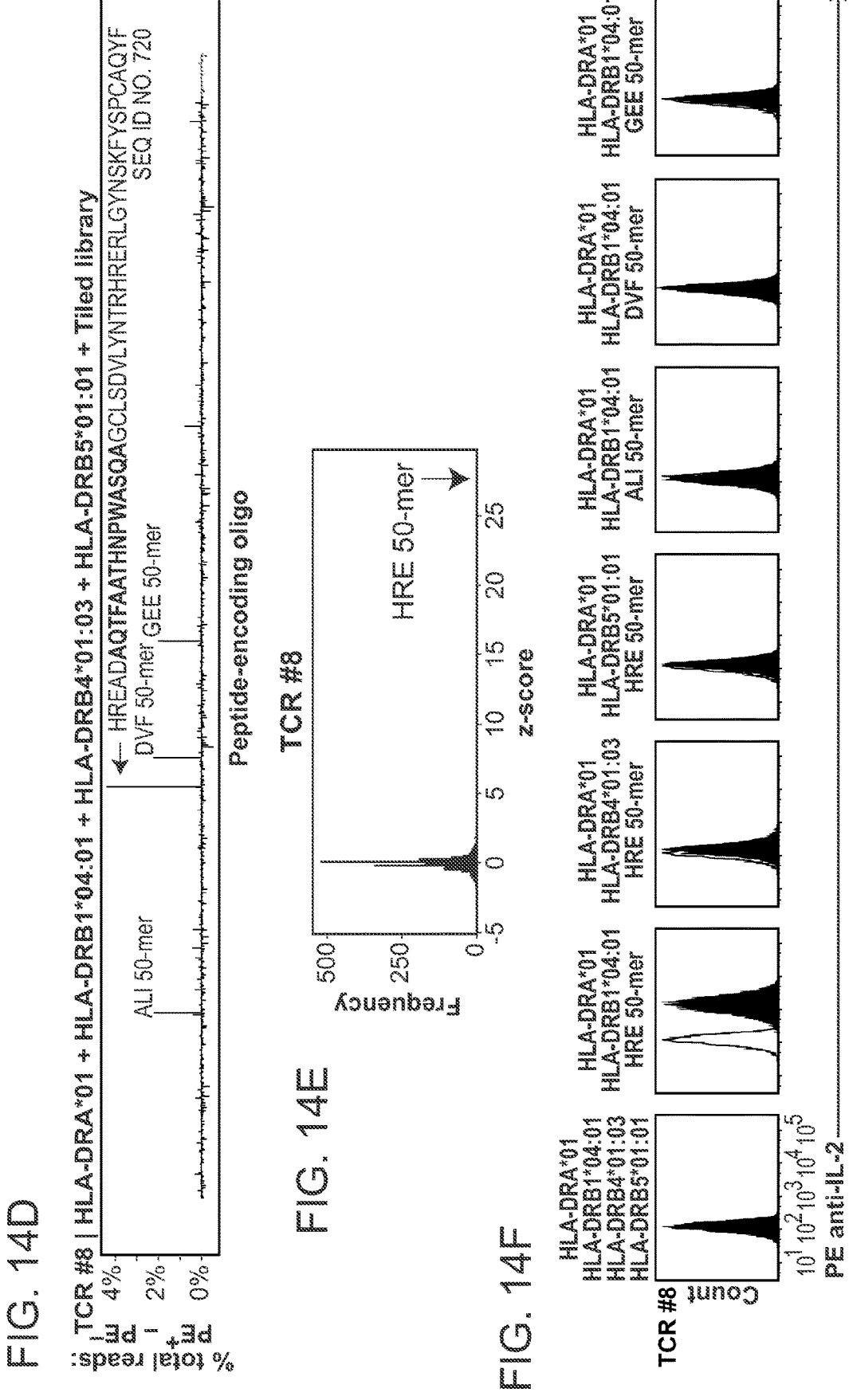
Figure 14G:
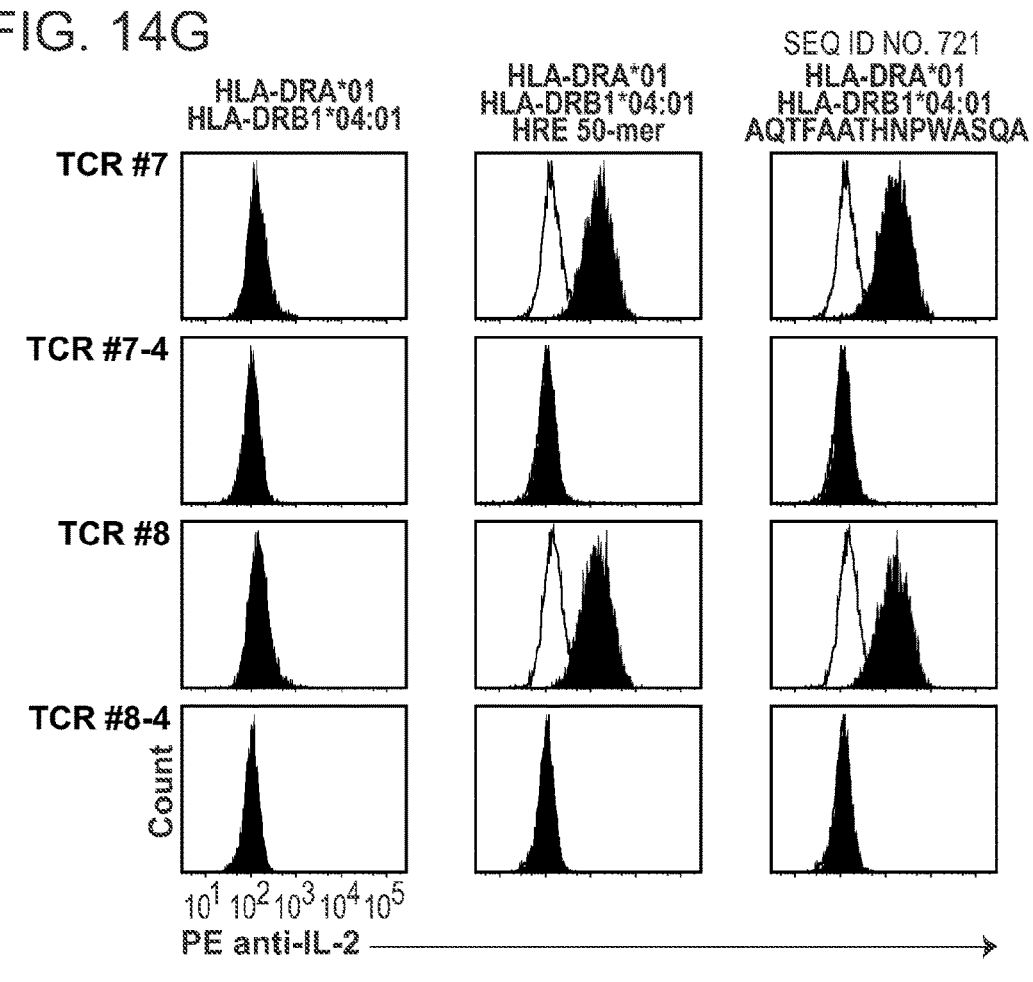

For TCR #8, the same HRE 50-mer as the top hit was identified (FIG. 14D-FIG. 14F). This is not unexpected given sequence similarity between TCR #7 and TCR #8: i.e. both of the TCRβ and TCRα use the same V and J segments, and the TCRβ CDR3s (complementarity determining regions) differ by only one amino acid. In addition, 13 of 27 (48%) of the individuals with TCR #7-expressing T cells in peripheral blood also had TCRβ #8-expressing T cells (Emerson et al., 2017 Nat. Genet., 49:659-665). It was confirmed that TCR #8 was similarly restricted by HLA-DRB1*04:01 (FIG. 14F), and that AQTFAATHNPWASQA (SEQ ID NO. 691) stimulated TCR #8-expressing T cells when presented on HLA-DRB1*04:01 (FIG. 14G).

Of note, TCR #7 and TCR #8 use the TRBV12-3 gene segment. TCRβ sequencing (Emerson et al., 2017 Nat. Genet., 49:659-665; Tanno et al., 2020 Proc. Natl. Acad. Sci. U.S.A., 117:532-540) had been unable to resolve TRBV12-3 from TRBV12-4. In contrast to T cells expressing TCR #7 or TCR #8, T cells expressing TCRs with the corresponding TRBV12-4-containing sequences (TCR #7-4 and TCR #8-4) were not activated by the HRE 50-mer nor AQTFAATH-NPWASQA (SEQ ID NO. 691) (FIG. 14G). This suggests that TRBV12-3 CASSLGGPGDTQYF TRBJ2-3 (SEQ ID NO. 692) and TRBV12-3 CASSLGGAGDTQYF TRBJ2-3 (SEQ ID NO. 693) are the TCRβ driving the statistical associations with CMV seropositivity (Emerson et al., 2017 Nat. Genet., 49:659-665), resolving the gene segment ambiguities.

Figure 7F:
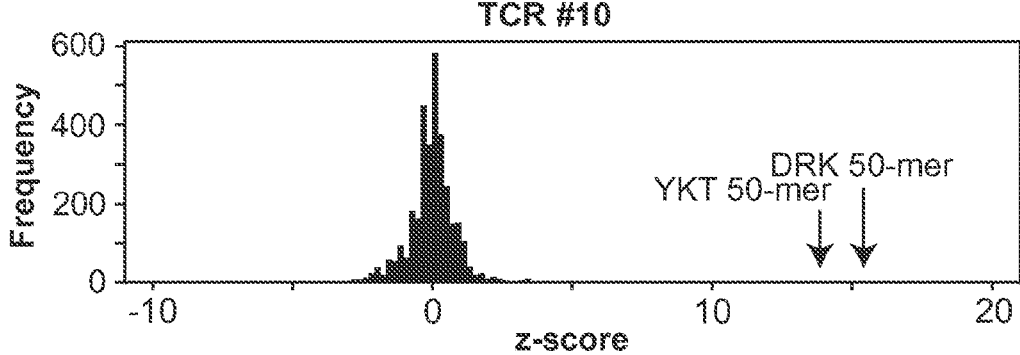
Figures 7I, 7J:
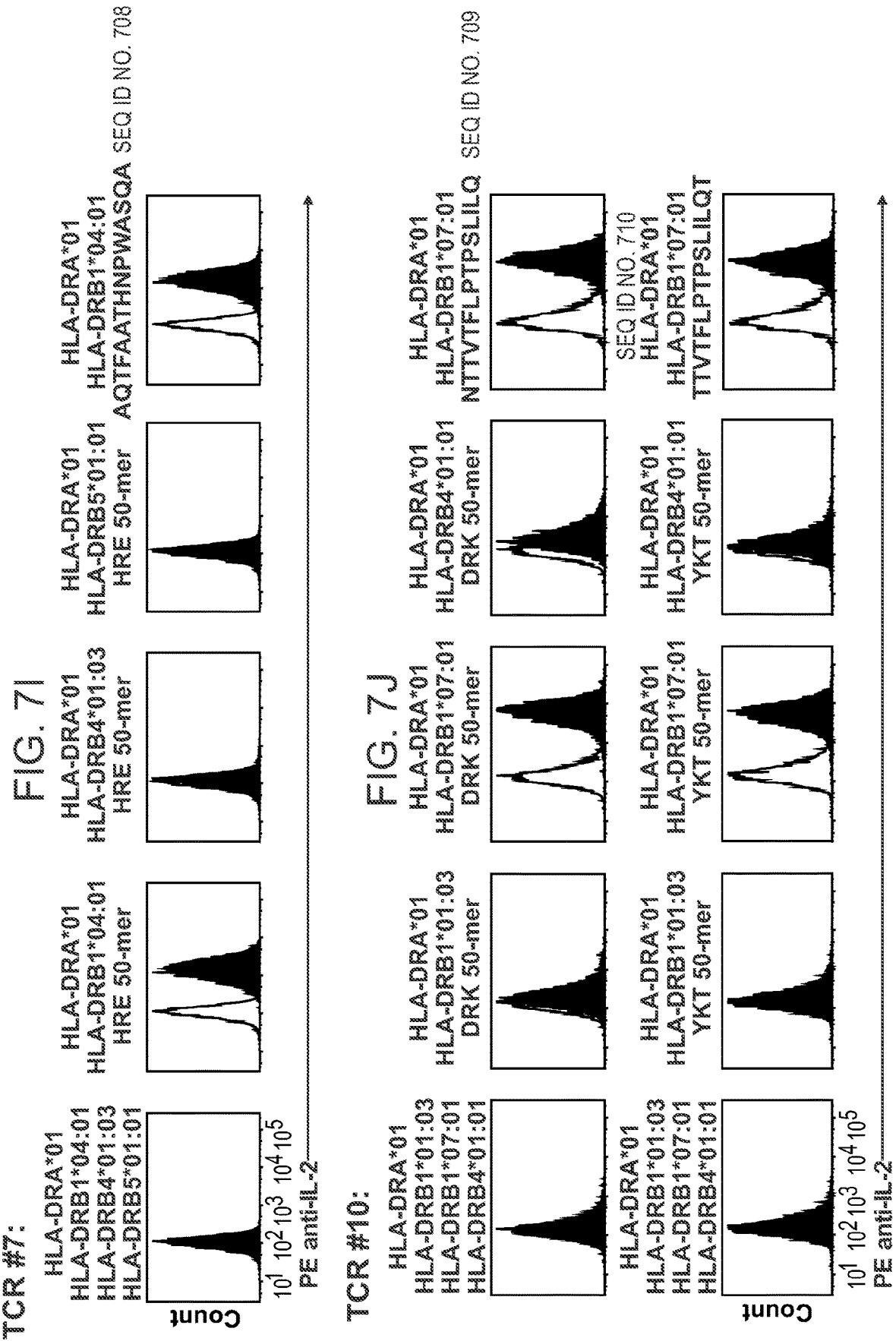
Figure 14H:
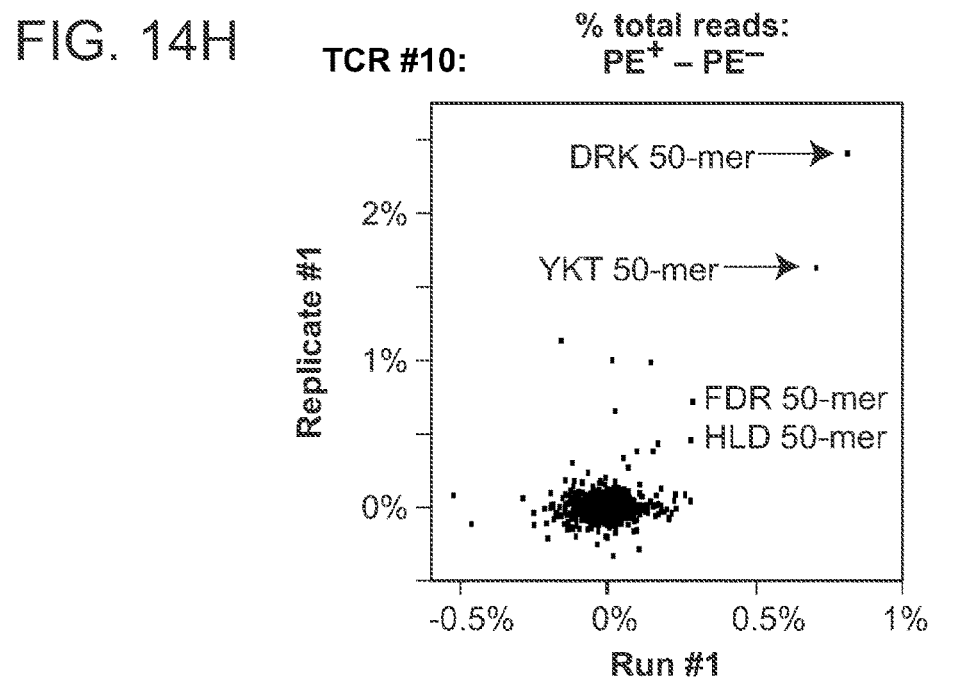
Figure 14I:
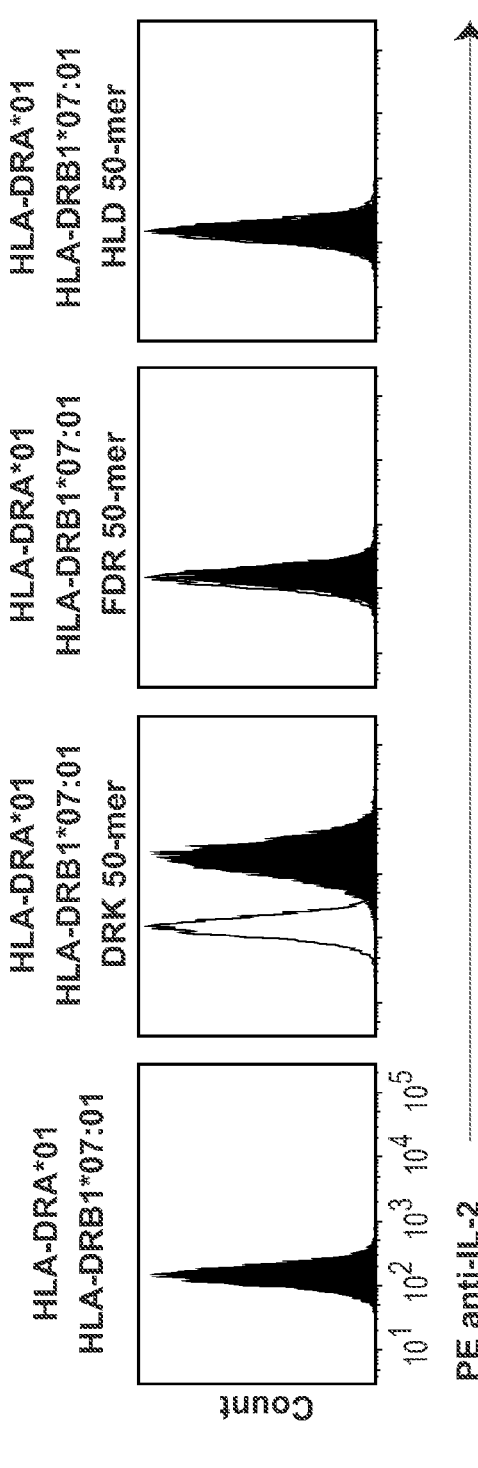
Figures 14J, 14K:
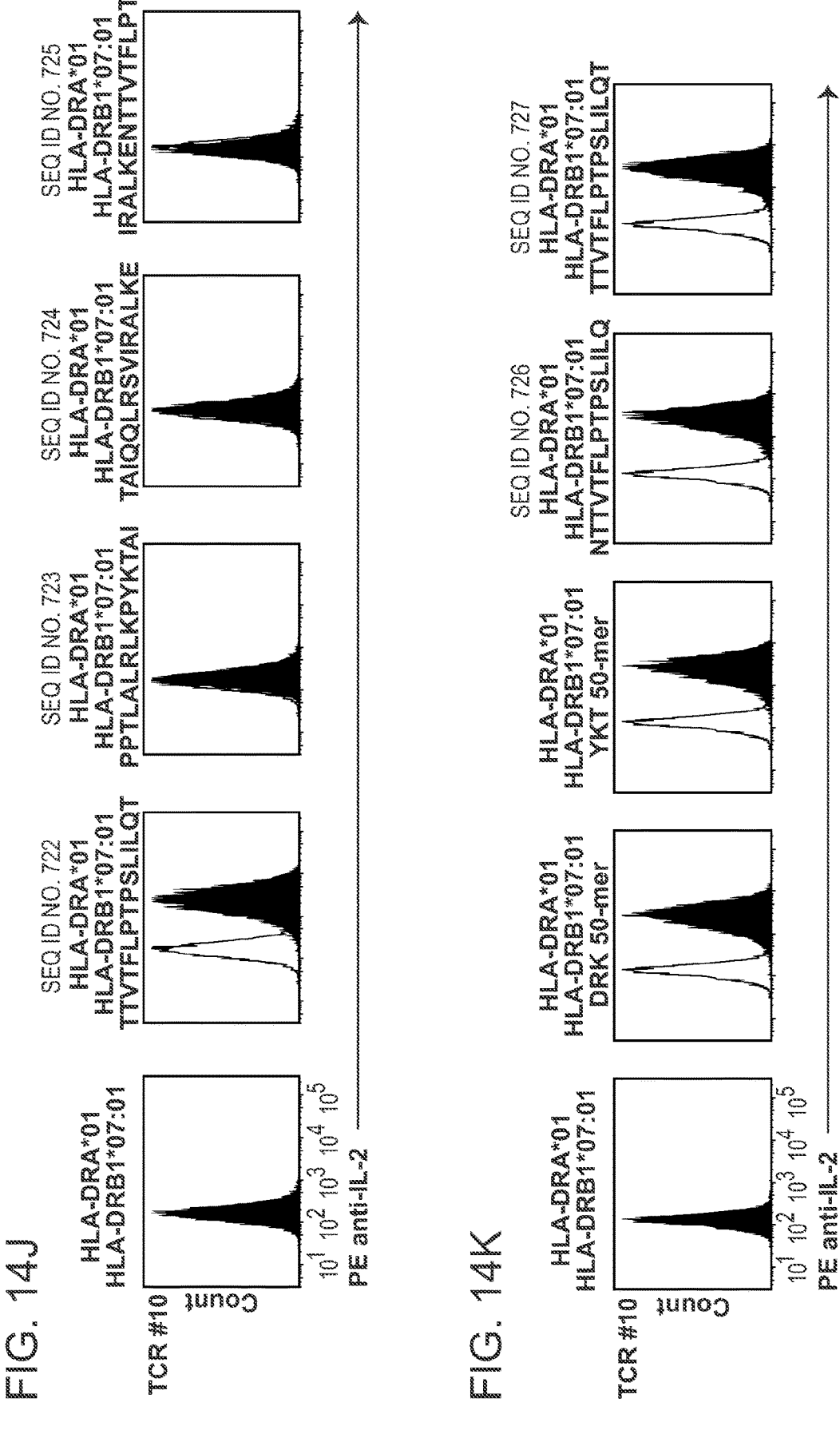
Figure 14L:
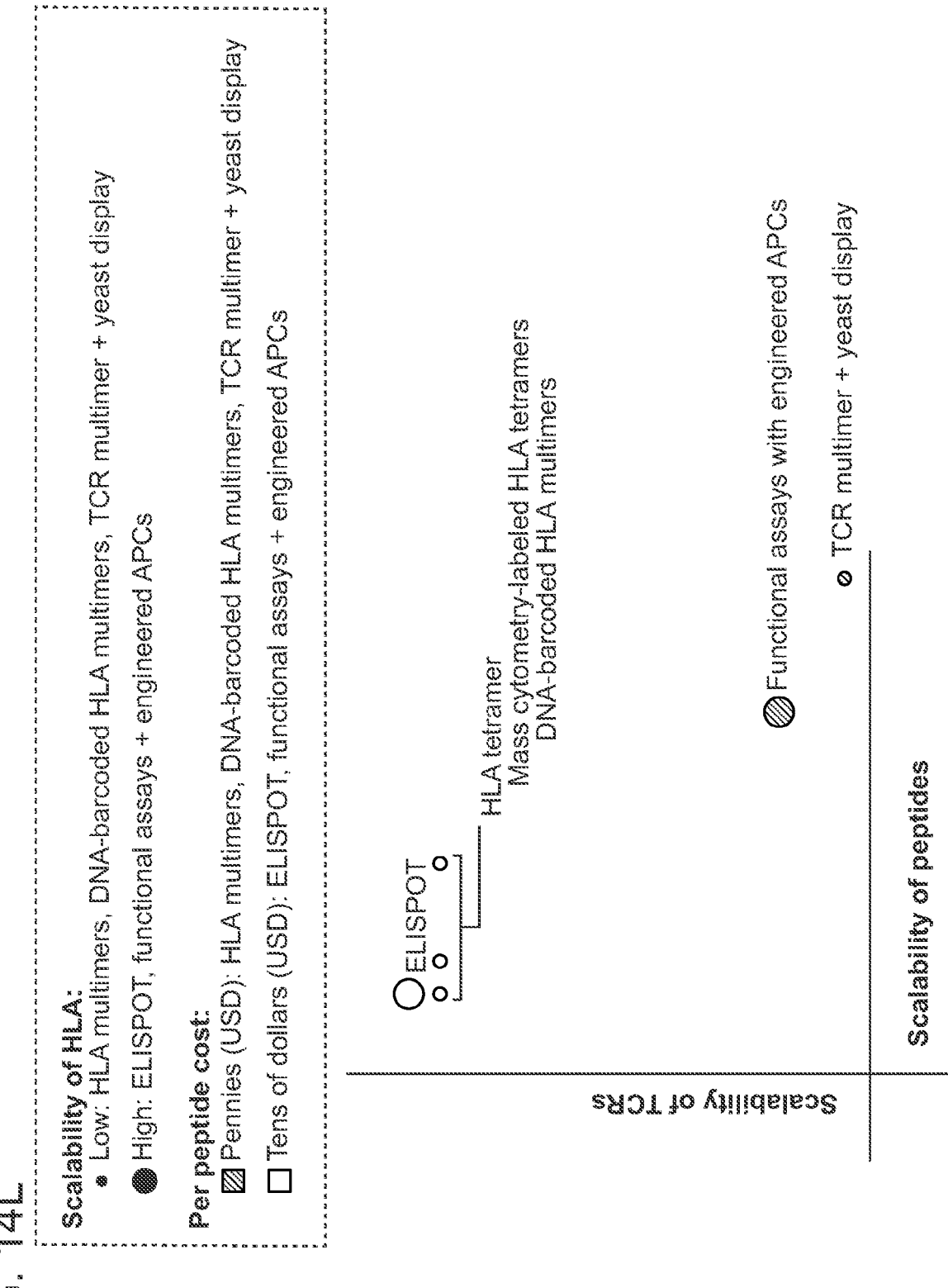

For TCR #10, DRKTRLSEPPTLALRLKPYKTAI-QQLRSVIRALKENTTVTFLPTPSLILQ (SEQ ID NO. 694) was identified from the CMV UL44 protein as the top hit using the tiled genomic library (FIG. 7E), with a z-score of 15.7 (FIG. 7F). The second highest-scoring hit (z-score of 13.7) was the adjacent 50-mer, YKTAIQQLRSVIRALK-ENTTVTFLPTPSLILQTVRSHCVSKITFNSSCLY (SEQ ID NO. 695) (FIG. 7E and FIG. 7F), which overlaps the DRK 50-mer by 32 amino acids (FIG. 7E and FIG. 7H). This suggested that the minimal epitope was in the overlap. Replication of the second round of screening showed similar results (FIG. 14H). It was confirmed that the DRK and YKT 50-mers stimulated TCR #10-expressing T cells, and found that recognition was restricted by HLA-DRB1*07:01 (FIG. 7J and FIG. 14I). Within the DRK 50-mer, the 15 amino acid peptide NTTVTFLPTPSLILQ (SEQ ID NO. 696) was the top ranked peptide predicted (by NetMHCIIpan 4.0 (Reynisson et al., 2020 J. Proteome Res., 19:2304-2315)) to bind to HLA-DRB1*07:01 (FIG. 7G); and within the YKT 50-mer, the overlapping peptide TTVTFLPTPSLILQT (SEQ ID NO. 697) was the top ranked peptide (FIG. 7G); with the HLA binding core (Reynisson et al., 2020 J. Proteome Res., 19:2304-2315) of both predicted to be FLPTPSLIL. It was confirmed that NTTVTFLPTPSLILQ (SEQ ID NO. 696) and TTVTFLPTPSLILQT (SEQ ID NO. 697) stimulated TCR #10-expressing T cells when presented on HLA-DRB1*07:01 (FIG. 7J and Supplementary FIG. 14J-FIG. 14K).

Altogether, epitopes for three of four TCRs with unique TCRβ genes that were screened on class II libraries were identified. For each epitope, the HLA class II restriction and fine map 50-mers to 15-mers was determined using HLA II binding prediction. One previous report had described peptides containing the FAATHNPWA (SEQ ID NO. 698) core (e.g. AQTFAATHNPWASQA (SEQ ID NO. 691) that stimulate CD4+ T cells in several individuals (Vita et al., 2019 Nucleic Acids Res. 47:D339-D343; Fuhrmann et al., 2008 J. Infect. Dis. 197:1455-1458) consistent with the associated TCRβ genes being public. Class II epitopes containing the FLPTPSLIL (SEQ ID NO. 699) core (e.g. TTVT-FLPTPSLILQT (SEQ ID NO. 697)) have not been previously described (Vita et al., 2019 Nucleic Acids Res. 47:D339-D343). Along with the class I screening data above, out of the ten CD8+ or CD4+ T cell receptors with unique TCRβ genes, we identified CMV epitopes for seven, including both known and previously undescribed epitopes.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying epitopes that activate T cells, comprising:

providing a plurality of antigen presenting cells (APCs), wherein each APC expresses a) a nucleic acid encoding a candidate epitope or a nucleic acid encoding a peptide that may be processed into a candidate epitope, b) a nucleic acid encoding an HLA molecule, and c) a nucleic acid encoding an anti-cytokine antibody;

mixing the plurality of APCs with a plurality of T cells, wherein each T cell expresses a T cell receptor (TCR) on its surface, wherein binding of the TCR on the T cells to the candidate epitope activates the T cells, wherein the activated T cells secrete a cytokine that binds to the anti-cytokine antibody; and identifying APCs bound to the cytokine; and sequencing the nucleic acid encoding the candidate epitope contained in the APCs to which the cytokine is bound.

2. The method of claim 1, wherein the APCs are professional APCs.

3. The method of claim 2, wherein the professional APCs are dendritic cells, macrophages, monocytes or B cells.

4. The method of claim 1, wherein the APCs are non-professional APCs.

5. The method of claim 1, wherein the APCs are human APCs.

6. The method of claim 1, wherein the candidate epitope is an infectious disease-associated candidate epitope, an autoimmune disease-associated candidate epitope, or a tumor-associated candidate epitope, or wherein the APCs are non-professional APCs of an immortalized cell line; or wherein the HLA molecule is a class I HLA molecule.

7. The method of claim 1, wherein the HLA molecule is a class II HLA molecule.

8. The method of claim 1, wherein the anti-cytokine antibody is an anti-IL-2 antibody, or wherein the anti-cytokine antibody is an anti-INF-γ antibody.

9. The method of claim 1, wherein the T cells comprise CD8$^+$ T cells.

10. The method of claim 1, wherein the T cells comprise CD4$^+$ T cells.

11. The method of claim 1, wherein the identifying comprises contacting the APCs after contact with the plurality of T cells with a detectable label that binds the cytokine; and detecting the label.

12. The method of claim 11, wherein the detectable label comprises a fluorescently-labeled, secondary anti-cytokine antibody.

13. The method of claim 1, further comprising sorting labeled APCs from non-labeled APCs that do not bear a T cell-activating epitope.

14. The method of claim 13, wherein the sorting is conducted by magnetic or flow cytometry; or wherein the sequencing is conducted using next generation sequencing.

15. The method of claim 1, wherein the plurality of APCs comprises a library of APCs that expresses a library of the candidate epitopes.

16. The method of claim 1, wherein the candidate epitope is 8-24 amino acids in length, or wherein the candidate epitope is 8-15 amino acids in length, or wherein the candidate epitope is 8-12 amino acids in length.

17. A modified APC, wherein the modified APC expresses a) an exogenous nucleic acid encoding a candidate epitope or an exogenous nucleic acid encoding a peptide that may be processed into a candidate epitope, b) an exogenous nucleic acid encoding an HLA molecule, and c) an exogenous nucleic acid encoding an anti-cytokine antibody.

18. The modified APC of claim 17, which is a professional APC.

19. The modified APC of claim 18, wherein the professional APC is a dendritic cell, macrophage, monocyte or a B cell.

20. The modified APC of claim 17, wherein the APC is a non-professional APC.

21. The modified APC of claim 20, wherein the non-professional APC is an immortalized cell line.

22. The modified APC of claim 17, wherein the APC is a human APC; or wherein the candidate epitope is an infectious disease-associated epitope, an autoimmune disease-associated epitope, or a tumor-associated epitope; or wherein the HLA molecule is a class I HLA molecule.

23. The modified APC of claim 17, wherein the HLA molecule is a class II HLA molecule.

24. The modified APC of claim 17, wherein the anti-cytokine antibody is an anti-IL-2 antibody, or wherein the anti-cytokine antibody is an anti-IFN-γ antibody.

25. A library of APCs of claim 17, wherein respective APCs comprise different nucleic acids that encode a different candidate epitope, thereby representing a library of candidate epitopes expressed by the library of APCs.

26. The library of claim 25, wherein the nucleic acids encoding the different candidate epitopes are obtained from a genomic library of candidate epitopes.

* * * * *

SEQUENCE LISTING

<160> NUMBER OF SEQ ID NOS: 777

<210> SEQ ID NO 1
<211> LENGTH: 1611

<212> TYPE: DNA
<213> ORGANISM: Homo sapiens

<400> SEQUENCE: 1

```
gagaagccaa tcagtgtcgt cgcggtcgct gttctaaagt ccgcacgcac ccaccgggac      60
tcagattctc cccagacgcc gaggatggcc gtcatggcgc cccgaacccct cctcctgcta     120 ctctcggggg ccctggccct gacccagacc tgggcgggct cccactccat gaggtatttc     180
ttcacatccg tgtcccggcc cggccgcggg agcccccgct tcatcgccgt gggctacgtg     240
gacgacacgc agttcgtgcg gttcgacagc gacgccgcga gccagaagat ggagccgcgg     300
gcgccgtgga tagagcagga ggggccggag tattgggacc aggagacacg gaatatgaag     360
gcccactcac agactgaccg agcgaacctg gggaccctgc gcggctacta caaccagagc     420
gaggacggtt ctcacaccat ccagataatg tatggctgcg acgtggggcc ggacgggcgc     480
ttcctccgcg ggtaccggca ggacgcctac gacggcaagg attacatcgc cctgaacgag     540
gacctgcgct cttggaccgc ggcggacatg gcagctcaga tcaccaagcg caagtgggag     600
gcggtccatg cggcggagca gcggagagtc tacctggagg ccggtgcgt ggacgggctc     660 cgcagatacc tggagaacgg gaaggagacg ctgcagcgca cggacccccc caagacacat     720
atgacccacc accccatctc tgaccatgag gccaccctga ggtgctgggc cctgggcttc     780
taccctgcgg agatcacact gacctggcag cgggatgggg aggaccagac ccaggacacg     840
gagctcgtgg agaccaggcc tgcaggggat ggaaccttcc agaagtgggc ggctgtggtg     900
gtgccttctg agaggagca gagatacacc tgccatgtgc agcatgaggg tctgcccaag     960
cccctcaccc tgagatggga gctgtcttcc cagcccacca tccccatcgt gggcatcatt    1020
gctggcctgg ttctccttgg agctgtgatc actggagctg tggtcgctgc cgtgatgtgg    1080
aggaggaaga gctcagatag aaaaggaggg agttacactc aggctgcaag cagtgacagt    1140
gcccagggct ctgatgtgtc tctcacagct tgtaaagtgt gagacagctg ccttgtgtgg    1200
gactgagagg caagagttgt tcctgccctt ccctttgtga cttgaagaac cctgactttg    1260
tttctgcaaa ggcacctgca tgtgtctgtg ttcgtgtagg cataatgtga ggaggtgggg    1320
agagcacccc accccatgt ccaccatgac cctcttccca cgctgacctg tgctccctct    1380
ccaatcatct ttcctgttcc agagaggtgg ggctgaggtg tctccatctc tgtctcaact    1440
tcatggtgca ctgagctgta acttcttcct tccctattaa aattagaacc tgagtataaa    1500
tttactttct caaattcttg ccatgagagg ttgatgagtt aattaaagga gaagattcct    1560
aaaatttgag agacaaaatt aatggaacgc atgagaacct ccagagtcc a              1611
```

<210> SEQ ID NO 2
<211> LENGTH: 365
<212> TYPE: PRT
<213> ORGANISM: Homo sapiens

<400> SEQUENCE: 2

```
Met Ala Val Met Ala Pro Arg Thr Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60
```

-continued

```
Ala Ser Gln Lys Met Glu Pro Arg Ala Pro Trp Ile Glu Gln Glu Gly
65              70              75                  80

Pro Glu Tyr Trp Asp Gln Glu Thr Arg Asn Met Lys Ala His Ser Gln
                85              90                  95

Thr Asp Arg Ala Asn Leu Gly Thr Leu Arg Gly Tyr Tyr Asn Gln Ser
            100             105             110

Glu Asp Gly Ser His Thr Ile Gln Ile Met Tyr Gly Cys Asp Val Gly
        115             120             125

Pro Asp Gly Arg Phe Leu Arg Gly Tyr Arg Gln Asp Ala Tyr Asp Gly
        130             135             140

Lys Asp Tyr Ile Ala Leu Asn Glu Asp Leu Arg Ser Trp Thr Ala Ala
145             150             155                 160

Asp Met Ala Ala Gln Ile Thr Lys Arg Lys Trp Glu Ala Val His Ala
            165             170             175

Ala Glu Gln Arg Arg Val Tyr Leu Glu Gly Arg Cys Val Asp Gly Leu
            180             185             190

Arg Arg Tyr Leu Glu Asn Gly Lys Glu Thr Leu Gln Arg Thr Asp Pro
            195             200             205

Pro Lys Thr His Met Thr His His Pro Ile Ser Asp His Glu Ala Thr
        210             215             220

Leu Arg Cys Trp Ala Leu Gly Phe Tyr Pro Ala Glu Ile Thr Leu Thr
225             230             235                 240

Trp Gln Arg Asp Gly Glu Asp Gln Thr Gln Asp Thr Glu Leu Val Glu
            245             250             255

Thr Arg Pro Ala Gly Asp Gly Thr Phe Gln Lys Trp Ala Ala Val Val
            260             265             270

Val Pro Ser Gly Glu Glu Gln Arg Tyr Thr Cys His Val Gln His Glu
        275             280             285

Gly Leu Pro Lys Pro Leu Thr Leu Arg Trp Glu Leu Ser Ser Gln Pro
        290             295             300

Thr Ile Pro Ile Val Gly Ile Ile Ala Gly Leu Val Leu Leu Gly Ala
305             310             315                 320

Val Ile Thr Gly Ala Val Val Ala Ala Val Met Trp Arg Arg Lys Ser
            325             330             335

Ser Asp Arg Lys Gly Gly Ser Tyr Thr Gln Ala Ala Ser Ser Asp Ser
            340             345             350

Ala Gln Gly Ser Asp Val Ser Leu Thr Ala Cys Lys Val
            355             360             365
```

<210> SEQ ID NO 3
<211> LENGTH: 1536
<212> TYPE: DNA
<213> ORGANISM: Homo sapiens

<400> SEQUENCE: 3

```
agagtctcct cagacgccga gatgctggtc atggcgcccc gaaccgtcct cctgctgctc      60
tcggcggccc tggccctgac cgagacctgg gccggctccc actccatgag gtatttctac     120
acctccgtgt cccggcccgg ccgcggggag ccccgcttca tctcagtggg ctacgtggac     180
gacacccagt tcgtgaggtt cgacagcgac gccgcgagtc cgagagagga gccgcgggcg     240
ccgtggatag agcaggaggg gccggagtat tgggaccgga acacacagat ctacaaggcc     300
caggcacaga ctgaccgaga gagcctgcgg aacctgcgcg gctactacaa ccagagcgag     360
gccgggtctc acaccctcca gagcatgtac ggctgcgacg tggggccgga cgggcgcctc     420
```

-continued

```
ctccgcgggc atgaccagta cgcctacgac ggcaaggatt acatcgccct gaacgaggac      480
ctgcgctcct ggaccgccgc ggacacggcg gctcagatca cccagcgcaa gtgggaggcg      540
gcccgtgagg cggagcagcg gagagcctac ctggagggcg agtgcgtgga gtggctccgc      600
agatacctgg agaacgggaa ggacaagctg gagcgcgctg accccccaaa gacacacgtg      660
acccaccacc ccatctctga ccatgaggcc accctgaggt gctgggccct gggtttctac      720
cctgcggaga tcacactgac ctggcagcgg gatggcgagg accaaactca ggacactgag      780
cttgtggaga ccagaccagc aggagataga accttccaga agtgggcagc tgtggtggtg      840
ccttctggag aagagcagag atacacatgc catgtacagc atgaggggct gccgaagccc      900
ctcaccctga gatgggagcc gtcttcccag tccaccgtcc ccatcgtggg cattgttgct      960
ggcctggctg tcctagcagt tgtggtcatc ggagctgtgg tcgctgctgt gatgtgtagg     1020
aggaagagtt caggtggaaa aggagggagc tactctcagg ctgcgtgcag cgacagtgcc     1080
cagggctctg atgtgtctct cacagcttga aaagcctgag acagctgtct tgtgagggac     1140
tgagatgcag gatttcttca cgcctcccct ttgtgacttc aagagcctct ggcatctctt     1200
tctgcaaagg cacctgaatg tgtctgcgtc cctgttagca taatgtgagg aggtggagag     1260
acagcccacc cttgtgtcca ctgtgacccc tgttcccatg ctgacctgtg tttcctcccc     1320
agtcatcttt cttgttccag agaggtgggg ctggatgtct ccatctctgt ctcaacttta     1380
cgtgcactga gctgcaactt cttacttccc tactgaaaat aagaatctga atataaattt     1440
gttttctcaa atatttgcta tgagaggttg atggattaat taaataagtc aattcctgga     1500
atttgagaga gcaaataaag acctgagaac cttcca                              1536
```

<210> SEQ ID NO 4
<211> LENGTH: 362
<212> TYPE: PRT
<213> ORGANISM: Homo sapiens

<400> SEQUENCE: 4

```
Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
            115                 120                 125

Pro Asp Gly Arg Leu Leu Arg Gly His Asp Gln Tyr Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175
```

-continued

```
Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
            195                 200                 205

Pro Lys Thr His Val Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360
```

<210> SEQ ID NO 5
<211> LENGTH: 1586
<212> TYPE: DNA
<213> ORGANISM: Homo sapiens

<400> SEQUENCE: 5

```
tccgcagtcc cggttctaaa gtccccagtc acccacccgg actcacattc tccccagagg      60
ccgagatgcg ggtcatggcg ccccgagccc tcctcctgct gctctcggga ggcctggccc     120
tgaccgagac ctgggcctgc tcccactcca tgaggtattt cgacaccgcc gtgtcccggc     180
ccggccgcgg agagccccgc ttcatctcag tgggctacgt ggacgacacg cagttcgtgc     240
ggttcgacag cgacgccgcg agtccgagag gggagccgcg ggcgccgtgg gtggagcagg     300
aggggccgga gtattgggac cgggagacac agaactacaa gcgccaggca caggctgacc     360
gagtgagcct gcggaacctg cgcggctact acaaccagag cgaggacggg tctcacaccc     420
tccagaggat gtatggctgc gacctggggc ccgacgggcg cctcctccgc gggtatgacc     480
agtccgccta cgacggcaag gattacatcg ccctgaacga ggacctgcgc tcctggaccg     540
ccgcggacac cgcggctcag atcacccagc gcaagttgga ggcggccgt gcggcggagc      600 agctgagagc ctacctggag ggcacgtgcg tggagtggct ccgcagatac ctggagaacg     660
ggaaggagac gctgcagcgc gcagaacccc caaagacaca cgtgacccac cacccctct       720 ctgaccatga ggccaccctg aggtgctggg ccctgggctt ctaccctgcg gagatcacac     780
tgacctggca gcgggatggg gaggaccaga cccaggacac cgagcttgtg agaccaggc      840 cagcaggaga tggaaccttc cagaagtggg cagctgtggt ggtgccttct ggacaagagc     900
agagatacac cgtgccatat cagcacgagg ggctgcaaga gccctcacc ctgagctggg      960 agccatcttc ccagcccacc atccccatca tgggcatcgt gctggcctg gctgtcctgg     1020 ttgtcctagc tgtccttgga gctgtggtca ccgctatgat gtgtaggagg aagagctcag    1080
```

-continued

```
gtggaaaagg agggagctgc tctcaggctg cgtgcagcaa cagtgcccag ggctctgatg    1140
agtctctcat cacttgtaaa gcctgagaca gctgcctgtg tgggactgag atgcaggatt    1200
tcttcacacc tctcctttgt gacttcaaga gcctctggca tctctttctg caaaggcgtc    1260
tgaatgtgtc tgcgttcctg ttagcataat gtgaggaggt ggagagacag cccacccccg    1320
tgtccaccgt gacccctgtc cccacactga cctgtgttcc ctccccgatc atctttcctg    1380
ttccagagag gtggggctgg atgtctccat ctctgtctca aattcatggt gcactgagct    1440
gcaacttctt acttccctaa tgaagttaag aacctgaata taaatttgtg ttctcaaata    1500
tttgctatga agcgttgatg gattaattaa ataagtcaat tcctagaagt tgagagagca    1560
aataaagacc tgagaacctt ccagaa    1586
```

```
<210> SEQ ID NO 6
<211> LENGTH: 366
<212> TYPE: PRT
<213> ORGANISM: Homo sapiens

<400> SEQUENCE: 6

Met Arg Val Met Ala Pro Arg Ala Leu Leu Leu Leu Ser Gly Gly
1               5                   10                  15

Leu Ala Leu Thr Glu Thr Trp Ala Cys Ser His Ser Met Arg Tyr Phe
                20                  25                  30

Asp Thr Ala Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Asn Tyr Lys Arg Gln Ala Gln
                85                  90                  95

Ala Asp Arg Val Ser Leu Arg Asn Leu Arg Gly Tyr Tyr Asn Gln Ser
                100                 105                 110

Glu Asp Gly Ser His Thr Leu Gln Arg Met Tyr Gly Cys Asp Leu Gly
            115                 120                 125

Pro Asp Gly Arg Leu Leu Arg Gly Tyr Asp Gln Ser Ala Tyr Asp Gly
        130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Leu Glu Ala Ala Arg Ala
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu Pro
        195                 200                 205

Pro Lys Thr His Val Thr His His Pro Leu Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Gln Glu Gln Arg Tyr Thr Cys His Met Gln His Glu
```

```
              275                280                285

Gly Leu Gln Glu Pro Leu Thr Leu Ser Trp Glu Pro Ser Ser Gln Pro
    290                295                300

Thr Ile Pro Ile Met Gly Ile Val Ala Gly Leu Ala Val Leu Val Val
305                310                315                320

Leu Ala Val Leu Gly Ala Val Val Thr Ala Met Met Cys Arg Arg Lys
                325                330                335

Ser Ser Gly Gly Lys Gly Gly Ser Cys Ser Gln Ala Ala Cys Ser Asn
                340                345                350

Ser Ala Gln Gly Ser Asp Glu Ser Leu Ile Thr Cys Lys Ala
        355                360                365

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caccgaggtc agtgtgatct ccgca                                      25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaactgcgga gatcacactg acctc                                      25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 13
caccgcggct actacaacca gagcg                                          25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaaccgctct ggttgtagta gccgc                                          25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccggctgg tacacggcag ggtca                                          25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaactgaccc tgccgtgtac cagcc                                          25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caccgcgtag aactggactt gacag                                          25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaacctgtca agtccagttc tacgc                                          25

<210> SEQ ID NO 19
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caggctactg ctgaattaga tttaaaatcc atagacctca tgtctagcac agt          53

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggattttaaa tctaattcag cagtagcctg gagcaacaaa tctgactttg ca           52

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
accataaaat tgtacctggc atcgaaagtg gttgcggggg ttc                     43

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcgatgccag gtacaatttt atggtctctc ggagaatgac gagtgga                 47

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgatgtgcaa ctcctgtctt gcattg                                        26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acatgtgcaa ctcctgtctt gcattg                                        26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gccaatgcaa ctcctgtctt gcattg                                          26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tagcttgcaa ctcctgtctt gcattg                                          26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggctaggcaa ctcctgtctt gcattg                                          26

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgatgtccac atagcgtaaa aggagca                                         27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acatgtccac atagcgtaaa aggagca                                         27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gccaatccac atagcgtaaa aggagca                                         27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
```

-continued

```
gatcagccac atagcgtaaa aggagca                                          27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggctagccac atagcgtaaa aggagca                                          27

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagcttaccg cctacttcct gtacca                                           26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggctagaccg cctacttcct gtacca                                           26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgatgtcgta ttttgtggca ttctgc                                          26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gccaatcgta ttttgtggca ttctgc                                          26

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caccgcgtca catggctgtg caatg                                           25
```

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaaccattgc acagccatgt gacgc                                          25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caccgcgaag cgcgcgtact cctcc                                          25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aaacggagga gtacgcgcgc ttcgc                                          25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caccgaatgg gcagtcagtc acaga                                          25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaactctgtg actgactgcc cattc                                          25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caccgaacta cgaggtggcg taccg                                          25

-continued

```
<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaaccggtac gccacctcgt agttc                                        25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caccgaagat gcatctataa ccaag                                        25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaaccttggt tatagatgca tcttc                                        25

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgatgtccac atagcgtaaa aggagca                                      27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acatgtccac atagcgtaaa aggagca                                      27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccaatccac atagcgtaaa aggagca                                      27
```

```
<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cagatcccac atagcgtaaa aggagca                                                27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gatcagccac atagcgtaaa aggagca                                                27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggctagccac atagcgtaaa aggagca                                                27

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggtgtgacca agcaggatct                                                        20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtgaccaagc aggatctgg                                                         19

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgatgtaccg cctacttcct gtacca                                                 26

<210> SEQ ID NO 56
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acatgtaccg cctacttcct gtacca                                    26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tagcttaccg cctacttcct gtacca                                    26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggctagaccg cctacttcct gtacca                                    26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgatgtcgta ttttgtggca ttctgc                                    26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gccaatcgta ttttgtggca ttctgc                                    26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tagcttcgta ttttgtggca ttctgc                                    26

<210> SEQ ID NO 62
<211> LENGTH: 26
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gccaatcgta ttttgtggca ttctgc                                                26

<210> SEQ ID NO 63
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Tyr Arg Met Gln Leu Leu Ser Cys Ile Ala Leu Ser Leu Ala Leu
1               5                   10                  15

Val Thr Asn Ser Gln Val Gln Leu Val Gln Ser Gly Gly Gly Trp Gln
            20                  25                  30

Pro Gly Arg Ser Leu Arg Leu Ser Cys Ala Ala Ser Gly Phe Thr Phe
        35                  40                  45

Ser Asn Tyr Ala Met Asn Trp Val Arg Gln Ala Pro Gly Lys Gly Leu
    50                  55                  60

Glu Trp Val Thr Leu Ile Ser Tyr Asp Gly Ser Gln Lys Tyr Tyr Ala
65                  70                  75                  80

Asp Ser Val Lys Gly Arg Phe Thr Thr Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Ser Thr Thr Leu Gly Ala Phe Asp Val Trp
        115                 120                 125

Gly Gln Gly Thr Met Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr

```
305                  310                  315                  320

Tyr Arg Val Val Ser Val Leu Thr Val Leu His Gln Asp Trp Leu Asn
                325                  330                  335

Gly Lys Glu Tyr Lys Cys Lys Val Ser Asn Lys Ala Leu Pro Ala Pro
                340                  345                  350

Ile Glu Lys Thr Ile Ser Lys Ala Lys Gly Gln Pro Arg Glu Pro Gln
                355                  360                  365

Val Tyr Thr Leu Pro Pro Ser Arg Glu Glu Met Thr Lys Asn Gln Val
        370                  375                  380

Ser Leu Thr Cys Leu Val Lys Gly Phe Tyr Pro Ser Asp Ile Ala Val
385                  390                  395                  400

Glu Trp Glu Ser Asn Gly Gln Pro Glu Asn Asn Tyr Lys Thr Thr Pro
                405                  410                  415

Pro Val Leu Asp Ser Asp Gly Ser Phe Phe Leu Tyr Ser Lys Leu Thr
                420                  425                  430

Val Asp Lys Ser Arg Trp Gln Gln Gly Asn Val Phe Ser Cys Ser Val
                435                  440                  445

Met His Glu Ala Leu His Asn His Tyr Thr Gln Lys Ser Leu Ser Leu
        450                  455                  460

Ser Pro Gly Lys
465

<210> SEQ ID NO 64
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Tyr Arg Met Gln Leu Leu Ser Cys Ile Ala Leu Ser Leu Ala Leu
1               5                   10                  15

Val Thr Asn Ser Ser Tyr Glu Leu Thr Gln Pro Pro Ser Val Ser Val
                20                  25                  30

Ser Pro Gly Gln Thr Ala Arg Ile Thr Cys Ser Gly Asp Ala Leu Pro
        35                  40                  45

Arg Lys Phe Ala Tyr Trp Tyr Gln Gln Lys Ser Gly Gln Ala Pro Val
        50                  55                  60

Met Val Ile Tyr Glu Asp Ser Lys Arg Pro Pro Gly Ile Pro Glu Arg
65                  70                  75                  80

Phe Ser Gly Ser Ser Ser Gly Thr Met Ala Thr Leu Thr Ile Thr Gly
                85                  90                  95

Ala Gln Val Glu Asp Glu Ala Asp Tyr Tyr Cys Tyr Ser Thr Asp Ser
                100                 105                 110

Gly Gly Asp Val Ser Val Phe Gly Gly Gly Thr Lys Leu Thr Val Leu
                115                 120                 125

Gly Gln Pro Lys Ala Ala Pro Ser Val Thr Leu Phe Pro Pro Ser Ser
        130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190
```

-continued

```
Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230

<210> SEQ ID NO 65
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Tyr Arg Met Gln Leu Leu Ser Cys Ile Ala Leu Ser Leu Ala Leu
1               5                   10                  15

Val Thr Asn Ser Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Ala Met Ser Trp Val Arg Gln Ala Pro Gly Lys Gly
        50                  55                  60

Leu Glu Trp Val Ser Ala Ile Ser Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Asp Gly Ser Ser Gly Trp Tyr Val Pro His
            115                 120                 125

Trp Phe Asp Pro Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470
```

```
<210> SEQ ID NO 66
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Tyr Arg Met Gln Leu Leu Ser Cys Ile Ala Leu Ser Leu Ala Leu
1               5                   10                  15

Val Thr Asn Ser Asn Phe Met Leu Thr Gln Pro His Ser Val Ser Glu
            20                  25                  30

Ser Pro Gly Lys Thr Val Thr Ile Ser Cys Thr Arg Ser Ser Gly Ser
        35                  40                  45

Ile Ala Ser Asn Tyr Val Gln Trp Tyr Gln Gln Arg Gly Ser Ser Pro
    50                  55                  60

Thr Thr Val Ile Tyr Glu Asp Asn Gln Arg Pro Ser Gly Val Pro Asp
65                  70                  75                  80

Arg Phe Ser Gly Ser Ile Asp Ser Ser Ser Asn Ser Ala Ser Leu Thr
                85                  90                  95

Ile Ser Gly Met Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
```

-continued

```
        195                 200                 205

Thr Val Ala Pro Thr Glu Cys Ser
    210                 215

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Tyr Arg Met Gln Leu Leu Ser Cys Ile Ala Leu Ser Leu Ala Leu
1               5                   10                  15

Val Thr Asn Ser
            20

<210> SEQ ID NO 68
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230
```

-continued

```
<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Trp His Thr Val Gly Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met Arg Met Ala Thr Pro Leu Leu Met
1               5

<210> SEQ ID NO 71
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atgtacagga tgcaactcct gtcttgcatt gcactaagtc ttgcacttgt cacgaattca      60
caggtacagc ttgtccaatc tgggggtggc tggcaaccag ggcgcagcct gagactttcc     120
tgtgcggcct cagggtttac ttttagtaat tacgcaatga attgggtcag gcaagctccg     180
ggtaaaggtc ttgagtgggt cactctcatc tcatacgatg gtagccagaa atattacgct     240
gacagtgtta agggtaggtt caccacatct cgagataata gtaagaacac cctgtacctt     300
cagatgaaca gtctgcgagc cgaagacacc gctgtttact actgtgcgcg agatagtacc     360
acactcggag cgttcgacgt ttggggacag ggcacgatgg tgaccgtctc aagtgctagc     420
accaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct tgggcaccca gacctacatc     660
tgcaacgtga atcacaagcc cagcaacacc aaggtggaca gaaagttga gcccaaatct     720 tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca aagccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga ggagatgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
```

-continued

```
tccgacggct ccttcttcct ctacagcaag ctcaccgtgg acaagagcag gtggcagcag      1320
gggaacgtct tctcatgctc cgtgatgcat gaggctctgc acaaccacta cacgcagaag      1380
agcctctccc tgtctccggg taaatga                                          1407

<210> SEQ ID NO 72
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
atgtacagga tgcaactcct gtcttgcatt gcactaagtc ttgcacttgt cacgaattca        60 tcatcgaac tgactcagcc tccgtcagtc tcagttagcc ccggtcaaac cgcacggatc        120
acgtgctccg gggatgcttt gccccggaag tttgcttatt ggtatcagca gaagtccggg       180
caagcaccag tcatggttat ctacgaggat agcaagcgac ccctggaat ccctgagaga        240 ttcagcgggt ccagtagcgg gactatggca acactgacaa taaccggcgc acaagtcgag       300
gacgaggcgg attactactg ttatagcact gatagtggtg gcgacgttag cgtctttggt       360
ggcggaacca agctgacggt tcttggacag cccaaggctg cccctcggt cactctgttc        420 ccgccctcct ctgaggagct tcaagccaac aaggccacac tggtgtgtct cataagtgac       480
ttctacccgg gagccgtgac agtggcctgg aaggcagata gcagccccgt caaggcggga       540
gtggagacca ccacaccctc caaacaaagc aacaacaagt acgcggccag cagctatctg       600
agcctgacgc ctgagcagtg gaagtcccac agaagctaca gctgccaggt cacgcatgaa       660
gggagcaccg tggagaagac agtggcccct acagaatgtt catag                       705

<210> SEQ ID NO 73
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgtacagga tgcaactcct gtcttgcatt gcactaagtc ttgcacttgt cacgaattca        60
gaggtgcagc tgttggagtc tggggggaggc ttggtacagc ctggggggtc cctgagactc      120
tcctgtgcag cctctggatt cacctttagc agctatgcca tgagctgggt ccgccaggct       180
ccagggaagg ggctggagtg ggtctcagct attagtggta gtggtggtag cacatactac       240
gcagactccg tgaagggccg gttcaccatc tccagagaca attccaagaa cacgctgtat       300
ctgcaaatga acagcctgag agccgaggac acggccgtat attactgtgc gaaagatggt       360
agcagtggct ggtacgtacc acactggttc gaccccctggg ccagggcac cctggtcacc      420 gtctcctcag ctagcaccaa gggcccatcg gtcttccccc tggcaccctc ctccaagagc      480
acctctgggg gcacagcggc cctgggctgc ctggtcaagg actacttccc cgaaccggtg      540
acggtgtcgt ggaactcagg cgccctgacc agcggcgtgc acaccttccc ggctgtccta      600
cagtcctcag gactctactc cctcagcagc gtggtgaccg tgccctccag cagcttgggc      660
acccagacct acatctgcaa cgtgaatcac aagcccagca acaccaaggt ggacaagaaa      720
gttgagccca aatcttgtga caaaactcac acatgcccac cgtgcccagc acctgaactc      780
```

-continued

```
ctgggggac cgtcagtctt cctcttcccc ccaaaaccca aggacaccct catgatctcc      840 cggaccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg      1020
aatggcaagg agtacaagtg caaggtctcc aacaaagccc tcccagcccc catcgagaaa      1080
accatctcca aagccaaagg gcagccccga gaaccacagg tgtacaccct gcccccatcc      1140
cgggaggaga tgaccaagaa ccaggtcagc ctgacctgcc tggtcaaagg cttctatccc      1200
agcgacatcg ccgtggagtg ggagagcaat gggcagccgg agaacaacta caagaccacg      1260
cctcccgtgc tggactccga cggctccttc ttcctctaca gcaagctcac cgtggacaag      1320
agcaggtggc agcaggggaa cgtcttctca tgctccgtga tgcatgaggc tctgcacaac      1380
cactacacgc agaagagcct ctccctgtct ccgggtaaat ga                        1422
```

<210> SEQ ID NO 74
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
atgtacagga tgcaactcct gtcttgcatt gcactaagtc ttgcacttgt cacgaattca      60
aattttatgc tgactcagcc ccactctgtg tcggagtctc cggggaagac ggtaaccatc      120
tcctgcaccc gcagcagtgg cagcattgcc agcaactatg tgcagtggta ccagcagcgc      180
ccgggcagtt cccccaccac tgtgatctat gaggataacc aaagaccttc tggggtccct      240
gatcggttct ctggctccat cgacagctcc tccaattctg cctccctcac catctctggg      300
atgttcggcg gagggaccaa gctgaccgtc ctaggtcagc ccaaggctgc ccctcggtc       360 actctgttcc cgccctcctc tgaggagctt caagccaaca ggccacact ggtgtgtctc       420 ataagtgact tctacccggg agccgtgaca gtggcctgga aggcagatag cagccccgtc      480
aaggcgggag tggagaccac cacaccctcc aaacaaagca acaacaagta cgcggccagc      540
agctatctga gcctgacgcc tgagcagtgg aagtcccaca gaagctacag ctgccaggtc      600
acgcatgaag ggagcaccgt ggagaagaca gtggcccta cagaatgttc atag            654
```

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75

```
atgtacagga tgcaactcct gtcttgcatt gcactaagtc ttgcacttgt cacgaattca      60
```

<210> SEQ ID NO 76
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

-continued

```
atgcacagga ggagaagcag gagctgtcgg gaagatcaga agccagtcat ggatgaccag        60
cgcgacctta tctccaacaa tgagcaactg cccatgctgg gacggcgccc tggtgcacca       120
gaatcaaaat gttcaagagg agccctatac acaggctttt ccatcctggt gactctgctc       180
ctcgctggcc aggccaccac cgcctacttc ctgtaccagc agcagggccg gctggacaaa       240
ctgacagtca cctcccagaa cctgcagctg gagaacctgc gcatgaagct tcccaagcct       300
cccaagcctg tgagcaagat gcgcatggcc accccgctgc tgatgcaggc gctgcccatg       360
ggagccctgc cccagggggcc catgcagaat gccacaaaat acggtaatat gactgaagac       420
catgtgatgc acctgctcca gaatgctgac cccctgaagg tgtacccgcc actgaagggg       480
agcttcccgg agaacctcag gcatttgaaa aatacgatgg agaccataga ctggaaggtc       540
tttgagagct ggatgcacca ttggctcctg tttgaaatga gcaggcactc cttggagcaa       600
aagcccactg acgctccacc gaaagagtca ctggaactgg aggacccgtc ttctgggctg       660
ggtgtgacca agcaggatct gggcccagtc cccatgtga                             699
```

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 77

```
ggaagatggc acaccgtggg actg                                              24
```

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 78

```
Gly Arg Trp His Thr Val Gly Leu
1               5
```

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 79

```
Met Arg Met Ala Thr Pro Leu Leu Met
1               5
```

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 80

```
Asn Leu Val Pro Met Val Ala Thr Val
1               5
```

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ile Leu Gly Phe Val Phe Thr Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Leu Leu Met Trp Ile Thr Gln Val
1               5

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ala Gly Gly Val Gly Lys Ser Ala Leu
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ala Asp Gly Val Gly Lys Ser Ala Leu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ala Cys Gly Val Gly Lys Ser Ala Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ala Val Gly Val Gly Lys Ser Ala Leu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Ala Arg Gly Val Gly Lys Ser Ala Leu
1               5                   10

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Asn Pro Val Val His Phe Phe Lys Asn Ile Val Thr Pro Arg
1               5                   10                  15

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val His Phe Phe Lys Asn Ile Val Thr Pro Arg Thr Pro
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Lys Tyr Val Lys Gln Asn Thr Leu Lys Leu Ala Thr
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Val Lys Gln Asn Thr Leu Lys Leu
1               5

<210> SEQ ID NO 92
<211> LENGTH: 30
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 92
aacctcgttc ctatggtcgc caccgtctag                                   30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 93
ggcattctgg ggttcgtttt caccctgtaa                                   30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 94
agcctcttga tgtggatcac gcaggtttag                                   30

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 95
ggagcaggag gcgtgggtaa gtcagctctg tga                               33

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 96
ggagcagacg gcgtgggtaa gtcagctctg tga                               33

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 97
ggagcatgcg gcgtgggtaa gtcagctctg tga                               33

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggagcagtgg gcgtgggtaa gtcagctctg tga                                    33

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggagcaagag gcgtgggtaa gtcagctctg tga                                    33

<210> SEQ ID NO 100
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gaaaacccag tggtgcactt ttttaagaat atagtcactc cccggtga                    48

<210> SEQ ID NO 101
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccgaagtatg tgaagcaaaa tacattgaaa ctcgctacgt ga                          42

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Leu Val Pro Met Val Ala Thr Val
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ile Leu Gly Phe Val Phe Thr Leu
1               5

<210> SEQ ID NO 104
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 104

Ser Leu Leu Met Trp Ile Thr Gln Val
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Pro Arg Val Thr Gly Gly Gly Ala Met
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Pro Ser Ile Asn Val His His Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Ala Phe Thr Ile Pro Ser Ile
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Ala Asp Gly Val Gly Lys Ser Ala Leu
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Lys Tyr Val Lys Gln Asn Thr Leu Lys Leu Ala Thr
1               5                   10

-continued

```
<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Asn Pro Val Val His Phe Phe Lys Asn Ile Val Thr Pro Arg
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Glu Asn Pro Val Val His Phe Phe Lys Asn Ile Val Thr Pro Arg
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Ala Ser Ser Leu Ala Pro Gly Thr Thr Asn Glu Lys Leu Phe Phe
1               5                   10                  15

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Ala Ser Ser Ser Arg Ser Ser Tyr Glu Gln Tyr Phe
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Ala Ser Ser Tyr Val Gly Asn Thr Gly Glu Leu Phe Phe
1               5                   10

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 115

Cys Ala Ser Ser Asp His Ser Val Thr Gly Ile Ser Ser Pro Leu His
1               5                   10                  15

Phe

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Ala Ser Ser Ala Asp Ser Asn Gly Glu Leu Phe Phe
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Cys Ala Ser Ser Leu Thr Gly Gly Gly Glu Leu Phe Phe
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Ala Ser Ser Asp Pro Gly Thr Glu Ala Phe Phe
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Cys Ala Ser Ser Ser Thr Gly Leu Pro Tyr Gly Tyr Thr Phe
1               5                   10

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Ser Ala Arg Asp Leu Thr Ser Gly Ala Asn Asn Glu Gln Phe Phe
1               5                   10                  15

```
<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ser Ala Arg Asp Leu Thr Ser Gly Ser Leu Asn Glu Gln Phe Phe
1               5                   10                  15

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ile Leu Asp Asn Asn Asn Asp Met Arg Phe
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys Ala Gly Ala Gly Ser Gln Gly Asn Leu Ile Phe
1               5                   10

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Ala Val Arg Pro Thr Ser Gly Gly Ser Tyr Ile Pro Thr Phe
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Ala Tyr Arg Ser Ala Arg Asp Ser Ser Tyr Lys Leu Ile Phe
1               5                   10                  15

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126
```

-continued

```
Cys Ala Glu Arg Gly Trp Asp Asn Asp Met Arg Phe
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Ala Thr Asp Asp Asp Ser Ala Arg Gln Leu Thr Phe
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Cys Ala Ala Ala Met Asp Ser Ser Tyr Lys Leu Ile Phe
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Ala Val Ser Glu Ser Pro Phe Gly Asn Glu Lys Leu Thr Phe
1               5                   10                  15

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Ala Thr Asp Thr Thr Ser Gly Thr Tyr Lys Tyr Ile Phe
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Cys Ala Thr Asp Ala Thr Ser Gly Thr Tyr Lys Tyr Ile Phe
1               5                   10

<210> SEQ ID NO 132
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 132

Ile Pro Ser Ile Asn Val His His Tyr
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Pro Ser Ile Asn Val His His Tyr
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asn Leu Val Pro Met Val Ala Thr Val
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Leu Val Pro Met Val Ala Thr Val
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Ala Val Pro Met Val Ala Thr Val
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asn Leu Ala Pro Met Val Ala Thr Val
1               5
```

```
<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asn Leu Val Ala Met Val Ala Thr Val
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Leu Val Pro Ala Val Ala Thr Val
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Leu Val Pro Met Ala Ala Thr Val
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asn Leu Val Pro Met Val Ala Ala Val
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Leu Val Pro Met Val Ala Thr Ala
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 143

Thr Ala Phe Thr Ile Pro Ser Ile
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Thr Ala Phe Thr Ile Pro Ser Ile
1               5

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Thr Pro Arg Val Thr Gly Gly Gly Ala Met
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Thr Pro Arg Val Thr Gly Gly Gly Ala Met
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Pro Arg Val Thr Gly Gly Gly Ala Met
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Pro Arg Val Thr Gly Gly Gly Ala Met
1               5                   10

<210> SEQ ID NO 149
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 149

Gly Ile Leu Gly Phe Val Phe Thr Leu
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Leu Val Pro Met Val Ala Thr Val
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Leu Val Pro Met Val Ala Thr Val
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Ala Val Pro Met Val Ala Thr Val
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Leu Ala Pro Met Val Ala Thr Val
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asn Leu Val Ala Met Val Ala Thr Val
1               5
```

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn Leu Val Pro Ala Val Ala Thr Val
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asn Leu Val Pro Met Ala Ala Thr Val
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Leu Val Pro Met Val Ala Ala Val
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asn Leu Val Pro Met Val Ala Thr Ala
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Ile Leu Gly Phe Val Phe Thr Leu
1               5

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Pro Arg Val Thr Gly Gly Gly Ala Met
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Ala Asp Gly Val Gly Lys Ser Ala Leu
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asn Leu Val Pro Met Val Ala Thr Val
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Phe Phe Trp Asp Ala Asn Asp Ile Tyr
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Pro Arg Val Thr Gly Gly Gly Ala Met
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Asp Glu Glu Glu Ala Ile Val Ala Tyr Thr Leu
1               5                   10

<210> SEQ ID NO 166
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Ala Lys Phe Lys Gln Leu Leu
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Thr Ile Gly Thr Ala Met Tyr Lys
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Leu Gly Gly Leu Leu Thr Met Val
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Leu Cys Thr Leu Val Ala Met Leu
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Leu Arg Gly Arg Ala Tyr Gly Leu
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ile Val Thr Asp Phe Ser Val Ile Lys
```

```
1               5
```

```
<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ala Lys Trp Arg Leu Gln Thr Leu
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Arg Leu Arg Ala Glu Ala Gln Val Lys
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Pro Pro Ile Phe Ile Arg Arg Leu
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Arg Ile Tyr Asp Leu Ile Glu Leu
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Val Arg Ala Tyr Thr Tyr Ser Lys
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 177

Tyr Pro Leu His Glu Gln His Gly Met
1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Val Phe Asp Arg Lys Ser Asp Ala Lys
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Tyr Cys Asn Val Leu Asn Lys Glu Phe
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Glu Glu Asn Leu Leu Asp Phe Val Arg Phe
1               5                   10

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Ser Cys Met Gly Leu Ile Tyr
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Thr Glu Leu Lys Leu Ser Asp Tyr
1               5

<210> SEQ ID NO 183

US 12,624,349 B2

133

134

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Glu Leu Arg Ser Arg Tyr Trp Ala Ile
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Phe Met Tyr Ser Asp Phe His Phe Ile
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Ile Leu Gly Phe Val Phe Thr Leu
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Leu Arg Gly Ser Val Ala His Lys
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Lys Thr Gly Gly Pro Ile Tyr Lys Arg
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188
```

```
Leu Pro Phe Asp Lys Thr Thr Val Met
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Ile Ile Pro Ser Gly Pro Leu Lys
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Arg Tyr Trp Ala Ile Arg Thr Arg
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Val Ser Asp Gly Gly Pro Asn Leu Tyr
1               5

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Val Leu Ser Phe Ile Lys Gly Thr Lys
1               5                   10

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asn Leu Val Pro Met Val Ala Thr Val
1               5

<210> SEQ ID NO 194
<211> LENGTH: 10
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 194

Glu Phe Phe Trp Asp Ala Asn Asp Ile Tyr
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Pro Arg Val Thr Gly Gly Gly Ala Met
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ser Asp Glu Glu Glu Ala Ile Val Ala Tyr Thr Leu
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Arg Ala Lys Phe Lys Gln Leu Leu
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Thr Ile Gly Thr Ala Met Tyr Lys
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Leu Gly Gly Leu Leu Thr Met Val
1               5

-continued

```
<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Leu Cys Thr Leu Val Ala Met Leu
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Phe Leu Arg Gly Arg Ala Tyr Gly Leu
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Val Thr Asp Phe Ser Val Ile Lys
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Ala Lys Trp Arg Leu Gln Thr Leu
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Arg Leu Arg Ala Glu Ala Gln Val Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205
```

```
Arg Pro Pro Ile Phe Ile Arg Arg Leu
1               5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Arg Ile Tyr Asp Leu Ile Glu Leu
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Val Arg Ala Tyr Thr Tyr Ser Lys
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Tyr Pro Leu His Glu Gln His Gly Met
1               5

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Val Phe Asp Arg Lys Ser Asp Ala Lys
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asp Tyr Cys Asn Val Leu Asn Lys Glu Phe
1               5                   10

<210> SEQ ID NO 211
<211> LENGTH: 10
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 211

Glu Glu Asn Leu Leu Asp Phe Val Arg Phe
1               5                   10

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Ser Cys Met Gly Leu Ile Tyr
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Thr Glu Leu Lys Leu Ser Asp Tyr
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Leu Arg Ser Arg Tyr Trp Ala Ile
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Phe Met Tyr Ser Asp Phe His Phe Ile
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Ile Leu Gly Phe Val Phe Thr Leu
1               5

-continued

```
<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile Leu Arg Gly Ser Val Ala His Lys
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Lys Thr Gly Gly Pro Ile Tyr Lys Arg
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Leu Pro Phe Asp Lys Thr Thr Val Met
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Ile Ile Pro Ser Gly Pro Leu Lys
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Arg Tyr Trp Ala Ile Arg Thr Arg
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 222

Val Ser Asp Gly Gly Pro Asn Leu Tyr
1               5

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Val Leu Ser Phe Ile Lys Gly Thr Lys
1               5                   10

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Ile Leu Gly Phe Val Phe Thr Leu
1               5

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Ala Asp Gly Val Gly Lys Ser Ala Leu
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Ala Asp Gly Val Gly Lys Ser Ala Leu
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Ala Asp Gly Val Gly Lys Ser Ala Leu
1               5                   10

<210> SEQ ID NO 228
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 228

Leu Val Val Val Gly Ala Asp Gly
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Val Val Val Gly Ala Asp Gly Val
1               5

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Val Val Gly Ala Asp Gly Val Gly
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Val Gly Ala Asp Gly Val Gly Lys
1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Ala Asp Gly Val Gly Lys Ser
1               5

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Asp Gly Val Gly Lys Ser Ala
1               5

```
<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Gly Val Gly Lys Ser Ala Leu
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Tyr Lys Leu Val Val Val Gly Ala Asp
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys Leu Val Val Val Gly Ala Asp Gly
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Val Val Val Gly Ala Asp Gly Val
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Val Val Val Gly Ala Asp Gly Val Gly
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 239

Val Val Gly Ala Asp Gly Val Gly Lys
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Val Gly Ala Asp Gly Val Gly Lys Ser
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Ala Asp Gly Val Gly Lys Ser Ala
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Asp Gly Val Gly Lys Ser Ala Leu
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Gly Val Gly Lys Ser Ala Leu Thr
1               5

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Glu Tyr Lys Leu Val Val Val Gly Ala Asp
1               5                   10

<210> SEQ ID NO 245
<211> LENGTH: 10

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Tyr Lys Leu Val Val Val Gly Ala Asp Gly
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Lys Leu Val Val Val Gly Ala Asp Gly Val
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Leu Val Val Val Gly Ala Asp Gly Val Gly
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Val Val Val Gly Ala Asp Gly Val Gly Lys
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Val Val Gly Ala Asp Gly Val Gly Lys Ser
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Val Gly Ala Asp Gly Val Gly Lys Ser Ala
```

-continued

```
1                   5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gly Ala Asp Gly Val Gly Lys Ser Ala Leu
1                   5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Asp Gly Val Gly Lys Ser Ala Leu Thr
1                   5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Gly Val Gly Lys Ser Ala Leu Thr Ile
1                   5                   10

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Thr Glu Tyr Lys Leu Val Val Val Gly Ala Asp
1                   5                   10

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Tyr Lys Leu Val Val Val Gly Ala Asp Gly
1                   5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 256

Tyr Lys Leu Val Val Val Gly Ala Asp Gly Val
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Lys Leu Val Val Val Gly Ala Asp Gly Val Gly
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Leu Val Val Val Gly Ala Asp Gly Val Gly Lys
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Val Val Val Gly Ala Asp Gly Val Gly Lys Ser
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Val Gly Ala Asp Gly Val Gly Lys Ser Ala
1               5                   10

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Val Gly Ala Asp Gly Val Gly Lys Ser Ala Leu
1               5                   10

<210> SEQ ID NO 262

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Ala Asp Gly Val Gly Lys Ser Ala Leu Thr
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ala Asp Gly Val Gly Lys Ser Ala Leu Thr Ile
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Gly Val Gly Lys Ser Ala Leu Thr Ile Gln
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Met Thr Glu Tyr Lys Leu Val Val Val Gly Ala Asp
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Thr Glu Tyr Lys Leu Val Val Val Gly Ala Asp Gly
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267
```

```
Glu Tyr Lys Leu Val Val Val Gly Ala Asp Gly Val
1               5                   10
```

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

```
Tyr Lys Leu Val Val Val Gly Ala Asp Gly Val Gly
1               5                   10
```

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Lys Leu Val Val Val Gly Ala Asp Gly Val Gly Lys
1               5                   10
```

<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

```
Leu Val Val Val Gly Ala Asp Gly Val Gly Lys Ser
1               5                   10
```

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Val Val Val Gly Ala Asp Gly Val Gly Lys Ser Ala
1               5                   10
```

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

```
Val Val Gly Ala Asp Gly Val Gly Lys Ser Ala Leu
1               5                   10
```

<210> SEQ ID NO 273
<211> LENGTH: 12
<212> TYPE: PRT
<213> ORGANISM: Artificial Sequence
<220> FEATURE:

<223> OTHER INFORMATION: Description of Artificial Sequence: Synthetic
     peptide

<400> SEQUENCE: 273

Val Gly Ala Asp Gly Val Gly Lys Ser Ala Leu Thr
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 274

Ala Asp Gly Val Gly Lys Ser Ala Leu Thr Ile Gln
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 275

Asp Gly Val Gly Lys Ser Ala Leu Thr Ile Gln Leu
1               5                   10

<210> SEQ ID NO 276

<400> SEQUENCE: 276

000

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 277

Gly Ala Asp Gly Val Gly Lys Ser Ala Leu
1               5                   10

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 278

Ala Asp Gly Val Gly Lys Ser Ala Leu
1               5

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 279

Met Ala Ser Gln Lys Arg Pro Ser Gln Arg His Gly Ser Lys Tyr
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Ser Gln Lys Arg Pro Ser Gln Arg His Gly Ser Lys Tyr Leu
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ser Gln Lys Arg Pro Ser Gln Arg His Gly Ser Lys Tyr Leu Ala
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Lys Arg Pro Ser Gln Arg His Gly Ser Lys Tyr Leu Ala Thr
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Lys Arg Pro Ser Gln Arg His Gly Ser Lys Tyr Leu Ala Thr Ala
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Pro Ser Gln Arg His Gly Ser Lys Tyr Leu Ala Thr Ala Ser
1               5                   10                  15

<210> SEQ ID NO 285
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Met Ala Ser Gln Lys Arg Pro Ser Gln Arg His Gly Ser Lys Tyr
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Ser Gln Lys Arg Pro Ser Gln Arg His Gly Ser Lys Tyr Leu
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ser Gln Lys Arg Pro Ser Gln Arg His Gly Ser Lys Tyr Leu Ala
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Lys Arg Pro Ser Gln Arg His Gly Ser Lys Tyr Leu Ala Thr
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Lys Arg Pro Ser Gln Arg His Gly Ser Lys Tyr Leu Ala Thr Ala
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Arg Pro Ser Gln Arg His Gly Ser Lys Tyr Leu Ala Thr Ala Ser
```

-continued

```
1               5               10              15
```

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

```
Leu Gly Gly Arg Asp Ser Arg Ser Gly Ser Pro Met Ala Arg Arg
1               5               10              15
```

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

```
Ile Val Thr Pro Arg Thr Pro Pro Ser Gln Gly Lys Gly Ala
1               5               10              15
```

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

```
Lys Gly Ala Glu Gly Gln Arg Pro Gly Phe Gly Tyr Gly Gly Arg
1               5               10              15
```

<210> SEQ ID NO 294
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

```
Phe Gly Gly Asp Arg Gly Ala Pro Lys Arg Gly Ser Gly Lys Asp
1               5               10              15
```

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

```
Gly Lys Asp Ser His His Pro Ala Arg Thr Ala His Tyr Gly Ser
1               5               10              15
```

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Met Gly Asn His Ala Gly Lys Arg Glu Leu Asn Ala Glu Lys Ala
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Val Met Ala Ser Gln Lys Arg Pro Ser Gln Arg His Gly Ser Lys
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Gly Asp Arg Gly Ala Pro Lys Arg Gly Ser Gly Lys Val Ser
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Asp Arg Gly Ala Pro Lys Arg Gly Ser Gly Lys Val Ser Ser
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asp Arg Gly Ala Pro Lys Arg Gly Ser Gly Lys Val Ser Ser Glu
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Arg Gly Ala Pro Lys Arg Gly Ser Gly Lys Val Ser Ser Glu Glu
1               5                   10                  15

<210> SEQ ID NO 302

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

His Gly Arg Thr Gln Asp Glu Asn Pro Val Val His Phe Phe Lys
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gly Arg Thr Gln Asp Glu Asn Pro Val Val His Phe Phe Lys Asn
1               5                   10                  15

<210> SEQ ID NO 304
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Arg Thr Gln Asp Glu Asn Pro Val Val His Phe Phe Lys Asn Ile
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Thr Gln Asp Glu Asn Pro Val Val His Phe Phe Lys Asn Ile Val
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Asp Glu Asn Pro Val Val His Phe Phe Lys Asn Ile Val Thr
1               5                   10                  15

<210> SEQ ID NO 307
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307
```

-continued

```
Asp Glu Asn Pro Val Val His Phe Phe Lys Asn Ile Val Thr Pro
1               5                   10                  15
```

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

```
Glu Asn Pro Val Val His Phe Phe Lys Asn Ile Val Thr Pro Arg
1               5                   10                  15
```

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

```
Asn Pro Val Val His Phe Phe Lys Asn Ile Val Thr Pro Arg Thr
1               5                   10                  15
```

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

```
Pro Val Val His Phe Phe Lys Asn Ile Val Thr Pro Arg Thr Pro
1               5                   10                  15
```

<210> SEQ ID NO 311
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

```
Val Val His Phe Phe Lys Asn Ile Val Thr Pro Arg Thr Pro Pro
1               5                   10                  15
```

<210> SEQ ID NO 312
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

```
Gln Asp Glu Asn Pro Val Val His Phe Phe Lys Asn Ile Val Thr
1               5                   10                  15
```

<210> SEQ ID NO 313
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 313

Glu Asn Pro Val Val His Phe Phe Lys Asn Ile Val Thr Pro Arg
1               5                   10                  15

<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Pro Val Val His Phe Phe Lys Asn Ile Val Thr Pro Arg Thr Pro
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asn Pro Val Val His Phe Phe Lys Asn Ile Val Thr Pro Arg Thr
1               5                   10                  15

<210> SEQ ID NO 316
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Asp Glu Asn Pro Val Val His Phe Phe Lys Asn Ile Val Thr Pro
1               5                   10                  15

<210> SEQ ID NO 317

<400> SEQUENCE: 317

000

<210> SEQ ID NO 318
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Thr Gln Asp Glu Asn Pro Val Val His Phe Phe Lys Asn Asn
1               5                   10

<210> SEQ ID NO 319
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gln Asp Glu Asn Pro Val Val His Phe Phe Lys Asn Val Ile
1               5                   10

<210> SEQ ID NO 320
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asp Glu Asn Pro Val Val His Phe Phe Lys Asn Ile Val Thr Pro
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Glu Asn Pro Val Val His Phe Phe Lys Asn Ile Val Thr Pro Arg
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Asn Pro Val Val His Phe Phe Lys Asn Ile Val Thr Pro Arg Thr
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Pro Val Val His Phe Phe Lys Asn Ile Val Thr Pro Arg Thr Pro
1               5                   10                  15

<210> SEQ ID NO 324

<400> SEQUENCE: 324

000

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

```
Cys Ala Ser Ser Ser Gly Gln Glu Thr Gln Tyr Phe
1               5                   10

<210> SEQ ID NO 326
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Cys Ala Ser Ser Val Thr Gly Gly Thr Asp Thr Gln Tyr Phe
1               5                   10

<210> SEQ ID NO 327
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Cys Ala Ser Ser Ala Gly Gln Gly Val Thr Tyr Glu Gln Tyr Phe
1               5                   10                  15

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Cys Ala Val Ala Ser Tyr Gly Asn Lys Leu Val Phe
1               5                   10

<210> SEQ ID NO 329
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Cys Ala Leu Ser Glu Gly Phe Gln Thr Gly Ala Asn Asn Leu Phe Phe
1               5                   10                  15

<210> SEQ ID NO 330
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Cys Ala Val Arg Ser Gly Gly Tyr Gln Lys Val Thr Phe
1               5                   10

<210> SEQ ID NO 331

<400> SEQUENCE: 331
```

000

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Leu Pro Leu Lys Met Leu Asn Ile
1               5

<210> SEQ ID NO 333
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Gln Ile Phe Leu Glu Val Gln Ala Ile Arg Glu Thr Val Glu Leu
1               5                   10                  15

Arg Gln Tyr Asp Pro Val Ala Ala Leu Phe Phe Phe Asp Ile Asp Leu
            20                  25                  30

Leu Leu Gln Arg Gly Pro Gln Tyr Ser Glu His Pro Thr Phe Thr Ser
        35                  40                  45

Gln Tyr
    50

<210> SEQ ID NO 334
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Thr Leu Leu Asn Cys Ala Val Thr Lys Leu Pro Cys Thr Leu Arg Ile
1               5                   10                  15

Val Thr Glu His Asp Thr Leu Leu Tyr Val Ala Ser Arg Asn Gly Leu
            20                  25                  30

Phe Ala Val Glu Asn Phe Leu Thr Glu Glu Pro Phe Gly Arg Gly Asp
        35                  40                  45

Pro Phe
    50

<210> SEQ ID NO 335

<400> SEQUENCE: 335

000

<210> SEQ ID NO 336

<400> SEQUENCE: 336

000

<210> SEQ ID NO 337

```
<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348
```

-continued

```
000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Tyr Ser Glu His Pro Thr Phe Thr Ser Gln Tyr
1               5                   10

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 358

Val Thr Glu His Asp Thr Leu Leu Tyr
1               5

<210> SEQ ID NO 359
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Cys Ala Ser Ser Leu Gly Gly Pro Gly Asp Thr Gln Tyr Phe
1               5                   10

<210> SEQ ID NO 360
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Cys Ala Ser Ser Leu Asn Arg Gly Gln Glu Thr Gln Tyr Phe
1               5                   10

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Cys Ala Val Ser Gln Pro Ser Gly Gly Ser Tyr Ile Pro Thr Phe
1               5                   10                  15

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Cys Ala Val Arg Arg Gly Thr Asp Lys Leu Ile Phe
1               5                   10

<210> SEQ ID NO 363
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

His Arg Glu Ala Asp Ala Gln Thr Phe Ala Ala Thr His Asn Pro Trp
1               5                   10                  15

Ala Ser Gln Ala Gly Cys Leu Ser Asp Val Leu Tyr Asn Thr Arg His
            20                  25                  30

Arg Glu Arg Leu Gly Tyr Asn Ser Lys Phe Tyr Ser Pro Cys Ala Gln
        35                  40                  45

Tyr Phe
    50

<210> SEQ ID NO 364
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Tyr Lys Thr Ala Ile Gln Gln Leu Arg Ser Val Ile Arg Ala Leu Lys
1               5                   10                  15

Glu Asn Thr Thr Val Thr Phe Leu Pro Thr Pro Ser Leu Ile Leu Gln
            20                  25                  30

Thr Val Arg Ser His Cys Val Ser Lys Ile Thr Phe Asn Ser Ser Cys
        35                  40                  45

Leu Tyr
    50

<210> SEQ ID NO 365
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

His Arg Glu Ala Asp Ala Gln Thr Phe Ala Ala Thr His Asn Pro Trp
1               5                   10                  15

Ala Ser Gln Ala Gly Cys Leu Ser Asp Val Leu Tyr Asn Thr Arg His
            20                  25                  30

Arg Glu Arg Leu Gly Tyr Asn Ser Lys Phe Tyr Ser Pro Cys Ala Gln
        35                  40                  45

Tyr Phe
    50

<210> SEQ ID NO 366
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Gln Thr Phe Ala Ala Thr His Asn Pro Trp Ala Ser Gln Ala
1               5                   10                  15

<210> SEQ ID NO 367
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Asp Arg Lys Thr Arg Leu Ser Glu Pro Pro Thr Leu Ala Leu Arg Leu

-continued

```
1               5               10              15

Lys Pro Tyr Lys Thr Ala Ile Gln Gln Leu Arg Ser Val Ile Arg Ala
                20              25              30

Leu Lys Glu Asn Thr Thr Val Thr Phe Leu Pro Thr Pro Ser Leu Ile
        35              40              45

Leu Gln
    50
```

```
<210> SEQ ID NO 368
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Tyr Lys Thr Ala Ile Gln Gln Leu Arg Ser Val Ile Arg Ala Leu Lys
1               5               10              15

Glu Asn Thr Thr Val Thr Phe Leu Pro Thr Pro Ser Leu Ile Leu Gln
                20              25              30

Thr Val Arg Ser His Cys Val Ser Lys Ile Thr Phe Asn Ser Ser Cys
        35              40              45

Leu Tyr
    50
```

```
<210> SEQ ID NO 369
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
aatctggtgc cgatggttgc caccgtgtga                                      30
```

```
<210> SEQ ID NO 370
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
ggcatcctgg ggttcgtctt caccctgtga                                      30
```

```
<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
aatctggtgc cgatggttgc caccgtgtga                                      30
```

```
<210> SEQ ID NO 372
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 372
ggcatcctgg ggttcgtctt caccctgtga                                        30

<210> SEQ ID NO 373
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
aatctggtgc cgatggttgc caccgtgtga                                        30

<210> SEQ ID NO 374
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
ggcatcctgg ggttcgtctt caccctgtga                                        30

<210> SEQ ID NO 375
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
aatctggtgc cgatggttgc caccgtgtga                                        30

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
ggcatcctgg ggttcgtctt caccctgtga                                        30

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Ile Pro Ser Ile Asn Val His His Tyr
1               5

<210> SEQ ID NO 378
<211> LENGTH: 9
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 378

Asn Leu Val Pro Met Val Ala Thr Val
1               5

<210> SEQ ID NO 379
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Glu Phe Phe Trp Asp Ala Asn Asp Ile Tyr
1               5                   10

<210> SEQ ID NO 380
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Thr Pro Arg Val Thr Gly Gly Gly Ala Met
1               5                   10

<210> SEQ ID NO 381
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Asp Glu Glu Glu Ala Ile Val Ala Tyr Thr Leu
1               5                   10

<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Arg Ala Lys Phe Lys Gln Leu Leu
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Thr Ile Gly Thr Ala Met Tyr Lys
1               5
```

```
<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Cys Leu Gly Gly Leu Leu Thr Met Val
1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gly Leu Cys Thr Leu Val Ala Met Leu
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Phe Leu Arg Gly Arg Ala Tyr Gly Leu
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ile Val Thr Asp Phe Ser Val Ile Lys
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gln Ala Lys Trp Arg Leu Gln Thr Leu
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389
```

Arg Leu Arg Ala Glu Ala Gln Val Lys
1               5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Pro Pro Ile Phe Ile Arg Arg Leu
1               5

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Arg Arg Ile Tyr Asp Leu Ile Glu Leu
1               5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Arg Val Arg Ala Tyr Thr Tyr Ser Lys
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Tyr Pro Leu His Glu Gln His Gly Met
1               5

<210> SEQ ID NO 394
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Val Phe Asp Arg Lys Ser Asp Ala Lys
1               5                   10

<210> SEQ ID NO 395
<211> LENGTH: 10
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 395

Asp Tyr Cys Asn Val Leu Asn Lys Glu Phe
1               5                   10

<210> SEQ ID NO 396
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Glu Glu Asn Leu Leu Asp Phe Val Arg Phe
1               5                   10

<210> SEQ ID NO 397
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Ala Ser Cys Met Gly Leu Ile Tyr
1               5

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Cys Thr Glu Leu Lys Leu Ser Asp Tyr
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Glu Leu Arg Ser Arg Tyr Trp Ala Ile
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Phe Met Tyr Ser Asp Phe His Phe Ile
1               5
```

-continued

```
<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Ile Leu Gly Phe Val Phe Thr Leu
1               5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Ile Leu Arg Gly Ser Val Ala His Lys
1               5

<210> SEQ ID NO 403
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Lys Thr Gly Gly Pro Ile Tyr Lys Arg
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Leu Pro Phe Asp Lys Thr Thr Val Met
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ser Ile Ile Pro Ser Gly Pro Leu Lys
1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 406

Ser Arg Tyr Trp Ala Ile Arg Thr Arg
1               5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Val Ser Asp Gly Gly Pro Asn Leu Tyr
1               5

<210> SEQ ID NO 408
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Arg Val Leu Ser Phe Ile Lys Gly Thr Lys
1               5                   10

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Ile Pro Ser Ile Asn Val His His Tyr
1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Asn Leu Val Pro Met Val Ala Thr Val
1               5

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Glu Phe Phe Trp Asp Ala Asn Asp Ile Tyr
1               5                   10

<210> SEQ ID NO 412
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 412

Thr Pro Arg Val Thr Gly Gly Gly Ala Met
1               5                   10

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Ser Asp Glu Glu Glu Ala Ile Val Ala Tyr Thr Leu
1               5                   10

<210> SEQ ID NO 414
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Arg Ala Lys Phe Lys Gln Leu Leu
1               5

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Ala Thr Ile Gly Thr Ala Met Tyr Lys
1               5

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Cys Leu Gly Gly Leu Leu Thr Met Val
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gly Leu Cys Thr Leu Val Ala Met Leu
1               5

```
<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Phe Leu Arg Gly Arg Ala Tyr Gly Leu
1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Ile Val Thr Asp Phe Ser Val Ile Lys
1               5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Gln Ala Lys Trp Arg Leu Gln Thr Leu
1               5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Arg Leu Arg Ala Glu Ala Gln Val Lys
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Arg Pro Pro Ile Phe Ile Arg Arg Leu
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 423

Arg Arg Ile Tyr Asp Leu Ile Glu Leu
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Arg Val Arg Ala Tyr Thr Tyr Ser Lys
1               5

<210> SEQ ID NO 425
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Tyr Pro Leu His Glu Gln His Gly Met
1               5

<210> SEQ ID NO 426
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Ala Val Phe Asp Arg Lys Ser Asp Ala Lys
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Asp Tyr Cys Asn Val Leu Asn Lys Glu Phe
1               5                   10

<210> SEQ ID NO 428
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Glu Glu Asn Leu Leu Asp Phe Val Arg Phe
1               5                   10

<210> SEQ ID NO 429
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Ala Ser Cys Met Gly Leu Ile Tyr
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Cys Thr Glu Leu Lys Leu Ser Asp Tyr
1               5

<210> SEQ ID NO 431
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Glu Leu Arg Ser Arg Tyr Trp Ala Ile
1               5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Phe Met Tyr Ser Asp Phe His Phe Ile
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Gly Ile Leu Gly Phe Val Phe Thr Leu
1               5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Ile Leu Arg Gly Ser Val Ala His Lys
```

-continued

```
1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Lys Thr Gly Gly Pro Ile Tyr Lys Arg
1               5

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Leu Pro Phe Asp Lys Thr Thr Val Met
1               5

<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Ser Ile Ile Pro Ser Gly Pro Leu Lys
1               5

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ser Arg Tyr Trp Ala Ile Arg Thr Arg
1               5

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Val Ser Asp Gly Gly Pro Asn Leu Tyr
1               5

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 440

Arg Val Leu Ser Phe Ile Lys Gly Thr Lys
1               5                   10

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Ile Pro Ser Ile Asn Val His His Tyr
1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Asn Leu Val Pro Met Val Ala Thr Val
1               5

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Glu Phe Phe Trp Asp Ala Asn Asp Ile Tyr
1               5                   10

<210> SEQ ID NO 444
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Thr Pro Arg Val Thr Gly Gly Gly Ala Met
1               5                   10

<210> SEQ ID NO 445
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ser Asp Glu Glu Glu Ala Ile Val Ala Tyr Thr Leu
1               5                   10

<210> SEQ ID NO 446

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Arg Ala Lys Phe Lys Gln Leu Leu
1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Ala Thr Ile Gly Thr Ala Met Tyr Lys
1               5

<210> SEQ ID NO 448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Cys Leu Gly Gly Leu Leu Thr Met Val
1               5

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Gly Leu Cys Thr Leu Val Ala Met Leu
1               5

<210> SEQ ID NO 450
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Phe Leu Arg Gly Arg Ala Tyr Gly Leu
1               5

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451
```

```
Ile Val Thr Asp Phe Ser Val Ile Lys
1               5

<210> SEQ ID NO 452
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Gln Ala Lys Trp Arg Leu Gln Thr Leu
1               5

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Arg Leu Arg Ala Glu Ala Gln Val Lys
1               5

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Arg Pro Pro Ile Phe Ile Arg Arg Leu
1               5

<210> SEQ ID NO 455
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Arg Arg Ile Tyr Asp Leu Ile Glu Leu
1               5

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Arg Val Arg Ala Tyr Thr Tyr Ser Lys
1               5

<210> SEQ ID NO 457
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 457

Tyr Pro Leu His Glu Gln His Gly Met
1               5

<210> SEQ ID NO 458
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Ala Val Phe Asp Arg Lys Ser Asp Ala Lys
1               5                   10

<210> SEQ ID NO 459
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Asp Tyr Cys Asn Val Leu Asn Lys Glu Phe
1               5                   10

<210> SEQ ID NO 460
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Glu Glu Asn Leu Leu Asp Phe Val Arg Phe
1               5                   10

<210> SEQ ID NO 461
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Ala Ser Cys Met Gly Leu Ile Tyr
1               5

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Cys Thr Glu Leu Lys Leu Ser Asp Tyr
1               5

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Glu Leu Arg Ser Arg Tyr Trp Ala Ile
1               5

<210> SEQ ID NO 464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Phe Met Tyr Ser Asp Phe His Phe Ile
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Gly Ile Leu Gly Phe Val Phe Thr Leu
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ile Leu Arg Gly Ser Val Ala His Lys
1               5

<210> SEQ ID NO 467
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Lys Thr Gly Gly Pro Ile Tyr Lys Arg
1               5

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

```
Leu Pro Phe Asp Lys Thr Thr Val Met
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ser Ile Ile Pro Ser Gly Pro Leu Lys
1               5

<210> SEQ ID NO 470
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Ser Arg Tyr Trp Ala Ile Arg Thr Arg
1               5

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Val Ser Asp Gly Gly Pro Asn Leu Tyr
1               5

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Arg Val Leu Ser Phe Ile Lys Gly Thr Lys
1               5                   10

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Gly Ile Leu Gly Phe Val Phe Thr Leu
1               5

<210> SEQ ID NO 474
<211> LENGTH: 15
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 474

Pro Asp Asp Tyr Ser Asn Thr His Ser Thr Arg Tyr Val Thr Val
1               5                   10                  15

<210> SEQ ID NO 475
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Asp Lys Arg Glu Met Trp Met Ala Cys Ile Lys Glu Leu His
1               5                   10

<210> SEQ ID NO 476
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Tyr Glu Tyr Val Asp Tyr Leu Phe Lys Arg Met Ile Asp
1               5                   10

<210> SEQ ID NO 477
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Thr Ser Leu Tyr Asn Leu Arg Arg Gly Thr Ala Leu Ala
1               5                   10

<210> SEQ ID NO 478
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Thr Gly His Gly Ala Arg Thr Ser Thr Glu Pro Thr Thr Asp Tyr
1               5                   10                  15

<210> SEQ ID NO 479
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Lys Glu Leu Lys Arg Gln Tyr Glu Lys Lys Leu Arg Gln
1               5                   10
```

<210> SEQ ID NO 480
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Thr Val Phe Tyr Asn Ile Pro Pro Met Pro Leu
1               5                   10

<210> SEQ ID NO 481
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Ala Glu Gly Leu Arg Ala Leu Leu Ala Arg Ser His Val Glu Arg
1               5                   10                  15

<210> SEQ ID NO 482
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Phe Val Phe Thr Leu Thr Val Pro Ser Glu Arg
1               5                   10

<210> SEQ ID NO 483
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ser Gly Pro Leu Lys Ala Glu Ile Ala Gln Arg Leu Glu Asp Val
1               5                   10                  15

<210> SEQ ID NO 484
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Pro Lys Tyr Val Lys Gln Asn Thr Leu Lys Leu Ala
1               5                   10

<210> SEQ ID NO 485
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 485

Pro Lys Tyr Val Lys Gln Asn Thr Leu Lys Leu Ala Thr
1               5                   10

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Asp Arg Leu Arg Arg Asp Gln Lys Ser
1               5

<210> SEQ ID NO 487
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Pro Tyr Tyr Thr Gly Glu His Ala Lys Ala Ile Gly Asn
1               5                   10

<210> SEQ ID NO 488
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gly Gln Ile Gly Asn Asp Pro Asn Arg Asp Ile Leu
1               5                   10

<210> SEQ ID NO 489
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Gln Tyr Ile Lys Ala Asn Ser Lys Phe Ile Gly Ile Thr Glu Leu
1               5                   10                  15

<210> SEQ ID NO 490
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gln Tyr Ile Lys Ala Asn Ser Lys Phe Ile Gly Ile Thr Glu
1               5                   10

<210> SEQ ID NO 491
<211> LENGTH: 16
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 491

Lys Phe Ile Ile Lys Arg Tyr Thr Pro Asn Asn Glu Ile Asp Ser Phe
1               5                   10                  15

<210> SEQ ID NO 492
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Val Ser Ile Asp Lys Phe Arg Ile Phe Cys Lys Ala Leu Asn Pro Lys
1               5                   10                  15

<210> SEQ ID NO 493
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Pro Asp Asp Tyr Ser Asn Thr His Ser Thr Arg Tyr Val Thr Val
1               5                   10                  15

<210> SEQ ID NO 494
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Asp Lys Arg Glu Met Trp Met Ala Cys Ile Lys Glu Leu His
1               5                   10

<210> SEQ ID NO 495
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Tyr Glu Tyr Val Asp Tyr Leu Phe Lys Arg Met Ile Asp
1               5                   10

<210> SEQ ID NO 496
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Thr Ser Leu Tyr Asn Leu Arg Arg Gly Thr Ala Leu Ala
1               5                   10

<210> SEQ ID NO 497
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Thr Gly His Gly Ala Arg Thr Ser Thr Glu Pro Thr Thr Asp Tyr
1               5                   10                  15

<210> SEQ ID NO 498
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Lys Glu Leu Lys Arg Gln Tyr Glu Lys Lys Leu Arg Gln
1               5                   10

<210> SEQ ID NO 499
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Thr Val Phe Tyr Asn Ile Pro Pro Met Pro Leu
1               5                   10

<210> SEQ ID NO 500
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Ala Glu Gly Leu Arg Ala Leu Leu Ala Arg Ser His Val Glu Arg
1               5                   10                  15

<210> SEQ ID NO 501
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Phe Val Phe Thr Leu Thr Val Pro Ser Glu Arg
1               5                   10

<210> SEQ ID NO 502
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Ser Gly Pro Leu Lys Ala Glu Ile Ala Gln Arg Leu Glu Asp Val
1               5                   10                  15

<210> SEQ ID NO 503
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Pro Lys Tyr Val Lys Gln Asn Thr Leu Lys Leu Ala
1               5                   10

<210> SEQ ID NO 504
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Pro Lys Tyr Val Lys Gln Asn Thr Leu Lys Leu Ala Thr
1               5                   10

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Asp Arg Leu Arg Arg Asp Gln Lys Ser
1               5

<210> SEQ ID NO 506
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Pro Tyr Tyr Thr Gly Glu His Ala Lys Ala Ile Gly Asn
1               5                   10

<210> SEQ ID NO 507
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Gly Gln Ile Gly Asn Asp Pro Asn Arg Asp Ile Leu
1               5                   10

<210> SEQ ID NO 508
<211> LENGTH: 15

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Gln Tyr Ile Lys Ala Asn Ser Lys Phe Ile Gly Ile Thr Glu Leu
1               5                   10                  15

<210> SEQ ID NO 509
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Gln Tyr Ile Lys Ala Asn Ser Lys Phe Ile Gly Ile Thr Glu
1               5                   10

<210> SEQ ID NO 510
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Lys Phe Ile Ile Lys Arg Tyr Thr Pro Asn Asn Glu Ile Asp Ser Phe
1               5                   10                  15

<210> SEQ ID NO 511
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Val Ser Ile Asp Lys Phe Arg Ile Phe Cys Lys Ala Leu Asn Pro Lys
1               5                   10                  15

<210> SEQ ID NO 512
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Pro Asp Asp Tyr Ser Asn Thr His Ser Thr Arg Tyr Val Thr Val
1               5                   10                  15

<210> SEQ ID NO 513
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Asp Lys Arg Glu Met Trp Met Ala Cys Ile Lys Glu Leu His
```

-continued

```
1               5                    10
```

```
<210> SEQ ID NO 514
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Tyr Glu Tyr Val Asp Tyr Leu Phe Lys Arg Met Ile Asp
1               5                    10

<210> SEQ ID NO 515
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Thr Ser Leu Tyr Asn Leu Arg Arg Gly Thr Ala Leu Ala
1               5                    10

<210> SEQ ID NO 516
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Thr Gly His Gly Ala Arg Thr Ser Thr Glu Pro Thr Thr Asp Tyr
1               5                    10                   15

<210> SEQ ID NO 517
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Lys Glu Leu Lys Arg Gln Tyr Glu Lys Lys Leu Arg Gln
1               5                    10

<210> SEQ ID NO 518
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Thr Val Phe Tyr Asn Ile Pro Pro Met Pro Leu
1               5                    10

<210> SEQ ID NO 519
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 519

Ala Glu Gly Leu Arg Ala Leu Leu Ala Arg Ser His Val Glu Arg
1               5                   10                  15

<210> SEQ ID NO 520
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Phe Val Phe Thr Leu Thr Val Pro Ser Glu Arg
1               5                   10

<210> SEQ ID NO 521
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Ser Gly Pro Leu Lys Ala Glu Ile Ala Gln Arg Leu Glu Asp Val
1               5                   10                  15

<210> SEQ ID NO 522
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Pro Lys Tyr Val Lys Gln Asn Thr Leu Lys Leu Ala
1               5                   10

<210> SEQ ID NO 523
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Pro Lys Tyr Val Lys Gln Asn Thr Leu Lys Leu Ala Thr
1               5                   10

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Asp Arg Leu Arg Arg Asp Gln Lys Ser
1               5

<210> SEQ ID NO 525
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Pro Tyr Tyr Thr Gly Glu His Ala Lys Ala Ile Gly Asn
1               5                   10

<210> SEQ ID NO 526
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Gly Gln Ile Gly Asn Asp Pro Asn Arg Asp Ile Leu
1               5                   10

<210> SEQ ID NO 527
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Gln Tyr Ile Lys Ala Asn Ser Lys Phe Ile Gly Ile Thr Glu Leu
1               5                   10                  15

<210> SEQ ID NO 528
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Gln Tyr Ile Lys Ala Asn Ser Lys Phe Ile Gly Ile Thr Glu
1               5                   10

<210> SEQ ID NO 529
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Lys Phe Ile Ile Lys Arg Tyr Thr Pro Asn Asn Glu Ile Asp Ser Phe
1               5                   10                  15

<210> SEQ ID NO 530
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530
```

```
Val Ser Ile Asp Lys Phe Arg Ile Phe Cys Lys Ala Leu Asn Pro Lys
1               5                   10                  15
```

<210> SEQ ID NO 531
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

```
Pro Lys Tyr Val Lys Gln Asn Thr Leu Lys Leu Ala Thr
1               5                   10
```

<210> SEQ ID NO 532
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

```
Pro Lys Tyr Val Lys Gln Asn Thr Leu Lys Leu Ala Thr
1               5                   10
```

<210> SEQ ID NO 533
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

```
Gly Ala Asp Gly Val Gly Lys Ser Ala Leu
1               5                   10
```

<210> SEQ ID NO 534
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

```
Gly Ala Asp Gly Val Gly Lys Ser Ala Leu
1               5                   10
```

<210> SEQ ID NO 535
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

```
Gly Ala Asp Gly Val Gly Lys Ser Ala Leu
1               5                   10
```

<210> SEQ ID NO 536
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 536

Gly Ala Asp Gly Val Gly Lys Ser Ala Leu
1               5                   10

<210> SEQ ID NO 537
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 537

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
                20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln
    50                  55                  60

<210> SEQ ID NO 538
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
                20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln
    50                  55                  60

<210> SEQ ID NO 539
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Asp Thr Ala Val Thr Asp Ser Lys Arg Thr Ala Asp Pro Lys Asn Ala
1               5                   10                  15

Trp Gln Asp Ala His Pro Ala Asp Pro Gly Ser Arg Pro His Leu Ile
                20                  25                  30

Arg Leu Phe Ser Arg Asp Ala Pro Gly Arg Glu Asp Asn Thr Phe Lys
        35                  40                  45

Asp Arg Pro Ser Glu Ser Asp Glu Leu Gln Thr Ile
    50                  55                  60

<210> SEQ ID NO 540

-continued

```
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 540

Asp Thr Ala Val Thr Asp Ser Lys Arg Thr Ala Asp Pro Lys Asn Ala
1               5                   10                  15

Trp Gln Asp Ala His Pro Ala Asp Pro Gly Ser Arg Pro His Leu Ile
            20                  25                  30

Arg Leu Phe Ser Arg Asp Ala Pro Gly Arg Glu Asp Asn Thr Phe Lys
        35                  40                  45

Asp Arg Pro Ser Glu Ser Asp Glu Leu Gln Thr Ile
    50                  55                  60

<210> SEQ ID NO 541
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 541

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly
        35                  40                  45

<210> SEQ ID NO 542
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 542

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly
        35                  40                  45

<210> SEQ ID NO 543
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly
```

35 40 45

<210> SEQ ID NO 544
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 544

Met Ala Ser Gln Lys Arg Pro Ser Gln Arg His Gly Ser Lys Tyr Leu
1 5 10 15

Ala Thr Ala Ser Thr Met Asp His Ala Arg His Gly Phe Leu Pro Arg
20 25 30

His Arg Asp Thr Gly Ile Leu Asp Ser Ile Gly Arg Phe Phe Gly
35 40 45

<210> SEQ ID NO 545
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 545

Gln Glu Asp Ser Ala Ala Thr Ser Glu Ser Leu Asp Val Met Ala Ser
1 5 10 15

Gln Lys Arg Pro Ser Gln Arg His Gly Ser Lys Tyr Leu Ala Thr Ala
20 25 30

Ser Thr Met Asp His Ala Arg His Gly Phe Leu Pro Arg His Arg Asp
35 40 45

Thr Gly Ile Leu Asp Ser Ile Gly Arg Phe Phe Gly
50 55 60

<210> SEQ ID NO 546
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 546

Gln Glu Asp Ser Ala Ala Thr Ser Glu Ser Leu Asp Val Met Ala Ser
1 5 10 15

Gln Lys Arg Pro Ser Gln Arg His Gly Ser Lys Tyr Leu Ala Thr Ala
20 25 30

Ser Thr Met Asp His Ala Arg His Gly Phe Leu Pro Arg His Arg Asp
35 40 45

Thr Gly Ile Leu Asp Ser Ile Gly Arg Phe Phe Gly
50 55 60

<210> SEQ ID NO 547
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 547

```
Gly Asp Arg Gly Ala Pro Lys Arg Gly Ser Gly Lys Val Pro Trp Leu
1               5                   10                  15

Lys Pro Gly Arg Ser Pro Leu Pro Ser His Ala Arg Ser Gln Pro Gly
            20                  25                  30

Leu Cys Asn Met Tyr Lys Asp Ser His His Pro Ala Arg Thr Ala His
        35                  40                  45

Tyr Gly Ser Leu Pro Gln Lys Ser His Gly Arg Thr
    50                  55                  60

<210> SEQ ID NO 548
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Gly Asp Arg Gly Ala Pro Lys Arg Gly Ser Gly Lys Val Pro Trp Leu
1               5                   10                  15

Lys Pro Gly Arg Ser Pro Leu Pro Ser His Ala Arg Ser Gln Pro Gly
            20                  25                  30

Leu Cys Asn Met Tyr Lys Asp Ser His His Pro Ala Arg Thr Ala His
        35                  40                  45

Tyr Gly Ser Leu Pro Gln Lys Ser His Gly Arg Thr
    50                  55                  60

<210> SEQ ID NO 549
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 549

Gly Asp Arg Gly Ala Pro Lys Arg Gly Ser Gly Lys Asp Ser His His
1               5                   10                  15

Pro Ala Arg Thr Ala His Tyr Gly Ser Leu Pro Gln Lys Ser His Gly
            20                  25                  30

Arg Thr

<210> SEQ ID NO 550
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

Gly Asp Arg Gly Ala Pro Lys Arg Gly Ser Gly Lys Asp Ser His His
1               5                   10                  15

Pro Ala Arg Thr Ala His Tyr Gly Ser Leu Pro Gln Lys Ser His Gly
            20                  25                  30

Arg Thr

<210> SEQ ID NO 551
<211> LENGTH: 34
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 551

Gly Asp Arg Gly Ala Pro Lys Arg Gly Ser Gly Lys Asp Ser His His
1               5                   10                  15

Pro Ala Arg Thr Ala His Tyr Gly Ser Leu Pro Gln Lys Ser His Gly
            20                  25                  30

Arg Thr

<210> SEQ ID NO 552
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Gly Asp Arg Gly Ala Pro Lys Arg Gly Ser Gly Lys Val Ser Ser Glu
1               5                   10                  15

Glu

<210> SEQ ID NO 553
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Gln Asp Glu Asn Pro Val Val His Phe Phe Lys Asn Ile Val Thr Pro
1               5                   10                  15

Arg Thr Pro Pro Pro Ser Gln Gly Lys Gly Arg Gly Leu Ser Leu Ser
            20                  25                  30

Arg Phe Ser Trp Gly Ala Glu Gly Gln Arg Pro Gly Phe Gly Tyr Gly
        35                  40                  45

Gly Arg Ala Ser Asp Tyr Lys Ser Ala His Lys Gly
    50                  55                  60

<210> SEQ ID NO 554
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

Gln Asp Glu Asn Pro Val Val His Phe Phe Lys Asn Ile Val Thr Pro
1               5                   10                  15

Arg Thr Pro Pro Pro Ser Gln Gly Lys Gly Ala Glu Gly Gln Arg Pro
            20                  25                  30

Gly Phe Gly Tyr Gly Gly Arg Ala Ser Asp Tyr Lys Ser Ala His Lys
        35                  40                  45

Gly

<210> SEQ ID NO 555
<211> LENGTH: 60
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 555

Gln Asp Glu Asn Pro Val Val His Phe Phe Lys Asn Ile Val Thr Pro
1               5                   10                  15

Arg Thr Pro Pro Pro Ser Gln Gly Lys Gly Arg Gly Leu Ser Leu Ser
            20                  25                  30

Arg Phe Ser Trp Gly Ala Glu Gly Gln Arg Pro Gly Phe Gly Tyr Gly
        35                  40                  45

Gly Arg Ala Ser Asp Tyr Lys Ser Ala His Lys Gly
    50                  55                  60

<210> SEQ ID NO 556
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Gln Asp Glu Asn Pro Val Val His Phe Phe Lys Asn Ile Val Thr Pro
1               5                   10                  15

Arg Thr Pro Pro Pro Ser Gln Gly Lys Gly Ala Glu Gly Gln Arg Pro
            20                  25                  30

Gly Phe Gly Tyr Gly Gly Arg Ala Ser Asp Tyr Lys Ser Ala His Lys
        35                  40                  45

Gly

<210> SEQ ID NO 557
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Gln Asp Glu Asn Pro Val Val His Phe Phe Lys Asn Ile Val Thr Pro
1               5                   10                  15

Arg Thr Pro Pro Pro Ser Gln Gly Lys Gly Arg Gly Leu Ser Leu Ser
            20                  25                  30

Arg Phe Ser Trp Gly Ala Glu Gly Gln Arg Pro Gly Phe Gly Tyr Gly
        35                  40                  45

Gly Arg Ala Ser Asp Tyr Lys Ser Ala His Lys Gly
    50                  55                  60

<210> SEQ ID NO 558
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala Arg Arg
            20                  25                  30
```

<210> SEQ ID NO 559
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 559

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala Arg Arg
            20                  25                  30

<210> SEQ ID NO 560
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 560

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala Arg Arg
            20                  25                  30

<210> SEQ ID NO 561
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 561

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala Arg Arg
            20                  25                  30

<210> SEQ ID NO 562
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 562

Phe Lys Gly Val Asp Ala Gln Gly Thr Leu Ser Lys Ile Phe Lys Leu
1               5                   10                  15

Gly Gly Arg Asp Ser Arg Ser Gly Ser Pro Met Ala Arg Arg
            20                  25                  30

<210> SEQ ID NO 563
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Glu Asn Pro Val Val His Phe Phe Lys Asn Ile Val Thr Pro Arg
1               5                   10                  15

<210> SEQ ID NO 564
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Asp Glu Asn Pro Val Val His Phe Phe Lys Asn Ile Val Thr Pro
1               5                   10                  15

<210> SEQ ID NO 565
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Pro Val Val His Phe Phe Lys Asn Ile Val Thr Pro Arg Thr Pro
1               5                   10                  15

<210> SEQ ID NO 566
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Asn Pro Val Val His Phe Phe Lys Asn Ile Val Thr Pro Arg Thr
1               5                   10                  15

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gln Asp Glu Asn Pro Val Val His Phe Phe Lys Asn Ile Val Thr
1               5                   10                  15

<210> SEQ ID NO 568
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Glu Asn Pro Val Val His Phe Phe Lys Asn Ile Val Thr Pro Arg
1               5                   10                  15

<210> SEQ ID NO 569
<211> LENGTH: 15
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 569

Asn Pro Val Val His Phe Phe Lys Asn Ile Val Thr Pro Arg Thr
1               5                   10                  15

<210> SEQ ID NO 570
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Pro Val Val His Phe Phe Lys Asn Ile Val Thr Pro Arg Thr Pro
1               5                   10                  15

<210> SEQ ID NO 571
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Asp Glu Asn Pro Val Val His Phe Phe Lys Asn Ile Val Thr Pro
1               5                   10                  15

<210> SEQ ID NO 572
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Gln Asp Glu Asn Pro Val Val His Phe Phe Lys Asn Ile Val Thr
1               5                   10                  15

<210> SEQ ID NO 573

<400> SEQUENCE: 573

000

<210> SEQ ID NO 574
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gln Asp Glu Asn Pro Val Val His Phe Phe Lys Asn Ile Val Thr
1               5                   10                  15

<210> SEQ ID NO 575
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 575

Glu Asn Pro Val Val His Phe Phe Lys Asn Ile Val Thr Pro Arg
1               5                   10                  15

<210> SEQ ID NO 576
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Asn Pro Val Val His Phe Phe Lys Asn Ile Val Thr Pro Arg Thr
1               5                   10                  15

<210> SEQ ID NO 577
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Glu Asn Pro Val Val His Phe Phe Lys Asn Ile Val Thr Pro Arg
1               5                   10                  15

<210> SEQ ID NO 578
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Pro Val Val His Phe Phe Lys Asn Ile Val Thr Pro Arg Thr Pro
1               5                   10                  15

<210> SEQ ID NO 579
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Val Val His Phe Phe Lys Asn Ile Val Thr Pro Arg Thr Pro Pro
1               5                   10                  15

<210> SEQ ID NO 580
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Asp Glu Asn Pro Val Val His Phe Phe Lys Asn Ile Val Thr Pro
1               5                   10                  15

<210> SEQ ID NO 581

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Gln Asp Glu Asn Pro Val Val His Phe Phe Lys Asn Ile Val Thr
1               5                   10                  15

<210> SEQ ID NO 582
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Thr Gln Asp Glu Asn Pro Val Val His Phe Phe Lys Asn Ile Val
1               5                   10                  15

<210> SEQ ID NO 583

<400> SEQUENCE: 583

000

<210> SEQ ID NO 584

<400> SEQUENCE: 584

000

<210> SEQ ID NO 585
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Ser Val Val Glu Gly Val Ala Thr Phe
1               5

<210> SEQ ID NO 586
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Val Phe Asn Glu Arg Leu Pro Val Phe
1               5

<210> SEQ ID NO 587
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587
```

```
Ala Tyr Gly Val Leu Ala Phe Leu Val Phe
1               5                   10

<210> SEQ ID NO 588
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Glu Tyr Leu His Pro Phe Gly Phe
1               5

<210> SEQ ID NO 589
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Ile Phe Asp Gly Gln His Phe Phe
1               5

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Asp Tyr Leu Asp Ser Leu Leu Phe Leu
1               5

<210> SEQ ID NO 591
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Ala Pro Ile Gly Val Ser Ser Leu Ile Leu
1               5                   10

<210> SEQ ID NO 592
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Ala Trp Met Pro Ala Glu Thr Phe
1               5

<210> SEQ ID NO 593
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 593

Ser Phe Pro Val Leu Thr Ala Phe
1               5

<210> SEQ ID NO 594
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Val Ser Pro Ser Thr Pro Pro Ala Ala Leu
1               5                   10

<210> SEQ ID NO 595
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Ile Pro Asn Gln Gly Arg Ser Leu
1               5

<210> SEQ ID NO 596
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Ile Tyr Gly Leu Glu His Phe Phe Leu
1               5

<210> SEQ ID NO 597
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Asp Pro His Ala Phe His Leu Leu
1               5

<210> SEQ ID NO 598
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Phe Pro Val Tyr Glu Val Arg Val
1               5

-continued

```
<210> SEQ ID NO 599
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Ala Tyr Ile Tyr Thr Thr Tyr Leu Leu
1               5

<210> SEQ ID NO 600
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Ser Pro Tyr Asp Arg Phe Arg Leu
1               5

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Asn Pro Phe Gly Ala Phe Thr Ile Ile
1               5

<210> SEQ ID NO 602

<400> SEQUENCE: 602

000

<210> SEQ ID NO 603

<400> SEQUENCE: 603

000

<210> SEQ ID NO 604
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Pro Lys Tyr Val Lys Gln Asn Thr Leu Lys Leu Ala Thr
1               5                   10

<210> SEQ ID NO 605
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605
```

```
Gly Ile Leu Gly Phe Val Phe Thr Leu
1               5

<210> SEQ ID NO 606
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gly Ile Leu Gly Phe Val Phe Thr Leu
1               5

<210> SEQ ID NO 607
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Thr Pro Arg Val Thr Gly Gly Gly Ala Met
1               5                   10

<210> SEQ ID NO 608
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Thr Pro Arg Val Thr Gly Gly Gly Ala Met
1               5                   10

<210> SEQ ID NO 609
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Ile Pro Ser Ile Asn Val His His Tyr
1               5

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Ile Pro Ser Ile Asn Val His His Tyr
1               5

<210> SEQ ID NO 611
<211> LENGTH: 8
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 611

Thr Ala Phe Thr Ile Pro Ser Ile
1               5

<210> SEQ ID NO 612
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Thr Ala Phe Thr Ile Pro Ser Ile
1               5

<210> SEQ ID NO 613
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Gly Ala Asp Gly Val Gly Lys Ser Ala Leu
1               5                   10

<210> SEQ ID NO 614
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Gly Ala Asp Gly Val Gly Lys Ser Ala Leu
1               5                   10

<210> SEQ ID NO 615
<211> LENGTH: 1235
<212> TYPE: DNA
<213> ORGANISM: Homo sapiens

<400> SEQUENCE: 615
attcttgtct gttctgcctc actcccgagc tctactgact cccaacagag cgcccaagaa      60
gaaaatggcc ataagtggag tccctgtgct aggattttc atcatagctg tgctgatgag     120
cgctcaggaa tcatgggcta tcaaagaaga acatgtgatc atccaggccg agttctatct     180
gaatcctgac caatcaggcg agtttatgtt tgactttgat ggtgatgaga ttttccatgt     240
ggatatggca aagaaggaga cggtctggcg gcttgaagaa tttggacgat ttgccagctt     300
tgaggctcaa ggtgcattgg ccaacatagc tgtggacaaa gccaacctgg aaatcatgac     360
aaagcgctcc aactatactc cgatcaccaa tgtacctcca gaggtaactg tgctcacaaa     420
cagccctgtg gaactgagag agcccaacgt cctcatctgt ttcatagaca gttcacccc     480 accagtggtc aatgtcacgt ggcttcgaaa tggaaaacct gtcaccacag gagtgtcaga     540
gacagtcttc ctgcccaggg aagaccacct tttccgcaag ttccactatc tccccttcct     600
```

```
gccctcaact gaggacgttt acgactgcag ggtggagcac tggggcttgg atgagcctct     660
tctcaagcac tgggagtttg atgctccaag ccctctccca gagactacag agaacgtggt     720
gtgtgccctg ggcctgactg tgggtctggt gggcatcatt attgggacca tcttcatcat     780
caagggattg cgcaaaagca atgcagcaga acgcagggg cctctgtaag gcacatggag       840
gtgatggtgt ttcttagaga aagatcact gaagaaactt ctgctttaat ggctttacaa      900
agctggcaat attacaatcc ttgacctcag tgaaagcagt catcttcagc attttccagc     960
cctatagcca ccccaagtgt ggatatgcct cttcgattgc tccgtactct aacatctagc    1020
tggcttccct gtctattgcc tttcctgta tctattttcc tctatttcct atcattttat     1080
tatcaccatg caatgcctct ggaataaaac atacaggagt ctgtctctgc tatggaatgc    1140
cccatggggc atctcttgtg tacttattgt ttaaggtttc ctcaaactgt gatttttctg    1200
aacacaataa actattttga tgatcttggg tggaa                              1235
```

```
<210> SEQ ID NO 616
<211> LENGTH: 254
<212> TYPE: PRT
<213> ORGANISM: Homo sapiens

<400> SEQUENCE: 616

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
    130                 135                 140

Thr Trp Leu Arg Asn Gly Lys Pro Val Thr Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Leu Arg Lys Ser Asn Ala Ala Glu Arg Arg Gly Pro Leu
                245                 250
```

-continued

```
<210> SEQ ID NO 617
<211> LENGTH: 1223
<212> TYPE: DNA
<213> ORGANISM: Homo sapiens

<400> SEQUENCE: 617
agtaacttcc tccctataac ttggaatgtg ggtggagggg ttcatagttc tccctgagtg      60
agacttgcct gcttctctgg cccctggtcc tgtcctgttc tccagcatgg tgtgtctgaa     120
gctccctgga ggctcctgca tgacagcgct gacagtgaca ctgatggtgc tgagctcccc     180
actggctttg tctggggaca cccgaccacg tttcctgtgg cagcctaaga gggagtgtca     240
tttcttcaat gggacggagc gggtgcggtt cctggacaga tacttctata accaggagga     300
gtccgtgcgc ttcgacagcg acgtggggga gttccgggcg gtgacggagc tggggcggcc     360
tgacgctgag tactggaaca gccagaagga catcctggag caggcgcggg ccgcggtgga     420
cacctactgc agacacaact acggggttgt ggagagcttc acagtgcagc ggcgagtcca     480
acctaaggtg actgtatatc cttcaaagac ccagcccctg cagcaccaca acctcctggt     540
ctgctctgtg agtggtttct atccaggcag cattgaagtc aggtggttcc tgaacggcca     600
ggaagagaag gctgggatgg tgtccacagg cctgatccag aatggagact ggaccttcca     660
gaccctggtg atgctggaaa cagttcctcg aagtggagag gtttacacct gccaagtgga     720
gcacccaagc gtgacaagcc ctctcacagt ggaatggaga gcacggtctg aatctgcaca     780
gagcaagatg ctgagtggag tcgggggctt tgtgctgggc ctgctcttcc ttggggccgg     840
gctgttcatc tacttcagga atcagaaagg cactctggac cttcagccaa caggattcct     900
gagctgaaat gcagatgacc acattcaagg aagaactttc tgccccggct ttgcaggatg     960
aaaagctttc ctgcttggca gttattcttc cacaagagag ggctttctca ggacctggtt    1020
gctactggtt cggcaactgc agaaaatgtc ctcccttgtg gcttcctcag ctcctgccct    1080
tggcctgaag tccagcatt gatggcagcg cctcatcttc aacttttgtg ctcccctttg    1140
cctaaaccgt atggcctccc gtgcatctgt attcaccctg tatgacaaac acattacatt    1200
attaaatgtt tctcaaagat gga                                             1223

<210> SEQ ID NO 618
<211> LENGTH: 266
<212> TYPE: PRT
<213> ORGANISM: Homo sapiens

<400> SEQUENCE: 618

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ser Gly Asp Thr
                20                  25                  30

Arg Pro Arg Phe Leu Trp Gln Pro Lys Arg Glu Cys His Phe Phe Asn
            35                  40                  45

Gly Thr Glu Arg Val Arg Phe Leu Asp Arg Tyr Phe Tyr Asn Gln Glu
        50                  55                  60

Glu Ser Val Arg Phe Asp Ser Asp Val Gly Glu Phe Arg Ala Val Thr
65                  70                  75                  80

Glu Leu Gly Arg Pro Asp Ala Glu Tyr Trp Asn Ser Gln Lys Asp Ile
                85                  90                  95

Leu Glu Gln Ala Arg Ala Ala Val Asp Thr Tyr Cys Arg His Asn Tyr
            100                 105                 110

Gly Val Val Glu Ser Phe Thr Val Gln Arg Arg Val Gln Pro Lys Val
```

-continued

```
            115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Leu Asn Gly Gln Glu Glu Lys Ala Gly Met Val Ser Thr Gly Leu
                165                 170                 175

Ile Gln Asn Gly Asp Trp Thr Phe Gln Thr Leu Val Met Leu Glu Thr
                180                 185                 190

Val Pro Arg Ser Gly Glu Val Tyr Thr Cys Gln Val Glu His Pro Ser
                195                 200                 205

Val Thr Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
                260                 265

<210> SEQ ID NO 619
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Cys Ala Ser Ser Ser Gly Gln Val Gln Glu Thr Gln Tyr Phe
1               5                   10

<210> SEQ ID NO 620
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Cys Ala Ser Ser Phe Pro Thr Ser Gly Gln Glu Thr Gln Tyr Phe
1               5                   10                  15

<210> SEQ ID NO 621
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Cys Ala Ser Ser His Arg Asp Arg Asn Tyr Glu Gln Tyr Phe
1               5                   10

<210> SEQ ID NO 622
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 622

Cys Ala Thr Ser Arg Val Ala Gly Glu Thr Gln Tyr Phe
1               5                   10

<210> SEQ ID NO 623
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Cys Ala Ser Ser Val Thr Gly Gly Thr Asp Thr Gln Tyr Phe
1               5                   10

<210> SEQ ID NO 624
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Cys Ala Ser Ser Val Thr Gly Gly Thr Asp Thr Gln Tyr Phe
1               5                   10

<210> SEQ ID NO 625
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Cys Ala Ser Ser Ala Gly Gln Gly Val Thr Tyr Glu Gln Tyr Phe
1               5                   10                  15

<210> SEQ ID NO 626
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Cys Ala Ser Ser Leu Gly Gly Pro Gly Asp Thr Gln Tyr Phe
1               5                   10

<210> SEQ ID NO 627
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Cys Ala Ser Ser Leu Gly Gly Pro Gly Asp Thr Gln Tyr Phe
1               5                   10

<210> SEQ ID NO 628
<211> LENGTH: 14
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Cys Ala Ser Ser Leu Gly Gly Ala Gly Asp Thr Gln Tyr Phe
1               5                   10

<210> SEQ ID NO 629
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Cys Ala Ser Ser Leu Gly Gly Ala Gly Asp Thr Gln Tyr Phe
1               5                   10

<210> SEQ ID NO 630
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Cys Ser Ala Ser Asp His Glu Gln Tyr Phe
1               5                   10

<210> SEQ ID NO 631
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Cys Ala Ser Ser Leu Asn Arg Gly Gln Glu Thr Gln Tyr Phe
1               5                   10

<210> SEQ ID NO 632
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Cys Ala Val Ala Ser Tyr Gly Asn Lys Leu Val Phe
1               5                   10

<210> SEQ ID NO 633
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Cys Ala Leu Ser Asp Asn Tyr Gly Gln Asn Phe Val Phe
```

```
1               5                    10

<210> SEQ ID NO 634
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Cys Ala Val Asn Val Asp Thr Asp Lys Leu Ile Phe
1               5                    10

<210> SEQ ID NO 635
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Cys Ala Thr Glu Gly Asn Phe Gly Asn Glu Lys Leu Thr Phe
1               5                    10

<210> SEQ ID NO 636
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Cys Ala Leu Ser Glu Gly Phe Gln Thr Gly Ala Asn Asn Leu Phe Phe
1               5                    10                   15

<210> SEQ ID NO 637
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Cys Ala Ala Pro Gly Gly Ser Thr Leu Gly Arg Leu Tyr Phe
1               5                    10

<210> SEQ ID NO 638
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Cys Ala Val Arg Ser Gly Gly Tyr Gln Lys Val Thr Phe
1               5                    10

<210> SEQ ID NO 639
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 639

Cys Ala Val Ser Gln Pro Ser Gly Gly Ser Tyr Ile Pro Thr Phe
1               5                   10                  15

<210> SEQ ID NO 640
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Cys Ala Val Ser Gln Pro Ser Gly Gly Ser Tyr Ile Pro Thr Phe
1               5                   10                  15

<210> SEQ ID NO 641
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Cys Ala Val Thr Asp Ala Ser Gly Gly Ser Tyr Ile Pro Thr Phe
1               5                   10                  15

<210> SEQ ID NO 642
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Cys Ala Val Thr Asp Ala Ser Gly Gly Ser Tyr Ile Pro Thr Phe
1               5                   10                  15

<210> SEQ ID NO 643
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Cys Gly Ala Asp Ser Arg Gly Ser Thr Leu Gly Arg Leu Tyr Phe
1               5                   10                  15

<210> SEQ ID NO 644
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Cys Ala Val Arg Arg Gly Thr Asp Lys Leu Ile Phe
1               5                   10

<210> SEQ ID NO 645
```

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Val Tyr Ala Ile Phe Ile Phe Gln Leu
1               5

<210> SEQ ID NO 646
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Val Tyr Ala Ile Phe Ile Phe Gln Leu
1               5

<210> SEQ ID NO 647
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Val Tyr Ala Ile Phe Ile Phe Gln Leu
1               5

<210> SEQ ID NO 648
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Val Tyr Ala Ile Phe Ile Phe Gln Leu
1               5

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Val Tyr Ala Ile Phe Ile Phe Gln Leu
1               5

<210> SEQ ID NO 650
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650
```

```
Ala Tyr Gly Val Leu Ala Phe Leu Val Phe
1               5                   10

<210> SEQ ID NO 651
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Glu Tyr Leu His Pro Phe Gly Phe
1               5

<210> SEQ ID NO 652
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Ile Phe Asp Gly Gln His Phe Phe
1               5

<210> SEQ ID NO 653
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Ser Phe Pro Val Leu Thr Ala Phe
1               5

<210> SEQ ID NO 654
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Ala Tyr Ile Tyr Thr Thr Tyr Leu Leu
1               5

<210> SEQ ID NO 655
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Asn Leu Val Pro Met Val Ala Thr Val
1               5

<210> SEQ ID NO 656
<211> LENGTH: 10
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 656

Thr Pro Arg Val Thr Gly Gly Gly Ala Met
1               5                   10

<210> SEQ ID NO 657
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Ile Pro Ser Ile Asn Val His His Tyr
1               5

<210> SEQ ID NO 658
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Thr Ala Phe Thr Ile Pro Ser Ile
1               5

<210> SEQ ID NO 659
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Gly Ala Asp Gly Val Gly Lys Ser Ala Leu
1               5                   10

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Ala Leu Val Pro Met Val Ala Thr Val
1               5

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Asn Leu Val Pro Met Val Ala Ala Val
1               5

-continued

```
<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Gly Ile Leu Gly Phe Val Phe Thr Leu
1               5

<210> SEQ ID NO 663
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Thr Pro Arg Val Thr Gly Gly Gly Ala Met
1               5                   10

<210> SEQ ID NO 664
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Gly Ala Asp Gly Val Gly Lys Ser Ala Leu
1               5                   10

<210> SEQ ID NO 665
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Gly Ile Leu Gly Phe Val Phe Thr Leu
1               5

<210> SEQ ID NO 666
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Pro Lys Tyr Val Lys Gln Asn Thr Leu Lys Leu Ala Thr
1               5                   10

<210> SEQ ID NO 667
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667
```

```
Gly Ala Asp Gly Val Gly Lys Ser Ala Leu
1               5                   10

<210> SEQ ID NO 668
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Ala Asp Gly Val Gly Lys Ser Ala Leu Thr
1               5                   10

<210> SEQ ID NO 669
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Gly Ala Asp Gly Val Gly Lys Ser Ala
1               5

<210> SEQ ID NO 670
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Val Gly Ala Asp Gly Val Gly Lys Ser Ala Leu
1               5                   10

<210> SEQ ID NO 671
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Gln Asp Glu Asn Pro Val Val His Phe Phe Lys Asn Ile Val Thr
1               5                   10                  15

<210> SEQ ID NO 672
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Asp Glu Asn Pro Val Val His Phe Phe Lys Asn Ile Val Thr Pro
1               5                   10                  15

<210> SEQ ID NO 673
<211> LENGTH: 15
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 673

Glu Asn Pro Val Val His Phe Phe Lys Asn Ile Val Thr Pro Arg
1               5                   10                  15

<210> SEQ ID NO 674
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Asn Pro Val Val His Phe Phe Lys Asn Ile Val Thr Pro Arg Thr
1               5                   10                  15

<210> SEQ ID NO 675
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Pro Val Val His Phe Phe Lys Asn Ile Val Thr Pro Arg Thr Pro
1               5                   10                  15

<210> SEQ ID NO 676
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Thr Gln Asp Glu Asn Pro Val Val His Phe Phe Lys Asn Ile Val
1               5                   10                  15

<210> SEQ ID NO 677
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Gln Asp Glu Asn Pro Val Val His Phe Phe Lys Asn Ile Val Thr
1               5                   10                  15

<210> SEQ ID NO 678
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Thr Pro Arg Val Thr Gly Gly Gly Ala Met
1               5                   10

```
<210> SEQ ID NO 679
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Met Leu Asn Ile Pro Ser Ile Asn Val
1               5

<210> SEQ ID NO 680
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Arg Pro His Glu Arg Asn Gly Phe Thr Val Leu
1               5                   10

<210> SEQ ID NO 681
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Leu Pro Leu Lys Met Leu Asn Ile
1               5

<210> SEQ ID NO 682
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 682

Gln Gln Ile Phe Leu Glu Val Gln Ala Ile Arg Glu Thr Val Glu Leu
1               5                   10                  15

Arg Gln Tyr Asp Pro Val Ala Ala Leu Phe Phe Phe Asp Ile Asp Leu
            20                  25                  30

Leu Leu Gln Arg Gly Pro Gln Tyr Ser Glu His Pro Thr Phe Thr Ser
        35                  40                  45

Gln Tyr
    50

<210> SEQ ID NO 683
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Tyr Ser Glu His Pro Thr Phe Thr Ser Gln Tyr
1               5                   10
```

```
<210> SEQ ID NO 684
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 684

Thr Leu Leu Asn Cys Ala Val Thr Lys Leu Pro Cys Thr Leu Arg Ile
1               5                   10                  15

Val Thr Glu His Asp Thr Leu Leu Tyr Val Ala Ser Arg Asn Gly Leu
            20                  25                  30

Phe Ala Val Glu Asn Phe Leu Thr Glu Glu Pro Phe Gln Arg Gly Asp
        35                  40                  45

Pro Phe
    50

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Val Thr Glu His Asp Thr Leu Leu Tyr
1               5

<210> SEQ ID NO 686
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Val Tyr Ala Ile Phe Ile Phe Gln Leu
1               5

<210> SEQ ID NO 687
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Tyr Ser Glu His Pro Thr Phe Thr Ser Gln Tyr
1               5                   10

<210> SEQ ID NO 688
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 688

Val Thr Glu His Asp Thr Leu Leu Tyr
1               5
```

<210> SEQ ID NO 689
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Leu Pro Leu Lys Met Leu Asn Ile
1               5

<210> SEQ ID NO 690
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 690

His Arg Glu Ala Asp Ala Gln Thr Phe Ala Ala Thr His Asn Pro Trp
1               5                   10                  15

Ala Ser Gln Ala Gly Cys Leu Ser Asp Val Leu Tyr Asn Thr Arg His
            20                  25                  30

Arg Glu Arg Leu Gly Tyr Asn Ser Lys Phe Tyr Ser Pro Cys Ala Gln
        35                  40                  45

Tyr Phe
    50

<210> SEQ ID NO 691
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Ala Gln Thr Phe Ala Ala Thr His Asn Pro Trp Ala Ser Gln Ala
1               5                   10                  15

<210> SEQ ID NO 692
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Cys Ala Ser Ser Leu Gly Gly Pro Gly Asp Thr Gln Tyr Phe
1               5                   10

<210> SEQ ID NO 693
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Cys Ala Ser Ser Leu Gly Gly Ala Gly Asp Thr Gln Tyr Phe
1               5                   10

<210> SEQ ID NO 694
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 694

Asp Arg Lys Thr Arg Leu Ser Glu Pro Pro Thr Leu Ala Leu Arg Leu
1               5                   10                  15

Lys Pro Tyr Lys Thr Ala Ile Gln Gln Leu Arg Ser Val Ile Arg Ala
            20                  25                  30

Leu Lys Glu Asn Thr Thr Val Thr Phe Leu Pro Thr Pro Ser Leu Ile
        35                  40                  45

Leu Gln
    50

<210> SEQ ID NO 695
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 695

Tyr Lys Thr Ala Ile Gln Gln Leu Arg Ser Val Ile Arg Ala Leu Lys
1               5                   10                  15

Glu Asn Thr Thr Val Thr Phe Leu Pro Thr Pro Ser Leu Ile Leu Gln
            20                  25                  30

Thr Val Arg Ser His Cys Val Ser Lys Ile Thr Phe Asn Ser Ser Cys
        35                  40                  45

Leu Tyr
    50

<210> SEQ ID NO 696
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Asn Thr Thr Val Thr Phe Leu Pro Thr Pro Ser Leu Ile Leu Gln
1               5                   10                  15

<210> SEQ ID NO 697
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Thr Thr Val Thr Phe Leu Pro Thr Pro Ser Leu Ile Leu Gln Thr
1               5                   10                  15

<210> SEQ ID NO 698
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Phe Ala Ala Thr His Asn Pro Trp Ala
1               5

<210> SEQ ID NO 699
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Phe Leu Pro Thr Pro Ser Leu Ile Leu
1               5

<210> SEQ ID NO 700
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Gly Ile Leu Gly Phe Val Phe Thr Leu
1               5

<210> SEQ ID NO 701
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Leu Pro Leu Lys Met Leu Asn Ile
1               5

<210> SEQ ID NO 702
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Leu Pro Leu Lys Met Leu Asn Ile
1               5

<210> SEQ ID NO 703
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Leu Pro Leu Lys Met Leu Asn Ile
1               5

```
<210> SEQ ID NO 704
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Tyr Ser Glu His Pro Thr Phe Thr Ser Gln Tyr
1               5                   10

<210> SEQ ID NO 705
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Val Thr Glu His Asp Thr Leu Leu Tyr
1               5

<210> SEQ ID NO 706
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Thr Thr Val Thr Phe Leu Pro Thr Pro Ser Leu Ile Leu Gln Thr
1               5                   10                  15

<210> SEQ ID NO 707
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Asn Thr Thr Val Thr Phe Leu Pro Thr Pro Ser Leu Ile Leu Gln
1               5                   10                  15

<210> SEQ ID NO 708
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Ala Gln Thr Phe Ala Ala Thr His Asn Pro Trp Ala Ser Gln Ala
1               5                   10                  15

<210> SEQ ID NO 709
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 709

Asn Thr Thr Val Thr Phe Leu Pro Thr Pro Ser Leu Ile Leu Gln
1               5                   10                  15

<210> SEQ ID NO 710
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Thr Thr Val Thr Phe Leu Pro Thr Pro Ser Leu Ile Leu Gln Thr
1               5                   10                  15

<210> SEQ ID NO 711
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Asn Leu Val Pro Met Val Ala Thr Val
1               5

<210> SEQ ID NO 712
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Asn Leu Val Pro Met Val Ala Thr Val
1               5

<210> SEQ ID NO 713
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Leu Pro Leu Lys Met Leu Asn Ile
1               5

<210> SEQ ID NO 714
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Tyr Ser Glu His Pro Thr Phe Thr Ser Gln Tyr
1               5                   10

<210> SEQ ID NO 715
<211> LENGTH: 9
<212> TYPE: PRT

<213> ORGANISM: Artificial Sequence
<220> FEATURE:
<223> OTHER INFORMATION: Description of Artificial Sequence: Synthetic
     peptide

<400> SEQUENCE: 715

Gln Tyr Asp Pro Val Ala Ala Leu Phe
1               5

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720
<211> LENGTH: 50
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 720

His Arg Glu Ala Asp Ala Gln Thr Phe Ala Ala Thr His Asn Pro Trp
1               5                   10                  15

Ala Ser Gln Ala Gly Cys Leu Ser Asp Val Leu Tyr Asn Thr Arg His
            20                  25                  30

Arg Glu Arg Leu Gly Tyr Asn Ser Lys Phe Tyr Ser Pro Cys Ala Gln
        35                  40                  45

Tyr Phe
    50

<210> SEQ ID NO 721
<211> LENGTH: 15
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 721

Ala Gln Thr Phe Ala Ala Thr His Asn Pro Trp Ala Ser Gln Ala
1               5                   10                  15

<210> SEQ ID NO 722
<211> LENGTH: 15
<212> TYPE: PRT

<210> ORGANISM: Artificial Sequence
<220> FEATURE:
<223> OTHER INFORMATION: Description of Artificial Sequence: Synthetic
      peptide

<400> SEQUENCE: 722

Thr Thr Val Thr Phe Leu Pro Thr Pro Ser Leu Ile Leu Gln Thr
1               5                   10                  15

<210> SEQ ID NO 723
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Pro Pro Thr Leu Ala Leu Arg Leu Lys Pro Tyr Lys Thr Ala Ile
1               5                   10                  15

<210> SEQ ID NO 724
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Thr Ala Ile Gln Gln Leu Arg Ser Val Ile Arg Ala Leu Lys Glu
1               5                   10                  15

<210> SEQ ID NO 725
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Ile Arg Ala Leu Lys Glu Asn Thr Thr Val Thr Phe Leu Pro Thr
1               5                   10                  15

<210> SEQ ID NO 726
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Asn Thr Thr Val Thr Phe Leu Pro Thr Pro Ser Leu Ile Leu Gln
1               5                   10                  15

<210> SEQ ID NO 727
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

Thr Thr Val Thr Phe Leu Pro Thr Pro Ser Leu Ile Leu Gln Thr
1               5                   10                  15

<210> SEQ ID NO 728
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Gly Ala Cys Gly Val Gly Lys Ser Ala Leu
1               5                   10

<210> SEQ ID NO 729
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Gly Ala Asp Gly Val Gly Lys Ser Ala Leu
1               5                   10

<210> SEQ ID NO 730
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Gly Ala Asp Gly Val Gly Lys Ser Ala Leu
1               5                   10

<210> SEQ ID NO 731
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Gly Ala Asp Gly Val Gly Lys Ser Ala Leu
1               5                   10

<210> SEQ ID NO 732
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Gly Ala Gly Gly Val Gly Lys Ser Ala Leu
1               5                   10

<210> SEQ ID NO 733
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 733

Gly Ala Arg Gly Val Gly Lys Ser Ala Leu
1               5                   10

<210> SEQ ID NO 734
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Gly Ala Val Gly Val Gly Lys Ser Ala Leu
1               5                   10

<210> SEQ ID NO 735
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Gly Ile Leu Gly Phe Val Phe Thr Leu
1               5

<210> SEQ ID NO 736
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Gly Ile Leu Gly Phe Val Phe Thr Leu
1               5

<210> SEQ ID NO 737
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Gly Ile Leu Gly Phe Val Phe Thr Leu
1               5

<210> SEQ ID NO 738
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Ile Pro Ser Ile Asn Val His His Tyr
1               5

<210> SEQ ID NO 739
<211> LENGTH: 9
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Asn Leu Val Pro Met Val Ala Thr Val
1               5

<210> SEQ ID NO 740
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Ser Leu Leu Met Trp Ile Thr Gln Val
1               5

<210> SEQ ID NO 741
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Gly Ala Asp Gly Val Gly Lys Ser Ala Leu
1               5                   10

<210> SEQ ID NO 742
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Gly Ala Asp Gly Val Gly Lys Ser Ala
1               5

<210> SEQ ID NO 743
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Gly Ala Gly Gly Val Gly Lys Ser Ala Leu
1               5                   10

<210> SEQ ID NO 744
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Tyr Val Lys Gln Asn Thr Leu Lys Leu

```
1               5

<210> SEQ ID NO 745
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Val Ser Asp Gly Gly Pro Asn Leu Tyr
1               5

<210> SEQ ID NO 746
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Cys Thr Glu Leu Lys Leu Ser Asp Tyr
1               5

<210> SEQ ID NO 747
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Gly Ile Leu Gly Phe Val Phe Thr Leu
1               5

<210> SEQ ID NO 748
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Phe Met Tyr Ser Asp Phe His Phe Ile
1               5

<210> SEQ ID NO 749
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Cys Leu Gly Gly Leu Leu Thr Met Val
1               5

<210> SEQ ID NO 750
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 750

Gly Leu Cys Thr Leu Val Ala Met Leu
1               5

<210> SEQ ID NO 751
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Lys Thr Gly Gly Pro Ile Tyr Lys Arg
1               5

<210> SEQ ID NO 752
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Arg Val Leu Ser Phe Ile Lys Gly Thr Lys
1               5                   10

<210> SEQ ID NO 753
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Ile Leu Arg Gly Ser Val Ala His Lys
1               5

<210> SEQ ID NO 754
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Arg Val Arg Ala Tyr Thr Tyr Ser Lys
1               5

<210> SEQ ID NO 755
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Arg Leu Arg Ala Glu Ala Gln Val Lys
1               5

<210> SEQ ID NO 756

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Ser Ile Ile Pro Ser Gly Pro Leu Lys
1               5

<210> SEQ ID NO 757
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Ala Val Phe Asp Arg Lys Ser Asp Ala Lys
1               5                   10

<210> SEQ ID NO 758
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Ile Pro Ser Ile Asn Val His His Tyr
1               5

<210> SEQ ID NO 759
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Ile Pro Ser Ile Asn Val His His Tyr
1               5

<210> SEQ ID NO 760
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Lys Leu Val Val Val Gly Ala Asp
1               5

<210> SEQ ID NO 761
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 761
```

-continued

```
Gln Gln Ile Phe Leu Glu Val Gln Ala Ile Arg Glu Thr Val Glu Leu
1               5                   10                  15

Arg Gln Tyr Asp Pro Val Ala Ala Leu Phe Phe Phe Asp Ile Asp Leu
            20                  25                  30

Leu Leu Gln Arg Gly Pro Gln Tyr Ser Glu His Pro Thr Phe Thr Ser
        35                  40                  45

Gln Tyr
    50
```

```
<210> SEQ ID NO 762
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 762
```

```
Thr Leu Leu Asn Cys Ala Val Thr Lys Leu Pro Cys Thr Leu Arg Ile
1               5                   10                  15

Val Thr Glu His Asp Thr Leu Leu Tyr Val Ala Ser Arg Asn Gly Leu
            20                  25                  30

Phe Ala Val Glu Asn Phe Leu Thr Glu Glu Pro Phe Gln Arg Gly Asp
        35                  40                  45

Pro Phe
    50
```

```
<210> SEQ ID NO 763
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763
```

```
Val Val His Phe Phe Lys Asn Ile Val Thr Pro Arg Thr Pro Pro
1               5                   10                  15
```

```
<210> SEQ ID NO 764
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 764
```

```
Asp Arg Lys Thr Arg Leu Ser Glu Pro Pro Thr Leu Ala Leu Arg Leu
1               5                   10                  15

Lys Pro Tyr Lys Thr Ala Ile Gln Gln Leu Arg Ser Val Ile Arg Ala
            20                  25                  30

Leu Lys Glu Asn Thr Thr Val Thr Phe Leu Pro Thr Pro Ser Leu Ile
        35                  40                  45

Leu Gln
    50
```

```
<210> SEQ ID NO 765
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
          peptide

<400> SEQUENCE: 765

Val Tyr Ala Ile Phe Ile Phe Gln Leu
1               5

<210> SEQ ID NO 766
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Asn Leu Ala Pro Met Val Ala Thr Val
1               5

<210> SEQ ID NO 767
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Val Val His Phe Phe Lys
1               5

<210> SEQ ID NO 768
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Val Val His Phe Phe Lys Asn Ile Val Thr Pro Arg Thr Pro Pro
1               5                   10                  15

<210> SEQ ID NO 769
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

His Thr Val Gly Leu Tyr Met
1               5

<210> SEQ ID NO 770
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 770

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30
```

```
His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
                100                 105                 110

Val Val His Phe Phe Lys Asn Ile Val Thr Pro Arg Thr Pro Pro Pro
                115                 120                 125

Ser Gln Gly Lys Gly Arg Gly Leu Ser Leu Ser Arg Phe Ser Trp Gly
        130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
        180                 185                 190

Pro Met Ala Arg Arg
        195
```

```
<210> SEQ ID NO 771
<211> LENGTH: 186
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 771
```

```
Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
                100                 105                 110

Val Val His Phe Phe Lys Asn Ile Val Thr Pro Arg Thr Pro Pro Pro
                115                 120                 125

Ser Gln Gly Lys Gly Ala Glu Gly Gln Arg Pro Gly Phe Gly Tyr Gly
        130                 135                 140

Gly Arg Ala Ser Asp Tyr Lys Ser Ala His Lys Gly Phe Lys Gly Val
145                 150                 155                 160

Asp Ala Gln Gly Thr Leu Ser Lys Ile Phe Lys Leu Gly Gly Arg Asp
                165                 170                 175

Ser Arg Ser Gly Ser Pro Met Ala Arg Arg
```

-continued

```
        180                    185

<210> SEQ ID NO 772
<211> LENGTH: 171
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 772

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
        130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 773
<211> LENGTH: 160
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 773

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Ala Glu Gly Gln Arg
            100                 105                 110

Pro Gly Phe Gly Tyr Gly Gly Arg Ala Ser Asp Tyr Lys Ser Ala His
```

-continued

```
          115                 120                 125

Lys Gly Phe Lys Gly Val Asp Ala Gln Gly Thr Leu Ser Lys Ile Phe
    130                 135                 140

Lys Leu Gly Gly Arg Asp Ser Arg Ser Gly Ser Pro Met Ala Arg Arg
145                 150                 155                 160

<210> SEQ ID NO 774
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 774

Met Gly Asn His Ala Gly Lys Arg Glu Leu Asn Ala Glu Lys Ala Ser
1                 5                   10                  15

Thr Asn Ser Glu Thr Asn Arg Gly Glu Ser Glu Lys Lys Arg Asn Leu
              20                  25                  30

Gly Glu Leu Ser Arg Thr Thr Ser Glu Asp Asn Glu Val Phe Gly Glu
          35                  40                  45

Ala Asp Ala Asn Gln Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
              85                  90                  95

Arg Asp Ala Pro Gly Arg Glu Asp Asn Thr Phe Lys Asp Arg Pro Ser
              100                 105                 110

Glu Ser Asp Glu Leu Gln Thr Ile Gln Glu Asp Ser Ala Ala Thr Ser
          115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
              165                 170                 175

Arg Phe Phe Gly Gly Asp Arg Gly Ala Pro Lys Arg Gly Ser Gly Lys
              180                 185                 190

Asp Ser His His Pro Ala Arg Thr Ala His Tyr Gly Ser Leu Pro Gln
          195                 200                 205

Lys Ser His Gly Arg Thr Gln Asp Glu Asn Pro Val Val His Phe Phe
    210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
              245                 250                 255

Pro Gly Phe Gly Tyr Gly Gly Arg Ala Ser Asp Tyr Lys Ser Ala His
              260                 265                 270

Lys Gly Phe Lys Gly Val Asp Ala Gln Gly Thr Leu Ser Lys Ile Phe
          275                 280                 285

Lys Leu Gly Gly Arg Asp Ser Arg Ser Gly Ser Pro Met Ala Arg Arg
    290                 295                 300

<210> SEQ ID NO 775
<211> LENGTH: 197
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 775

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
            115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
                180                 185                 190

Val Ser Ser Glu Glu
        195

<210> SEQ ID NO 776
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Asn Pro Trp Ala Ser Gln Ala Gly Cys Leu Ser Asp Val Leu Tyr
1               5                   10                  15

<210> SEQ ID NO 777
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Arg Leu Gly Tyr Asn Ser Lys Phe Tyr Ser Pro Cys Ala Gln Tyr
1               5                   10                  15
```